United States Patent
Mainolfi

(10) Patent No.: US 11,091,451 B2
(45) Date of Patent: Aug. 17, 2021

(54) SHMT INHIBITORS AND USES THEREOF

(71) Applicant: Raze Therapeutics, Inc., Cambridge, MA (US)

(72) Inventor: Nello Mainolfi, Belmont, MA (US)

(73) Assignee: RAZE THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 16/466,479

(22) PCT Filed: Dec. 5, 2017

(86) PCT No.: PCT/US2017/064618
§ 371 (c)(1),
(2) Date: Jun. 4, 2019

(87) PCT Pub. No.: WO2018/106636
PCT Pub. Date: Jun. 14, 2018

(65) Prior Publication Data
US 2019/0345119 A1    Nov. 14, 2019

Related U.S. Application Data

(60) Provisional application No. 62/430,132, filed on Dec. 5, 2016.

(51) Int. Cl.
| | | |
|---|---|---|
| C07D 277/30 | (2006.01) | |
| C07C 233/50 | (2006.01) | |
| C07D 213/56 | (2006.01) | |
| C07D 417/04 | (2006.01) | |
| C07D 417/12 | (2006.01) | |

(52) U.S. Cl.
CPC .......... C07D 277/30 (2013.01); C07C 233/50 (2013.01); C07D 213/56 (2013.01); C07D 417/04 (2013.01); C07D 417/12 (2013.01)

(58) Field of Classification Search
CPC .......................... C07D 277/30; C07C 233/50
USPC ............................................... 514/326
See application file for complete search history.

(56) References Cited

U.S. PATENT DOCUMENTS

| | | | | |
|---|---|---|---|---|
| 3,502,673 A | * | 3/1970 | Hepworth | ............ C07D 239/42 544/319 |
| 3,538,107 A | * | 11/1970 | Gilbert | .................. C07D 277/22 548/204 |
| 3,749,787 A | * | 7/1973 | Hepworth et al. | ... C07D 277/30 514/365 |
| 5,639,600 A | | 6/1997 | McGrath et al. | |
| 6,552,065 B2 | | 4/2003 | Remiszewski et al. | |
| 7,071,189 B2 | | 7/2006 | Kawashima et al. | |
| 7,087,648 B1 | | 8/2006 | McGrath | |
| 7,390,799 B2 | | 6/2008 | Bruncko et al. | |
| 8,138,347 B2 | | 3/2012 | Knight et al. | |
| 2009/0275550 A1 | * | 11/2009 | Barrow | ................ C07D 213/65 514/210.2 |
| 2018/0117010 A1 | * | 5/2018 | Rabinowitz | ............ A61K 45/06 |

FOREIGN PATENT DOCUMENTS

| | | |
|---|---|---|
| WO | WO-2001042246 A2 | 6/2001 |
| WO | WO-2003063794 A2 | 8/2003 |
| WO | WO-2004019973 A1 | 3/2004 |
| WO | WO-2004089925 A1 | 10/2004 |
| WO | WO-2004106328 A1 | 12/2004 |
| WO | WO-2005007623 A2 | 1/2005 |
| WO | WO-2005113554 A2 | 12/2005 |
| WO | WO-2006078846 A1 | 7/2006 |
| WO | WO-2006122806 A2 | 11/2006 |
| WO | WO-2007016176 A2 | 2/2007 |
| WO | WO-2007044729 A2 | 4/2007 |
| WO | WO-2007053452 A1 | 5/2007 |
| WO | WO-2007070514 A1 | 6/2007 |
| WO | WO-2007084786 A1 | 7/2007 |
| WO | WO-2007129161 A2 | 11/2007 |
| WO | WO-2008039218 A2 | 4/2008 |
| WO | WO-2008109943 A1 | 9/2008 |
| WO | WO-2008118802 A1 | 10/2008 |
| WO | WO-2009114512 A1 | 9/2009 |
| WO | WO-2011090760 A1 | 7/2011 |
| WO | WO-2012007836 A1 * | 1/2012 ............. A61P 17/00 |
| WO | WO-2016145252 A1 * | 9/2016 ............. A61P 37/00 |

OTHER PUBLICATIONS

Ralph Howe et al. Metabolism of 2-(4-Chlorophenyl)thiazol-4-ylacetic Acid (Fenclozic Acid) and Related Compounds by Microorganisms (Year: 1972).*
PCT International Search Report and Written Opinion from PCT/US2017/064618, dated Mar. 13, 2018 (10 Pages).

* cited by examiner

*Primary Examiner* — Rita J Desai
(74) *Attorney, Agent, or Firm* — Dechert LLP; Andrea L.C. Reid; Todd K. Macklin

(57) ABSTRACT

The present invention provides compounds, compositions thereof, and methods of using the same.

11 Claims, No Drawings

SHMT INHIBITORS AND USES THEREOF

CROSS REFERENCE TO RELATED APPLICATIONS

This application claims the benefit of U.S. Provisional Application No. 62/430,132, filed Dec. 5, 2016, the entirety of which is hereby incorporated herein by reference.

TECHNICAL FIELD OF THE INVENTION

The present invention relates to compounds and methods useful for inhibiting serine hydroxymethyltransferase (SHMT1) and mitochondrial serine hydroxymethyltransferase (SHMT2). The invention also provides pharmaceutically acceptable compositions comprising compounds of the present invention and methods of using said compositions in the treatment of various disorders.

BACKGROUND OF THE INVENTION

Serine hydroxymethyltransferase (SHMT1) and mitochondrial serine hydroxymethyltransferase (SHMT2) catalyze the reversible conversion of serine to glycine, with the concurrent generation of methylene-tetrahydrofolate (methylene-THF), in a reaction dependent upon pyridoxal 5'-phosphate (PLP).

Certain cancers, including human melanomas, breast cancers, lung cancers, colon cancers, leukemias, lymphomas, and neuroblastoma, can have high levels of SHMT1 and/or SHMT2. These cancer cells are dependent on SHMT1 and/or SHMT2 for their growth and survival as SHMT1/2 catalyzes the production of glycine and methylene-THF, the latter of which is required for one-carbon unit anabolic metabolic reactions. SHMT1/2 may also be a significant source of NADPH in cancer cells. Targeting SHMT1 and/or SHMT2 by small molecule inhibitors could be a therapeutic strategy to reduce cancer cell growth and survival. Accordingly, there remains a need to find SHMT1/2 inhibitors useful as therapeutic agents.

SUMMARY OF THE INVENTION

It has now been found that compounds of this invention, and pharmaceutically acceptable compositions thereof, are effective as inhibitors of SHMT1 and/or SHMT2. Such compounds have the general formula I:

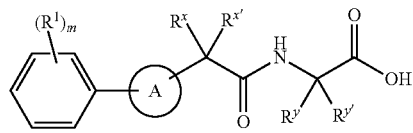

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with SHMT1 and/or SHMT2. Such diseases, disorders, or conditions include cellular proliferative disorders (e.g., cancer) such as those described herein.

DETAILED DESCRIPTION OF CERTAIN EMBODIMENTS

1. General Description of Certain Embodiments of the Invention

Compounds of the present invention, and compositions thereof, are useful as inhibitors of SHMT1 and/or SHMT2. Without wishing to be bound by any particular theory, it is believed that compounds of the present invention, and compositions thereof, may inhibit the activity of SHMT1 and/or SHMT2 and/or inhibit the production of NADPH, and thus reduce the growth of cells in proliferative disorders such as cancer.

In certain embodiments, the present invention provides a compound of formula I:

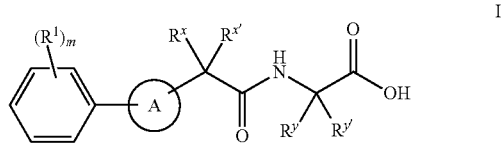

or a pharmaceutically acceptable salt thereof, wherein:
Ring A is an optionally substituted bivalent ring selected from S

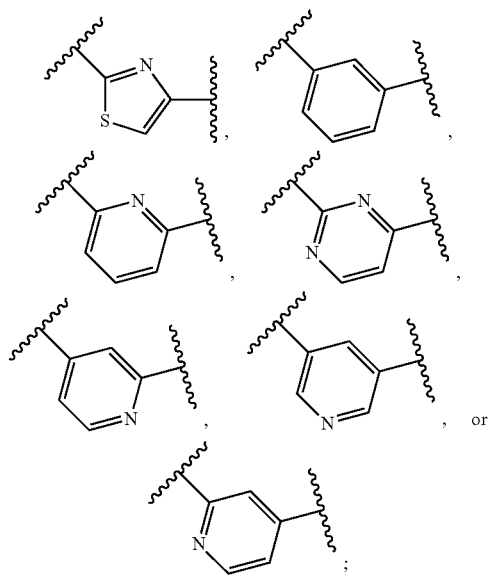

each $R^1$ is independently halogen, —CN, —$NO_2$, —OR, —Cy, or an optionally substituted $C_{1-6}$ aliphatic group; or two $R^1$ groups can be taken together with their intervening atoms to form a 5-8 membered partially unsaturated or aryl fused ring having 0-3 heteroatoms independently selected from nitrogen, oxygen or sulfur;
each R is independently hydrogen or an optionally substituted group selected from $C_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

Cy is an optionally substituted group selected from a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

$R^x$ and $R^y$ are independently hydrogen or an optionally substituted group selected from $C_{1-6}$ aliphatic or phenyl;

$R^{x'}$ and $R^{y'}$ are independently hydrogen or $C_{1-4}$ alkyl; or $R^y$ and $R^{y'}$ can be taken together with their intervening atoms to form a 3-6 membered saturated ring having 0-3 heteroatoms independently selected from nitrogen, oxygen or sulfur; and m is 1, 2, 3, 4 or 5.

In some embodiments, said compound of formulat I is other than a compound depicted in Table 2, below.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$C(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ_2$; —N(R$^\circ$)C(S)NR$^\circ_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NR$^\circ_2$; —C(S)NR$^\circ_2$; —C(S)SR$^\circ$; —SC(S)SR$^\circ$, —(CH$_2$)$_{0-4}$OC(O)NR$^\circ_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ_2$; —S(O)(NR$^\circ$)R$^\circ$; —S(O)$_2$N=C(NR$^\circ_2$)$_2$; —(CH$_2$)$_{0-4}$S(O)R$^\circ$; —N(R$^\circ$)S(O)$_2$NR$^\circ_2$; —N(R$^\circ$)S(O)$_2$R; —N(OR$^\circ$)R$^\circ$; —C(NH)NR$^\circ_2$; —P(O)$_2$R$^\circ$; —P(O)R$^\circ_2$; —OP(O)R$^\circ_2$; —OP(O)(OR$^\circ$)$_2$; —SiR$^\circ_3$; —(C$_{1-4}$ straight or branched alkylene)O—N(R$^\circ$)$_2$; or —(C$_{1-4}$ straight or branched alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\circ$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\circ$ is unsubstituted or where preceded by "halo" is substituted only with one or more halogens, and is independently C$_{1-4}$ aliphatic, —CH$_2$Ph, —O(CH$_2$)$_{0-1}$-Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention As used herein, the term "inhibitor" is defined as a compound that binds to and/or inhibits SHMT1 and/or SHMT2 with measurable affinity. In certain embodiments, an inhibitor has an IC$_{50}$ and/or binding constant of less than about 100 μM, less than about 50 μM, less than about 1 μM, less than about 500 nM, less than about 100 nM, less than about 10 nM, or less than about 1 nM.

The terms "measurable affinity" and "measurably inhibit," as used herein, means a measurable change in SHMT1 and/or SHMT2 activity between a sample comprising a compound of the present invention, or composition thereof, and SHMT1 or SHMT2, and an equivalent sample comprising SHMT1 or SHMT2, in the absence of said compound, or composition thereof.

3. Description of Exemplary Embodiments

In certain embodiments, the present invention provides a compound of Formula I:

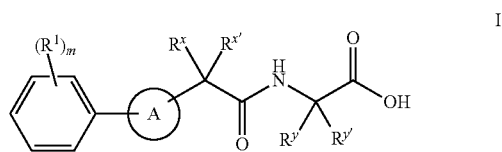

or a pharmaceutically acceptable salt thereof, wherein:
Ring A is an optionally substituted bivalent ring selected from

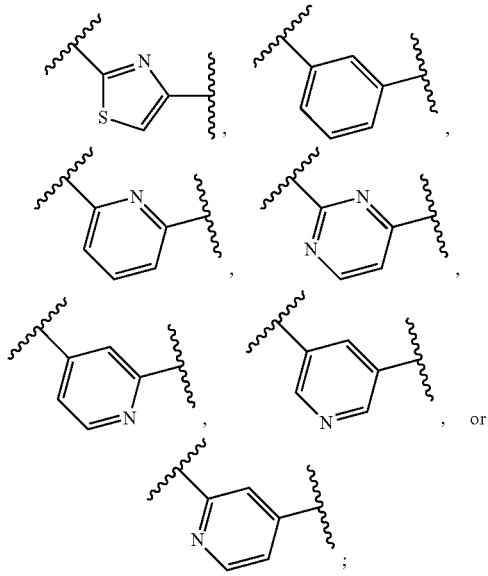
;

each R¹ is independently halogen, —CN, —NO₂, —OR, —Cy, or an optionally substituted C$_{1-6}$ aliphatic group; or two R¹ groups can be taken together with their intervening atoms to form a 5-8 membered partially unsaturated or aryl fused ring having 0-3 heteroatoms independently selected from nitrogen, oxygen or sulfur;

each R is independently hydrogen or an optionally substituted group selected from C$_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

Cy is an optionally substituted group selected from a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

R$^x$ and R$^y$ are independently hydrogen or an optionally substituted group selected from C$_{1-6}$ aliphatic or phenyl;
R$^{x'}$ and R$^{y'}$ are independently hydrogen or C$_{1-4}$ alkyl; or
Ry and Ry' can be taken together with their intervening atoms to form a 3-6 membered saturated ring having 0-3 heteroatoms independently selected from nitrogen, oxygen or sulfur; and m is 1, 2, 3, 4 or 5.

In some embodiments, said compound of formula I is other than a compound depicted in Table 2.

As defined above and described herein, Ring A is an optionally substituted bivalent ring selected from

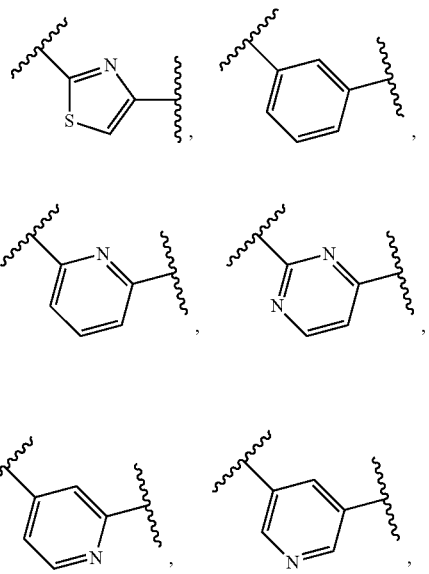

In some embodiments, Ring A is

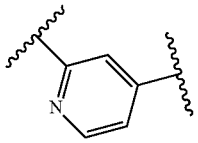

In some embodiments, Ring A is

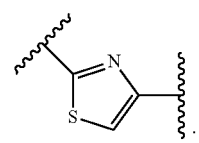 [SMILES: *c1csc(*)n1]

In some embodiments, Ring A is

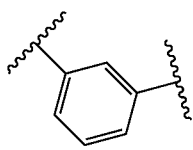

In some embodiments, Ring A is

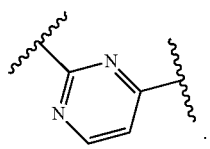 [SMILES: *c1ccnc(*)n1]

In some embodiments, Ring A is

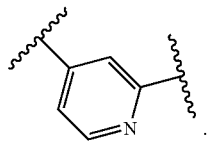 [SMILES: *c1ccnc(*)c1]

In some embodiments, Ring A is

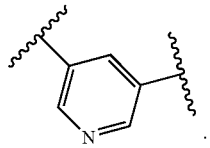 [SMILES: *c1cncc(*)c1]

In some embodiments, Ring A is

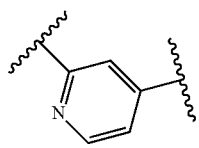

In some embodiments, Ring A is

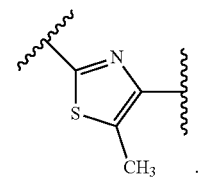

In some embodiments, Ring A is selected from those depicted in Table 1, below.

As defined above and described herein, each $R^1$ is independently halogen, —CN, —NO$_2$, —OR, —Cy, or an optionally substituted C$_{1-6}$ aliphatic group; or two $R^1$ groups can be taken together with their intervening atoms to form a 5-8 membered partially unsaturated or aryl fused ring having 0-3 heteroatoms independently selected from nitrogen, oxygen or sulfur.

In some embodiments, $R^1$ is halogen. In some embodiments, $R^1$ is —CN. In some embodiments, $R^1$ is —NO$_2$. In some embodiments, $R^1$ is —OR In some embodiments, $R^1$ is —Cy. In some embodiments, $R^1$ is an optionally substituted C$_{1-6}$ aliphatic group. In some embodiments, two $R^1$ groups are taken together with their intervening atoms to form a 5-8 membered partially unsaturated or aryl fused ring having 0-3 heteroatoms independently selected from nitrogen, oxygen or sulfur In some embodiments, $R^1$ is fluoro. In some embodiments, $R^1$ is bromo. In some embodiments, $R^1$ is chloro. In some embodiments, $R^1$ is —OCH$_3$. In some embodiments, $R^1$ is —OCF$_3$. In some embodiments, $R^1$ is ethyl. In some embodiments, $R^1$ is phenyl.

In some embodiments, $R^1$ is

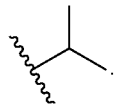

In some embodiments, $R^1$ is

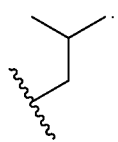

In some embodiments, $R^1$ is

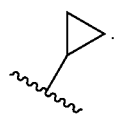 [SMILES: *C1CC1]

In some embodiments, $R^1$ is

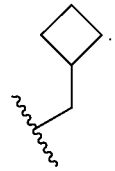 [SMILES: *CC1CCC1]

In some embodiments, $R^1$ is

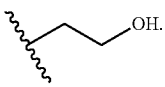 [SMILES: *CCO]

In some embodiments, $R^1$ is

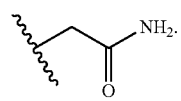

In some embodiments, $R^1$ is

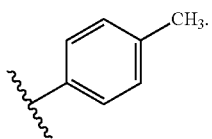 [SMILES: *c1ccc(C)cc1]

In some embodiments, $R^1$ is

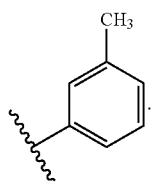 [SMILES: *c1cccc(C)c1]

In some embodiments, $R^1$ is

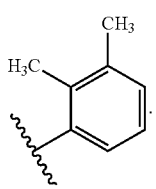

In some embodiments, $R^1$ is

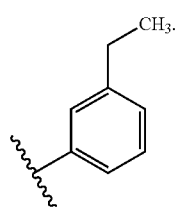 [SMILES: *c1cccc(CC)c1]

In some embodiments, $R^1$ is

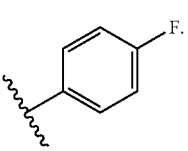 [SMILES: *c1ccc(F)cc1]

In some embodiments, $R^1$ is

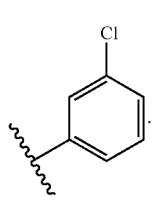 [SMILES: *c1cccc(Cl)c1]

In some embodiments, $R^1$ is

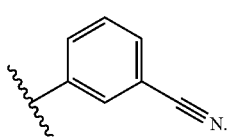 [SMILES: *c1cccc(C#N)c1]

In some embodiments, $R^1$ is

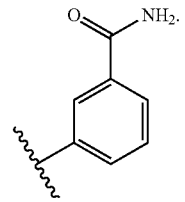 [SMILES: *c1cccc(C(N)=O)c1]

In some embodiments, $R^1$ is

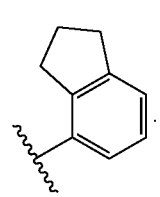 [SMILES: *c1cccc2c1CCC2]

In some embodiments, $R^1$ is

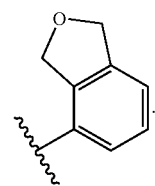

In some embodiments, $R^1$ is

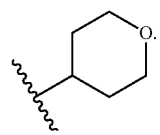

In some embodiments, $R^1$ is

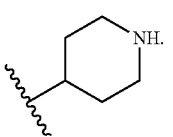 [SMILES: *C1CCNCC1]

In some embodiments, $R^1$ is

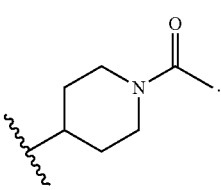 [SMILES: *C1CCN(C(C)=O)CC1]

In some embodiments, two $R^1$ groups are taken together with their intervening atoms to form

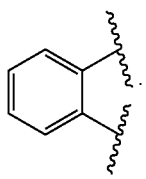

In some embodiments, two $R^1$ groups are taken together with their intervening atoms to form

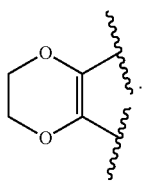

In some embodiments, $R^1$ is selected from those depicted in Table 1, below.

As defined above and described herein, $R^x$ and $R^y$ are independently hydrogen or an optionally substituted group selected from $C_{1-6}$ aliphatic or phenyl.

In some embodiments, $R^x$ is hydrogen. In some embodiments, $R^x$ is an optionally substituted group selected from $C_{1-6}$ aliphatic. In some embodiments, $R^x$ is phenyl.

In some embodiments, $R^x$ is methyl. In some embodiments, $R^x$ is

In some embodiments, $R^x$ is

In some embodiments, $R^x$ is

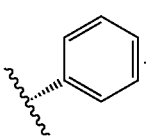

In some embodiments, $R^x$ is selected from those depicted in Table 1, below.

In some embodiments, $R^y$ is hydrogen. In some embodiments, $R^y$ is an optionally substituted group selected from $C_{1-6}$ aliphatic. In some embodiments, $R^y$ is phenyl.

In some embodiments, $R^y$ is methyl. In some embodiments, $R^y$ is

In some embodiments, $R^y$ is

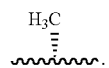

In some embodiments, $R^y$ is

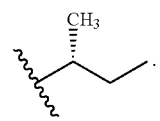

In some embodiments, $R^y$ is

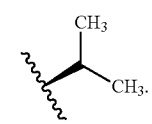

In some embodiments, $R^y$ is

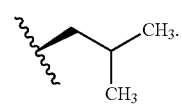

In some embodiments, $R^y$ is

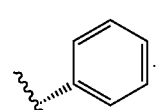

In some embodiments, $R^y$ is

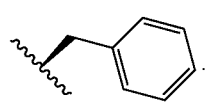

In some embodiments, $R^y$ is

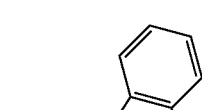

In some embodiments, $R^y$ is

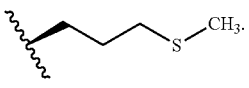

In some embodiments, $R^y$ is

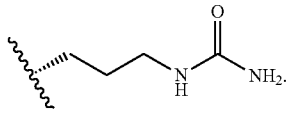

In some embodiments, $R^y$ is selected from those depicted in Table 1, below.

As defined above and described herein, $R^{x'}$ and $R^{y'}$ are independently hydrogen or $C_{1-4}$ alkyl.

In some embodiments, $R^{x'}$ is hydrogen. In some embodiments, $R^{x'}$ is $C_{1-4}$ alkyl.

In some embodiments, $R^{x'}$ is methyl.

In some embodiments, $R^{x'}$ is selected from those depicted in Table 1, below.

In some embodiments, $R^{y'}$ is hydrogen. In some embodiments, $R^{x'}$ is $C_{1-4}$ alkyl.

In some embodiments, $R^{y'}$ is methyl.

In some embodiments, $R^{y'}$ is selected from those depicted in Table 1, below.

As defined above and described herein, Ry and Ry' can be taken together with their intervening atoms to form a 3-6 membered saturated ring having 0-3 heteroatoms independently selected from nitrogen, oxygen or sulfur.

In some embodiments, $R^y$ and $R^{y'}$ are taken together with their intervening atoms to form a cyclobutylenyl ring. In some embodiments, $R^y$ and $R^{y'}$ are taken together with their intervening atoms to form a cyclopropylenyl ring. In some embodiments, $R^y$ and $R^{y'}$ are taken together with their intervening atoms to form a ring selected from those depicted in Table 1, below.

As defined above and described herein, m is 1, 2, 3, 4 or 5.

In some embodiments, m is 1. In some embodiments, m is 2. In some embodiments, m is 3. In some embodiments, m is 4. In some embodiments, m is 5.

In some embodiments, m is selected from those depicted in Table 1, below.

In certain embodiments, the present invention provides a compound of formula I-a:

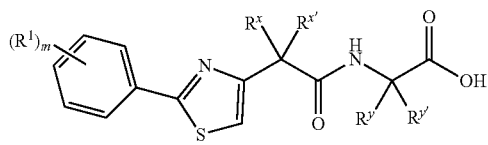

I-a or a pharmaceutically acceptable salt thereof, wherein each of $R^1$, $R^x$, $R^{x'}$, $R^y$, $R^{y'}$, and m is as defined above and in embodiments herein, both singly and in combination.

In certain embodiments, the present invention provides a compound of formula I-b:

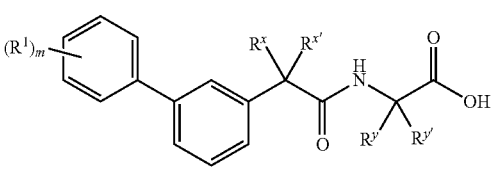

I-b or a pharmaceutically acceptable salt thereof, wherein each of $R^1$, $R^x$, $R^{x'}$, $R^y$, $R^{y'}$, and m is as defined above and in embodiments herein, both singly and in combination.

In certain embodiments, the present invention provides a compound of formula I-c:

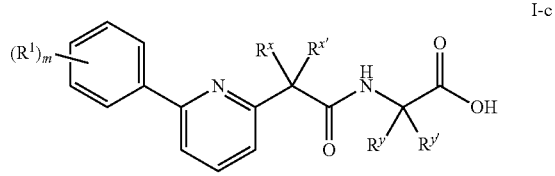

I-c or a pharmaceutically acceptable salt thereof, wherein each of $R^1$, $R^x$, $R^{x'}$, $R^y$, $R^{y'}$, and m is as defined above and in embodiments herein, both singly and in combination.

In certain embodiments, the present invention provides a compound of formula I-d:

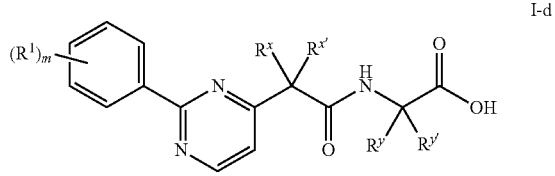

I-d or a pharmaceutically acceptable salt thereof, wherein each of $R^1$, $R^x$, $R^{x'}$, $R^y$, $R^{y'}$, and m is as defined above and in embodiments herein, both singly and in combination.

In certain embodiments, the present invention provides a compound of formula I-e:

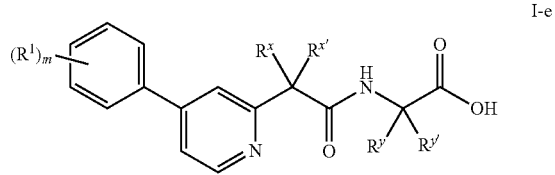

I-e or a pharmaceutically acceptable salt thereof, wherein each of $R^1$, $R^x$, $R^{x'}$, $R^y$, $R^{y'}$, and m is as defined above and in embodiments herein, both singly and in combination.

In certain embodiments, the present invention provides a compound of formula I-f:

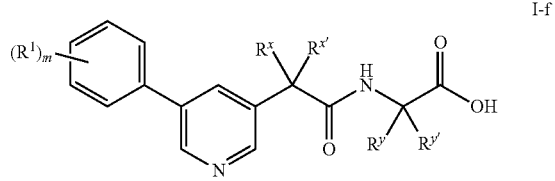

I-f or a pharmaceutically acceptable salt thereof, wherein each of $R^1$, $R^x$, $R^{x'}$, $R^y$, $R^{y'}$, and m is as defined above and in embodiments herein, both singly and in combination.

In certain embodiments, the present invention provides a compound of formula I-g:

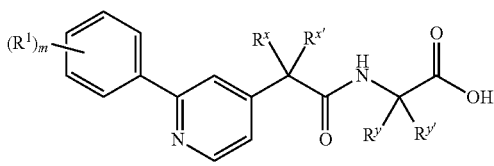

or a pharmaceutically acceptable salt thereof, wherein each of $R^1$, $R^x$, $R^{x'}$, $R^y$, $R^{y'}$, and m is as defined above and in embodiments herein, both singly and in combination.

In certain embodiments, the present invention provides a compound of formula II:

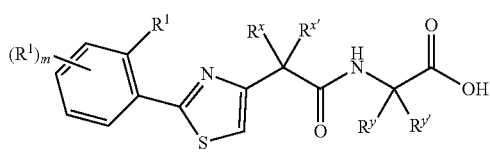

or a pharmaceutically acceptable salt thereof, wherein each of $R^1$, $R^x$, $R^{x'}$, $R^y$, $R^{y'}$, and m is as defined above and in embodiments herein, both singly and in combination.

In certain embodiments, the present invention provides a compound of formula II-a:

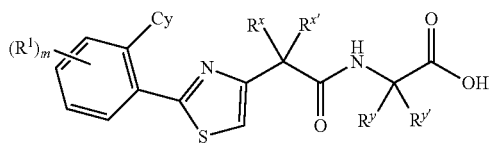

or a pharmaceutically acceptable salt thereof, wherein each of Cy, $R^1$, $R^x$, $R^{x'}$, $R^y$, $R^{y'}$, and m is as defined above and in embodiments herein, both singly and in combination.

In certain embodiments, the present invention provides a compound of formula II-b:

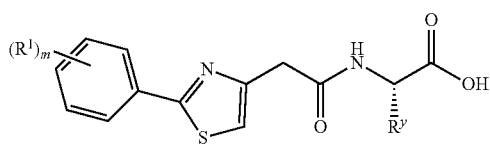

or a pharmaceutically acceptable salt thereof, wherein each of $R^1$, $R^y$, and m is as defined above and in embodiments herein, both singly and in combination.

In certain embodiments, the present invention provides a compound of formula II-c:

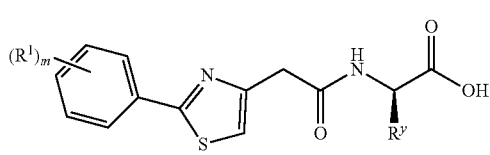

or a pharmaceutically acceptable salt thereof, wherein each of $R^1$, $R^y$, and m is as defined above and in embodiments herein, both singly and in combination.

Exemplary compounds of the invention are set forth in Table 1, below.

TABLE 1

Exemplary Compounds

TABLE 1-continued
Exemplary Compounds
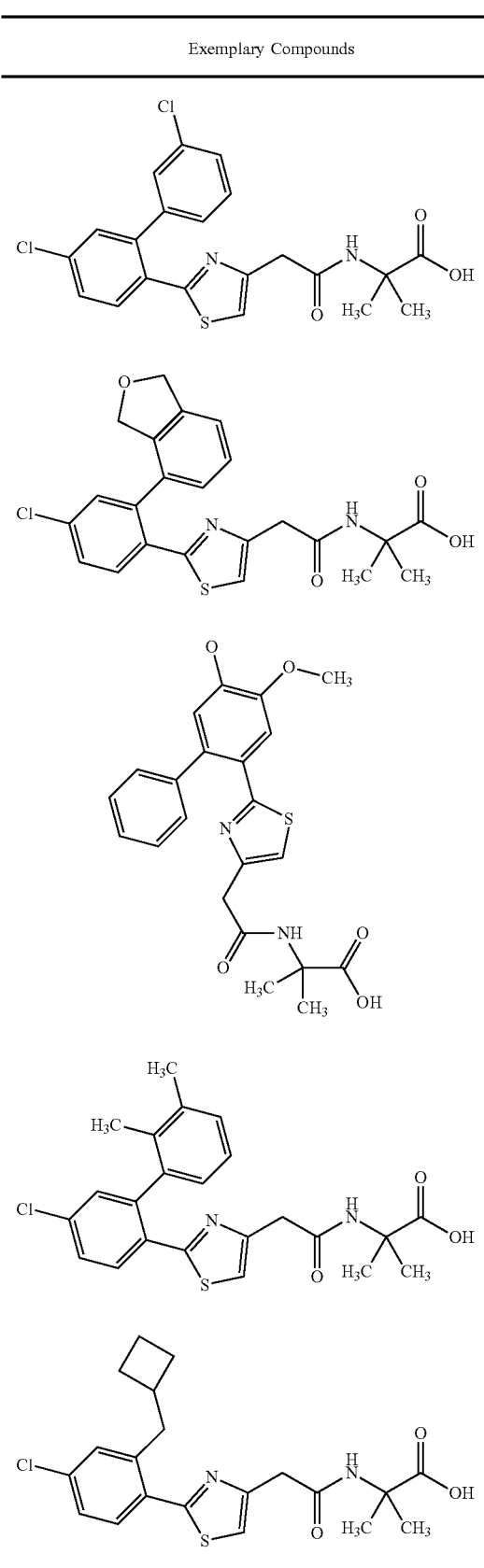
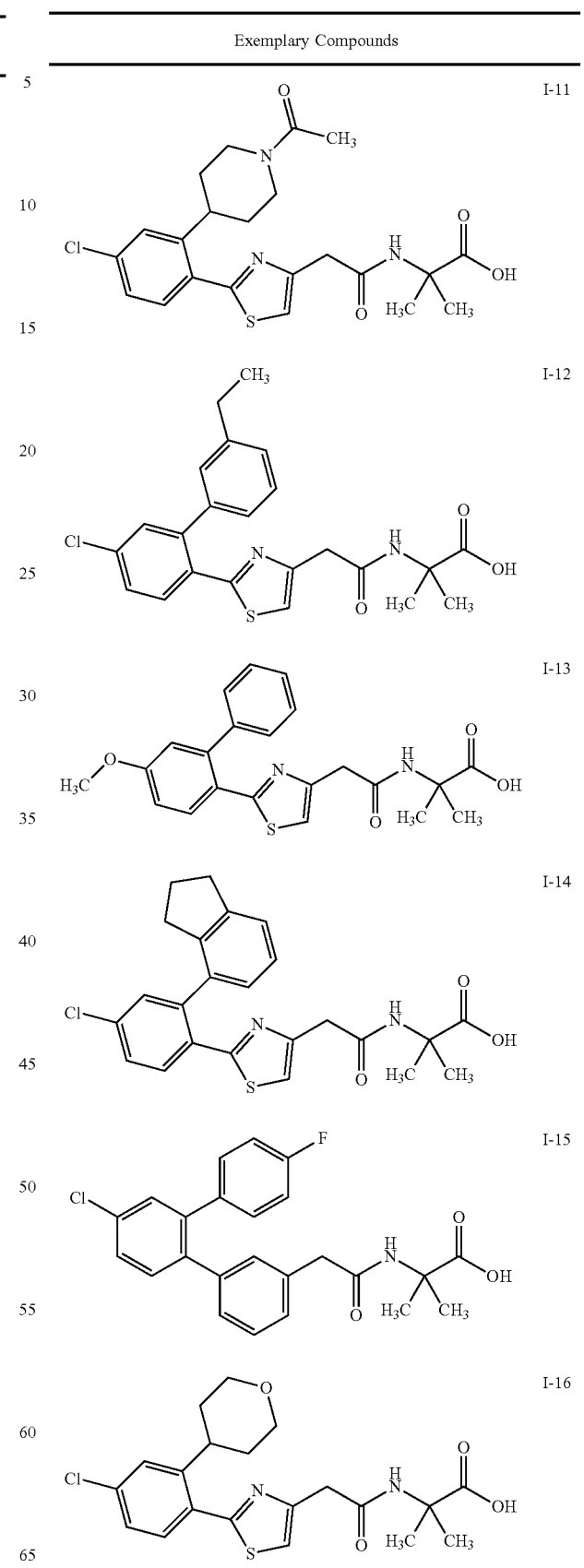

TABLE 1-continued

Exemplary Compounds

TABLE 1-continued

Exemplary Compounds

I-29, I-30, I-31, I-32, I-33, I-34, I-35, I-36, I-37, I-38, I-39, I-40, I-41

TABLE 1-continued
Exemplary Compounds
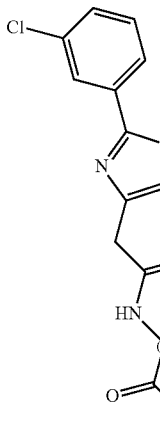

TABLE 1-continued
Exemplary Compounds
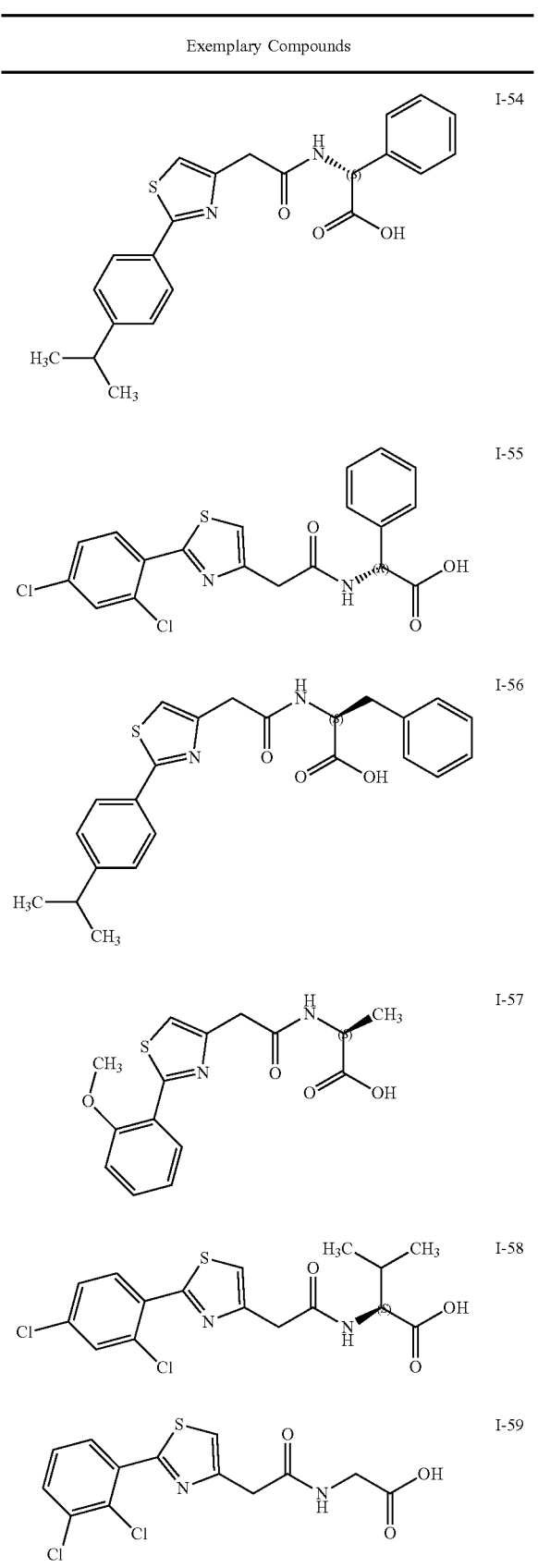
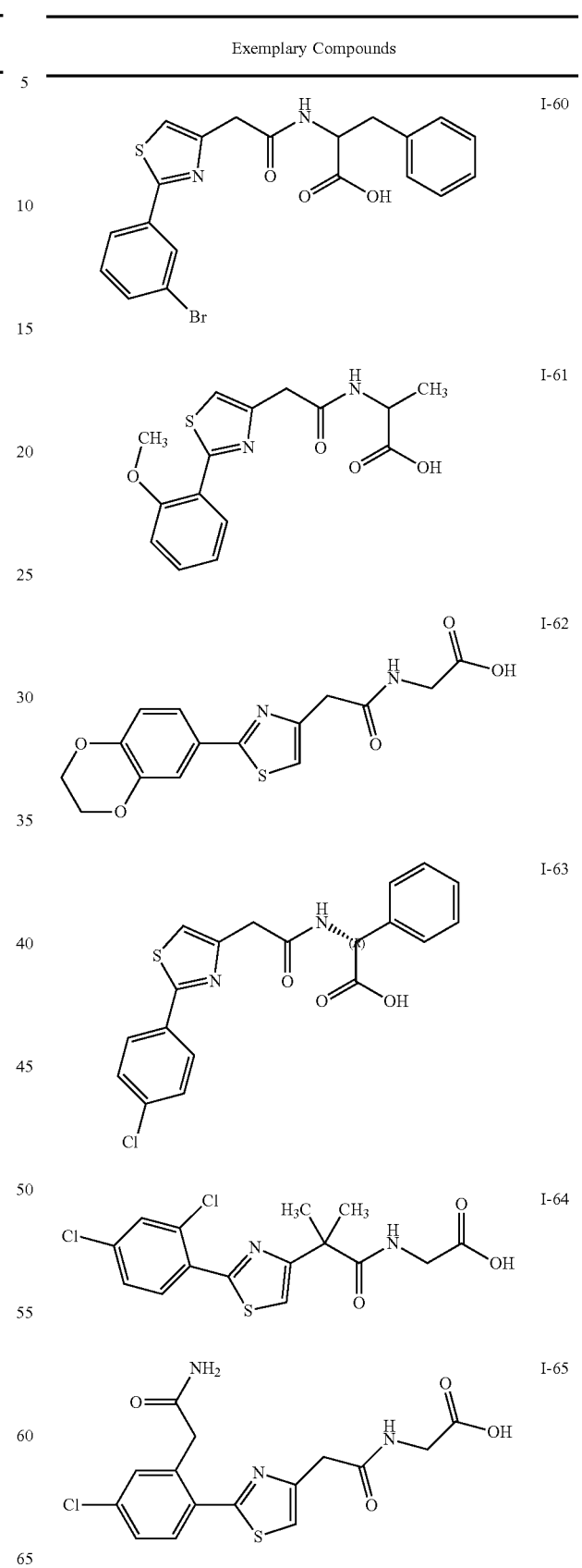

TABLE 1-continued

Exemplary Compounds

I-66

I-67

I-68

I-69

I-70

I-71

In some embodiments, the present invention provides a compound set forth in Table 1, above, or a pharmaceutically acceptable salt thereof. It will be appreciated that the present invention also provides a compound set forth in Table 1, above, as a racemic mixture, or a pharmaceutically acceptable salt thereof.

Additional exemplary compounds of the invention are set forth in Table 2, below.

TABLE 2

Exemplary Compounds

I-72

I-73

I-74

TABLE 2-continued

Exemplary Compounds

| Compound | Structure |
|---|---|
| I-75 | Glycine-NH-CH2-[thiazole-2-(4-methylphenyl)] |
| I-76 | Glycine-NH-CH2-[thiazole-2-(4-ethylphenyl)] |
| I-77 | Glycine-NH-CH2-[thiazole-2-(4-ethylphenyl)] |
| I-78 | (S)-Alanine-NH-CH2-[thiazole-2-(4-methylphenyl)] |
| I-79 | Glycine-NH-CH2-[thiazole-2-(3-aminophenyl)] |
| I-80 | Glycine-NH-CH2-[thiazole-2-(4-aminomethylphenyl)] |
| I-81 | (S)-Alanine-NH-CH2-[thiazole-2-(4-ethylphenyl)] |
| I-82 | Glycine-NH-CH2-[thiazole-2-(4-chlorophenyl)] |
| I-83 | Glycine-NH-CH2-[thiazole-2-(4-methoxyphenyl)] |
| I-84 | Glycine-NH-CH2-[thiazole-2-(2-aminophenyl)] |

TABLE 2-continued
Exemplary Compounds
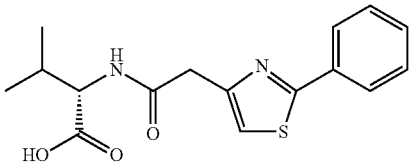 [SMILES: CC(C)[C@H](NC(=O)Cc1csc(-c2ccccc2)n1)C(=O)O] I-85
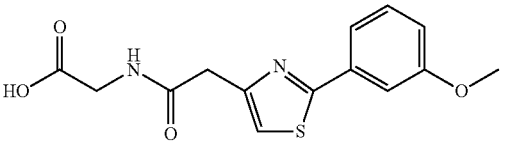 [SMILES: COc1cccc(-c2nc(CC(=O)NCC(=O)O)cs2)c1] I-86
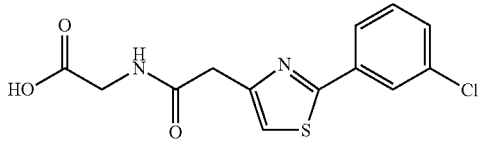 [SMILES: O=C(O)CNC(=O)Cc1csc(-c2cccc(Cl)c2)n1] I-87
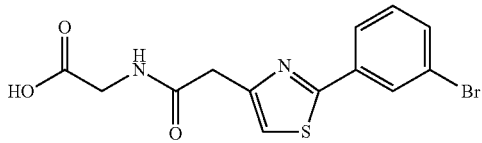 [SMILES: O=C(O)CNC(=O)Cc1csc(-c2cccc(Br)c2)n1] I-88
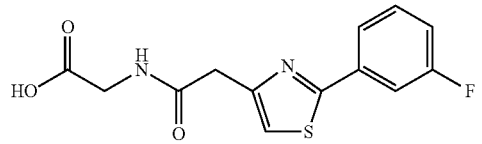 [SMILES: O=C(O)CNC(=O)Cc1csc(-c2cccc(F)c2)n1] I-89
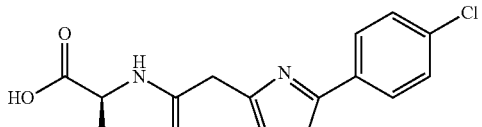 I-90
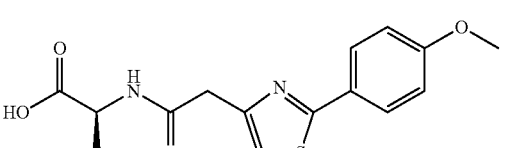 I-91
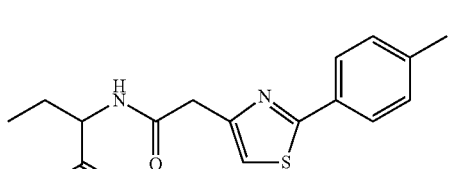 I-92
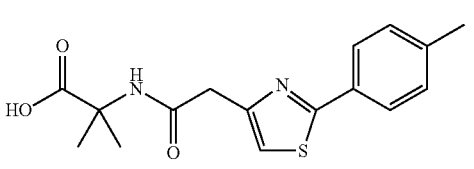 [SMILES: Cc1ccc(-c2nc(CC(=O)NC(C)(C)C(=O)O)cs2)cc1] I-93

TABLE 2-continued
Exemplary Compounds
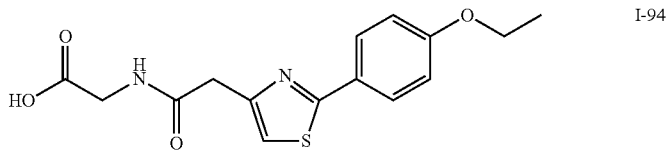 I-94
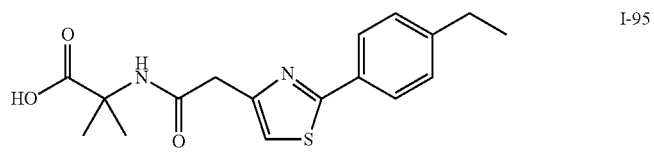 I-95
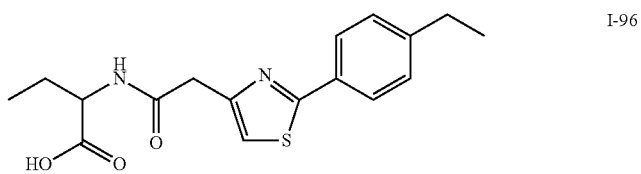 I-96
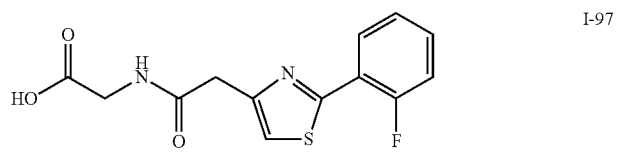 I-97
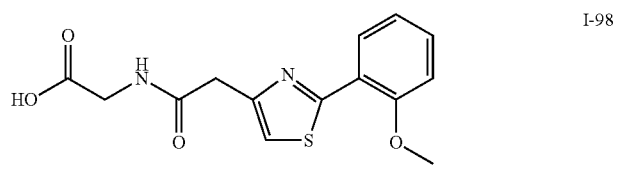 I-98
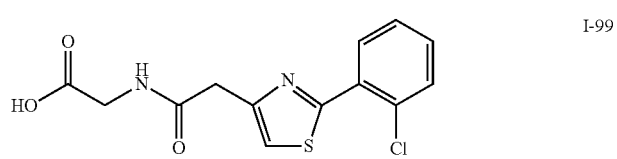 I-99
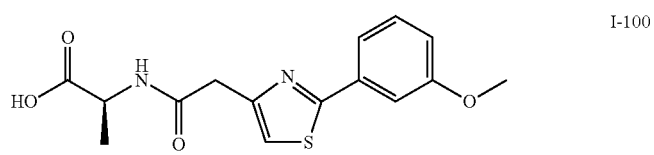 I-100
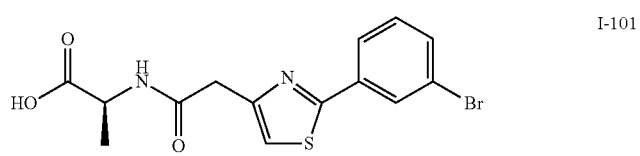 I-101
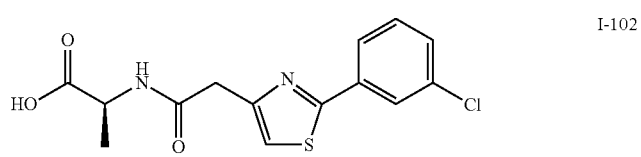 I-102

TABLE 2-continued
Exemplary Compounds
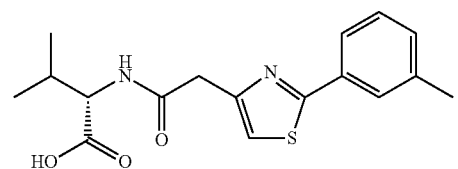 [SMILES: Cc1cccc(-c2nc(CC(=O)N[C@H](C(=O)O)C(C)C)cs2)c1]
I-103
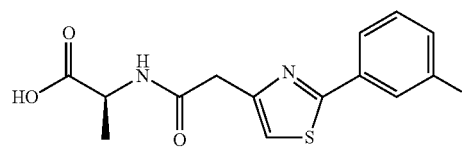
I-104
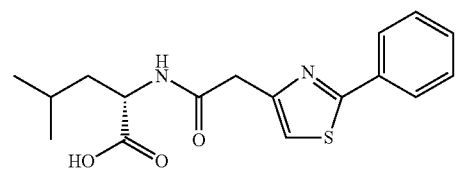 [SMILES: CC(C)C[C@H](NC(=O)Cc1csc(-c2ccccc2)n1)C(=O)O]
I-105
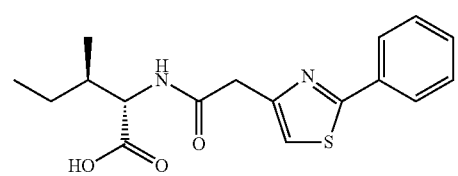 [SMILES: CC[C@@H](C)[C@H](NC(=O)Cc1csc(-c2ccccc2)n1)C(=O)O]
I-106
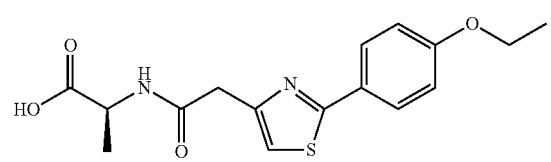 [SMILES: CCOc1ccc(-c2nc(CC(=O)N[C@@H](C)C(=O)O)cs2)cc1]
I-107
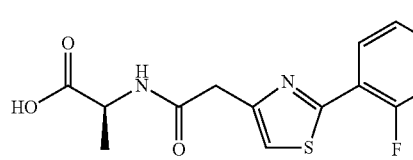
I-108
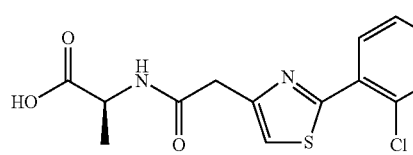
I-109
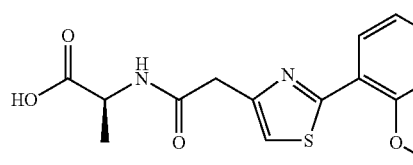
I-110
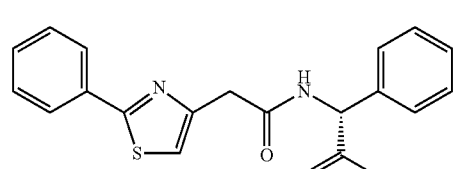
I-111

TABLE 2-continued
Exemplary Compounds
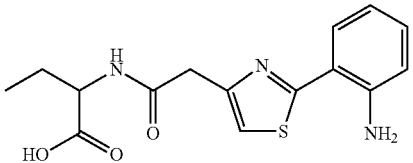 [SMILES: CCC(NC(=O)Cc1csc(-c2ccccc2N)n1)C(=O)O] I-112
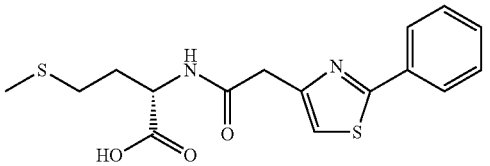 [SMILES: CSCC[C@H](NC(=O)Cc1csc(-c2ccccc2)n1)C(=O)O] I-113
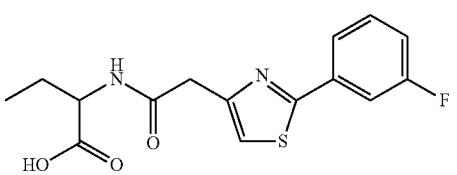 [SMILES: CCC(NC(=O)Cc1csc(-c2cccc(F)c2)n1)C(=O)O] I-114
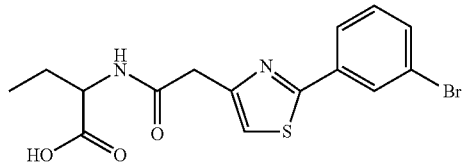 [SMILES: CCC(NC(=O)Cc1csc(-c2cccc(Br)c2)n1)C(=O)O] I-115
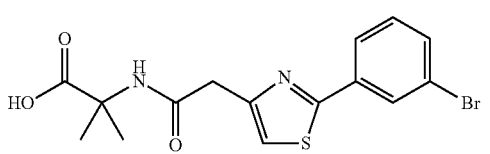 [SMILES: CC(C)(NC(=O)Cc1csc(-c2cccc(Br)c2)n1)C(=O)O] I-116
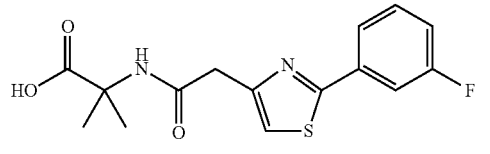 [SMILES: CC(C)(NC(=O)Cc1csc(-c2cccc(F)c2)n1)C(=O)O] I-117
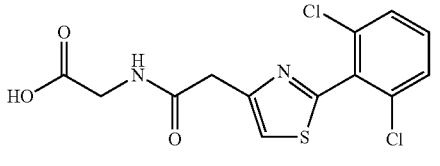 [SMILES: O=C(O)CNC(=O)Cc1csc(-c2c(Cl)cccc2Cl)n1] I-118
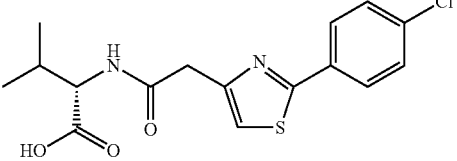 I-119
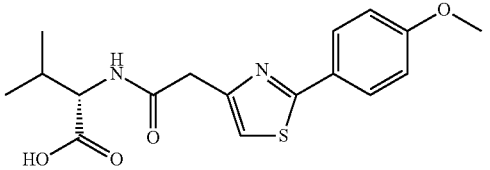 [SMILES: COc1ccc(-c2nc(CC(=O)N[C@H](C(=O)O)C(C)C)cs2)cc1] I-120

TABLE 2-continued
Exemplary Compounds
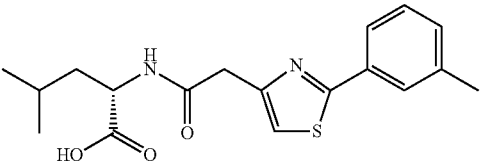 [SMILES: Cc1cccc(-c2nc(CC(=O)N[C@@H](CC(C)C)C(=O)O)cs2)c1]
I-121
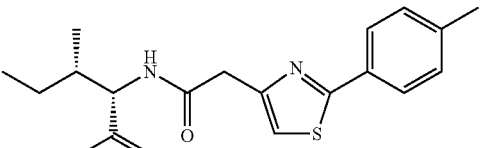
I-122
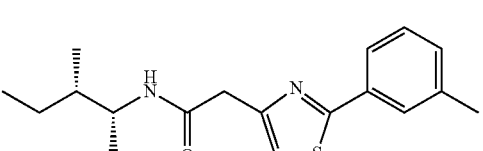
I-123
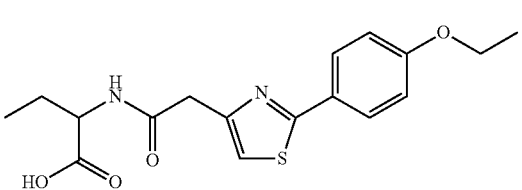 [SMILES: CCOc1ccc(-c2nc(CC(=O)NC(CC)C(=O)O)cs2)cc1]
I-124
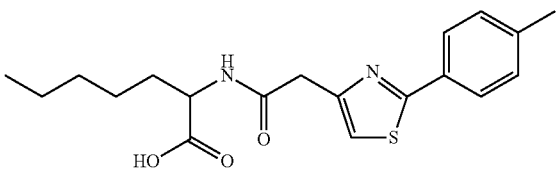 [SMILES: CCCCCC(NC(=O)Cc1csc(-c2ccc(C)cc2)n1)C(=O)O]
I-125
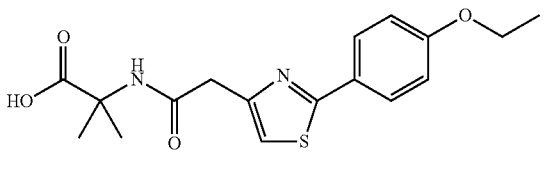 [SMILES: CCOc1ccc(-c2nc(CC(=O)NC(C)(C)C(=O)O)cs2)cc1]
I-126
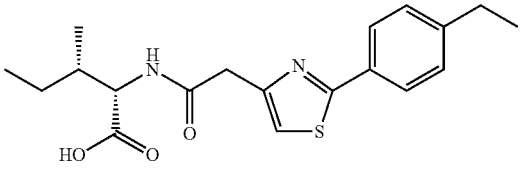 [SMILES: CCc1ccc(-c2nc(CC(=O)N[C@H](C(=O)O)[C@@H](C)CC)cs2)cc1]
I-127
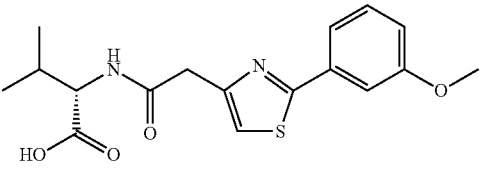 [SMILES: COc1cccc(-c2nc(CC(=O)N[C@H](C(=O)O)C(C)C)cs2)c1]
I-128
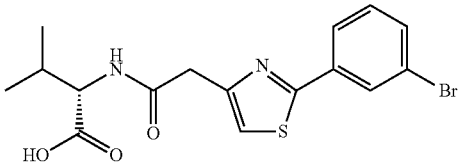 [SMILES: CC(C)[C@H](NC(=O)Cc1csc(-c2cccc(Br)c2)n1)C(=O)O]
I-129

TABLE 2-continued
Exemplary Compounds
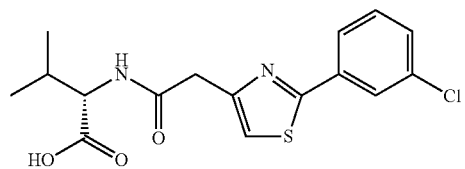 [SMILES: CC(C)[C@H](NC(=O)Cc1csc(-c2cccc(Cl)c2)n1)C(=O)O] I-130
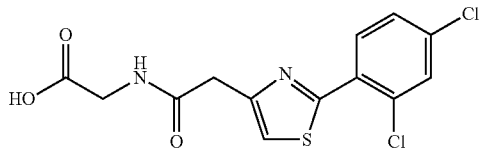 [SMILES: O=C(O)CNC(=O)Cc1csc(-c2ccc(Cl)cc2Cl)n1] I-131
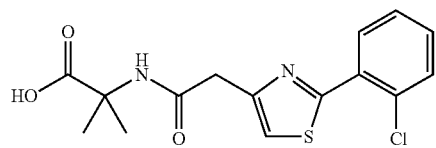 [SMILES: CC(C)(NC(=O)Cc1csc(-c2ccccc2Cl)n1)C(=O)O] I-132
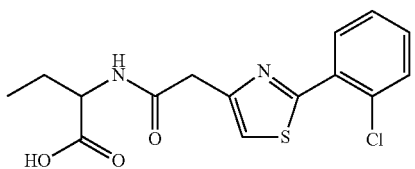 [SMILES: CCC(NC(=O)Cc1csc(-c2ccccc2Cl)n1)C(=O)O] I-133
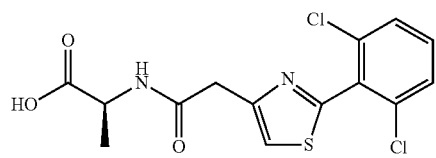 [SMILES: C[C@H](NC(=O)Cc1csc(-c2c(Cl)cccc2Cl)n1)C(=O)O] I-134
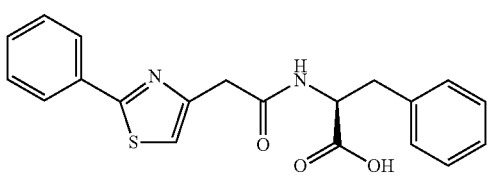 [SMILES: O=C(Cc1csc(-c2ccccc2)n1)N[C@@H](Cc1ccccc1)C(=O)O] I-135
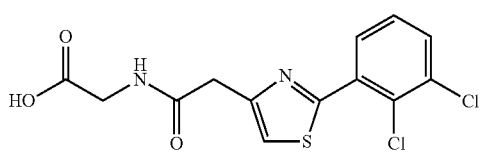 [SMILES: O=C(O)CNC(=O)Cc1csc(-c2cccc(Cl)c2Cl)n1] I-136
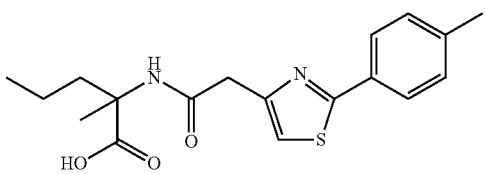 [SMILES: CCCC(C)(NC(=O)Cc1csc(-c2ccc(C)cc2)n1)C(=O)O] I-137
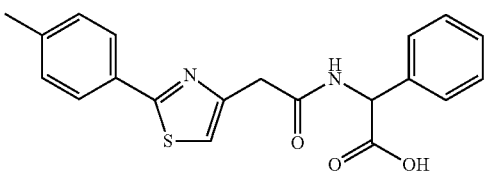 [SMILES: Cc1ccc(-c2nc(CC(=O)NC(C(=O)O)c3ccccc3)cs2)cc1] I-138

TABLE 2-continued
Exemplary Compounds
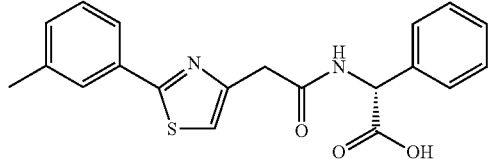 [SMILES: Cc1cccc(-c2nc(CC(=O)N[C@@H](C(=O)O)c3ccccc3)cs2)c1] I-139
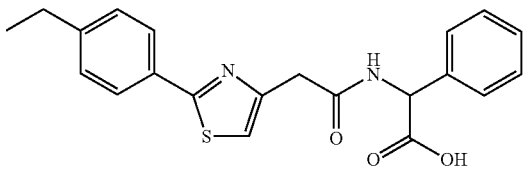 [SMILES: CCc1ccc(-c2nc(CC(=O)NC(C(=O)O)c3ccccc3)cs2)cc1] I-140
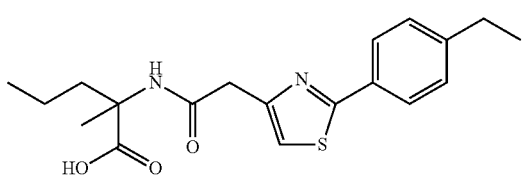 I-141
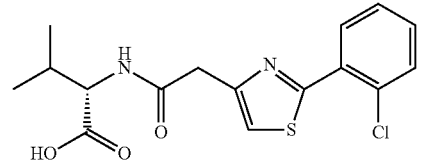 [SMILES: CC(C)[C@H](NC(=O)Cc1csc(-c2ccccc2Cl)n1)C(=O)O] I-142
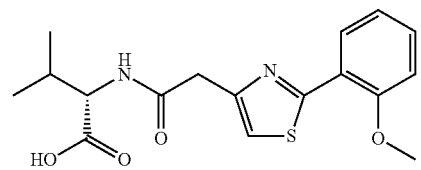 [SMILES: COc1ccccc1-c1nc(CC(=O)N[C@H](C(=O)O)C(C)C)cs1] I-143
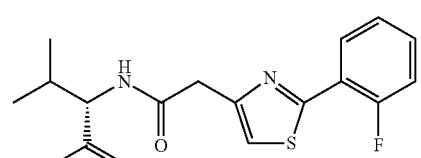 I-144
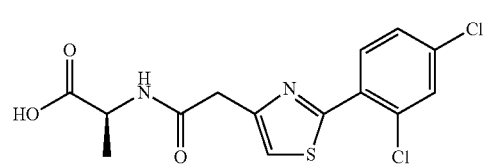 [SMILES: C[C@H](NC(=O)Cc1csc(-c2ccc(Cl)cc2Cl)n1)C(=O)O] I-145
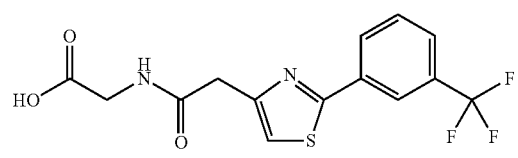 [SMILES: O=C(O)CNC(=O)Cc1csc(-c2cccc(C(F)(F)F)c2)n1] I-146
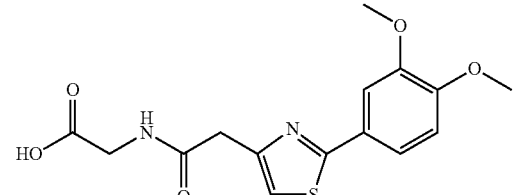 I-147

TABLE 2-continued
Exemplary Compounds
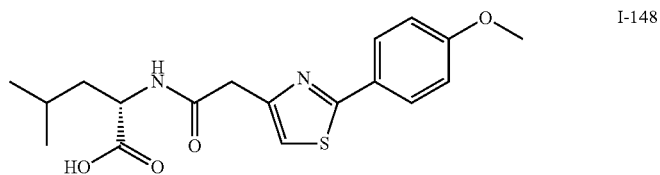 I-148
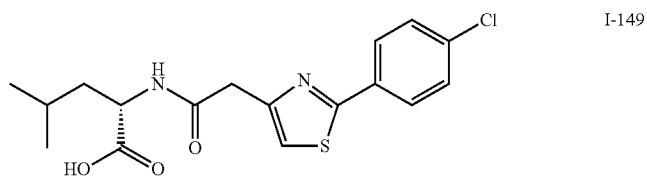 I-149
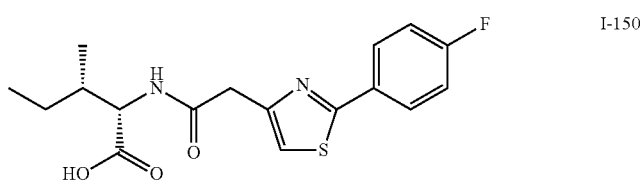 I-150
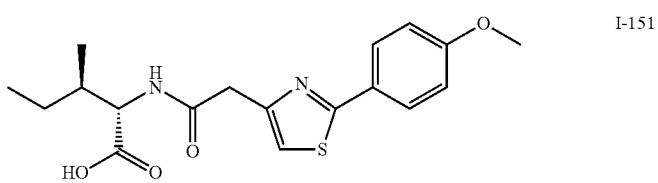 I-151
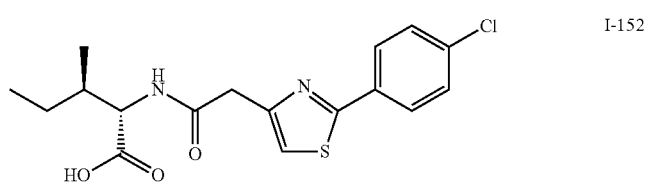 I-152
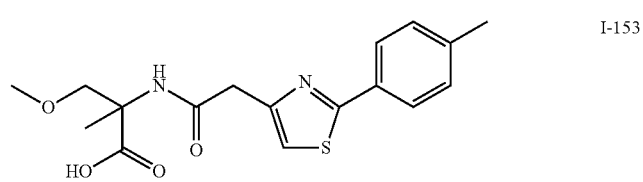 I-153
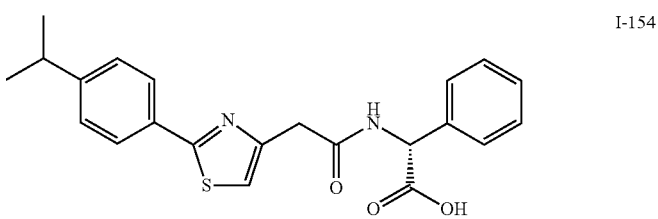 I-154
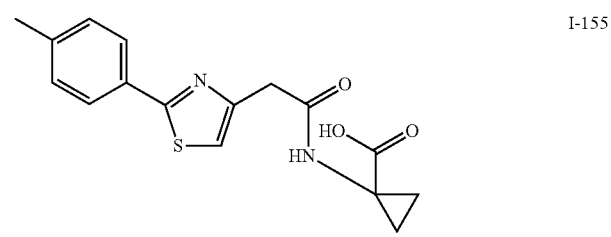 I-155

TABLE 2-continued

Exemplary Compounds

I-156

I-157

I-158

I-159

I-160

I-161

I-162

I-163

TABLE 2-continued

Exemplary Compounds

| Compound |
|---|
| I-164 |
| I-165 |
| I-166 |
| I-167 |
| I-168 |
| I-169 |
| I-170 |
| I-171 |

TABLE 2-continued
Exemplary Compounds
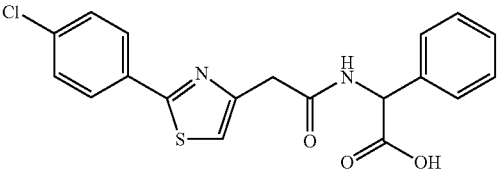 [SMILES: O=C(Cc1csc(-c2ccc(Cl)cc2)n1)NC(C(=O)O)c1ccccc1] I-172
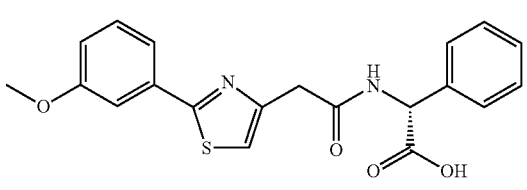 [SMILES: COc1cccc(-c2nc(CC(=O)N[C@@H](C(=O)O)c3ccccc3)cs2)c1] I-173
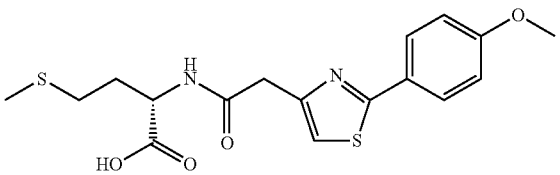 I-174
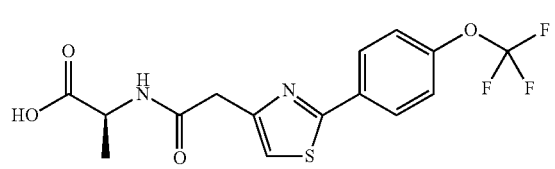 [SMILES: C[C@H](NC(=O)Cc1csc(-c2ccc(OC(F)(F)F)cc2)n1)C(=O)O] I-175
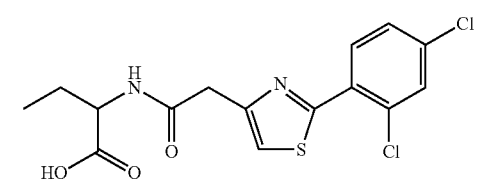 [SMILES: CCC(NC(=O)Cc1csc(-c2ccc(Cl)cc2Cl)n1)C(=O)O] I-176
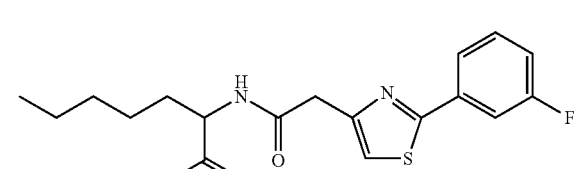 I-177
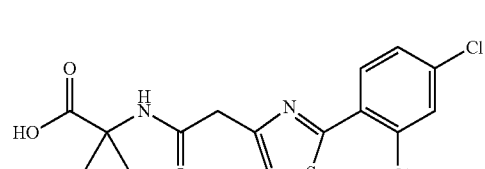 I-178
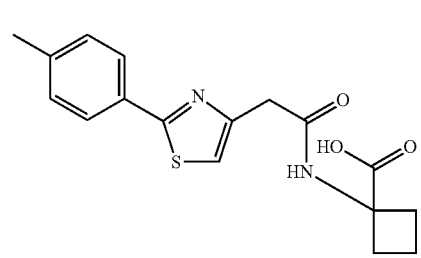 [SMILES: Cc1ccc(-c2nc(CC(=O)NC3(C(=O)O)CCC3)cs2)cc1] I-179

TABLE 2-continued

Exemplary Compounds

I-180
I-181
I-182
I-183
I-184
I-185
I-186
I-187
I-188

TABLE 2-continued
Exemplary Compounds
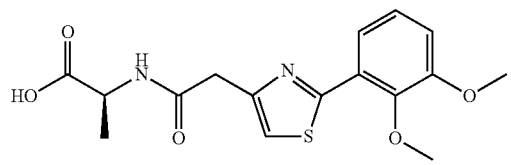 [SMILES: COc1cccc(-c2nc(CC(=O)N[C@@H](C)C(=O)O)cs2)c1OC]
I-189
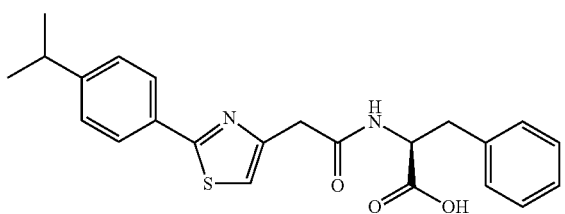 [SMILES: CC(C)c1ccc(-c2nc(CC(=O)N[C@@H](Cc3ccccc3)C(=O)O)cs2)cc1]
I-190
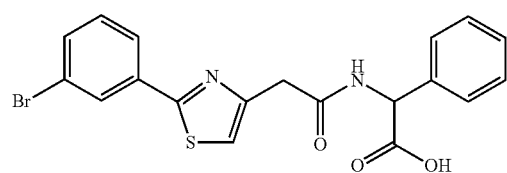
I-191
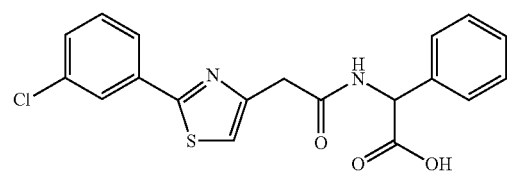 [SMILES: O=C(Cc1csc(-c2cccc(Cl)c2)n1)NC(C(=O)O)c1ccccc1]
I-192
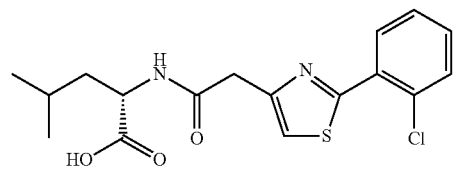 [SMILES: CC(C)C[C@H](NC(=O)Cc1csc(-c2ccccc2Cl)n1)C(=O)O]
I-193
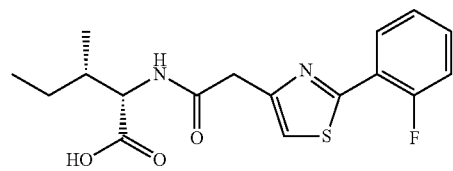 [SMILES: CC[C@H](C)[C@H](NC(=O)Cc1csc(-c2ccccc2F)n1)C(=O)O]
I-194
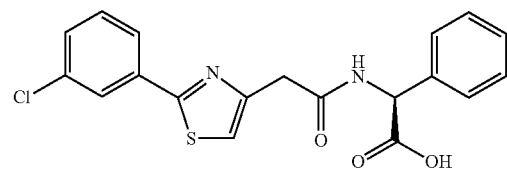 [SMILES: O=C(Cc1csc(-c2cccc(Cl)c2)n1)N[C@H](C(=O)O)c1ccccc1]
I-195
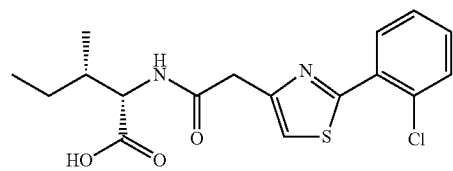 [SMILES: CC[C@H](C)[C@H](NC(=O)Cc1csc(-c2ccccc2Cl)n1)C(=O)O]
I-196

TABLE 2-continued
Exemplary Compounds
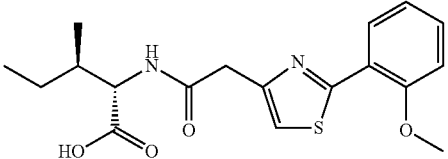 [SMILES: CC[C@@H](C)[C@H](NC(=O)Cc1csc(-c2ccccc2OC)n1)C(=O)O] I-197
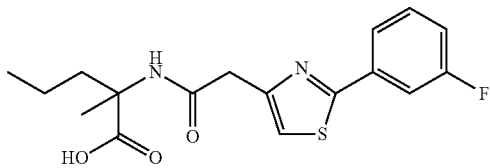 [SMILES: CCCC(C)(NC(=O)Cc1csc(-c2cccc(F)c2)n1)C(=O)O] I-198
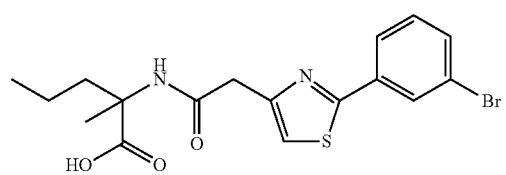 [SMILES: CCCC(C)(NC(=O)Cc1csc(-c2cccc(Br)c2)n1)C(=O)O] I-199
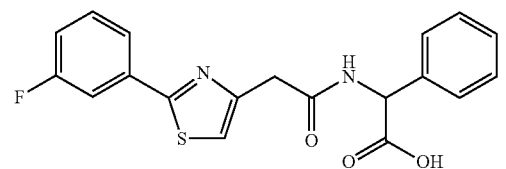 [SMILES: O=C(Cc1csc(-c2cccc(F)c2)n1)NC(C(=O)O)c1ccccc1] I-200
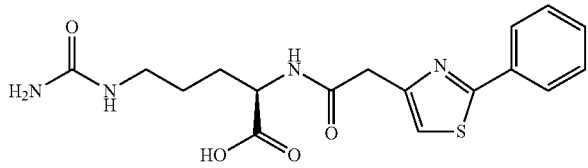 [SMILES: NC(=O)NCCC[C@@H](NC(=O)Cc1csc(-c2ccccc2)n1)C(=O)O] I-201
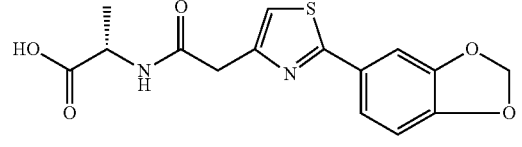 [SMILES: C[C@H](NC(=O)Cc1csc(-c2ccc3c(c2)OCO3)n1)C(=O)O] I-202
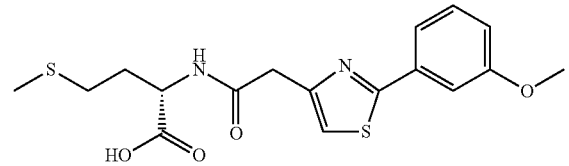 I-203
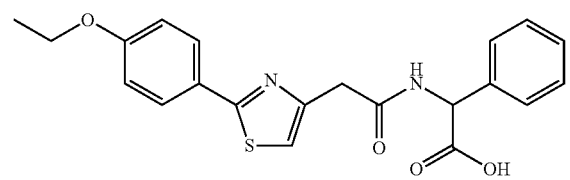 [SMILES: CCOc1ccc(-c2nc(CC(=O)NC(C(=O)O)c3ccccc3)cs2)cc1] I-204
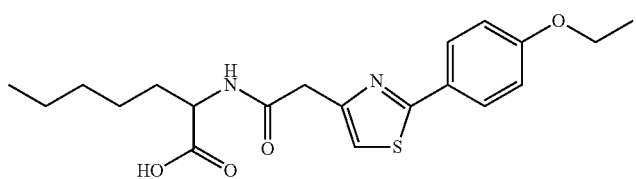 [SMILES: CCCCCC(NC(=O)Cc1csc(-c2ccc(OCC)cc2)n1)C(=O)O] I-205

TABLE 2-continued

Exemplary Compounds

| Structure | ID |
|---|---|
| (4-methoxyphenyl-thiazole-acetamide-phenylalanine) | I-206 |
| (methionine-acetamide-thiazole-3-bromophenyl) | I-207 |
| (methionine-acetamide-thiazole-3-chlorophenyl) | I-208 |
| (2-methoxyphenyl-thiazole-acetamide-phenylglycine) | I-209 |
| (valine-acetamide-thiazole-2,6-dichlorophenyl) | I-210 |
| (norleucine-acetamide-thiazole-2-chlorophenyl) | I-211 |
| (α-methyl-norvaline-acetamide-thiazole-4-ethoxyphenyl) | I-212 |
| (2-methoxyphenyl-thiazole-acetamide-phenylglycine) | I-213 |

TABLE 2-continued
Exemplary Compounds
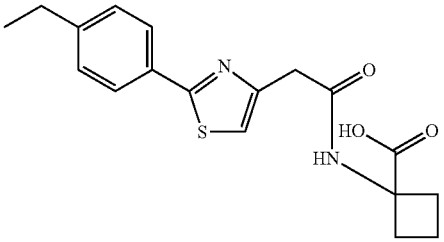 [SMILES: CCc1ccc(-c2nc(CC(=O)NC3(C(=O)O)CCC3)cs2)cc1] I-214
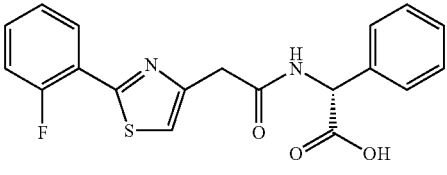 [SMILES: O=C(Cc1csc(-c2ccccc2F)n1)N[C@@H](C(=O)O)c1ccccc1] I-215
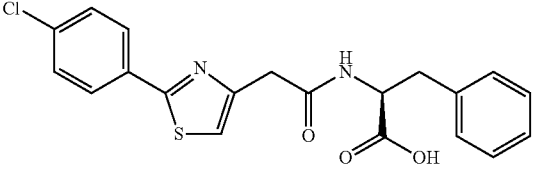 [SMILES: O=C(Cc1csc(-c2ccc(Cl)cc2)n1)N[C@@H](Cc1ccccc1)C(=O)O] I-216
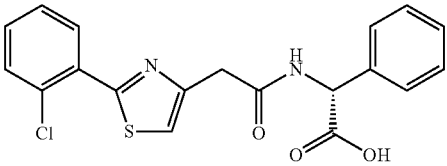 [SMILES: O=C(Cc1csc(-c2ccccc2Cl)n1)N[C@@H](C(=O)O)c1ccccc1] I-217
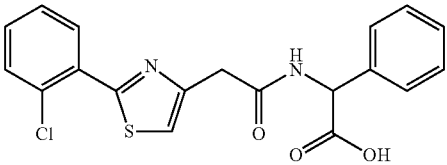 [SMILES: O=C(Cc1csc(-c2ccccc2Cl)n1)NC(C(=O)O)c1ccccc1] I-218
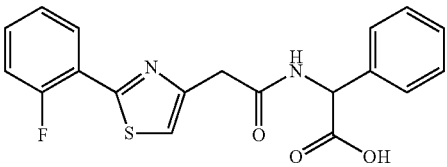 [SMILES: O=C(Cc1csc(-c2ccccc2F)n1)NC(C(=O)O)c1ccccc1] I-219
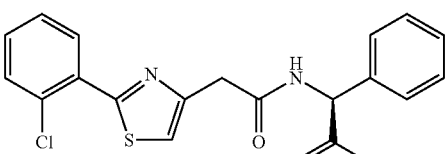 I-220
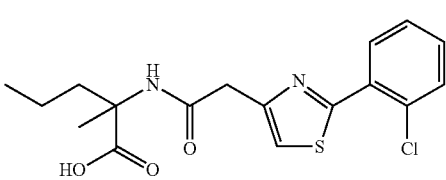 I-221

TABLE 2-continued
Exemplary Compounds
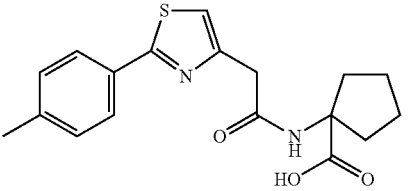 [SMILES: Cc1ccc(-c2nc(CC(=O)NC3(C(=O)O)CCCC3)cs2)cc1]
I-222
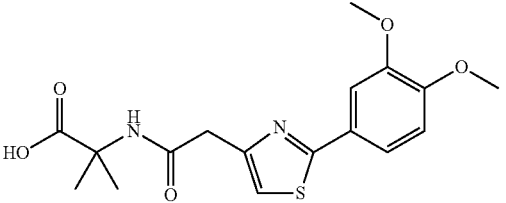 [SMILES: COc1ccc(-c2nc(CC(=O)NC(C)(C)C(=O)O)cs2)cc1OC]
I-223
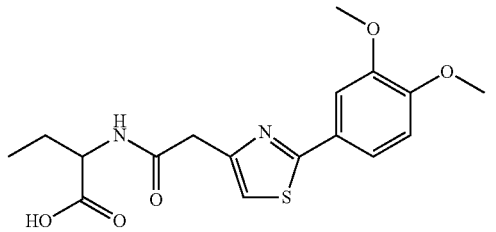 [SMILES: CCC(NC(=O)Cc1csc(-c2ccc(OC)c(OC)c2)n1)C(=O)O]
I-224
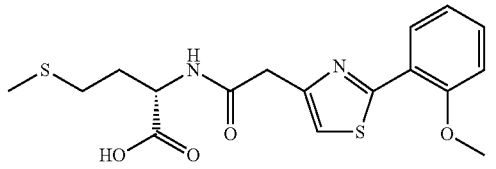
I-225
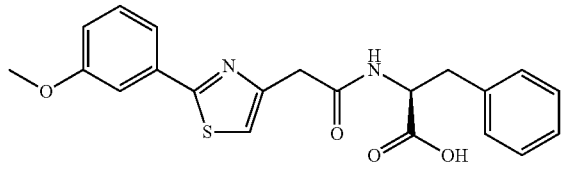 [SMILES: COc1cccc(-c2nc(CC(=O)N[C@@H](Cc3ccccc3)C(=O)O)cs2)c1]
I-226
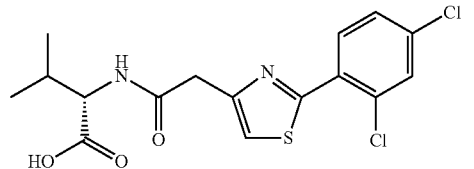
I-227
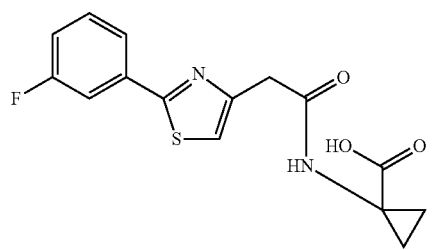 [SMILES: O=C(Cc1csc(-c2cccc(F)c2)n1)NC1(C(=O)O)CC1]
I-228

TABLE 2-continued

Exemplary Compounds

| Compound ID |
|---|
| I-229 |
| I-230 |
| I-231 |
| I-232 |
| I-233 |
| I-234 |
| I-235 |
| I-236 |

TABLE 2-continued
Exemplary Compounds
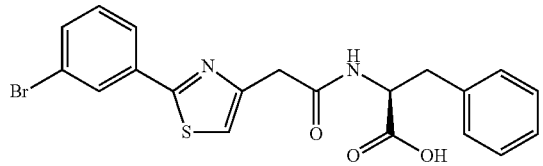 [SMILES: O=C(Cc1csc(-c2cccc(Cl)c2)n1)N[C@@H](Cc1ccccc1)C(=O)O]
I-237
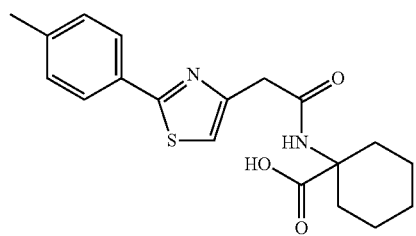 [SMILES: Cc1ccc(-c2nc(CC(=O)NC3(C(=O)O)CCCCC3)cs2)cc1]
I-238
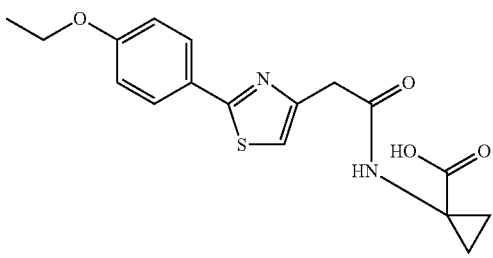 [SMILES: CCOc1ccc(-c2nc(CC(=O)NC3(C(=O)O)CC3)cs2)cc1]
I-239
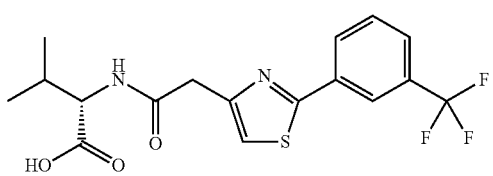 [SMILES: CC(C)[C@H](NC(=O)Cc1csc(-c2cccc(C(F)(F)F)c2)n1)C(=O)O]
I-240
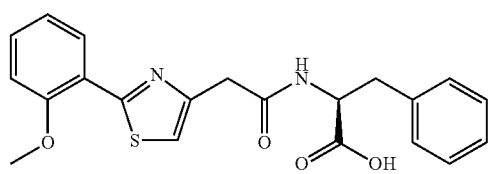 [SMILES: COc1ccccc1-c1nc(CC(=O)N[C@@H](Cc2ccccc2)C(=O)O)cs1]
I-241
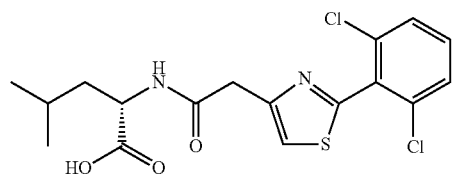 [SMILES: CC(C)C[C@H](NC(=O)Cc1csc(-c2c(Cl)cccc2Cl)n1)C(=O)O]
I-242
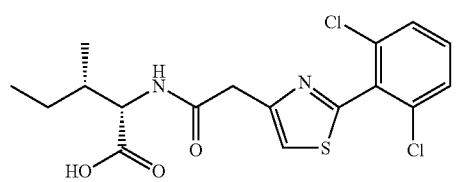 [SMILES: CC[C@H](C)[C@H](NC(=O)Cc1csc(-c2c(Cl)cccc2Cl)n1)C(=O)O]
I-243

TABLE 2-continued
Exemplary Compounds
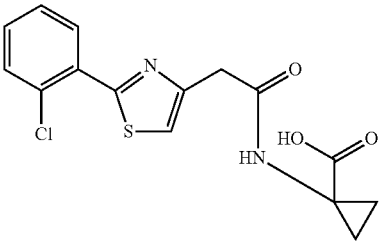 [SMILES: O=C(Cc1csc(-c2ccccc2Cl)n1)NC1(C(=O)O)CC1]
I-244
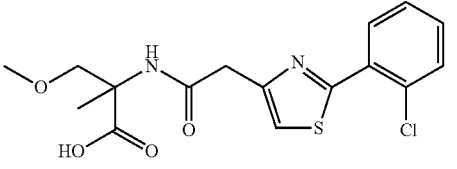 [SMILES: COCC(C)(NC(=O)Cc1csc(-c2ccccc2Cl)n1)C(=O)O]
I-245
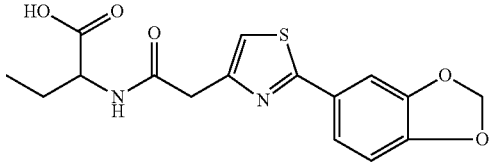 [SMILES: CCC(NC(=O)Cc1csc(-c2ccc3c(c2)OCO3)n1)C(=O)O]
I-246
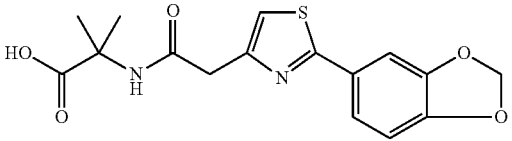 [SMILES: CC(C)(NC(=O)Cc1csc(-c2ccc3c(c2)OCO3)n1)C(=O)O]
I-247
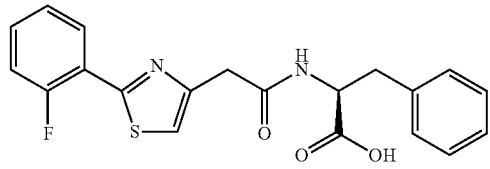 [SMILES: O=C(Cc1csc(-c2ccccc2F)n1)N[C@@H](Cc1ccccc1)C(=O)O]
I-248
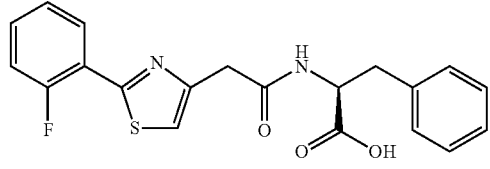
I-249
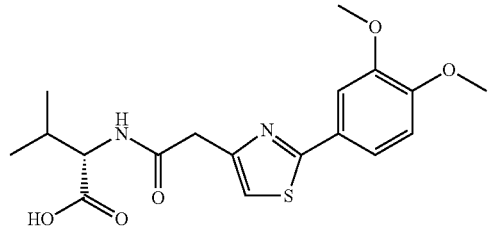 [SMILES: COc1ccc(-c2nc(CC(=O)N[C@H](C(=O)O)C(C)C)cs2)cc1OC]
I-250

TABLE 2-continued

Exemplary Compounds

| | |
|---|---|
| [Structure of compound I-251: 3-bromophenyl-thiazole-CH2-C(O)-NH-cyclobutane-COOH] | I-251 |
| [Structure of compound I-252: 3-fluorophenyl-thiazole-CH2-C(O)-NH-cyclobutane-COOH] | I-252 |
| [Structure of compound I-253: 4-methylphenyl-thiazole-CH2-C(O)-NH-cycloheptane-COOH] | I-253 |
| [Structure of compound I-254: valine-NH-C(O)-CH2-thiazole-4-(trifluoromethoxy)phenyl] | I-254 |
| [Structure of compound I-255: leucine-NH-C(O)-CH2-thiazole-2,4-dichlorophenyl] | I-255 |
| [Structure of compound I-256: isoleucine-NH-C(O)-CH2-thiazole-2,4-dichlorophenyl] | I-256 |
| [Structure of compound I-257: 4-methylphenyl-thiazole-CH2-C(O)-NH-tetrahydrothiophene-COOH] | I-257 |

TABLE 2-continued
Exemplary Compounds
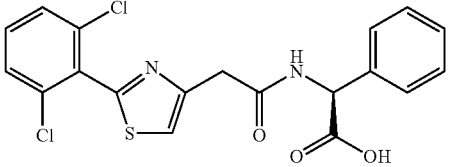 [SMILES: O=C(Cc1csc(-c2c(Cl)cccc2Cl)n1)N[C@H](C(=O)O)c1ccccc1] I-258
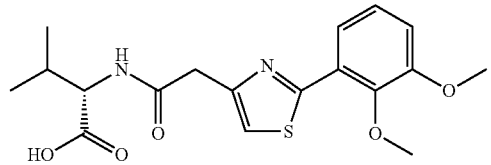 [SMILES: COc1cccc(-c2nc(CC(=O)N[C@H](C(=O)O)C(C)C)cs2)c1OC] I-259
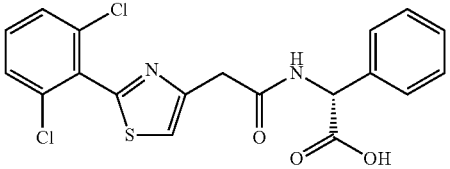 [SMILES: O=C(Cc1csc(-c2c(Cl)cccc2Cl)n1)N[C@@H](C(=O)O)c1ccccc1] I-260
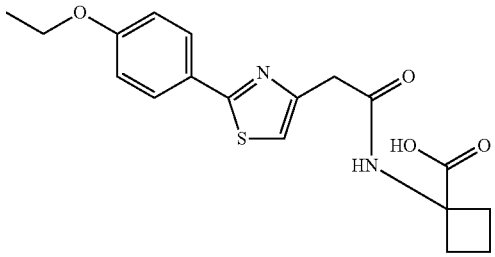 [SMILES: CCOc1ccc(-c2nc(CC(=O)NC3(C(=O)O)CCC3)cs2)cc1] I-261
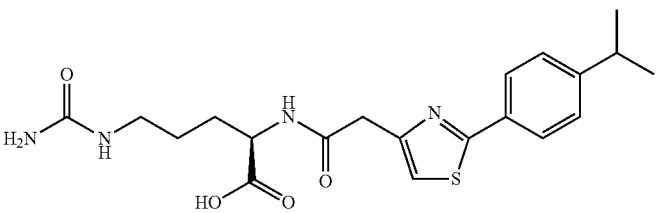 [SMILES: CC(C)c1ccc(-c2nc(CC(=O)N[C@H](CCCNC(N)=O)C(=O)O)cs2)cc1] I-262
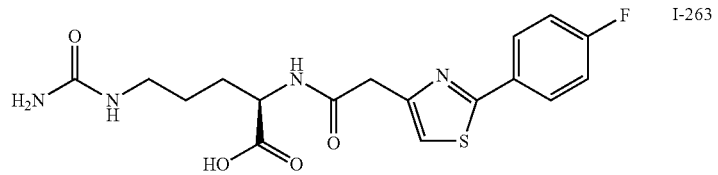 I-263
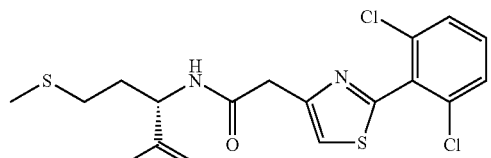 I-264
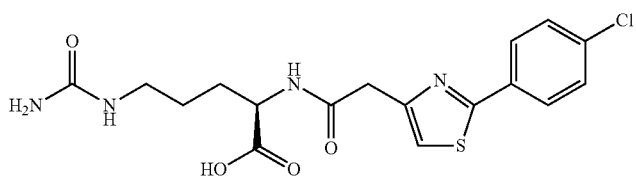 [SMILES: NC(=O)NCCC[C@@H](NC(=O)Cc1csc(-c2ccc(Cl)cc2)n1)C(=O)O] I-265

TABLE 2-continued
Exemplary Compounds
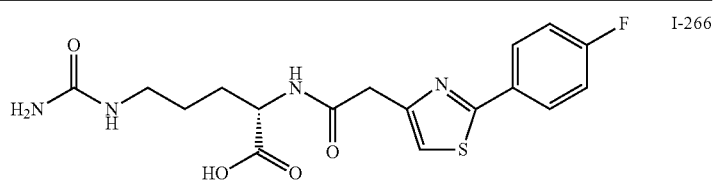 I-266
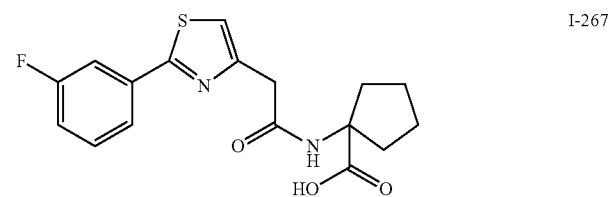 I-267
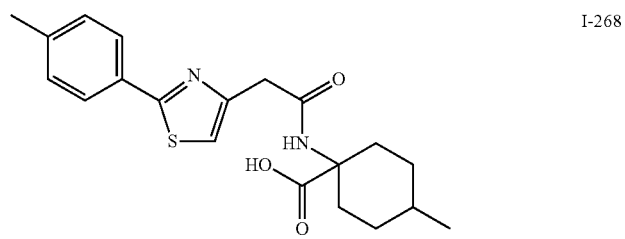 I-268
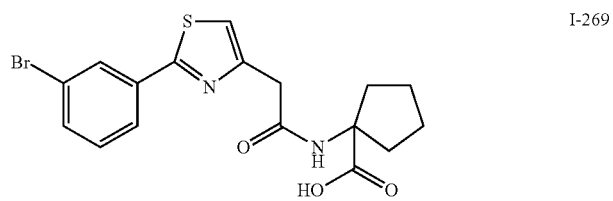 I-269
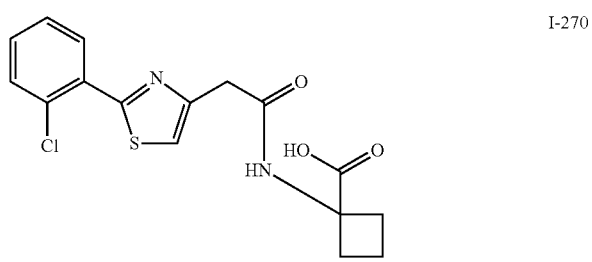 I-270
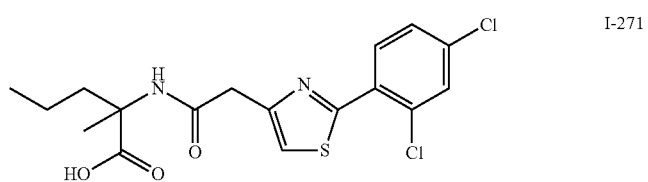 I-271
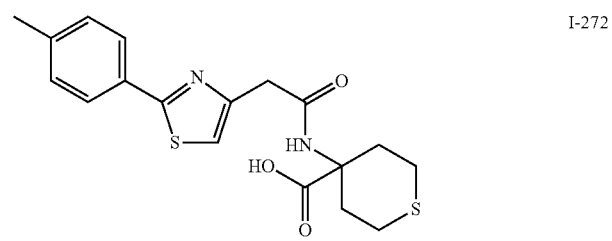 I-272

TABLE 2-continued
Exemplary Compounds
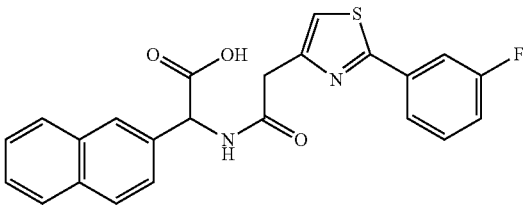 [SMILES: O=C(Cc1csc(-c2cccc(F)c2)n1)NC(C(=O)O)c1ccc2ccccc2c1]
I-273
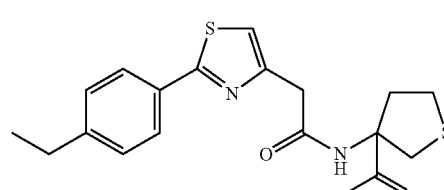
I-274
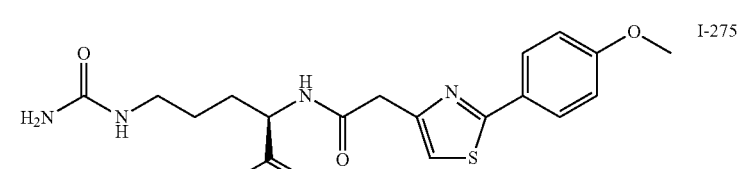
I-275
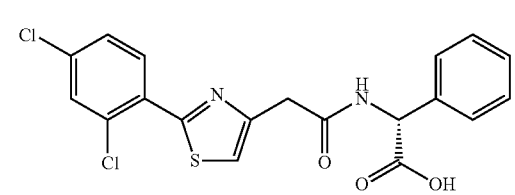 [SMILES: O=C(Cc1csc(-c2ccc(Cl)cc2Cl)n1)NC(C(=O)O)c1ccccc1]
I-276
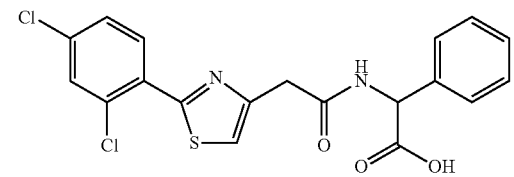
I-277
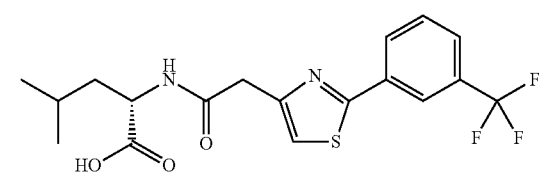 [SMILES: CC(C)C[C@H](NC(=O)Cc1csc(-c2cccc(C(F)(F)F)c2)n1)C(=O)O]
I-278
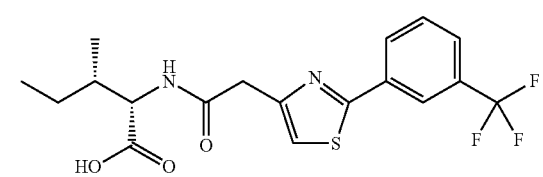 [SMILES: CC[C@H](C)[C@H](NC(=O)Cc1csc(-c2cccc(C(F)(F)F)c2)n1)C(=O)O]
I-279
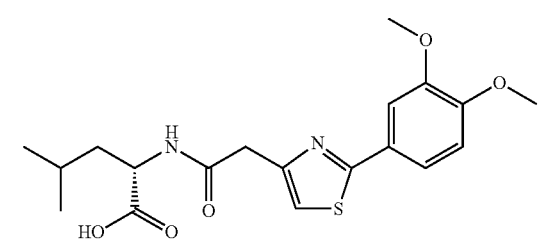 [SMILES: COc1ccc(-c2nc(CC(=O)N[C@@H](CC(C)C)C(=O)O)cs2)cc1OC]
I-280

TABLE 2-continued
Exemplary Compounds
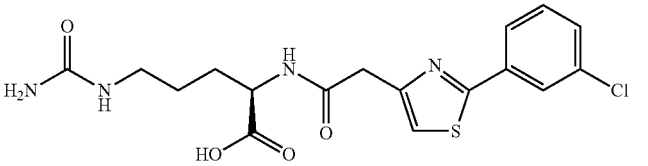 [SMILES: NC(=O)NCCC[C@@H](NC(=O)Cc1csc(-c2cccc(Br)c2)n1)C(=O)O]
I-281
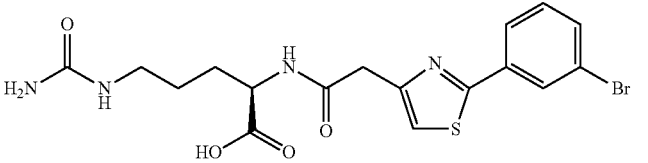
I-282
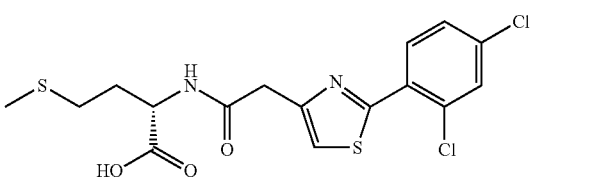 [SMILES: CSCC[C@H](NC(=O)Cc1csc(-c2ccc(Cl)cc2Cl)n1)C(=O)O]
I-283
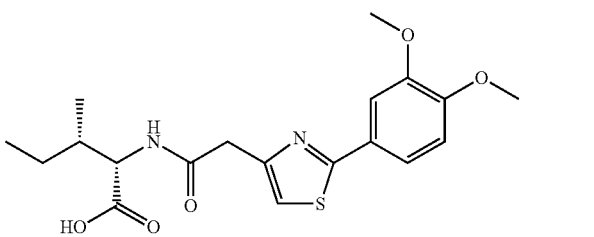 [SMILES: CC[C@H](C)[C@H](NC(=O)Cc1csc(-c2ccc(OC)c(OC)c2)n1)C(=O)O]
I-284
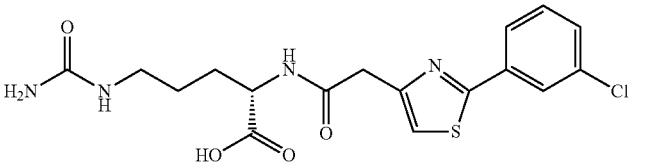 [SMILES: NC(=O)NCCC[C@H](NC(=O)Cc1csc(-c2cccc(Cl)c2)n1)C(=O)O]
I-285
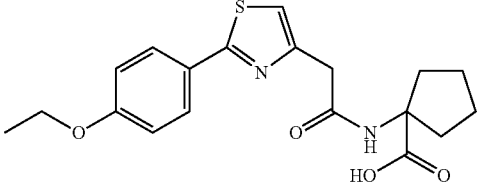 [SMILES: CCOc1ccc(-c2nc(CC(=O)NC3(C(=O)O)CCCC3)cs2)cc1]
I-286
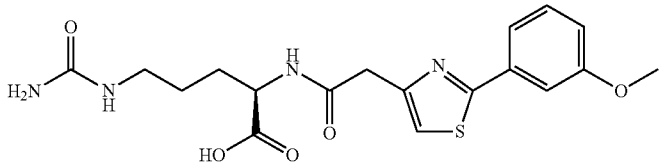 [SMILES: COc1cccc(-c2nc(CC(=O)N[C@H](CCCNC(N)=O)C(=O)O)cs2)c1]
I-287
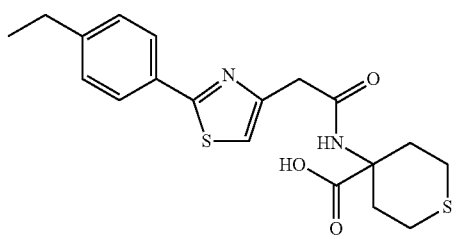 [SMILES: CCc1ccc(-c2nc(CC(=O)NC3(C(=O)O)CCSCC3)cs2)cc1]
I-288

TABLE 2-continued
Exemplary Compounds
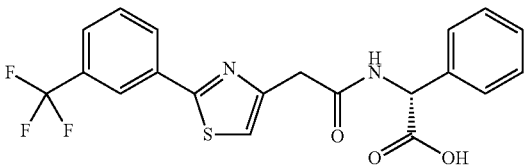
I-289
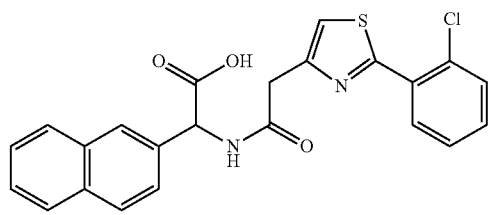 [SMILES: O=C(Cc1csc(-c2ccccc2Cl)n1)NC(C(=O)O)c1ccc2ccccc2c1]
I-290
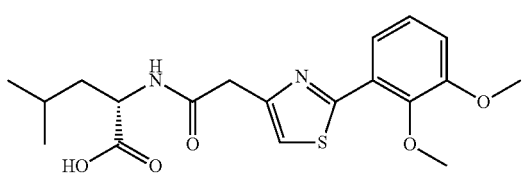 [SMILES: COc1cccc(-c2nc(CC(=O)N[C@@H](CC(C)C)C(=O)O)cs2)c1OC]
I-291
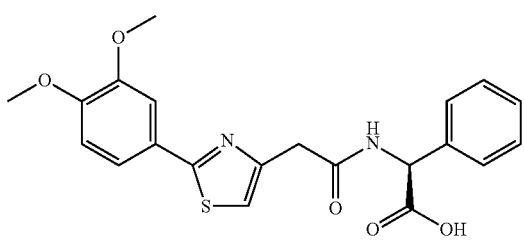 [SMILES: COc1ccc(-c2nc(CC(=O)N[C@H](C(=O)O)c3ccccc3)cs2)cc1OC]
I-292
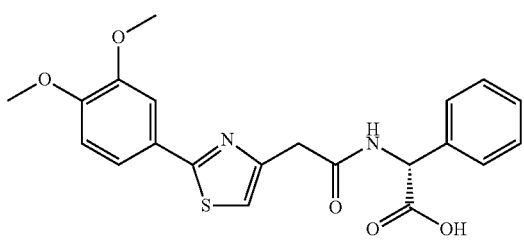 [SMILES: COc1ccc(-c2nc(CC(=O)N[C@@H](C(=O)O)c3ccccc3)cs2)cc1OC]
I-293
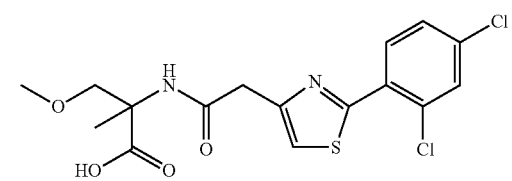 [SMILES: COCC(C)(NC(=O)Cc1csc(-c2ccc(Cl)cc2Cl)n1)C(=O)O]
I-294
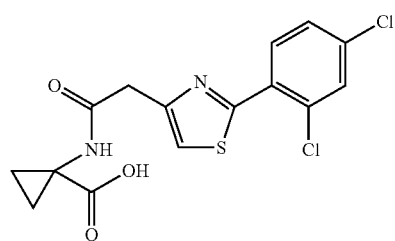 [SMILES: O=C(Cc1csc(-c2ccc(Cl)cc2Cl)n1)NC1(C(=O)O)CC1]
I-295

TABLE 2-continued
Exemplary Compounds
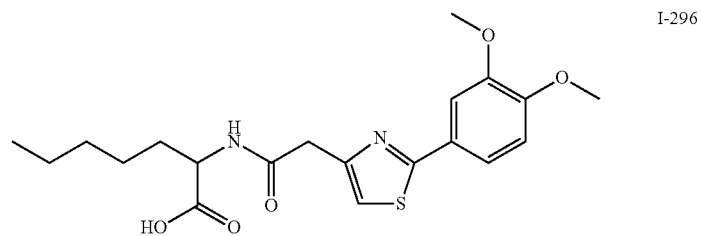
I-296
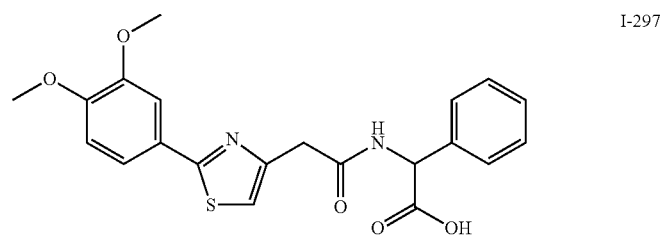
I-297
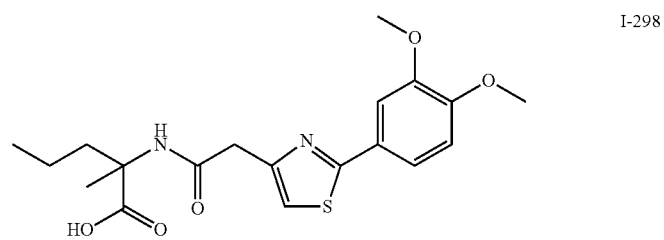
I-298
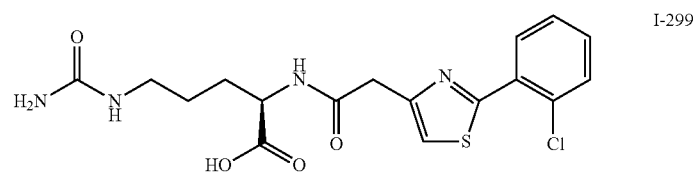
I-299
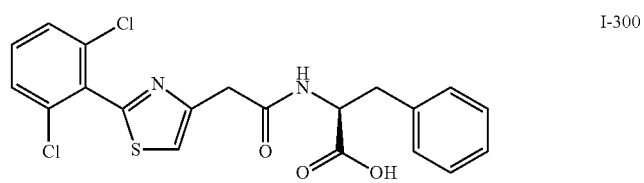
I-300
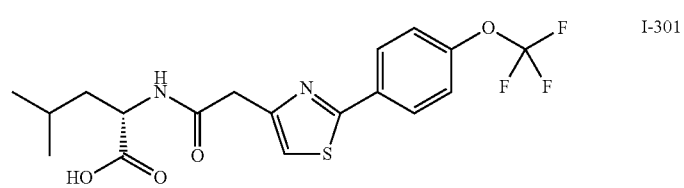
I-301
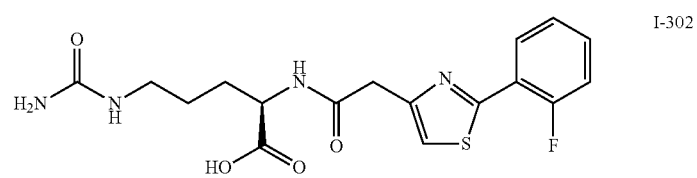
I-302

TABLE 2-continued
Exemplary Compounds
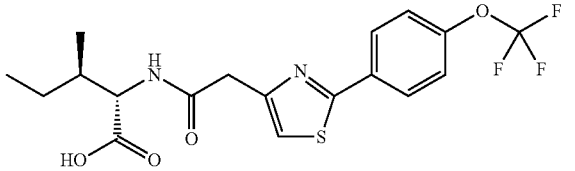 [SMILES: CC[C@@H](C)[C@H](NC(=O)Cc1csc(-c2ccc(OC(F)(F)F)cc2)n1)C(=O)O]
I-303
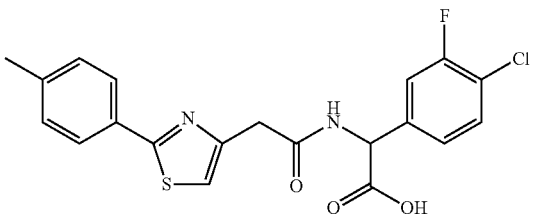 [SMILES: Cc1ccc(-c2nc(CC(=O)NC(C(=O)O)c3ccc(Cl)c(F)c3)cs2)cc1]
I-304
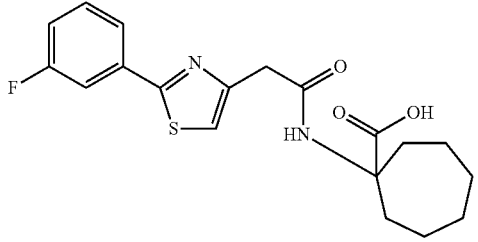 [SMILES: O=C(Cc1csc(-c2cccc(F)c2)n1)NC1(C(=O)O)CCCCCC1]
I-305
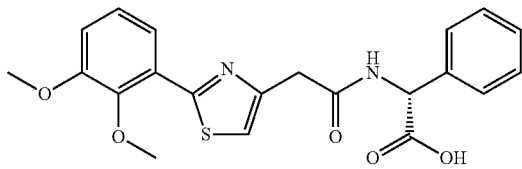 [SMILES: COc1cccc(-c2nc(CC(=O)N[C@@H](C(=O)O)c3ccccc3)cs2)c1OC]
I-306
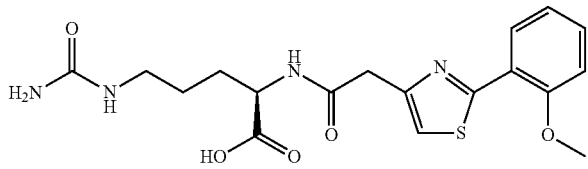 [SMILES: COc1ccccc1-c1nc(CC(=O)N[C@H](CCCNC(N)=O)C(=O)O)cs1]
I-307
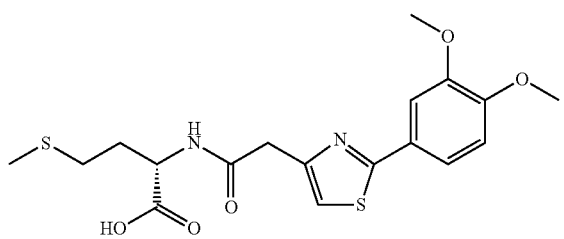
I-308
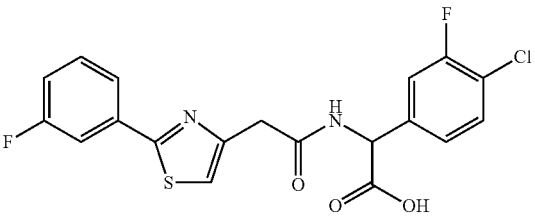 [SMILES: O=C(Cc1csc(-c2cccc(F)c2)n1)NC(C(=O)O)c1ccc(Cl)c(F)c1]
I-309

TABLE 2-continued

Exemplary Compounds

I-310

I-311

I-312

I-313

I-314

I-315

I-316

I-317

TABLE 2-continued

Exemplary Compounds

| | |
|---|---|
| (structure) | I-318 |
| (structure) | I-319 |
| (structure) | I-320 |
| (structure) | I-321 |
| (structure) | I-322 |
| (structure) | I-323 |
| (structure) | I-324 |

TABLE 2-continued

Exemplary Compounds

I-325

I-326

I-327

I-328

I-329

I-330

I-331

TABLE 2-continued
Exemplary Compounds
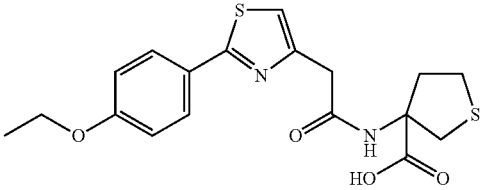 [SMILES: CCOc1ccc(-c2nc(CC(=O)NC3(C(=O)O)CCSC3)cs2)cc1] I-332
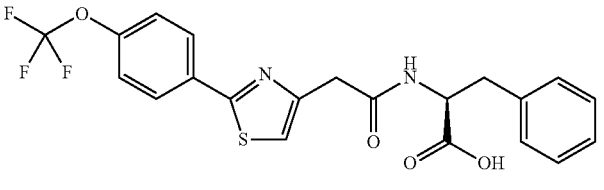 [SMILES: O=C(Cc1csc(-c2ccc(OC(F)(F)F)cc2)n1)N[C@@H](Cc1ccccc1)C(=O)O] I-333
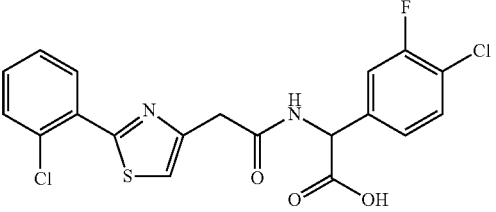 [SMILES: O=C(Cc1csc(-c2ccccc2Cl)n1)NC(C(=O)O)c1ccc(Cl)c(F)c1] I-334
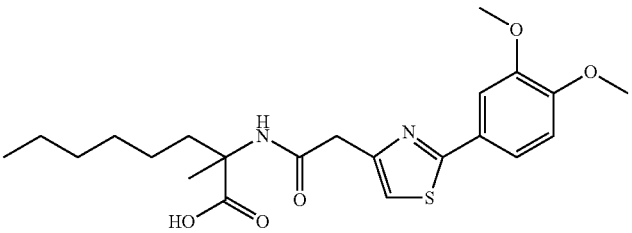 [SMILES: CCCCCCC(C)(NC(=O)Cc1csc(-c2ccc(OC)c(OC)c2)n1)C(=O)O] I-335
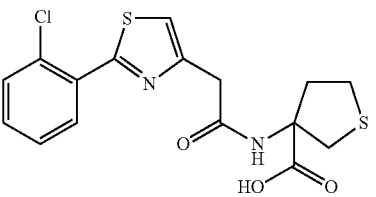 [SMILES: O=C(Cc1csc(-c2ccccc2Cl)n1)NC1(C(=O)O)CCSC1] I-336
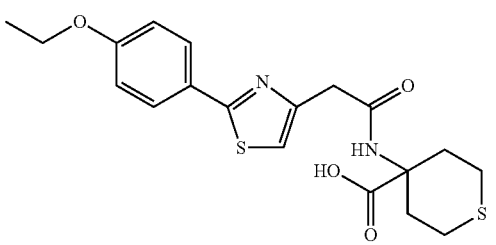 [SMILES: CCOc1ccc(-c2nc(CC(=O)NC3(C(=O)O)CCSCC3)cs2)cc1] I-337
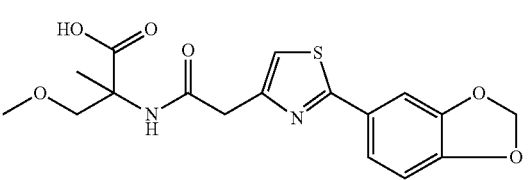 [SMILES: COCC(C)(NC(=O)Cc1csc(-c2ccc3c(c2)OCO3)n1)C(=O)O] I-338

TABLE 2-continued
Exemplary Compounds
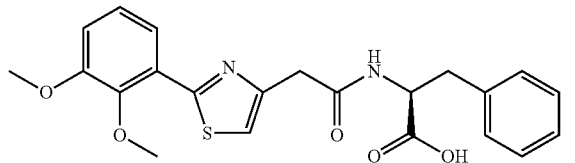 [SMILES: COc1cccc(-c2nc(CC(=O)N[C@@H](Cc3ccccc3)C(=O)O)cs2)c1OC]
I-339
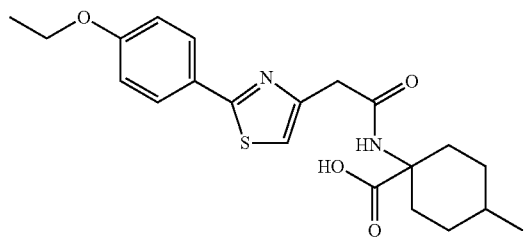 [SMILES: CCOc1ccc(-c2nc(CC(=O)NC3(C(=O)O)CCC(C)CC3)cs2)cc1]
I-340
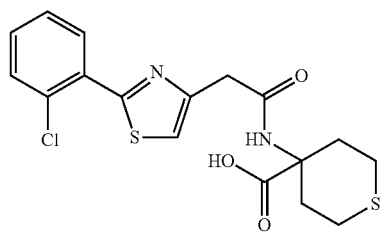 [SMILES: O=C(Cc1csc(-c2ccccc2Cl)n1)NC1(C(=O)O)CCSCC1]
I-341
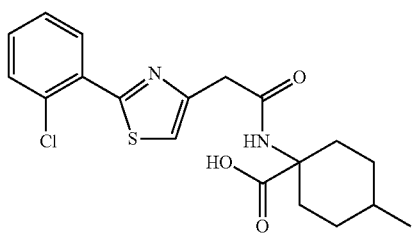 [SMILES: CC1CCC(NC(=O)Cc2csc(-c3ccccc3Cl)n2)(C(=O)O)CC1]
I-342
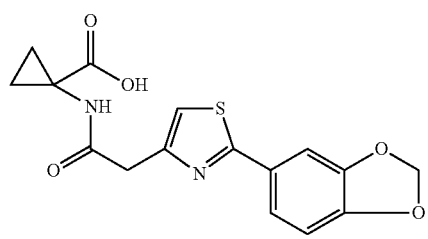 [SMILES: O=C(Cc1csc(-c2ccc3c(c2)OCO3)n1)NC1(C(=O)O)CC1]
I-343
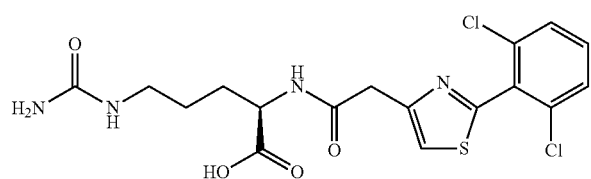 [SMILES: NC(=O)NCCC[C@@H](NC(=O)Cc1csc(-c2c(Cl)cccc2Cl)n1)C(=O)O]
I-344

101
TABLE 2-continued
Exemplary Compounds
I-345
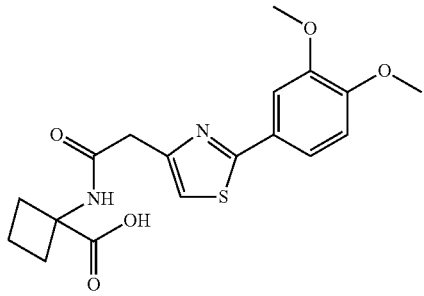 [SMILES: COc1ccc(-c2nc(CC(=O)NC3(C(=O)O)CCC3)cs2)cc1OC]
I-346
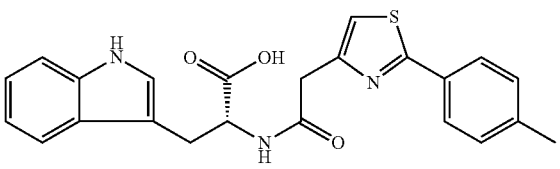 [SMILES: Cc1ccc(-c2nc(CC(=O)N[C@H](Cc3c[nH]c4ccccc34)C(=O)O)cs2)cc1]
I-347
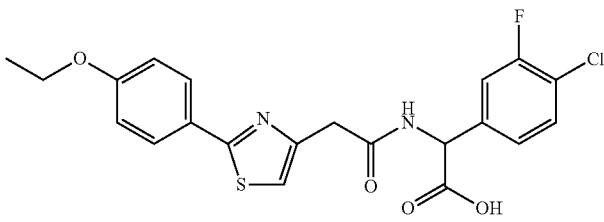 [SMILES: CCOc1ccc(-c2nc(CC(=O)NC(C(=O)O)c3ccc(Cl)c(F)c3)cs2)cc1]
I-348
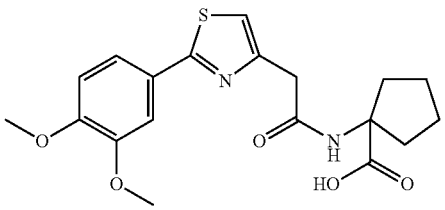 [SMILES: COc1ccc(-c2nc(CC(=O)NC3(C(=O)O)CCCC3)cs2)cc1OC]
I-349
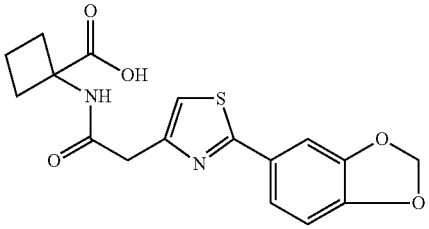 [SMILES: O=C(Cc1csc(-c2ccc3c(c2)OCO3)n1)NC1(C(=O)O)CCC1]
I-350
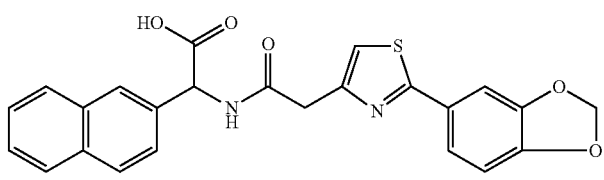 [SMILES: O=C(Cc1csc(-c2ccc3c(c2)OCO3)n1)NC(C(=O)O)c1ccc2ccccc2c1]
I-351
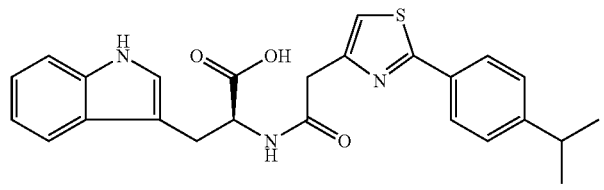 [SMILES: CC(C)c1ccc(-c2nc(CC(=O)N[C@@H](Cc3c[nH]c4ccccc34)C(=O)O)cs2)cc1]

TABLE 2-continued
Exemplary Compounds
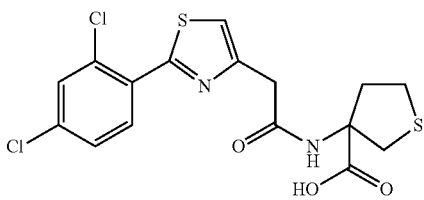 [SMILES: O=C(Cc1csc(-c2ccc(Cl)cc2Cl)n1)NC1(C(=O)O)CCSC1] I-352
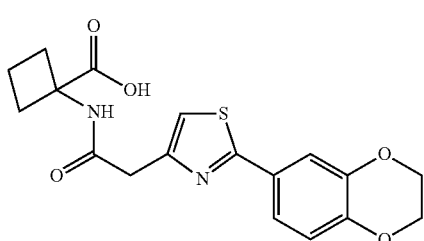 I-353
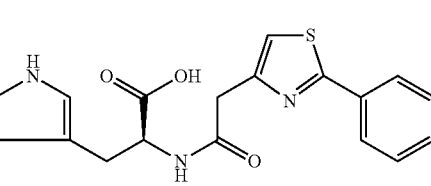 I-354
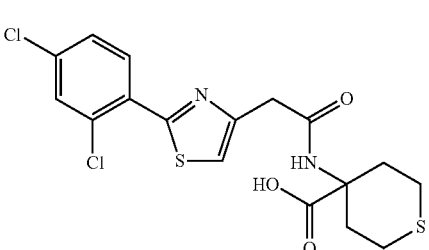 I-355
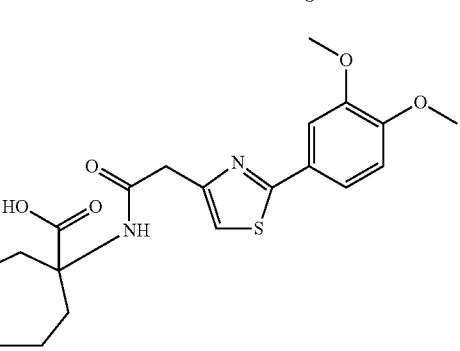 I-356
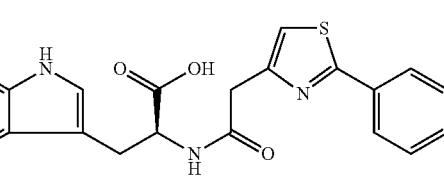 I-357
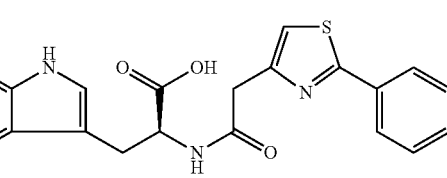 I-358

TABLE 2-continued
Exemplary Compounds
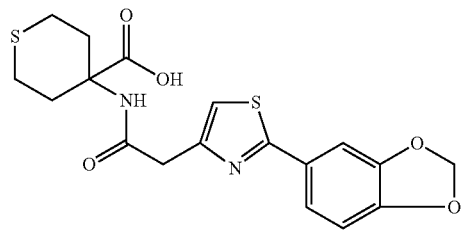 [SMILES: O=C(Cc1csc(-c2ccc3c(c2)OCO3)n1)NC1(C(=O)O)CCSCC1]
I-359
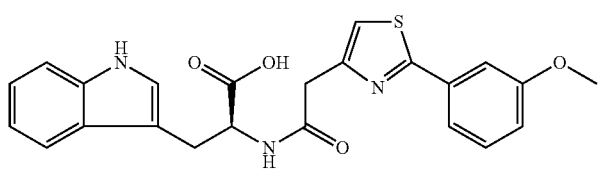 [SMILES: COc1cccc(-c2nc(CC(=O)N[C@@H](Cc3c[nH]c4ccccc34)C(=O)O)cs2)c1]
I-360
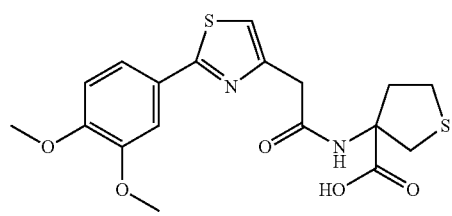 [SMILES: COc1ccc(-c2nc(CC(=O)NC3(C(=O)O)CCSC3)cs2)cc1OC]
I-361
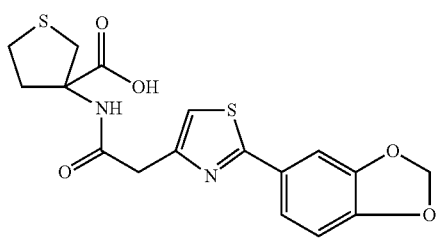 [SMILES: O=C(Cc1csc(-c2ccc3c(c2)OCO3)n1)NC1(C(=O)O)CCSC1]
I-362
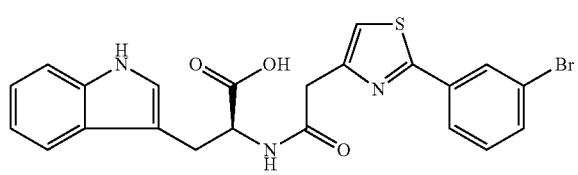 [SMILES: O=C(Cc1csc(-c2cccc(Br)c2)n1)N[C@@H](Cc1c[nH]c2ccccc12)C(=O)O]
I-363
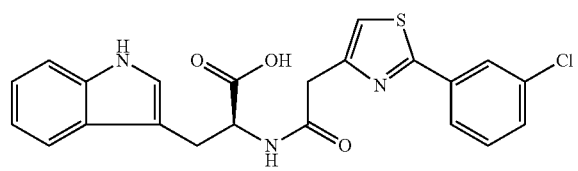 [SMILES: O=C(Cc1csc(-c2cccc(Cl)c2)n1)N[C@@H](Cc1c[nH]c2ccccc12)C(=O)O]
I-364
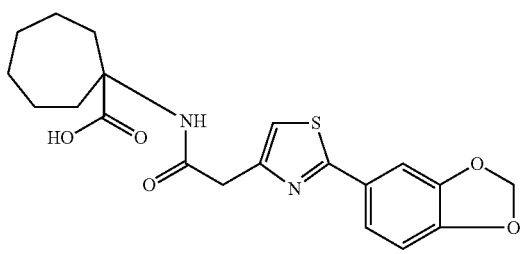 [SMILES: O=C(Cc1csc(-c2ccc3c(c2)OCO3)n1)NC1(C(=O)O)CCCCCC1]
I-365

TABLE 2-continued
Exemplary Compounds
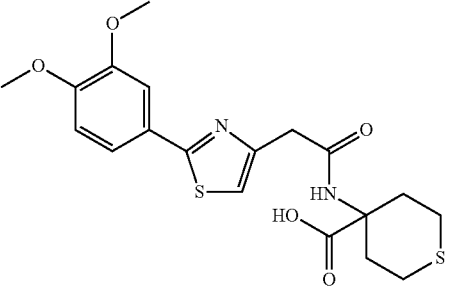 [SMILES: COc1ccc(-c2nc(CC(=O)NC3(C(=O)O)CCSCC3)cs2)cc1OC] I-366
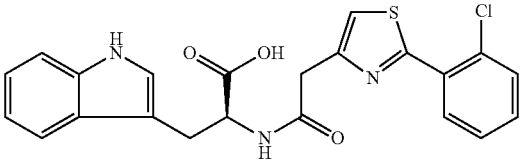 [SMILES: O=C(Cc1csc(-c2ccccc2Cl)n1)N[C@@H](Cc1c[nH]c2ccccc12)C(=O)O] I-367
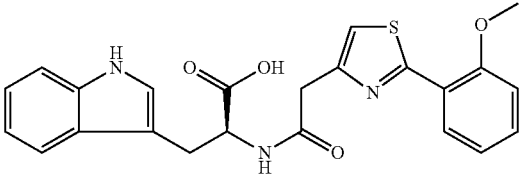 [SMILES: COc1ccccc1-c1nc(CC(=O)N[C@@H](Cc2c[nH]c3ccccc23)C(=O)O)cs1] I-368
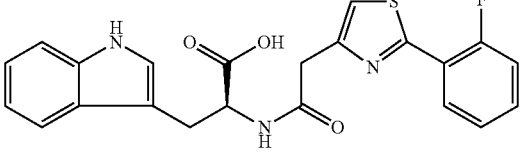 I-369
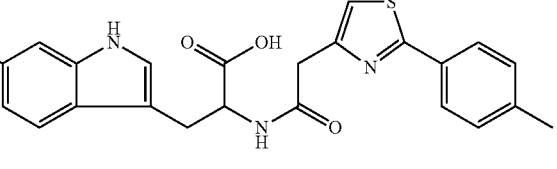 I-370
 I-371
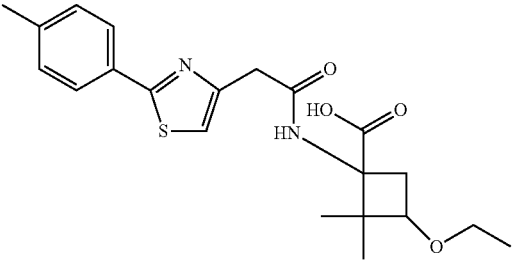 [SMILES: CCOC1CC(NC(=O)Cc2csc(-c3ccc(C)cc3)n2)(C(=O)O)C1(C)C] I-372

TABLE 2-continued
Exemplary Compounds
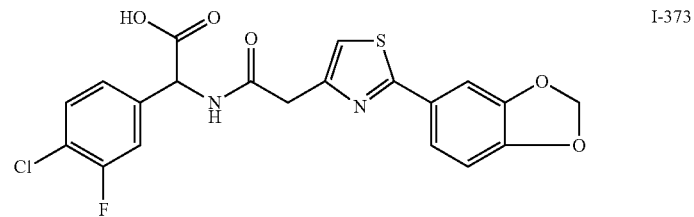 I-373
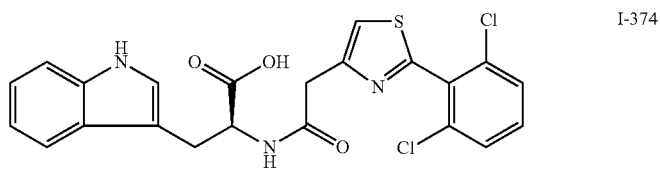 I-374
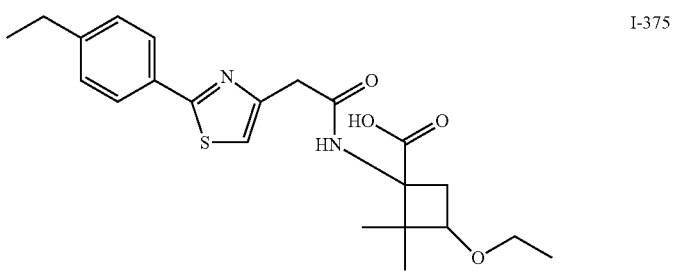 I-375
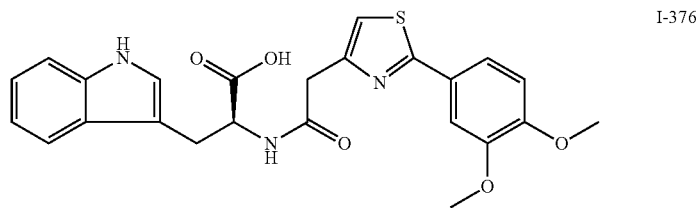 I-376
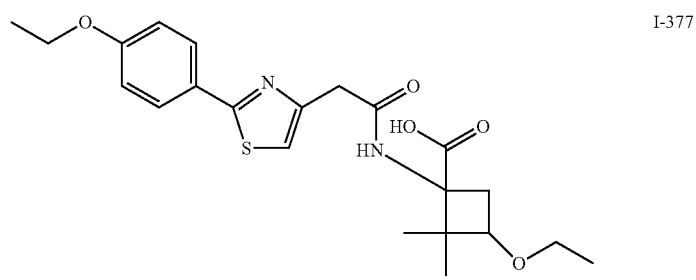 I-377
 I-378
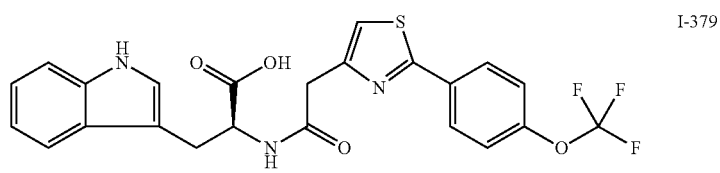 I-379

TABLE 2-continued
Exemplary Compounds
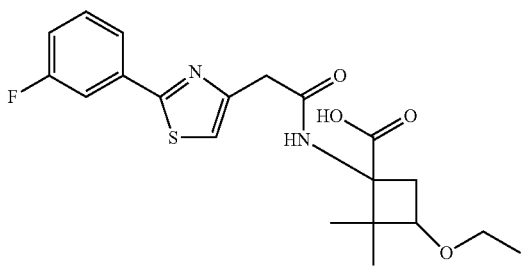 [SMILES: CCOC1CC(NC(=O)Cc2csc(-c3cccc(F)c3)n2)(C(=O)O)C1(C)C]
I-380
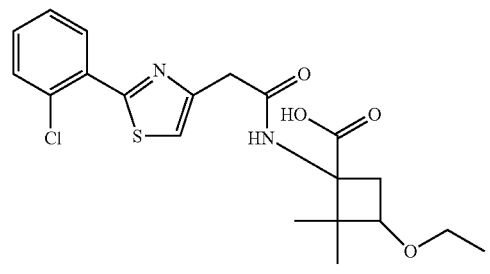 [SMILES: CCOC1CC(NC(=O)Cc2csc(-c3ccccc3Cl)n2)(C(=O)O)C1(C)C]
I-381
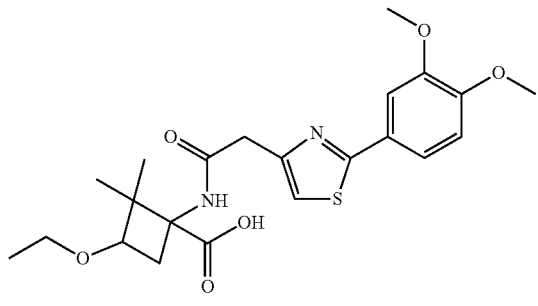 [SMILES: CCOC1CC(NC(=O)Cc2csc(-c3ccc(OC)c(OC)c3)n2)(C(=O)O)C1(C)C]
I-382
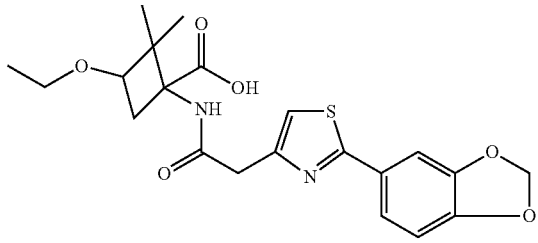 [SMILES: CCOC1CC(NC(=O)Cc2csc(-c3ccc4c(c3)OCO4)n2)(C(=O)O)C1(C)C]
I-383
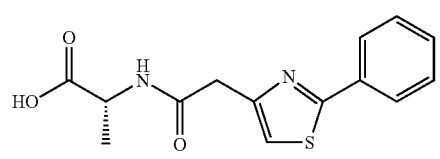
I-384
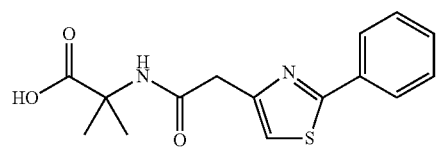 [SMILES: CC(C)(NC(=O)Cc1csc(-c2ccccc2)n1)C(=O)O]
I-385
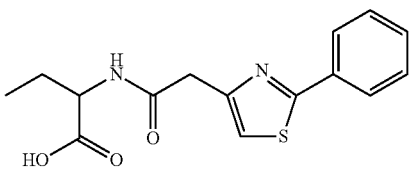 [SMILES: CCC(NC(=O)Cc1csc(-c2ccccc2)n1)C(=O)O]
I-386

TABLE 2-continued
Exemplary Compounds
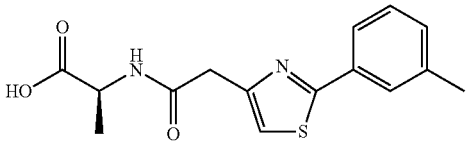 [SMILES: Cc1cccc(-c2nc(CC(=O)N[C@@H](C)C(=O)O)cs2)c1]
I-387
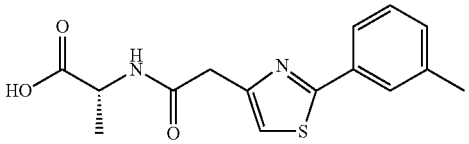 [SMILES: Cc1cccc(-c2nc(CC(=O)N[C@H](C)C(=O)O)cs2)c1]
I-388
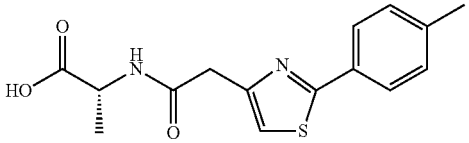 [SMILES: Cc1ccc(-c2nc(CC(=O)N[C@H](C)C(=O)O)cs2)cc1]
I-389
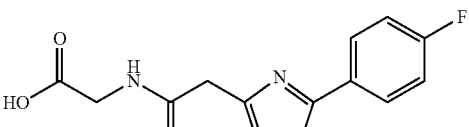
I-390
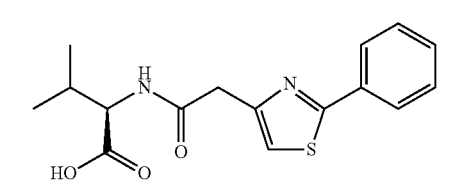 [SMILES: CC(C)[C@@H](NC(=O)Cc1csc(-c2ccccc2)n1)C(=O)O]
I-391
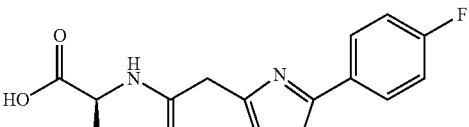
I-392
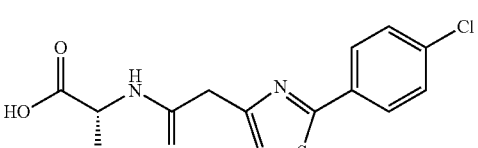
I-393
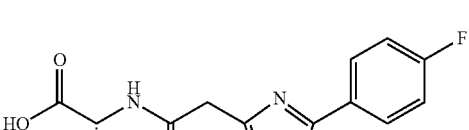
I-394
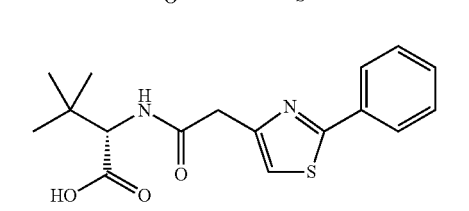
I-395

TABLE 2-continued

Exemplary Compounds

| | |
|---|---|
| (structure) | I-396 |
| (structure) | I-397 |
| (structure) | I-398 |
| (structure) | I-399 |
| (structure) | I-400 |
| (structure) | I-401 |
| (structure) | I-402 |
| (structure) | I-403 |
| (structure) | I-404 |

TABLE 2-continued
Exemplary Compounds
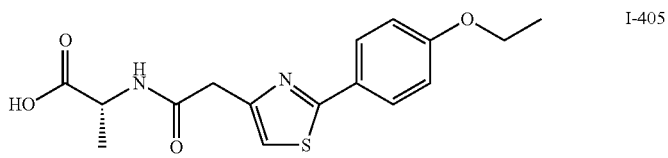 I-405
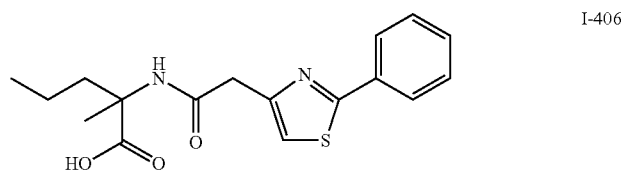 I-406
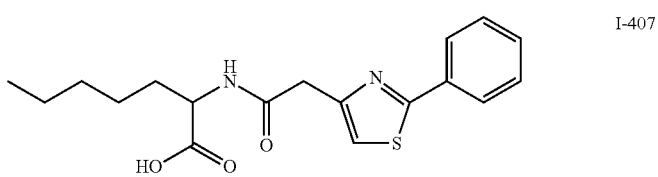 I-407
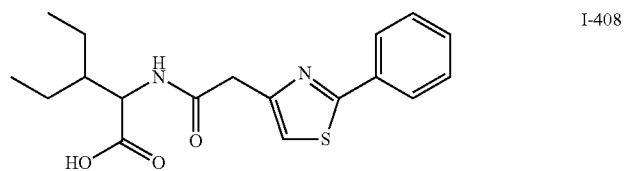 I-408
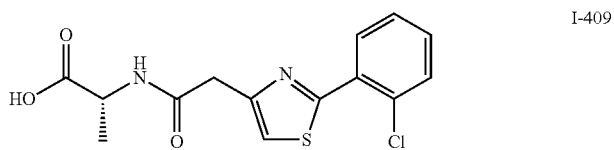 I-409
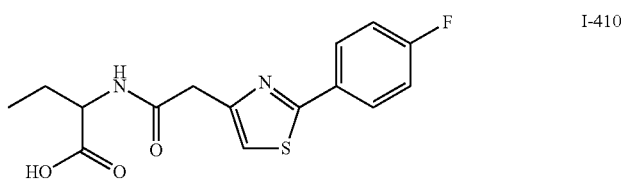 I-410
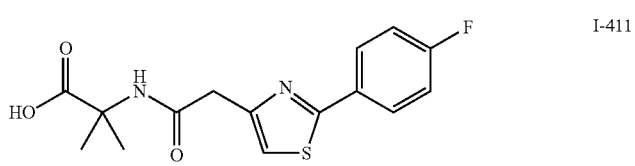 I-411
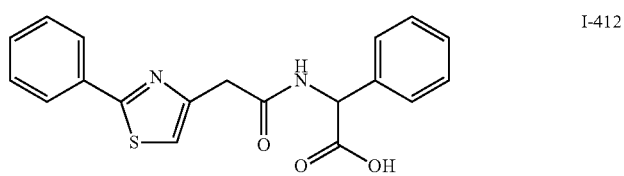 I-412
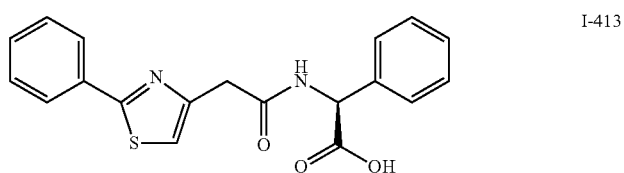 I-413

TABLE 2-continued
Exemplary Compounds
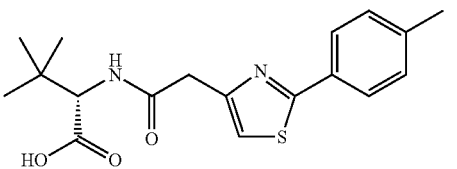 [SMILES: Cc1ccc(-c2nc(CC(=O)N[C@H](C(=O)O)C(C)(C)C)cs2)cc1]
I-414
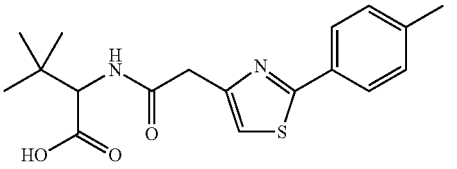 [SMILES: Cc1ccc(-c2nc(CC(=O)NC(C(=O)O)C(C)(C)C)cs2)cc1]
I-415
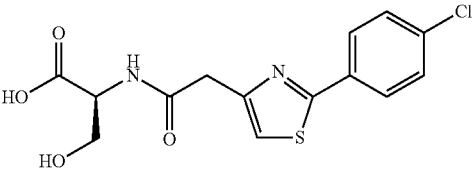 [SMILES: O=C(Cc1csc(-c2ccc(Cl)cc2)n1)N[C@@H](CO)C(=O)O]
I-416
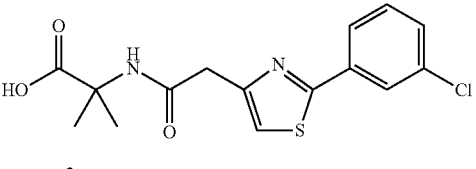
I-417
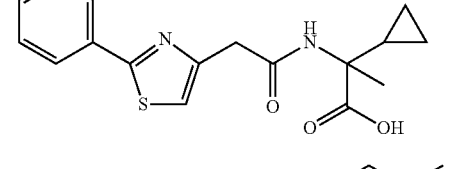
I-418
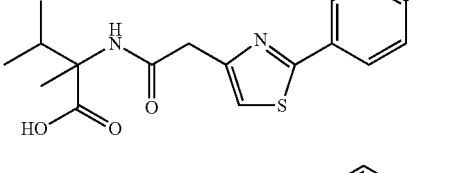
I-419
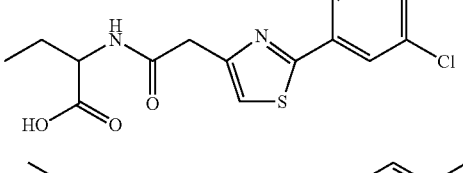
I-420
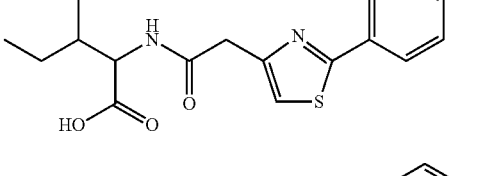
I-421
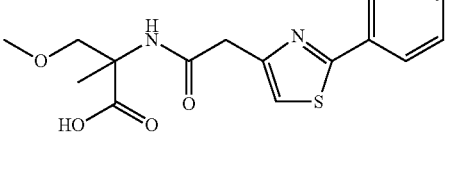
I-422

TABLE 2-continued
Exemplary Compounds
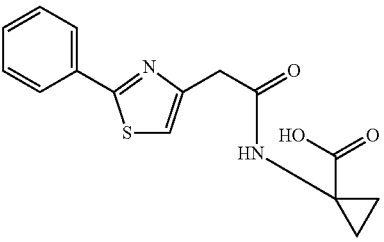 [SMILES: O=C(Cc1csc(-c2ccccc2)n1)NC1(C(=O)O)CC1] I-423
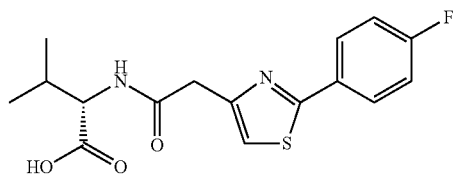 [SMILES: CC(C)[C@H](NC(=O)Cc1csc(-c2ccc(F)cc2)n1)C(=O)O] I-424
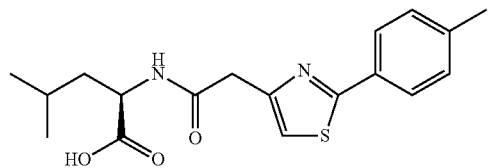 [SMILES: Cc1ccc(-c2nc(CC(=O)N[C@H](CC(C)C)C(=O)O)cs2)cc1] I-425
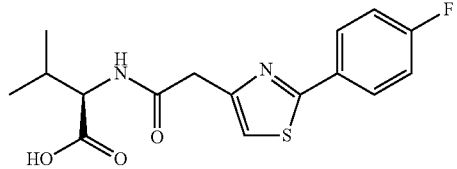 [SMILES: CC(C)[C@@H](NC(=O)Cc1csc(-c2ccc(F)cc2)n1)C(=O)O] I-426
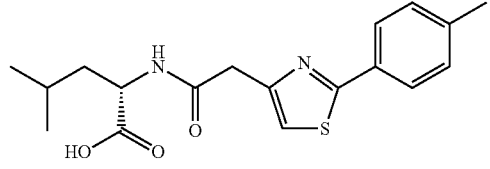 [SMILES: Cc1ccc(-c2nc(CC(=O)N[C@@H](CC(C)C)C(=O)O)cs2)cc1] I-427
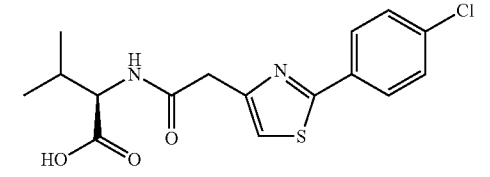 [SMILES: CC(C)[C@@H](NC(=O)Cc1csc(-c2ccc(Cl)cc2)n1)C(=O)O] I-428
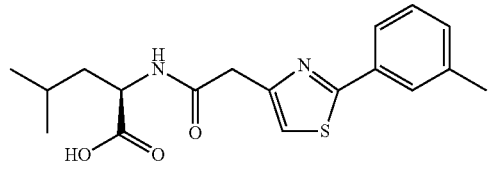 [SMILES: Cc1cccc(-c2nc(CC(=O)N[C@H](CC(C)C)C(=O)O)cs2)c1] I-429
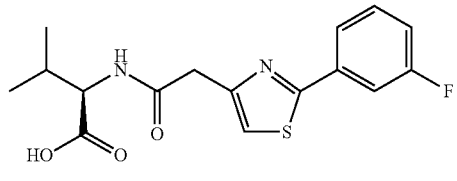 [SMILES: CC(C)[C@@H](NC(=O)Cc1csc(-c2cccc(F)c2)n1)C(=O)O] I-430

123
TABLE 2-continued
Exemplary Compounds
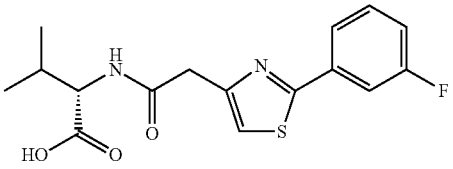 [SMILES: CC(C)[C@H](NC(=O)Cc1csc(-c2cccc(F)c2)n1)C(=O)O] I-431
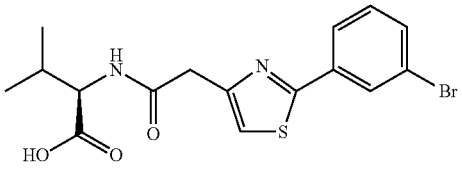 [SMILES: CC(C)[C@@H](NC(=O)Cc1csc(-c2cccc(Br)c2)n1)C(=O)O] I-432
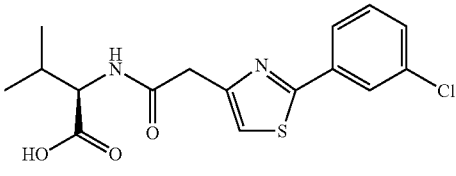 [SMILES: CC(C)[C@@H](NC(=O)Cc1csc(-c2cccc(Cl)c2)n1)C(=O)O] I-433
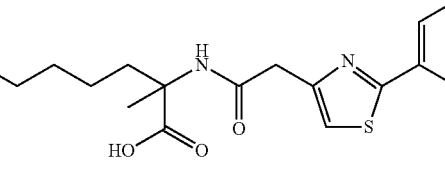 I-434
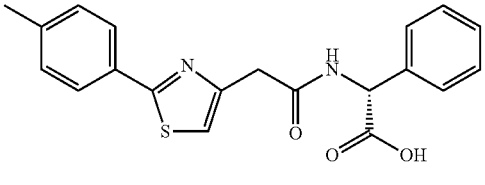 [SMILES: Cc1ccc(-c2nc(CC(=O)N[C@@H](C(=O)O)c3ccccc3)cs2)cc1] I-435
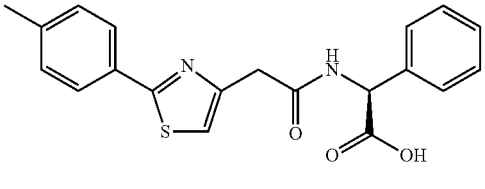 [SMILES: Cc1ccc(-c2nc(CC(=O)N[C@H](C(=O)O)c3ccccc3)cs2)cc1] I-436
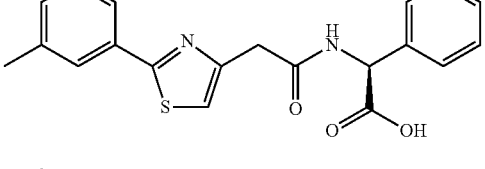 I-437
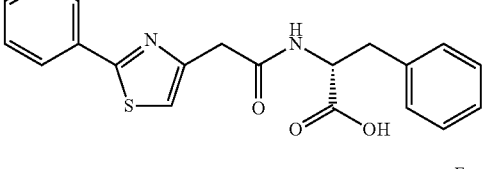 I-438
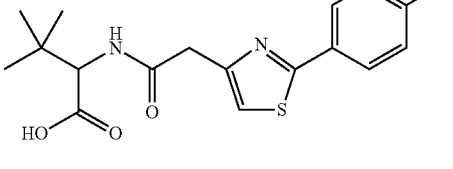 I-439
124

TABLE 2-continued
Exemplary Compounds
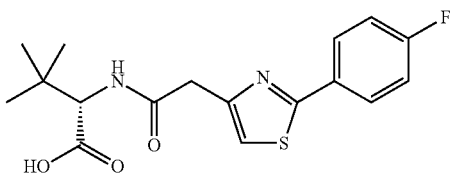 [SMILES: CC(C)(C)[C@H](NC(=O)Cc1csc(-c2ccc(F)cc2)n1)C(=O)O] I-440
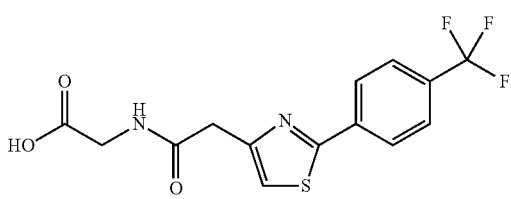 [SMILES: O=C(O)CNC(=O)Cc1csc(-c2ccc(C(F)(F)F)cc2)n1] I-441
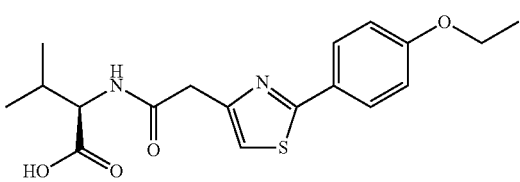 [SMILES: CCOc1ccc(-c2nc(CC(=O)N[C@@H](C(=O)O)C(C)C)cs2)cc1] I-442
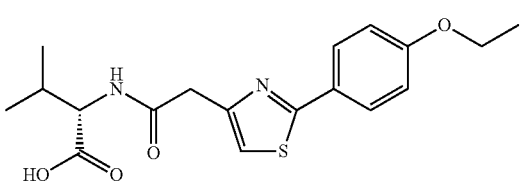 [SMILES: CCOc1ccc(-c2nc(CC(=O)N[C@H](C(=O)O)C(C)C)cs2)cc1] I-443
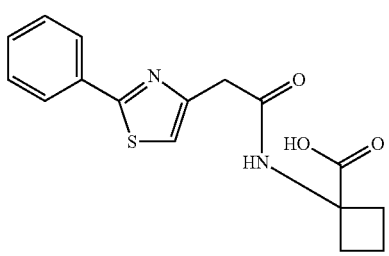 [SMILES: O=C(Cc1csc(-c2ccccc2)n1)NC1(C(=O)O)CCC1] I-444
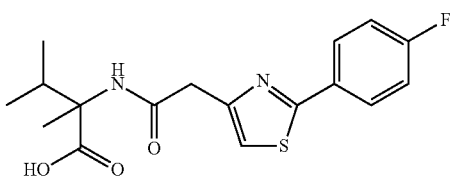 [SMILES: CC(C)C(C)(NC(=O)Cc1csc(-c2ccc(F)cc2)n1)C(=O)O] I-445
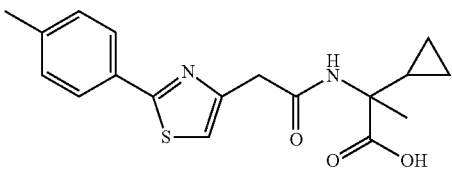 [SMILES: Cc1ccc(-c2nc(CC(=O)NC(C)(C(=O)O)C3CC3)cs2)cc1] I-446
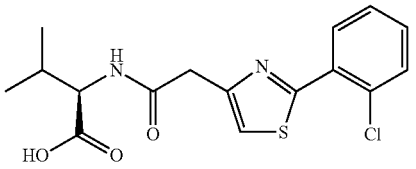 [SMILES: CC(C)[C@@H](NC(=O)Cc1csc(-c2ccccc2Cl)n1)C(=O)O] I-447

TABLE 2-continued
Exemplary Compounds
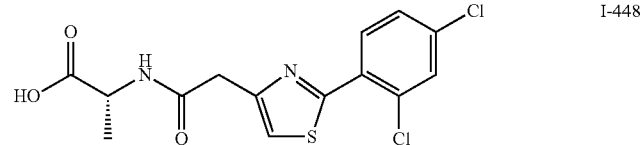 I-448
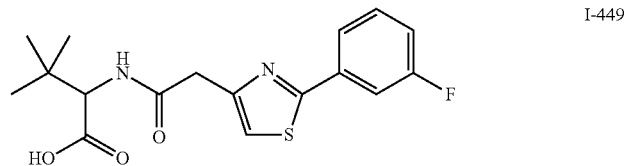 I-449
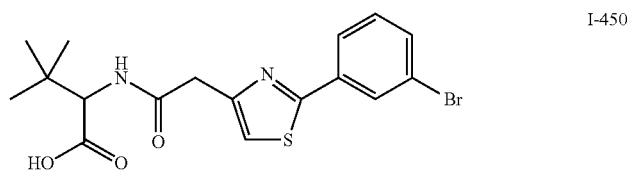 I-450
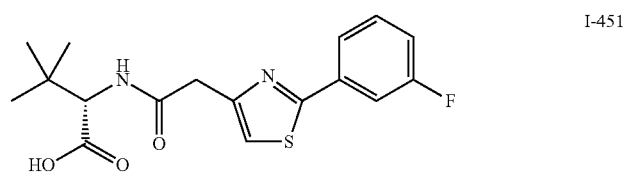 I-451
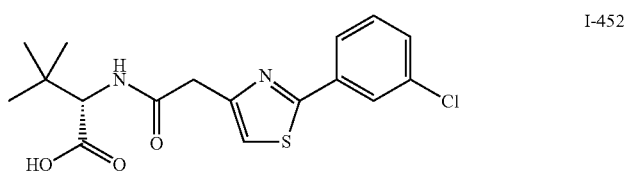 I-452
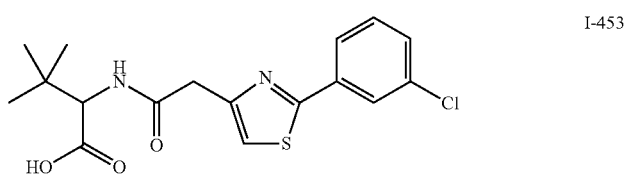 I-453
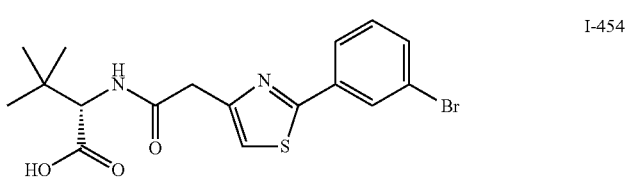 I-454
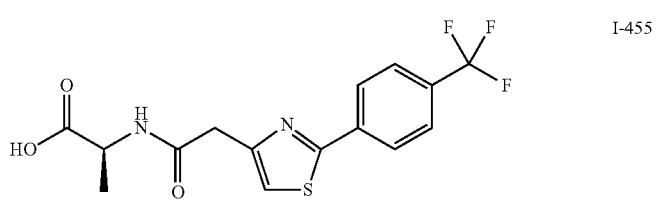 I-455

TABLE 2-continued

Exemplary Compounds

| Compound | ID |
|---|---|
| (structure) | I-456 |
| (structure) | I-457 |
| (structure) | I-458 |
| (structure) | I-459 |
| (structure) | I-460 |
| (structure) | I-461 |
| (structure) | I-462 |
| (structure) | I-463 |

TABLE 2-continued

Exemplary Compounds

I-464

I-465

I-466

I-467

I-468

I-469

I-470

I-471

I-472

TABLE 2-continued
Exemplary Compounds
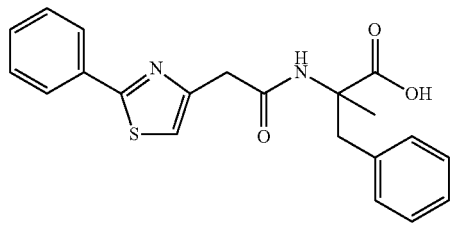 [SMILES: CC(Cc1ccccc1)(NC(=O)Cc1csc(-c2ccccc2)n1)C(=O)O] I-473
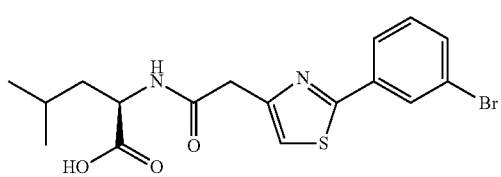 [SMILES: CC(C)C[C@@H](NC(=O)Cc1csc(-c2cccc(Br)c2)n1)C(=O)O] I-474
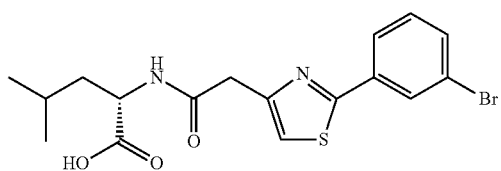 [SMILES: CC(C)C[C@H](NC(=O)Cc1csc(-c2cccc(Br)c2)n1)C(=O)O] I-475
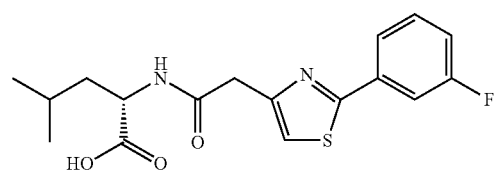 [SMILES: CC(C)C[C@H](NC(=O)Cc1csc(-c2cccc(F)c2)n1)C(=O)O] I-476
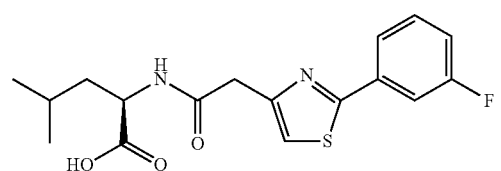 [SMILES: CC(C)C[C@@H](NC(=O)Cc1csc(-c2cccc(F)c2)n1)C(=O)O] I-477
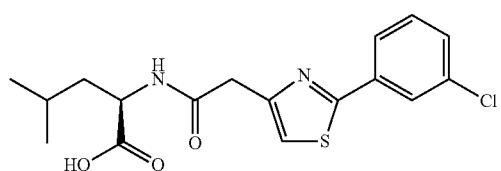 [SMILES: CC(C)C[C@@H](NC(=O)Cc1csc(-c2cccc(Cl)c2)n1)C(=O)O] I-478
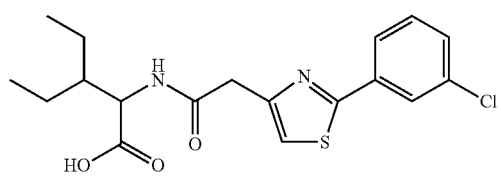 [SMILES: CCC(CC)C(NC(=O)Cc1csc(-c2cccc(Cl)c2)n1)C(=O)O] I-479
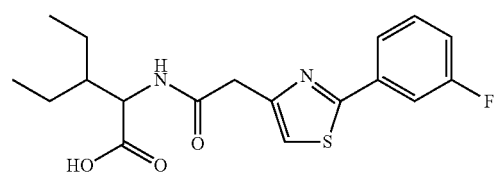 [SMILES: CCC(CC)C(NC(=O)Cc1csc(-c2cccc(F)c2)n1)C(=O)O] I-480

TABLE 2-continued
Exemplary Compounds
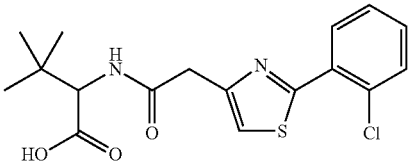 I-481
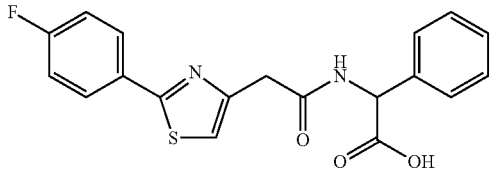 [SMILES: O=C(Cc1csc(-c2ccc(F)cc2)n1)NC(C(=O)O)c1ccccc1] I-482
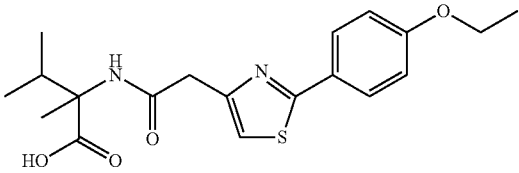 [SMILES: CCOc1ccc(-c2nc(CC(=O)NC(C)(C(=O)O)C(C)C)cs2)cc1] I-483
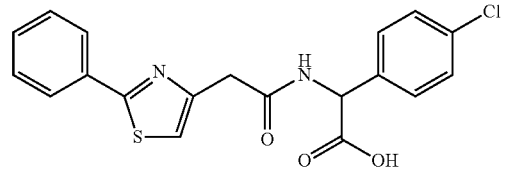 [SMILES: O=C(Cc1csc(-c2ccccc2)n1)NC(C(=O)O)c1ccc(Cl)cc1] I-484
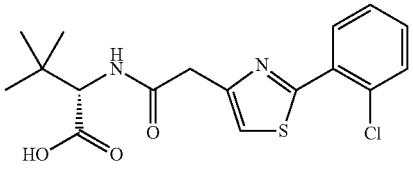 [SMILES: CC(C)(C)[C@H](NC(=O)Cc1csc(-c2ccccc2Cl)n1)C(=O)O] I-485
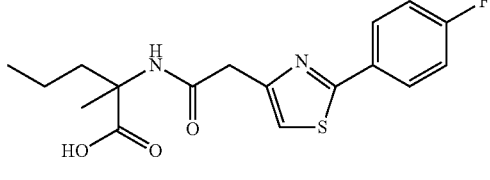 I-486
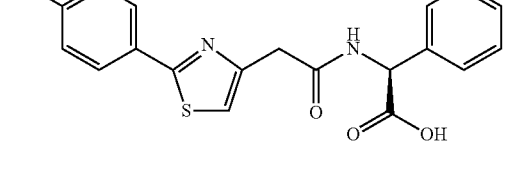 I-487
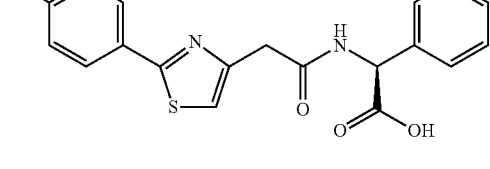 I-488

US 11,091,451 B2
TABLE 2-continued
Exemplary Compounds
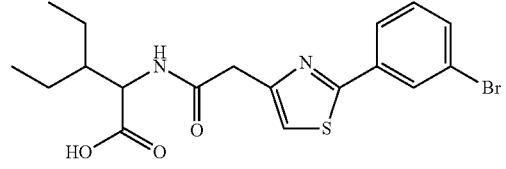 [SMILES: CCC(CC)C(NC(=O)Cc1csc(-c2cccc(Br)c2)n1)C(=O)O] I-489
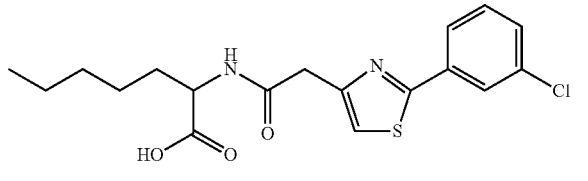 [SMILES: CCCCCC(NC(=O)Cc1csc(-c2cccc(Cl)c2)n1)C(=O)O] I-490
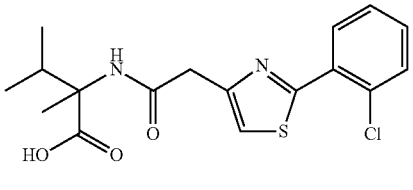 [SMILES: CC(C)C(C)(NC(=O)Cc1csc(-c2ccccc2Cl)n1)C(=O)O] I-491
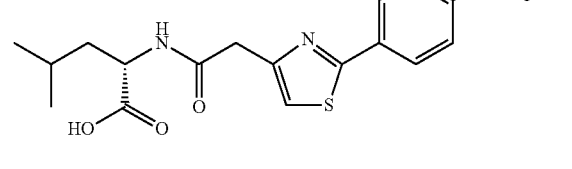 I-492
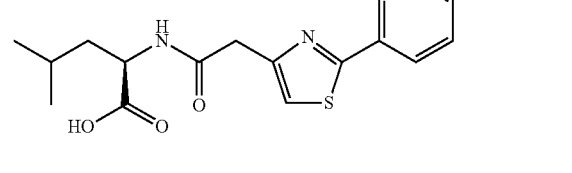 I-493
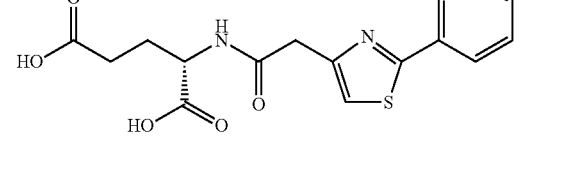 I-494
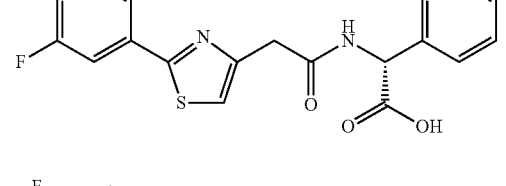 I-495
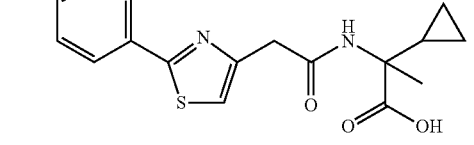 I-496

TABLE 2-continued
Exemplary Compounds
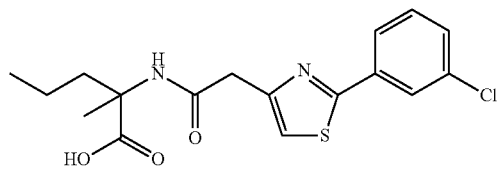 [SMILES: CCCC(C)(NC(=O)Cc1csc(-c2cccc(Cl)c2)n1)C(=O)O] I-497
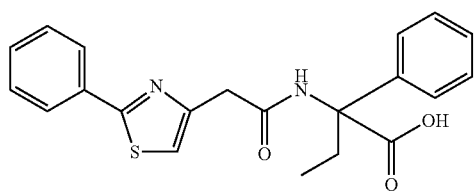 [SMILES: CCC(NC(=O)Cc1csc(-c2ccccc2)n1)(C(=O)O)c1ccccc1] I-498
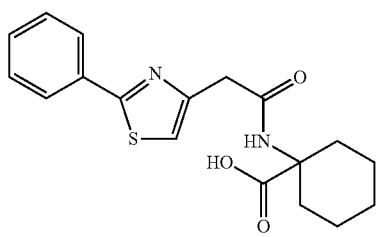 [SMILES: O=C(Cc1csc(-c2ccccc2)n1)NC1(C(=O)O)CCCCC1] I-499
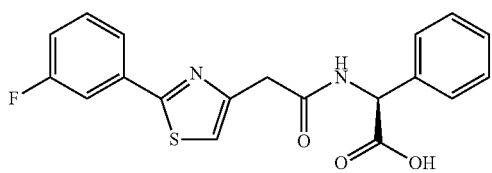 [SMILES: O=C(Cc1csc(-c2cccc(F)c2)n1)N[C@H](C(=O)O)c1ccccc1] I-500
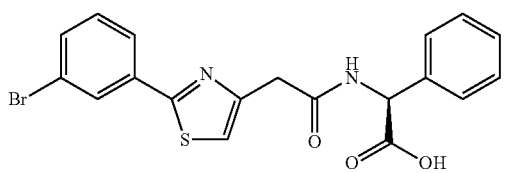 [SMILES: O=C(Cc1csc(-c2cccc(Br)c2)n1)N[C@H](C(=O)O)c1ccccc1] I-501
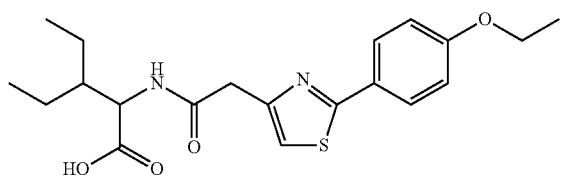 [SMILES: CCOc1ccc(-c2nc(CC(=O)NC(C(=O)O)C(CC)CC)cs2)cc1] I-502
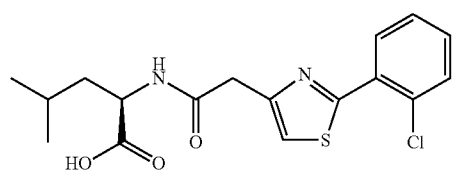 [SMILES: CC(C)C[C@@H](NC(=O)Cc1csc(-c2ccccc2Cl)n1)C(=O)O] I-503
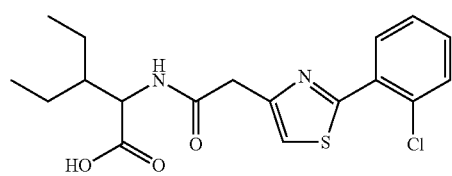 [SMILES: CCC(CC)C(NC(=O)Cc1csc(-c2ccccc2Cl)n1)C(=O)O] I-504

TABLE 2-continued
Exemplary Compounds
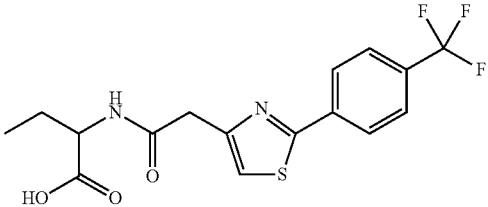 [SMILES: CCC(NC(=O)Cc1csc(-c2ccc(C(F)(F)F)cc2)n1)C(=O)O] I-505
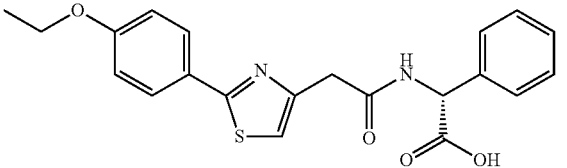 [SMILES: CCOc1ccc(-c2nc(CC(=O)N[C@@H](C(=O)O)c3ccccc3)cs2)cc1] I-506
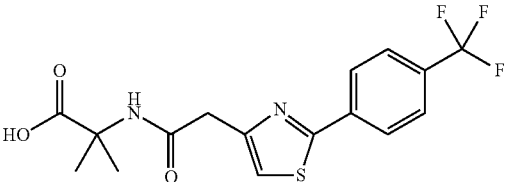 I-507
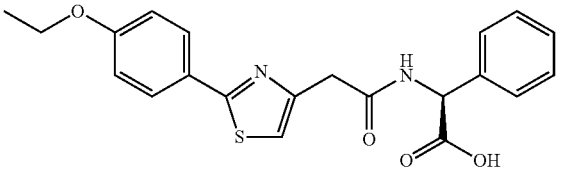 [SMILES: CCOc1ccc(-c2nc(CC(=O)N[C@H](C(=O)O)c3ccccc3)cs2)cc1] I-508
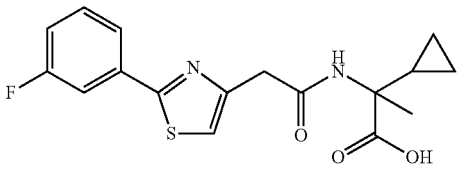 [SMILES: CC(NC(=O)Cc1csc(-c2cccc(F)c2)n1)(C(=O)O)C1CC1] I-509
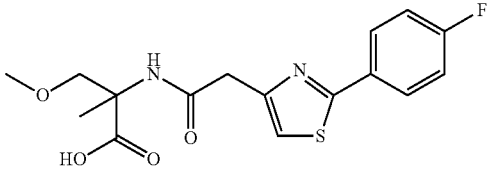 [SMILES: COCC(C)(NC(=O)Cc1csc(-c2ccc(F)cc2)n1)C(=O)O] I-510
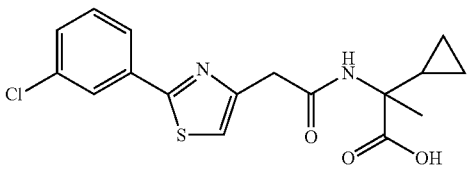 [SMILES: CC(NC(=O)Cc1csc(-c2cccc(Cl)c2)n1)(C(=O)O)C1CC1] I-511
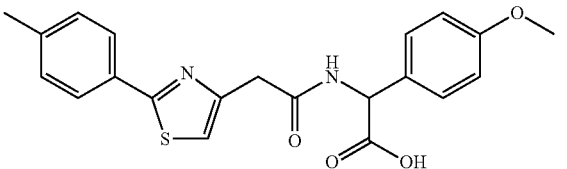 I-512

TABLE 2-continued

Exemplary Compounds

I-513

I-514

I-515

I-516

I-517

I-518

I-519

TABLE 2-continued
Exemplary Compounds
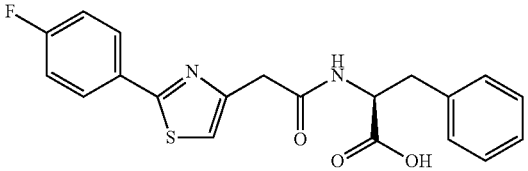 [SMILES: O=C(Cc1csc(-c2ccc(F)cc2)n1)N[C@@H](Cc1ccccc1)C(=O)O] I-520
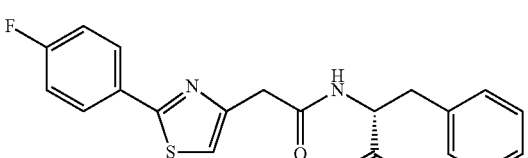 I-521
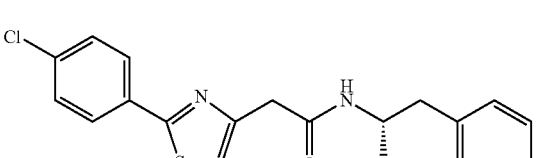 I-522
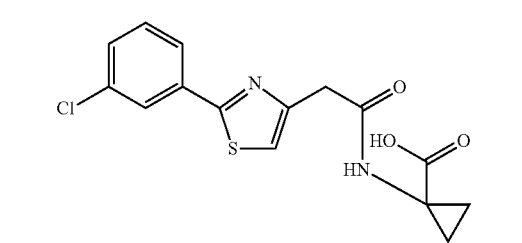 [SMILES: O=C(Cc1csc(-c2cccc(Cl)c2)n1)NC1(C(=O)O)CC1] I-523
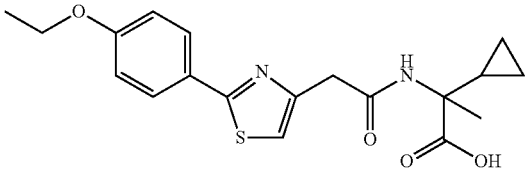 [SMILES: CCOc1ccc(-c2nc(CC(=O)NC(C)(C(=O)O)C3CC3)cs2)cc1] I-524
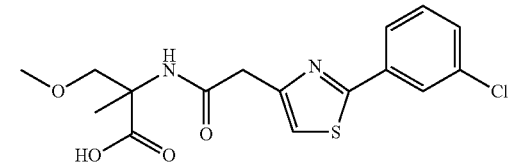 I-525
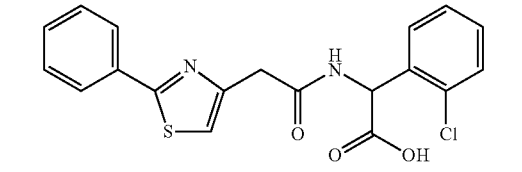 [SMILES: O=C(Cc1csc(-c2ccccc2)n1)NC(C(=O)O)c1ccccc1Cl] I-526
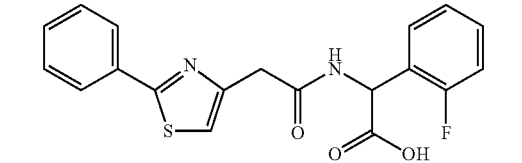 [SMILES: O=C(Cc1csc(-c2ccccc2)n1)NC(C(=O)O)c1ccccc1F] I-527

TABLE 2-continued
Exemplary Compounds
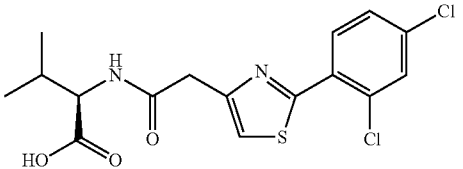 [SMILES: CC(C)[C@@H](NC(=O)Cc1csc(-c2ccc(Cl)cc2Cl)n1)C(=O)O] I-528
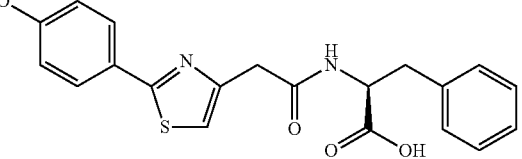 I-529
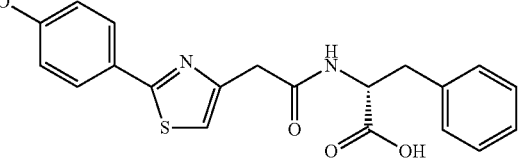 I-530
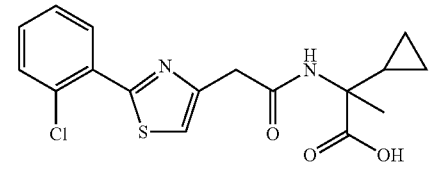 [SMILES: CC(NC(=O)Cc1csc(-c2ccccc2Cl)n1)(C(=O)O)C1CC1] I-531
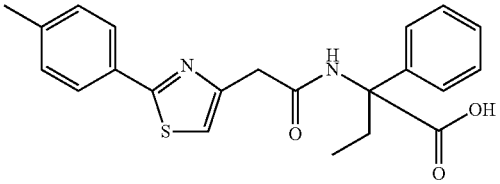 [SMILES: CCC(NC(=O)Cc1csc(-c2ccc(C)cc2)n1)(C(=O)O)c1ccccc1] I-532
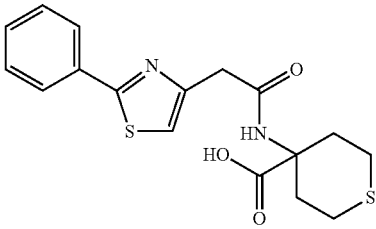 [SMILES: O=C(Cc1csc(-c2ccccc2)n1)NC1(C(=O)O)CCSCC1] I-533
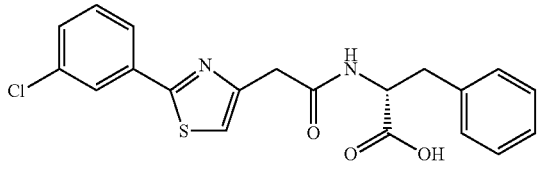 [SMILES: O=C(Cc1csc(-c2cccc(Cl)c2)n1)N[C@H](Cc1ccccc1)C(=O)O] I-534
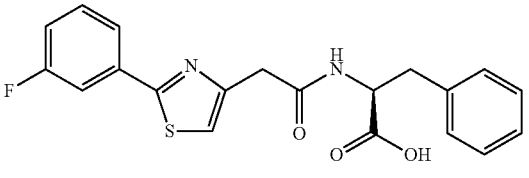 [SMILES: O=C(Cc1csc(-c2cccc(F)c2)n1)N[C@@H](Cc1ccccc1)C(=O)O] I-535

TABLE 2-continued
Exemplary Compounds
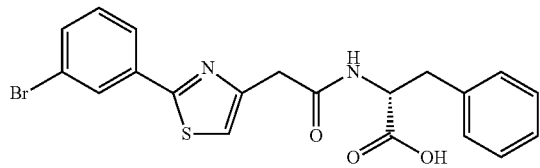
I-536
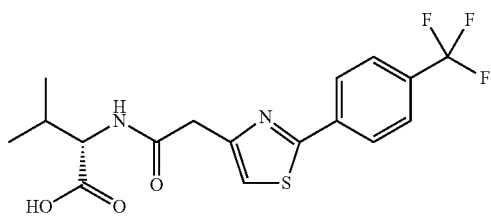 [SMILES: CC(C)[C@H](NC(=O)Cc1csc(-c2ccc(C(F)(F)F)cc2)n1)C(=O)O]
I-537
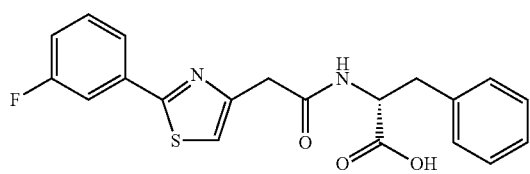 [SMILES: O=C(Cc1csc(-c2cccc(F)c2)n1)N[C@H](Cc1ccccc1)C(=O)O]
I-538
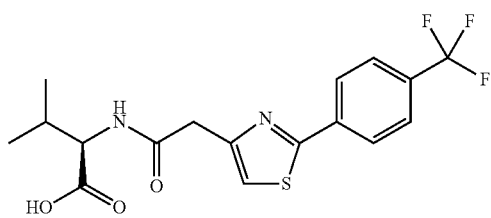 [SMILES: CC(C)[C@@H](NC(=O)Cc1csc(-c2ccc(C(F)(F)F)cc2)n1)C(=O)O]
I-539
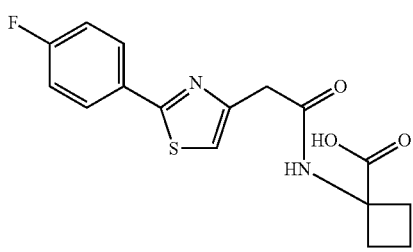 [SMILES: O=C(Cc1csc(-c2ccc(F)cc2)n1)NC1(C(=O)O)CCC1]
I-540
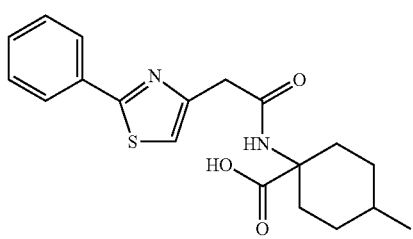 [SMILES: CC1CCC(NC(=O)Cc2csc(-c3ccccc3)n2)(C(=O)O)CC1]
I-541
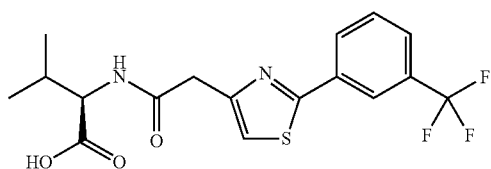 [SMILES: CC(C)[C@@H](NC(=O)Cc1csc(-c2cccc(C(F)(F)F)c2)n1)C(=O)O]
I-542

TABLE 2-continued
Exemplary Compounds
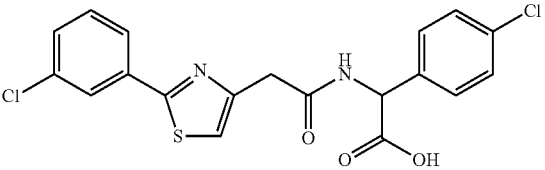 [SMILES: O=C(Cc1csc(-c2cccc(Cl)c2)n1)NC(C(=O)O)c1ccc(Cl)cc1] I-543
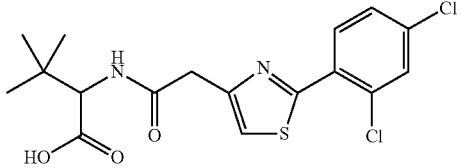 [SMILES: CC(C)(C)C(NC(=O)Cc1csc(-c2ccc(Cl)cc2Cl)n1)C(=O)O] I-544
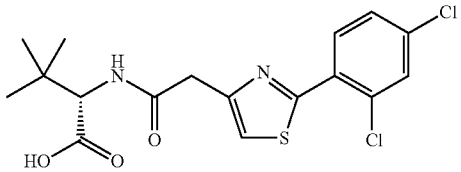 [SMILES: CC(C)(C)[C@H](NC(=O)Cc1csc(-c2ccc(Cl)cc2Cl)n1)C(=O)O] I-545
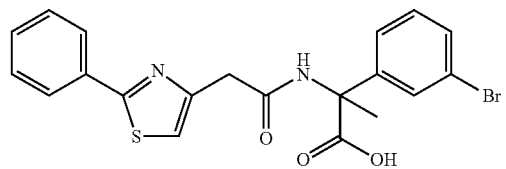 [SMILES: CC(NC(=O)Cc1csc(-c2ccccc2)n1)(C(=O)O)c1cccc(Br)c1] I-546
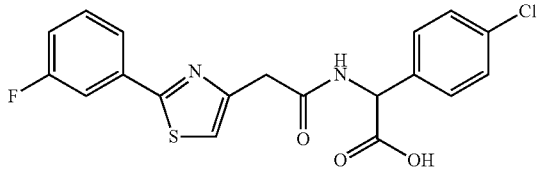 [SMILES: O=C(Cc1csc(-c2cccc(F)c2)n1)NC(C(=O)O)c1ccc(Cl)cc1] I-547
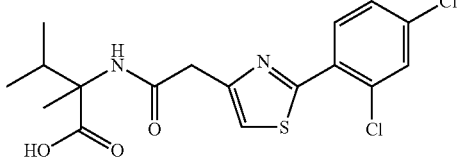 I-548
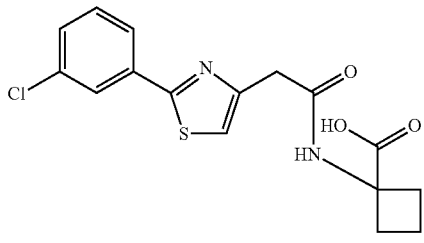 [SMILES: O=C(Cc1csc(-c2cccc(Cl)c2)n1)NC1(C(=O)O)CCC1] I-549
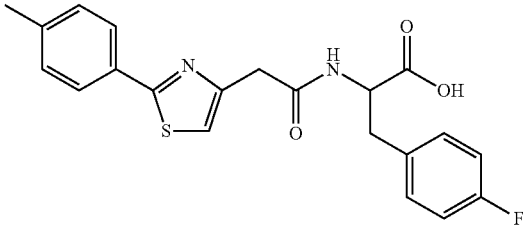 [SMILES: Cc1ccc(-c2nc(CC(=O)NC(Cc3ccc(F)cc3)C(=O)O)cs2)cc1] I-550

US 11,091,451 B2
TABLE 2-continued
Exemplary Compounds
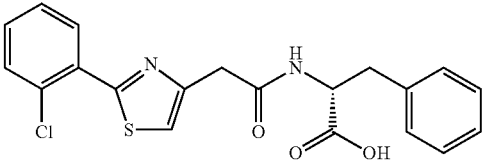 [SMILES: O=C(Cc1csc(-c2ccccc2Cl)n1)N[C@H](Cc1ccccc1)C(=O)O] I-551
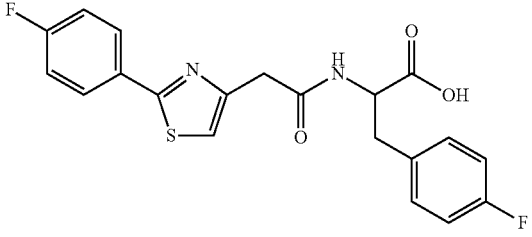 [SMILES: O=C(Cc1csc(-c2ccc(F)cc2)n1)NC(Cc1ccc(F)cc1)C(=O)O] I-552
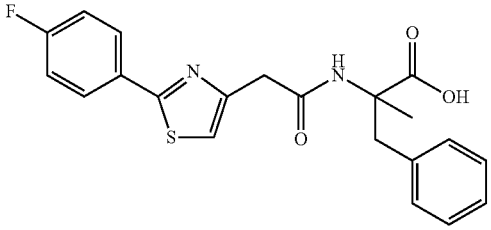 [SMILES: CC(Cc1ccccc1)(NC(=O)Cc1csc(-c2ccc(F)cc2)n1)C(=O)O] I-553
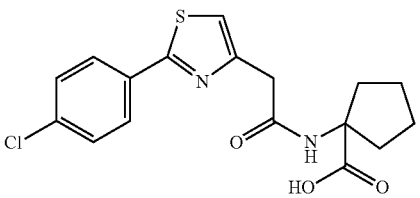 [SMILES: O=C(Cc1csc(-c2ccc(Cl)cc2)n1)NC1(C(=O)O)CCCC1] I-554
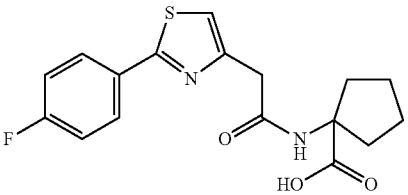 [SMILES: O=C(Cc1csc(-c2ccc(F)cc2)n1)NC1(C(=O)O)CCCC1] I-555
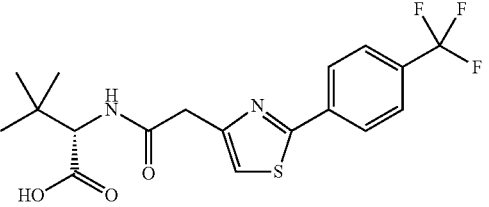 [SMILES: CC(C)(C)[C@H](NC(=O)Cc1csc(-c2ccc(C(F)(F)F)cc2)n1)C(=O)O] I-556
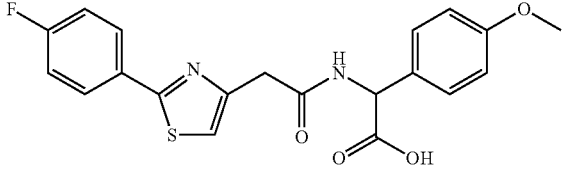 [SMILES: COc1ccc(C(NC(=O)Cc2csc(-c3ccc(F)cc3)n2)C(=O)O)cc1] I-557

TABLE 2-continued
Exemplary Compounds
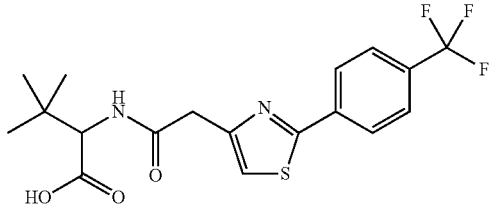 [SMILES: CC(C)(C)C(NC(=O)Cc1csc(-c2ccc(C(F)(F)F)cc2)n1)C(=O)O]
I-558
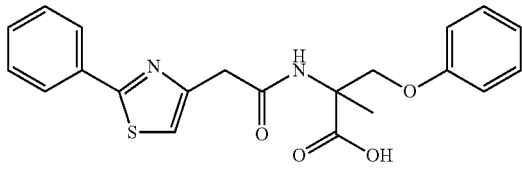 [SMILES: CC(COc1ccccc1)(NC(=O)Cc1csc(-c2ccccc2)n1)C(=O)O]
I-559
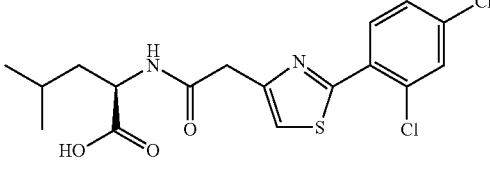
I-560
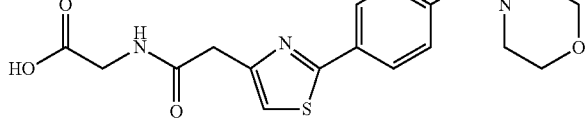
I-561
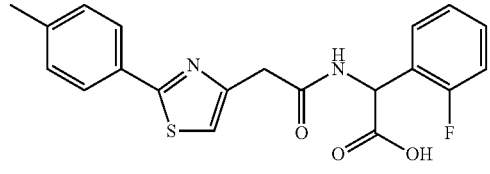 [SMILES: Cc1ccc(-c2nc(CC(=O)NC(C(=O)O)c3ccccc3F)cs2)cc1]
I-562
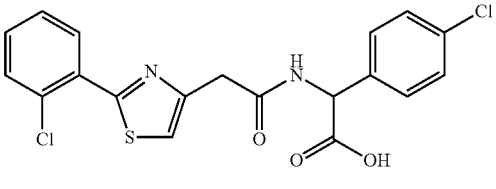 [SMILES: O=C(Cc1csc(-c2ccccc2Cl)n1)NC(C(=O)O)c1ccc(Cl)cc1]
I-563
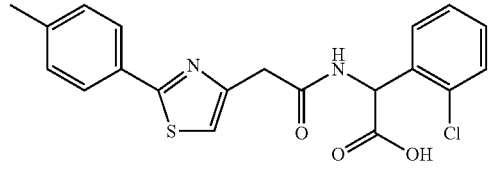 [SMILES: Cc1ccc(-c2nc(CC(=O)NC(C(=O)O)c3ccccc3Cl)cs2)cc1]
I-564
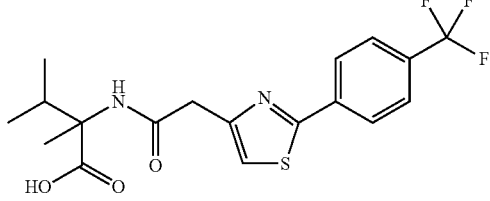
I-565

TABLE 2-continued
Exemplary Compounds
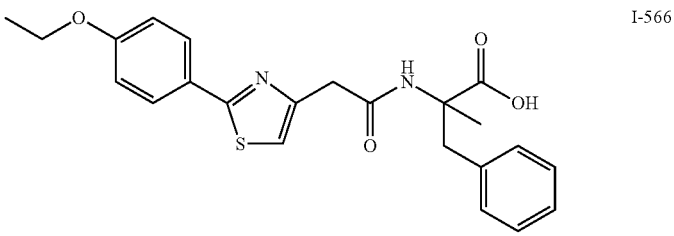 I-566
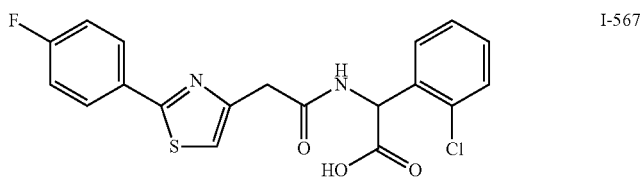 I-567
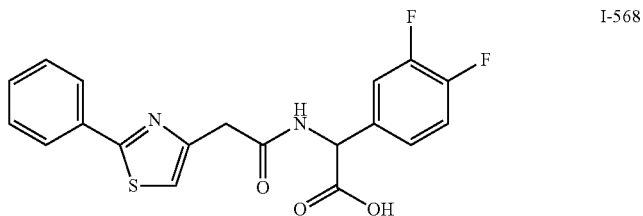 I-568
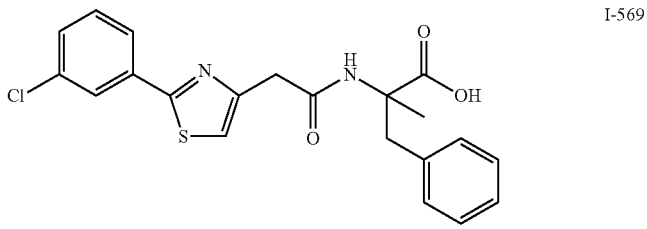 I-569
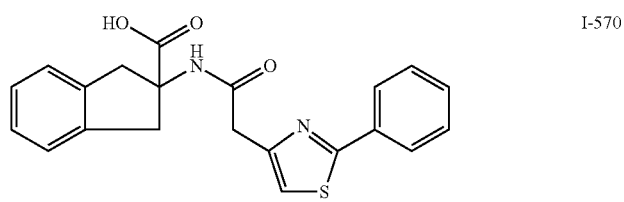 I-570
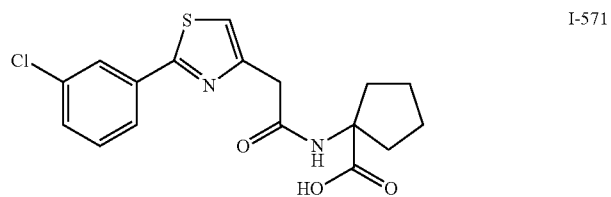 I-571
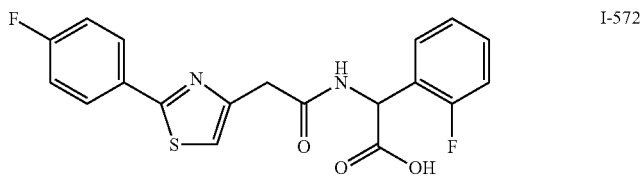 I-572

TABLE 2-continued
Exemplary Compounds
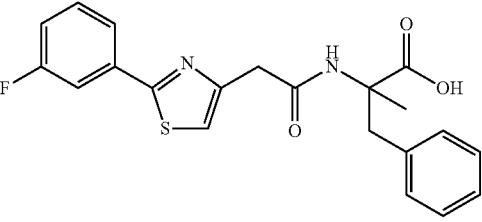 [SMILES: CC(Cc1ccccc1)(NC(=O)Cc1csc(-c2cccc(F)c2)n1)C(=O)O] I-573
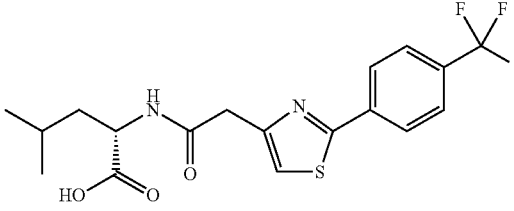 I-574
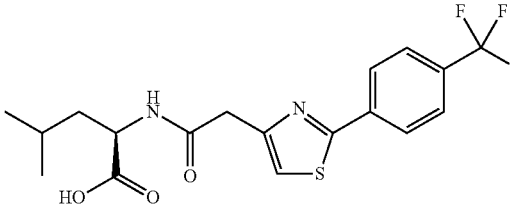 I-575
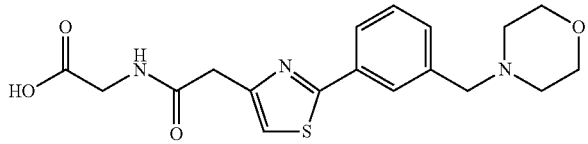 [SMILES: O=C(O)CNC(=O)Cc1csc(-c2cccc(CN3CCOCC3)c2)n1] I-576
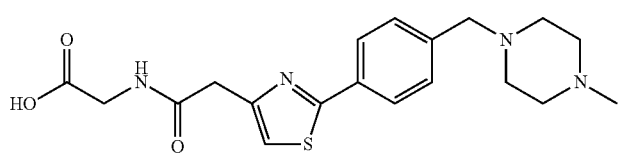 [SMILES: CN1CCN(Cc2ccc(-c3nc(CC(=O)NCC(=O)O)cs3)cc2)CC1] I-577
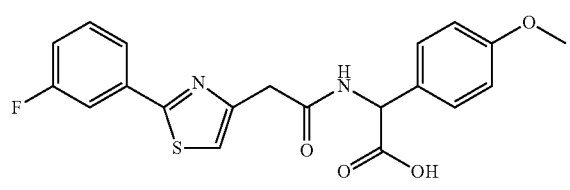 [SMILES: COc1ccc(C(NC(=O)Cc2csc(-c3cccc(F)c3)n2)C(=O)O)cc1] I-578
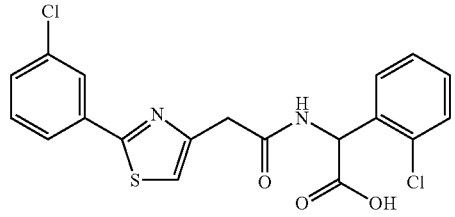 I-579
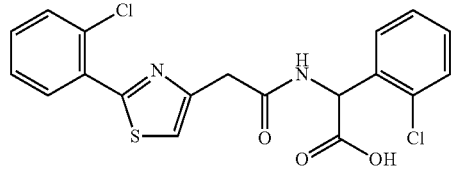 [SMILES: O=C(Cc1csc(-c2ccccc2Cl)n1)NC(C(=O)O)c1ccccc1Cl] I-580

TABLE 2-continued
Exemplary Compounds
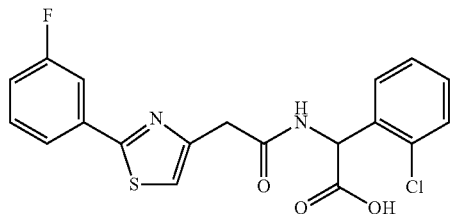 I-581
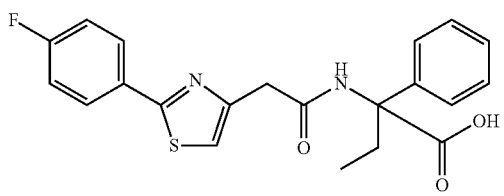 [SMILES: CCC(NC(=O)Cc1csc(-c2ccc(F)cc2)n1)(C(=O)O)c1ccccc1] I-582
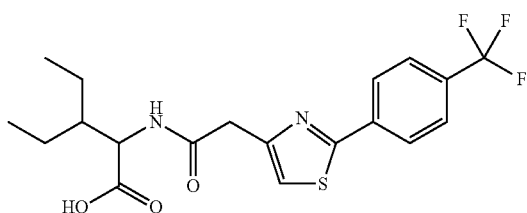 [SMILES: CCC(CC)C(NC(=O)Cc1csc(-c2ccc(C(F)(F)F)cc2)n1)C(=O)O] I-583
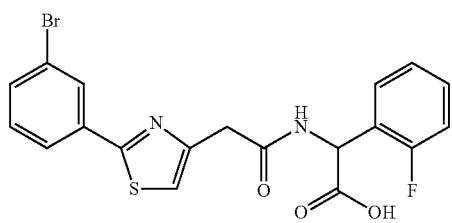 I-584
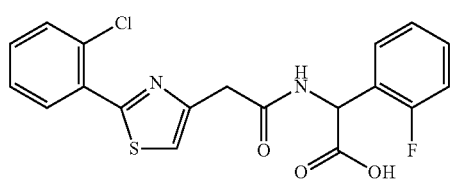 [SMILES: O=C(Cc1csc(-c2ccccc2Cl)n1)NC(C(=O)O)c1ccccc1F] I-585
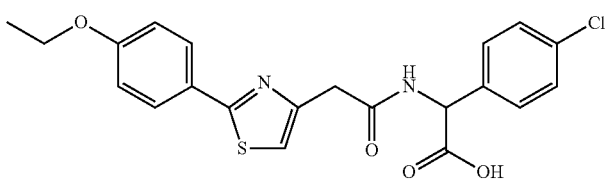 [SMILES: CCOc1ccc(-c2nc(CC(=O)NC(C(=O)O)c3ccc(Cl)cc3)cs2)cc1] I-586
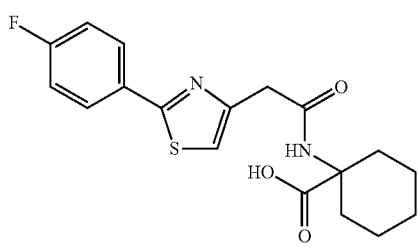 I-587

TABLE 2-continued
Exemplary Compounds
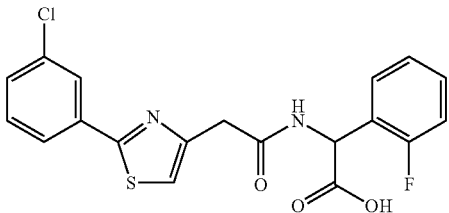 [SMILES: O=C(Cc1csc(-c2cccc(Cl)c2)n1)NC(C(=O)O)c1ccccc1F]
I-588
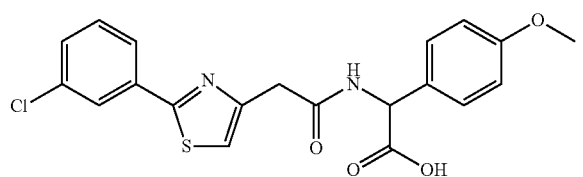 [SMILES: COc1ccc(C(NC(=O)Cc2csc(-c3cccc(Cl)c3)n2)C(=O)O)cc1]
I-589
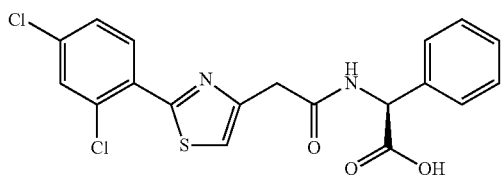
I-590
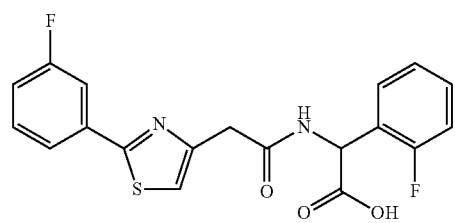 [SMILES: O=C(Cc1csc(-c2cccc(F)c2)n1)NC(C(=O)O)c1ccccc1F]
I-591
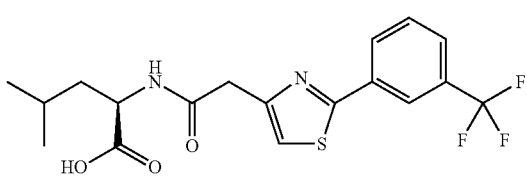 [SMILES: CC(C)C[C@@H](NC(=O)Cc1csc(-c2cccc(C(F)(F)F)c2)n1)C(=O)O]
I-592
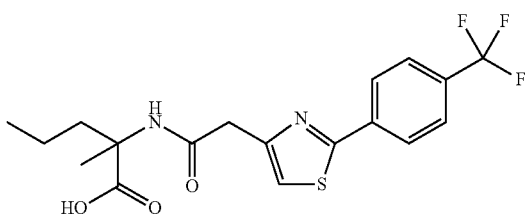 [SMILES: CCCC(C)(NC(=O)Cc1csc(-c2ccc(C(F)(F)F)cc2)n1)C(=O)O]
I-593
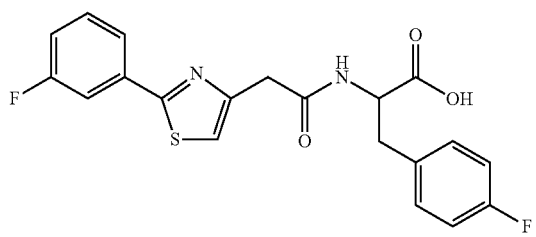 [SMILES: O=C(Cc1csc(-c2cccc(F)c2)n1)NC(Cc1ccc(F)cc1)C(=O)O]
I-594

TABLE 2-continued

Exemplary Compounds

I-595

I-596

I-597

I-598

I-599

I-600

I-601

I-602

TABLE 2-continued
Exemplary Compounds
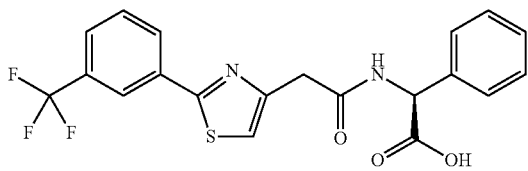 [SMILES: O=C(Cc1csc(-c2cccc(C(F)(F)F)c2)n1)N[C@H](C(=O)O)c1ccccc1] I-603
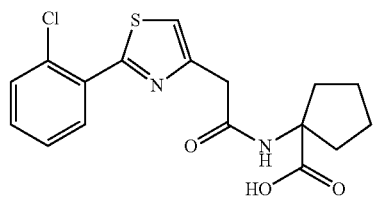 [SMILES: O=C(Cc1csc(-c2ccccc2Cl)n1)NC1(C(=O)O)CCCC1] I-604
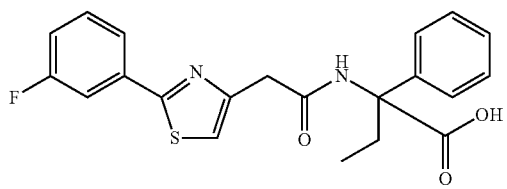 [SMILES: CCC(NC(=O)Cc1csc(-c2cccc(F)c2)n1)(C(=O)O)c1ccccc1] I-605
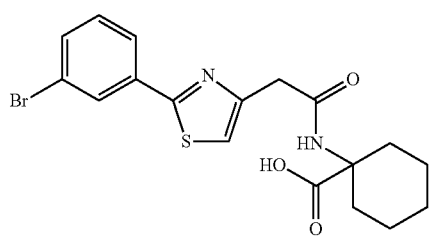 I-606
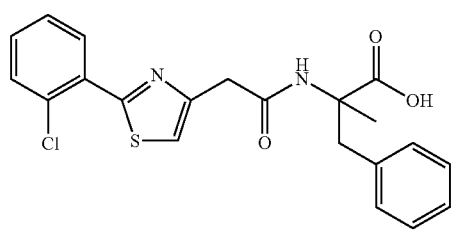 [SMILES: CC(Cc1ccccc1)(NC(=O)Cc1csc(-c2ccccc2Cl)n1)C(=O)O] I-607
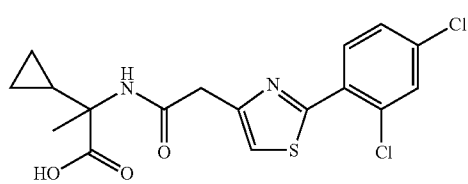 [SMILES: CC(NC(=O)Cc1csc(-c2ccc(Cl)cc2Cl)n1)(C(=O)O)C1CC1] I-608
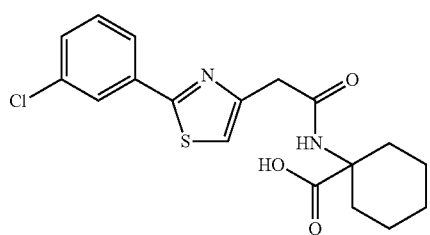 [SMILES: O=C(Cc1csc(-c2cccc(Cl)c2)n1)NC1(C(=O)O)CCCCC1] I-609

TABLE 2-continued
Exemplary Compounds
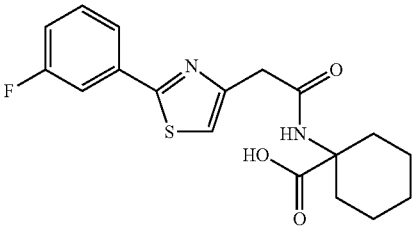 I-610
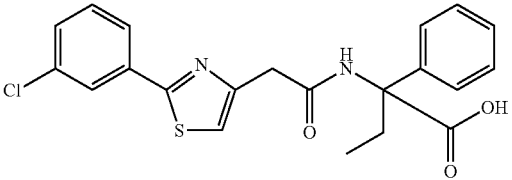 [SMILES: CCC(NC(=O)Cc1csc(-c2cccc(Cl)c2)n1)(C(=O)O)c1ccccc1] I-611
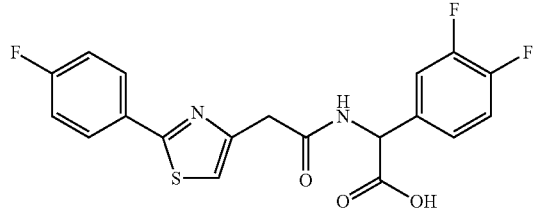 [SMILES: O=C(Cc1csc(-c2ccc(F)cc2)n1)NC(C(=O)O)c1ccc(F)c(F)c1] I-612
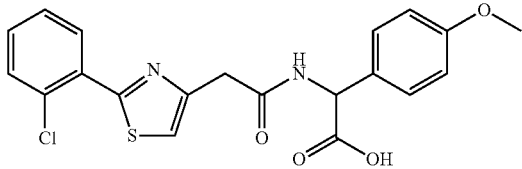 [SMILES: COc1ccc(C(NC(=O)Cc2csc(-c3ccccc3Cl)n2)C(=O)O)cc1] I-613
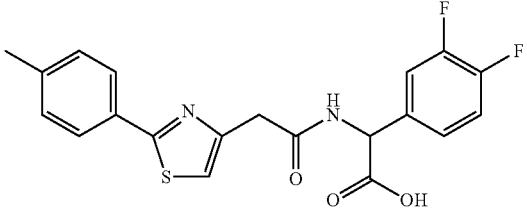 [SMILES: Cc1ccc(-c2nc(CC(=O)NC(C(=O)O)c3ccc(F)c(F)c3)cs2)cc1] I-614
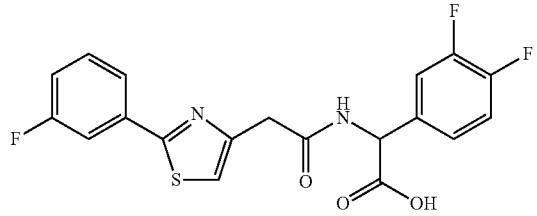 [SMILES: O=C(Cc1csc(-c2cccc(F)c2)n1)NC(C(=O)O)c1ccc(F)c(F)c1] I-615
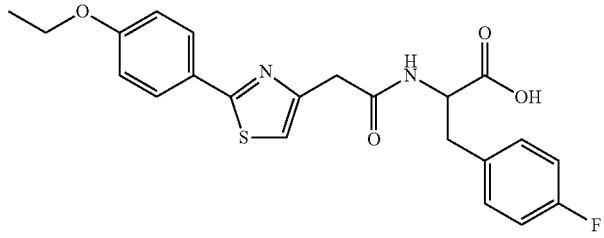 [SMILES: CCOc1ccc(-c2nc(CC(=O)NC(Cc3ccc(F)cc3)C(=O)O)cs2)cc1] I-616

TABLE 2-continued

Exemplary Compounds

| | |
|---|---|
| [structure] | I-617 |
| [structure] | I-618 |
| [structure] | I-619 |
| [structure] | I-620 |
| [structure] | I-621 |
| [structure] | I-622 |
| [structure] | I-623 |

TABLE 2-continued
Exemplary Compounds
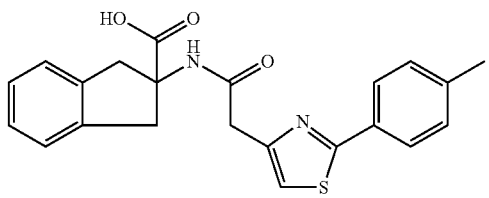 [SMILES: Cc1ccc(-c2nc(CC(=O)NC3(C(=O)O)Cc4ccccc4C3)cs2)cc1] I-624
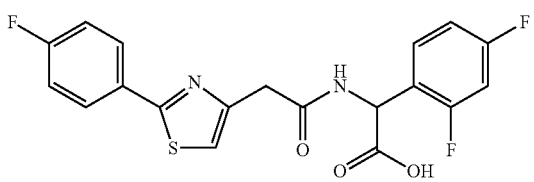 [SMILES: O=C(Cc1csc(-c2ccc(F)cc2)n1)NC(C(=O)O)c1ccc(F)cc1F] I-625
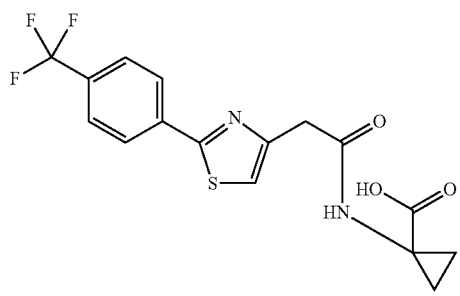 [SMILES: O=C(Cc1csc(-c2ccc(C(F)(F)F)cc2)n1)NC1(C(=O)O)CC1] I-626
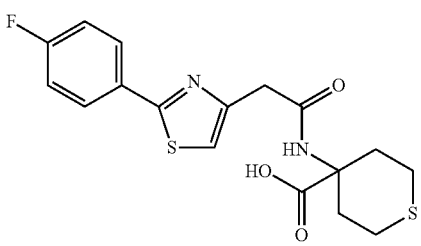 [SMILES: O=C(Cc1csc(-c2ccc(F)cc2)n1)NC1(C(=O)O)CCSCC1] I-627
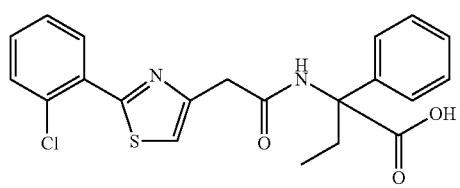 [SMILES: CCC(NC(=O)Cc1csc(-c2ccccc2Cl)n1)(C(=O)O)c1ccccc1] I-628
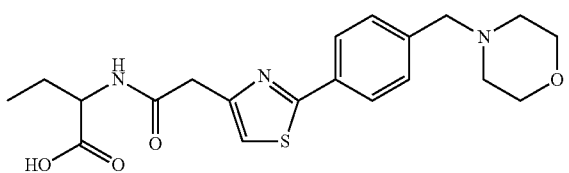 [SMILES: CCC(NC(=O)Cc1csc(-c2ccc(CN3CCOCC3)cc2)n1)C(=O)O] I-629
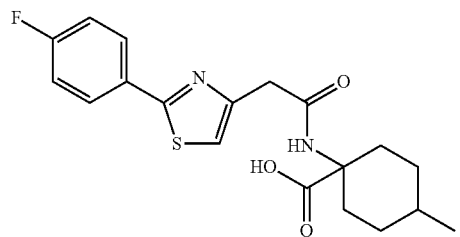 [SMILES: CC1CCC(NC(=O)Cc2csc(-c3ccc(F)cc3)n2)(C(=O)O)CC1] I-630

TABLE 2-continued
Exemplary Compounds
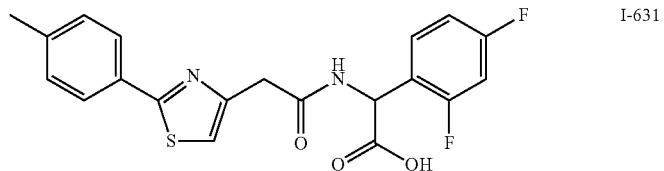 I-631
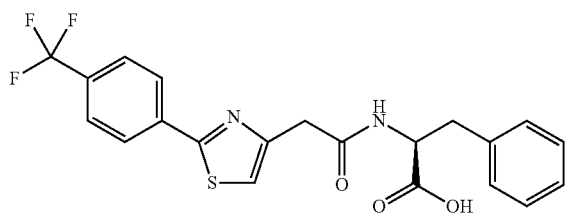 [SMILES: O=C(Cc1csc(-c2ccc(C(F)(F)F)cc2)n1)N[C@@H](Cc1ccccc1)C(=O)O] I-632
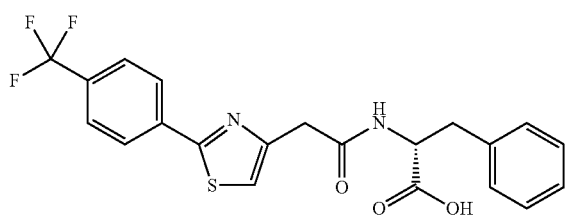 [SMILES: O=C(Cc1csc(-c2ccc(C(F)(F)F)cc2)n1)N[C@H](Cc1ccccc1)C(=O)O] I-633
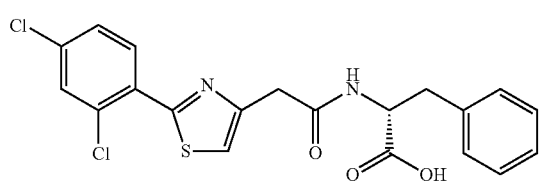 [SMILES: O=C(Cc1csc(-c2ccc(Cl)cc2Cl)n1)N[C@H](Cc1ccccc1)C(=O)O] I-634
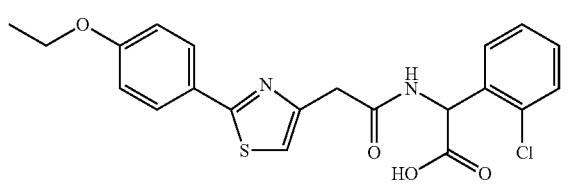 [SMILES: CCOc1ccc(-c2nc(CC(=O)NC(C(=O)O)c3ccccc3Cl)cs2)cc1] I-635
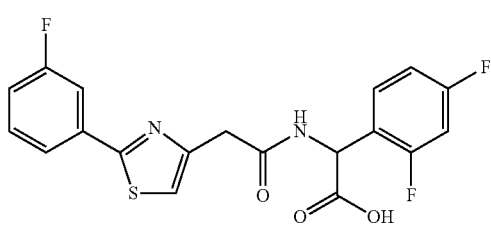 [SMILES: O=C(Cc1csc(-c2cccc(F)c2)n1)NC(C(=O)O)c1ccc(F)cc1F] I-636
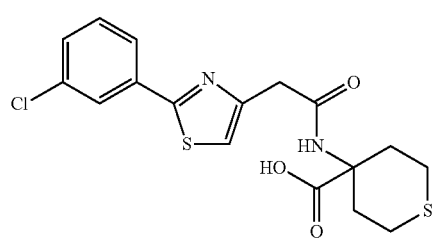 [SMILES: O=C(Cc1csc(-c2cccc(Cl)c2)n1)NC1(C(=O)O)CCSCC1] I-637

TABLE 2-continued

Exemplary Compounds

I-638

I-639

I-640

I-641

I-642

I-643

I-644

I-645

TABLE 2-continued

Exemplary Compounds

I-646

I-647

I-648

I-649

I-650

I-651

I-652

181

TABLE 2-continued

Exemplary Compounds

I-653

I-654

I-655

I-656

I-657

I-658

I-659

TABLE 2-continued
Exemplary Compounds
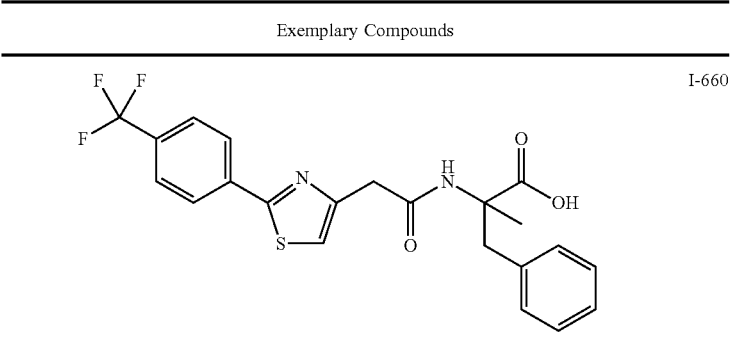
I-660
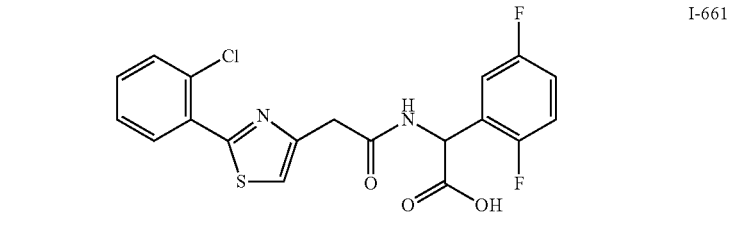
I-661
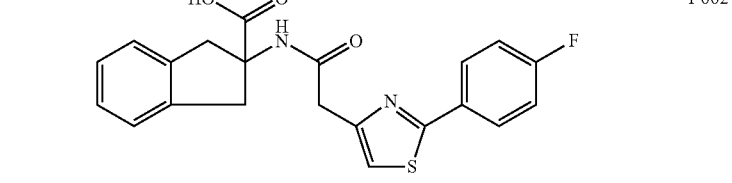
I-662
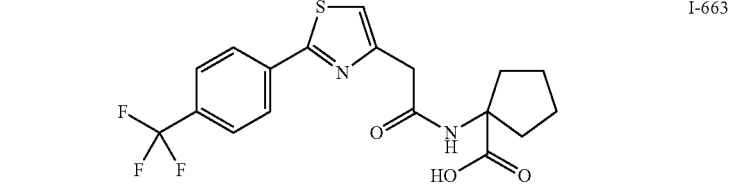
I-663
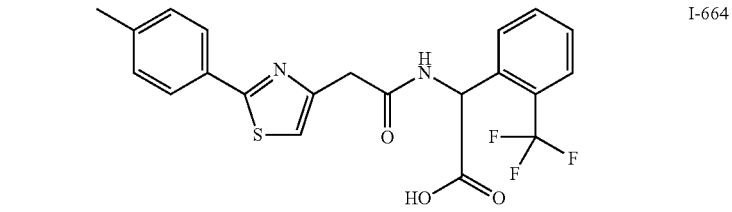
I-664
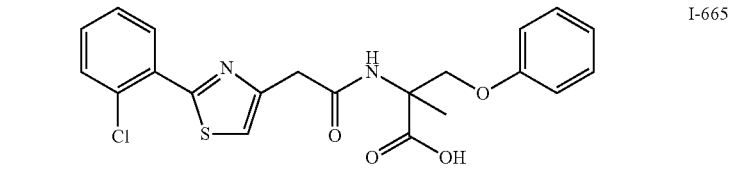
I-665
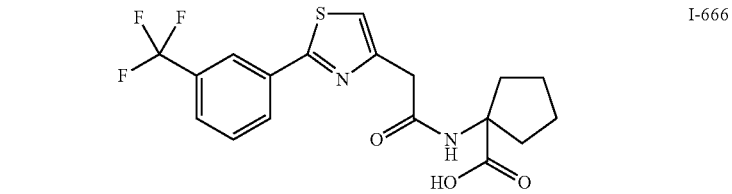
I-666

TABLE 2-continued
Exemplary Compounds
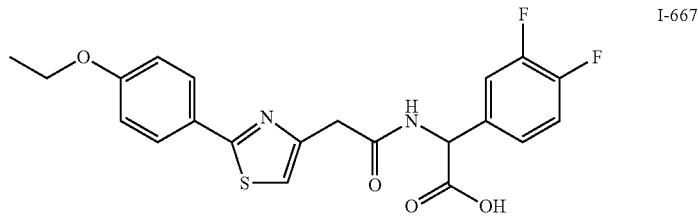 I-667
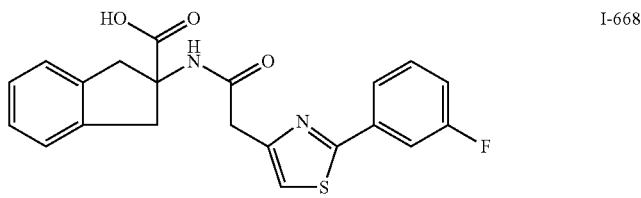 I-668
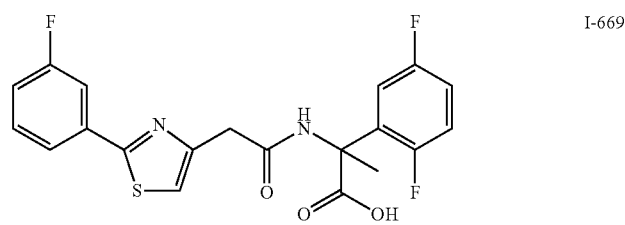 I-669
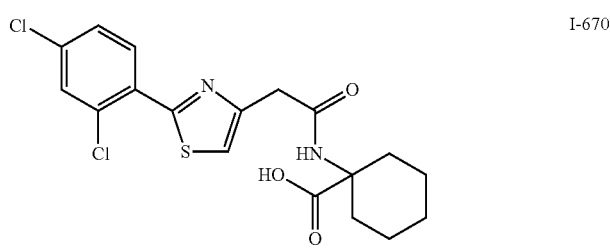 I-670
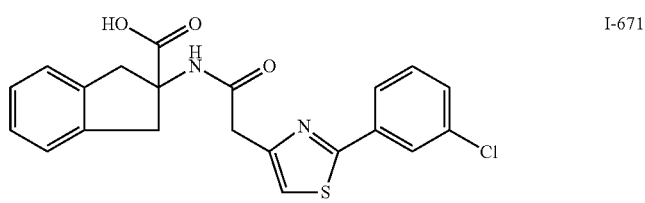 I-671
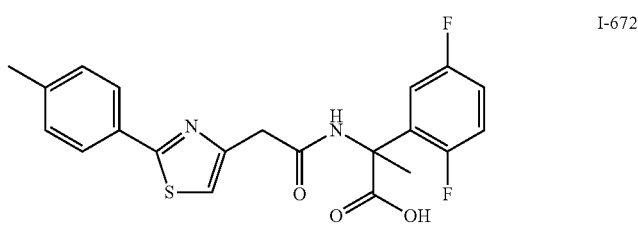 I-672
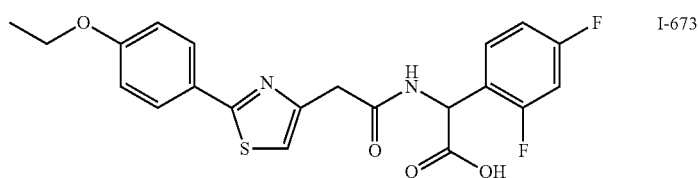 I-673

TABLE 2-continued

Exemplary Compounds

I-674

I-675

I-676

I-677

I-678

I-679

I-680

TABLE 2-continued
Exemplary Compounds
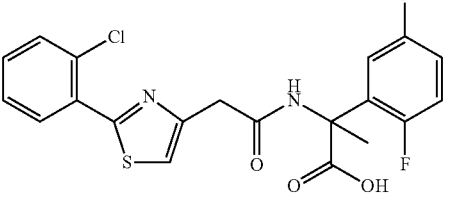
I-681
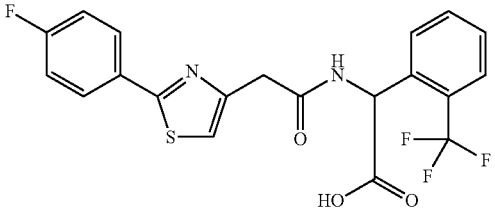 [SMILES: O=C(Cc1csc(-c2ccc(F)cc2)n1)NC(C(=O)O)c1ccccc1C(F)(F)F]
I-682
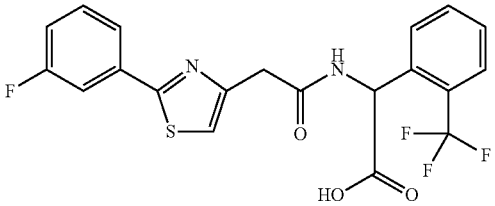 [SMILES: O=C(Cc1csc(-c2cccc(F)c2)n1)NC(C(=O)O)c1ccccc1C(F)(F)F]
I-683
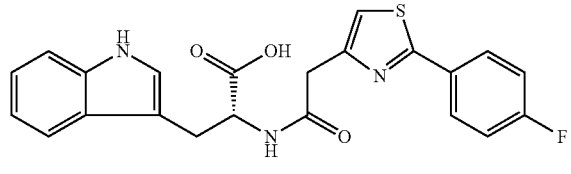 [SMILES: O=C(Cc1csc(-c2ccc(F)cc2)n1)N[C@H](Cc1c[nH]c2ccccc12)C(=O)O]
I-684
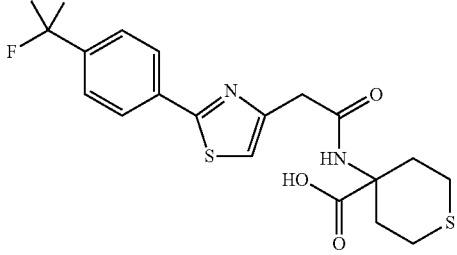
I-685
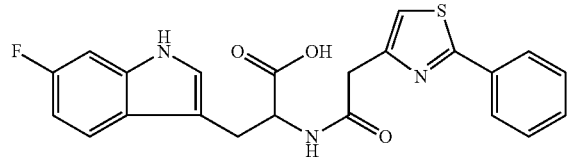 [SMILES: O=C(Cc1csc(-c2ccccc2)n1)NC(Cc1c[nH]c2cc(F)ccc12)C(=O)O]
I-686
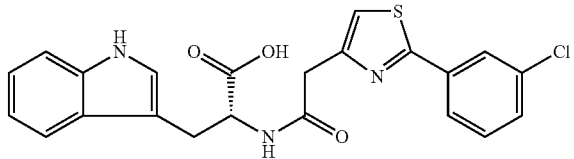 [SMILES: O=C(Cc1csc(-c2cccc(Cl)c2)n1)N[C@H](Cc1c[nH]c2ccccc12)C(=O)O]
I-687

TABLE 2-continued
Exemplary Compounds
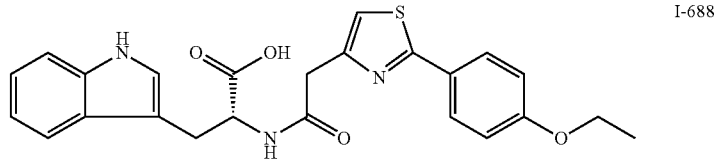 I-688
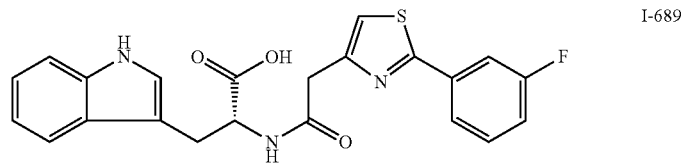 I-689
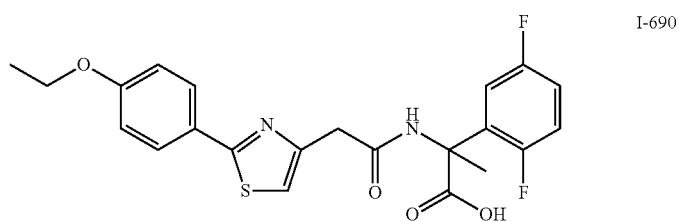 I-690
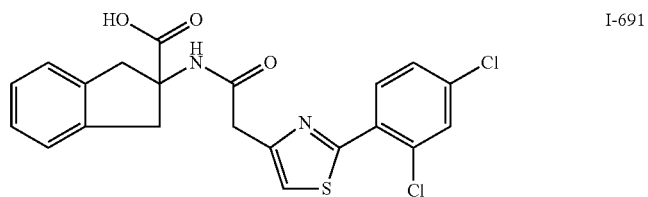 I-691
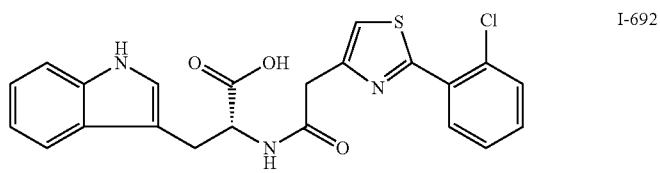 I-692
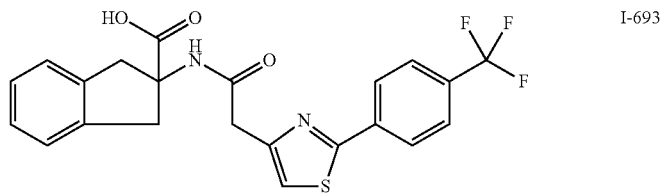 I-693
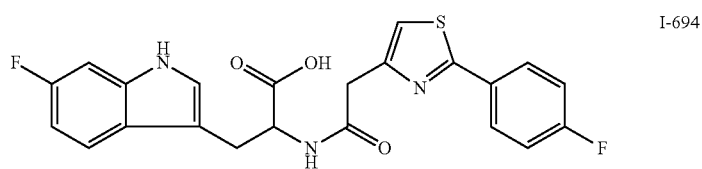 I-694

TABLE 2-continued

Exemplary Compounds

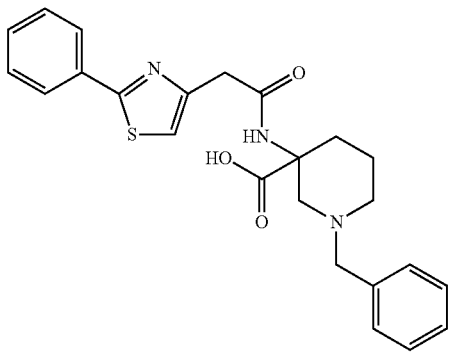 [SMILES: O=C(Cc1csc(-c2ccccc2)n1)NC1(C(=O)O)CCCN(Cc2ccccc2)C1]

I-695

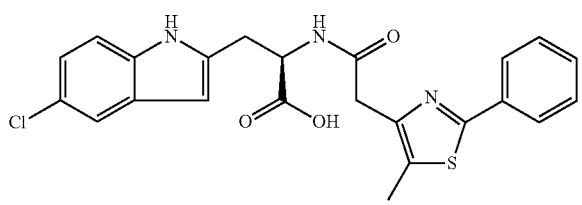 [SMILES: Cc1sc(-c2ccccc2)nc1CC(=O)N[C@H](Cc1cc2cc(Cl)ccc2[nH]1)C(=O)O]

I-696

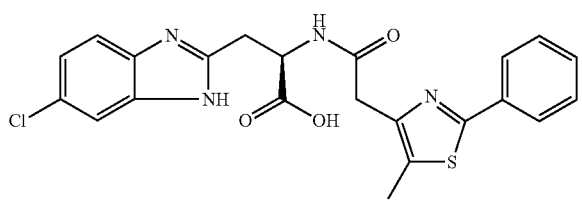 [SMILES: Cc1sc(-c2ccccc2)nc1CC(=O)N[C@H](Cc1nc2ccc(Cl)cc2[nH]1)C(=O)O]

I-697

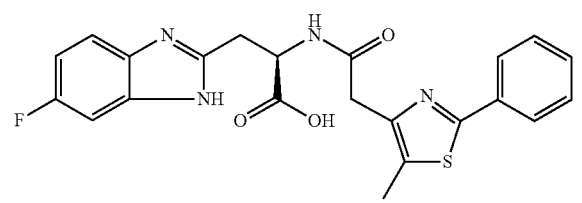 [SMILES: Cc1sc(-c2ccccc2)nc1CC(=O)N[C@H](Cc1nc2ccc(F)cc2[nH]1)C(=O)O]

I-698

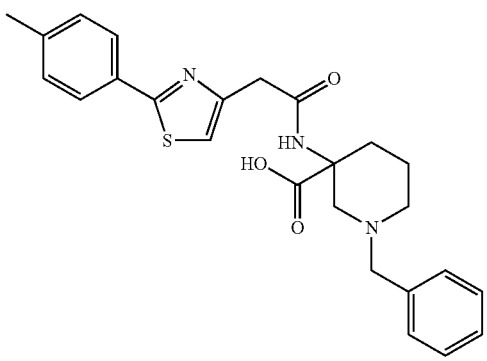 [SMILES: Cc1ccc(-c2nc(CC(=O)NC3(C(=O)O)CCCN(Cc4ccccc4)C3)cs2)cc1]

I-699

In some embodiments, the present invention provides a compound other than a compound set forth in Table 2.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry*: Reactions, Mechanisms, and Structure, M. B. Smith and J. March, 5$^{th}$ Edition, John Wiley & Sons, 2001, *Comprehensive Organic Transformations*, R. C. Larock, 2$^{nd}$ d Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, o-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

General Synthetic Methods

Compounds of the invention and intermediates useful for the preparation of compounds of the present invention were synthesized according to the general synthetic methods described in the following schemes 1-9:

Synthesis of Intermediates

In certain embodiments, intermediates useful for the preparation of compounds of the present invention of formula I are generally prepared according to Scheme 1 set forth below:

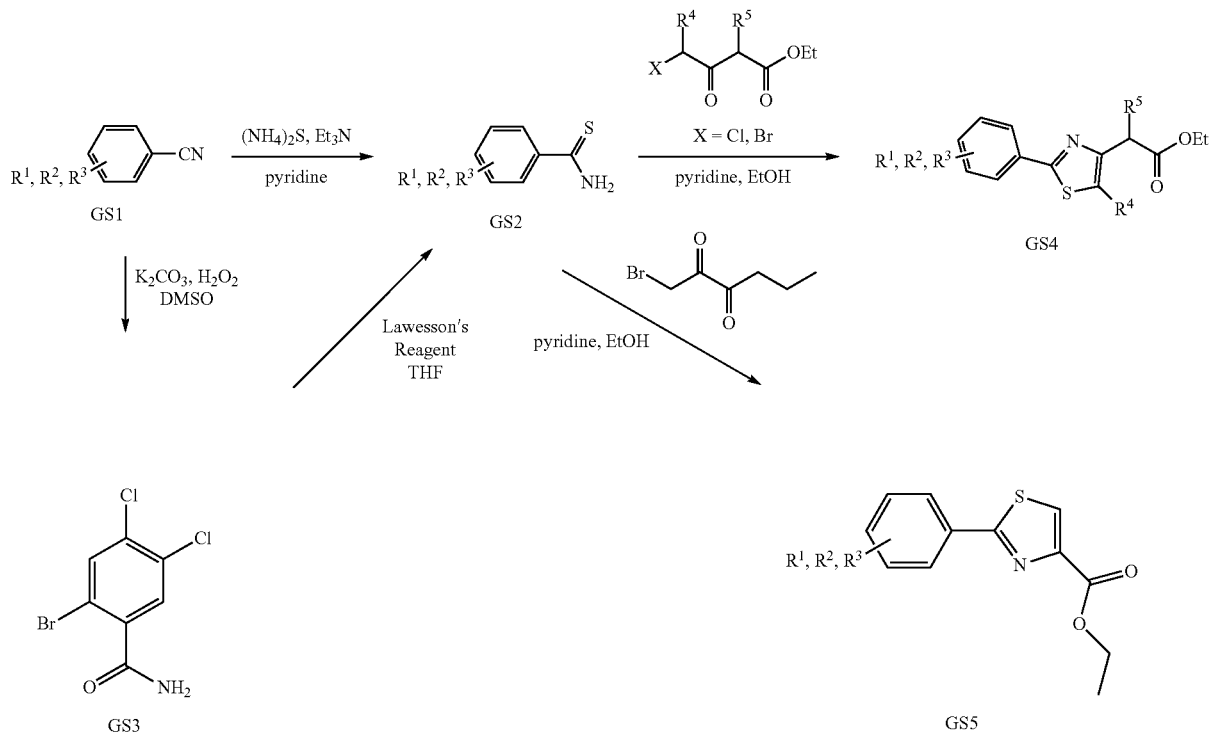

Scheme 1

-continued

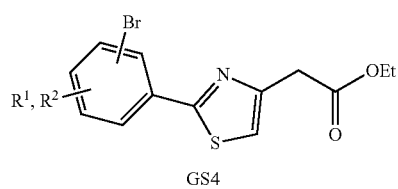
GS4

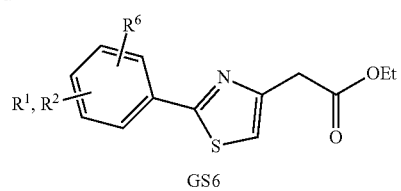
GS6

R[6]—B(OH)$_2$
Pd(dppf)Cl$_2$, Na$_2$CO$_3$
Dioxane/H$_2$O
or
R$_6$—SnBu$_3$
Pd(PPh$_3$)$_4$, toluene Compounds such as GS3-GS6 can be accessed as described in Scheme 1. An optionally substituted benzonitrile GS1 can be treated with (NH$_4$)$_2$S and triethylamine in pyridine or DMF with heat to form the benzenecarbothioamide GS2. Alternatively, the nitrile can be oxidized to amide GS3 under oxidation conditions such as with hydrogen peroxide and potassium carbonate in DMSO. Amide GS3 can then be converted to intermediate GS2 utilizing Lawesson's reagent in THF. Thiazole acetate GS4 can be formed by cyclization of the thioamide GS2 with a variety of substituted or non-substituted chloro or bromo ethyl-3-oxobutanoates in ethanol with heating and the addition of pyridine in some cases. Alternatively, benzenecarbothioamide GS2 can be treated with ethyl 3-bromo-2-oxopropanoate, ethanol and pyridine with heating to form intermediate thiazole carboxylate GS5.

Thiazole acetate GS4 can further be derivatized when one R group is bromide by cross coupling a variety of boronic esters or acids under standard conditions with Pd(dppf)Cl$_2$ and cesium or sodium carbonate in dioxane and water or with Pd(OAc)$_2$, PCy$_3$ or P(t-Bu)$_3$HBF$_4$, and K$_3$PO$_4$ in toluene and water with heating to form thiazole acetate GS6. Tin reagents, such as tributyl(ethenyl)stannane, can also be coupled under standard conditions using Pd(PPh$_3$)$_4$ as a catalyst in toluene under reflux, to form the further derivatized products GS6.

In certain embodiments, intermediates useful for the preparation of compounds of the present invention of formula I are generally prepared according to Scheme 2 set forth below:

Scheme 2

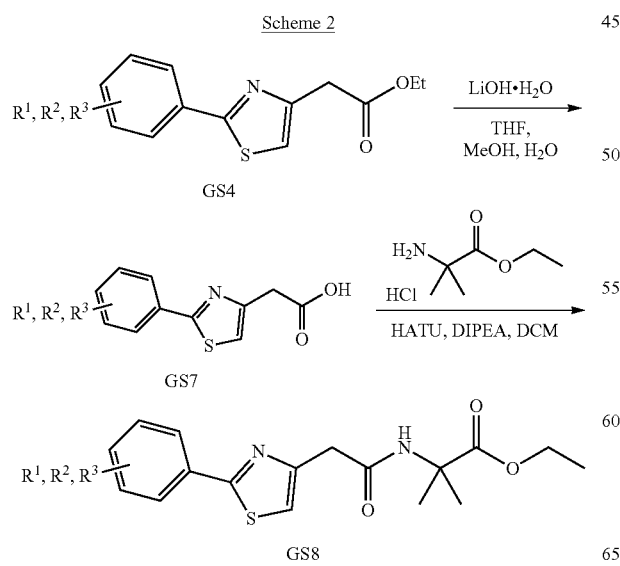

In another embodiment of the invention the required intermediate GS8 can be prepared as described in Scheme 2. Intermediate GS4 can be hydrolyzed with lithium or sodium hydroxide in a solvent mixture of THF, methanol and water to give acid GS7. This acid can then be coupled with a variety of amines, such as ethyl 2-amino-2-methyl-propanoate hydrochloride, under standard coupling conditions with HATU and disopropylethylamine in dichloromethane to give the ester GS8.

In certain embodiments, intermediates useful for the preparation of compounds of the present invention of formula I are generally prepared according to Scheme 3 set forth below:

Scheme 3

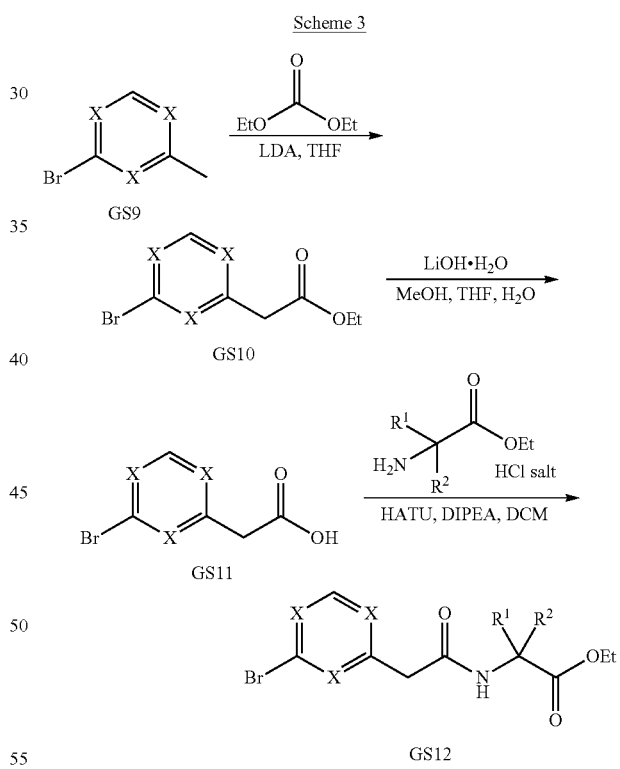

X = CH, N

Additional compounds of the invention can be synthesized using intermediate GS12 as described in Scheme 3. Starting from various methyl bromo-pyridines or pyrimidines GS9, deprotonation with LDA followed by condensation with diethyl carbonate forms ester GS10. The ester can be hydrolyzed under typical conditions described above in Scheme 2 to form acid GS11. This acid can be further coupled with amines as describe in Scheme 2 to form the intermediate GS12.

In certain embodiments, intermediates useful for the preparation of compounds of the present invention of formula I are generally prepared according to Scheme 4 set forth below:

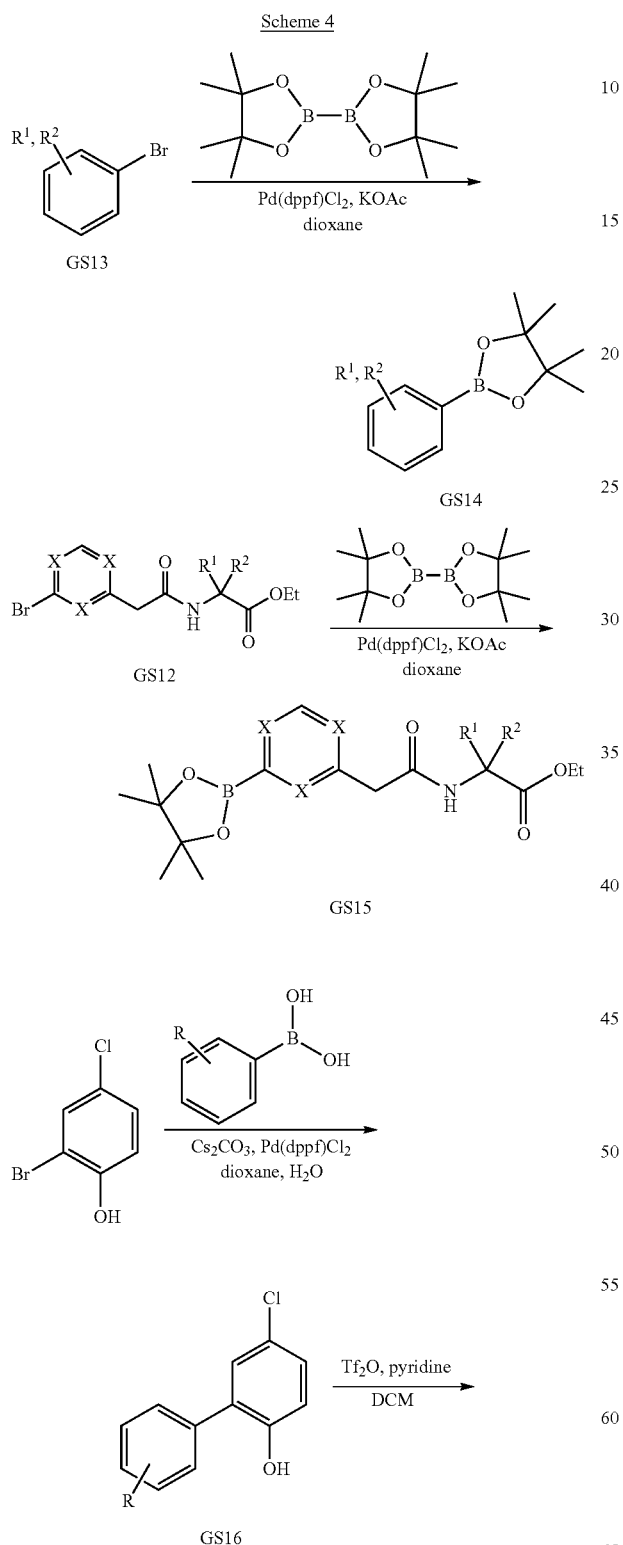

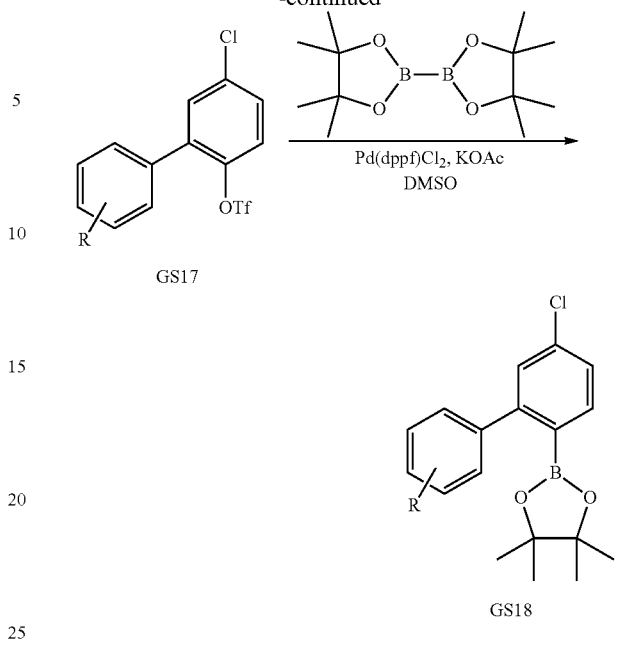

A variety of coupling partner boronic esters (GS14, GS15 and GS18) and triflates GS17 were prepared as described in Scheme 4. The boronic esters GS14 can be accessed from the corresponding substituted bromides GS13 under standard cross coupling conditions with bis(pinacolato)diboron, potassium acetate or other suitable base, Pd(dppf)Cl$_2$ in solvents such as dioxane or DMSO with heating. Key intermediate bromide GS12 can also be further converted to the boronic ester GS15 under the same conditions. Further biphenyl coupling partners can be obtained by first cross coupling 2-bromo-4-chlorophenol under standard cross coupling conditions with boronic acids or esters to obtain intermediate GS16. The phenol can then be converted to the triflate GS17 with trifluoromethanesulfonic anhydride and pyridine in DCM. These triflates could then be directly utilized to form compounds described in this claim or further converted to the boronic ester GS18 coupling partner as described previously for GS14 under typical conditions.

In certain embodiments, intermediates useful for the preparation of compounds of the present invention of formula I are generally prepared according to Scheme 5 set forth below:

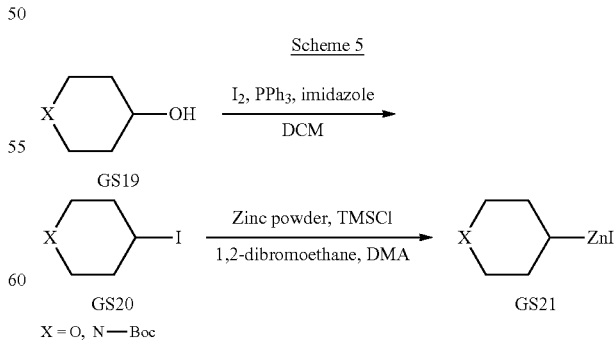

The zinc iodide coupling partners GS21 could be accessed by the two step procedure described in Scheme 5. Either tetrahydropyran-4-ol or tert-butyl 4-hydroxypiperidine-1- carboxylate GS19 were converted to the corresponding iodide GS20 with iodine, imidazole and PPh₃ in DCM. These iodides can then be converted to the zinc iodide GS21 with zinc powder and TMSCl in solvents such as 1,2 dibromoethane and DMA.

Synthesis of Examples

In certain embodiments, compounds of the present invention of formula I are generally prepared according to Scheme 6 set forth below:

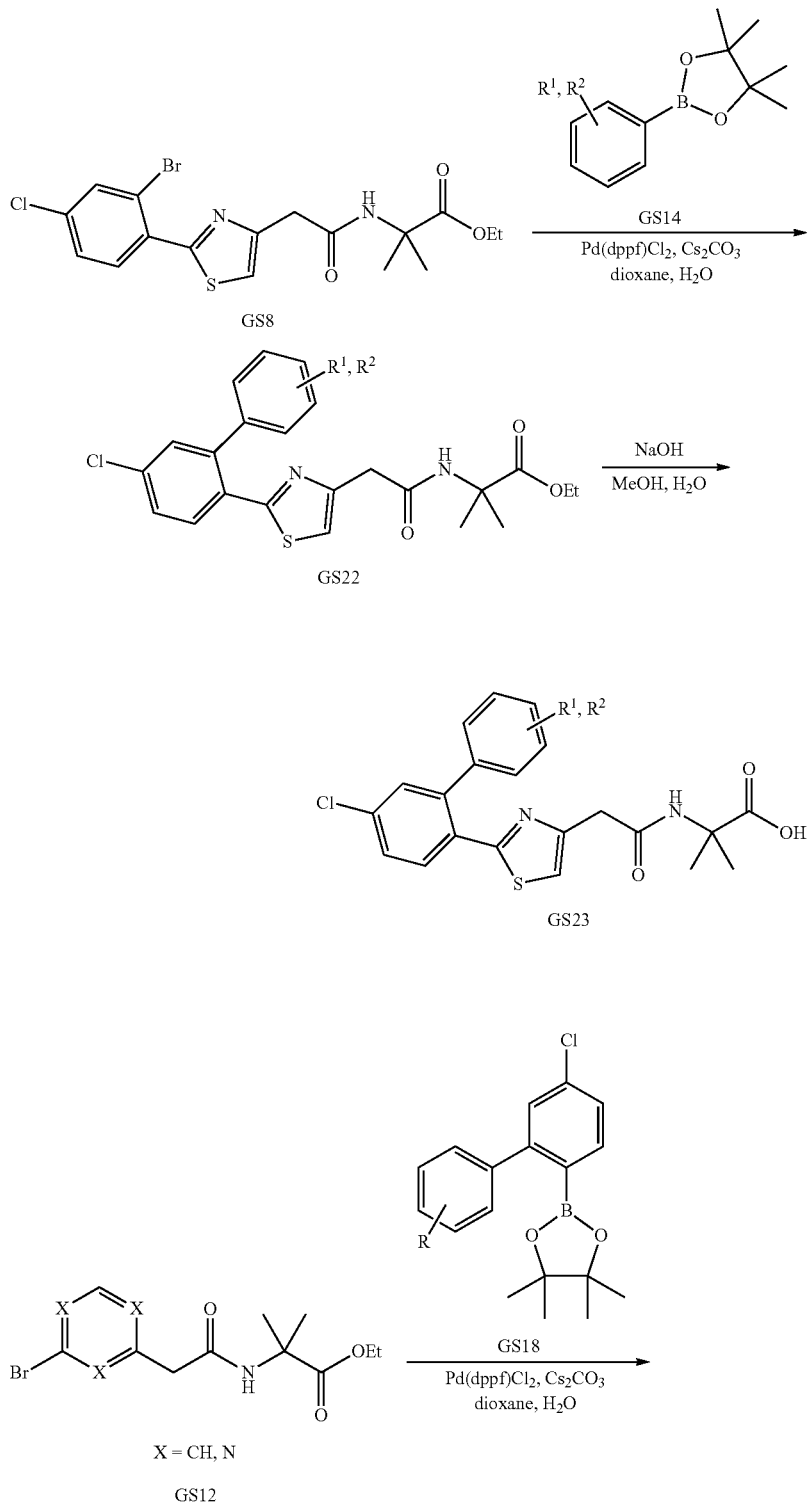

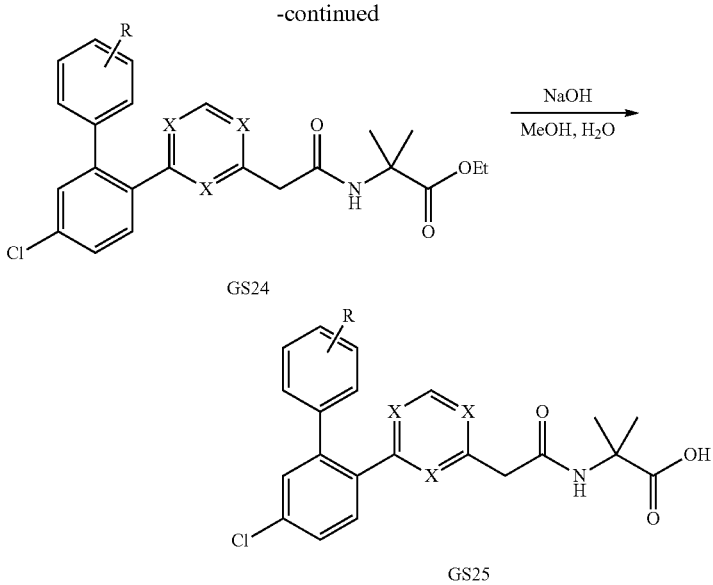

GS24

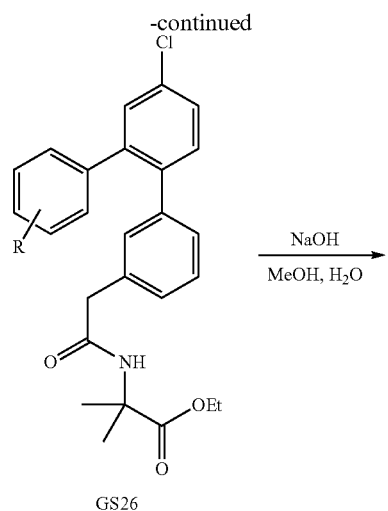

GS25

Final compounds of the invention such as GS23 and GS25 can be synthesized as described in Scheme 6. The key intermediate bromo esters such as GS8 and GS12 can be coupled with a variety of aryl boronic esters GS14 and GS18 to form intermediates GS22 and GS24, respectively. This is achieved under standard cross coupling conditions using, Pd(dppf)Cl$_2$, cesium carbonate or other suitable base in dioxane and water with heating. Intermediates GS22 and GS24 can then be hydrolyzed using sodium or lithium hydroxide in water and methanol or ethanol to form the claimed compounds as represented by GS23 and GS25.

In certain embodiments, compounds of the present invention of formula I are generally prepared according to Scheme 7 set forth below:

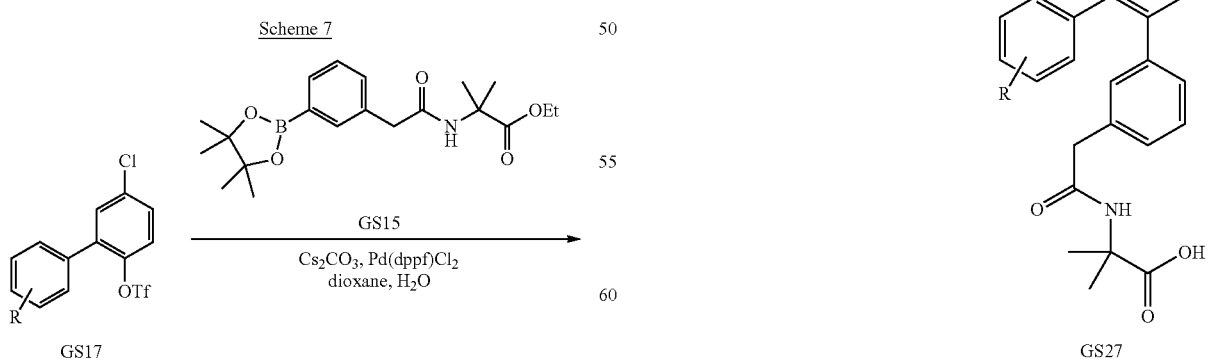

Final compounds GS27 of the invention can be synthesized as described in the two step procedure in Scheme 7. Coupling triflates GS17 with boronic ester GS15, using catalysts such as Pd(dppf)Cl₂ or Pd₂(dba)₃ with XPhos, and base such as cesium carbonate, in water and dioxane with heat gives intermediates GS26. These esters can be hydrolyized as described above for GS25 in Scheme 6 with sodium hydroxide to give the acid products GS27.

In certain embodiments, compounds of the present invention of formula I are generally prepared according to Scheme 8 set forth below:

Scheme 8

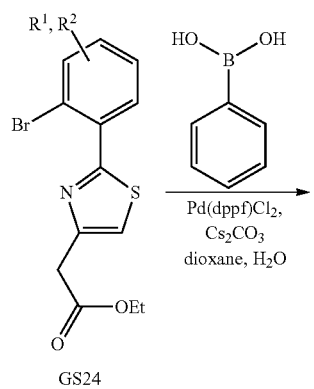

GS24

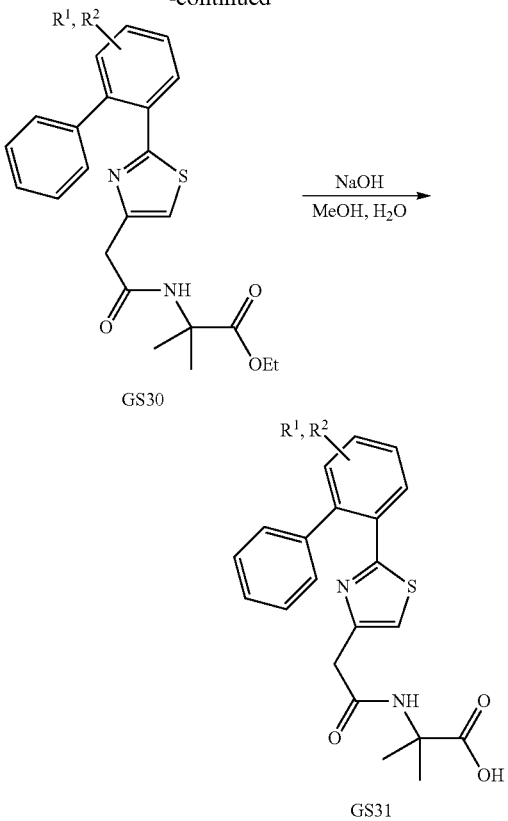

GS30

GS31

Compounds of the type GS31 can be synthesized via the method shown in Scheme 8. Phenyl boronic acid can be coupled with a variety of bromide intermediates GS4 under standard conditions described above for GS22 to form intermediate GS28. The ester can then be hydrolyzed using lithium or sodium hydroxide to form acid GS29. This acid can then be coupled with the amine of choice, in this case ethyl 2-amino-2-methylpropanoate, with HATU and diisopropylethylamine in DCM or DMF to form GS30. Final hydrolysis of the ester under conditions previously described yields the final acid products GS31.

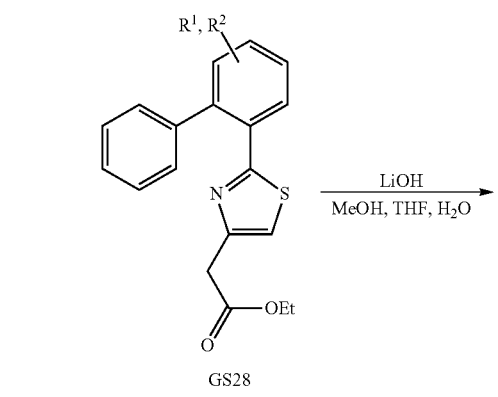

GS28

In certain embodiments, compounds of the present invention of formula I are generally prepared according to Scheme 9 set forth below:

Scheme 9

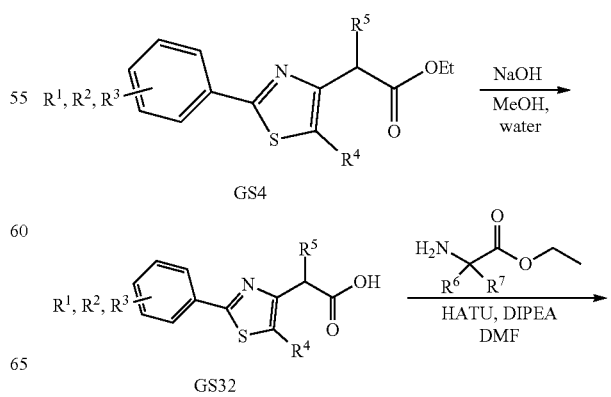

GS4

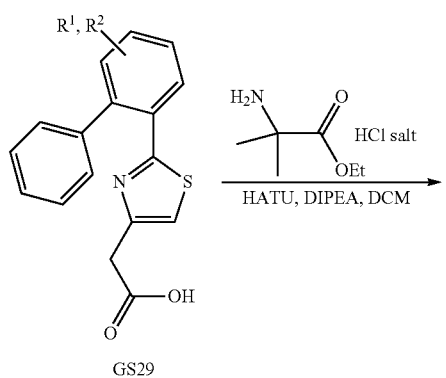

GS29

GS32

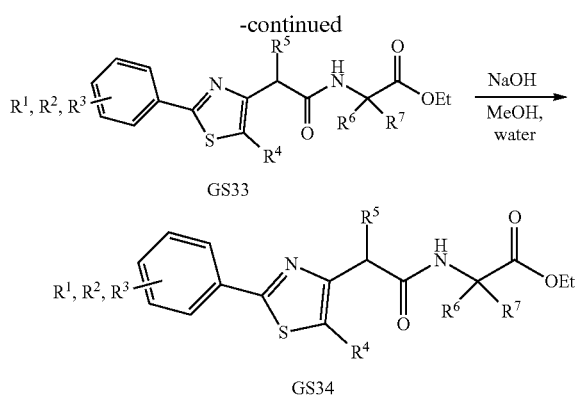

Final compounds of the type GS34 were synthesized as described in the three step procedure outlined in Scheme 9. A variety of substituted thiadiazole ester intermediates GS4 can first be hydrolyzed using sodium hydroxide in methanol and water to give acids GS32. These acids can then be coupled with the amine of choice under standard conditions described above for GS30 to give GS33. Final hydrolysis of the esters as previously described give the final compounds GS34 described within.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit SHMT1 and/or SHMT2, or a mutant thereof, in a biological sample or in a patient. In certain embodiments, the amount of compound in compositions of this invention is such that is effective to measurably inhibit SHMT1 and/or SHMT2, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of SHMT1 and/or SHMT2, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of SHMT1 and/or SHMT2 or a mutant thereof.

The activity of a compound utilized in this invention as an inhibitor of SHMT1 and/or SHMT2, or a mutant thereof, may be assayed in vitro, in vivo or in a cell line. In vitro assays include assays that determine inhibition of SHMT1 and/or SHMT2, or a mutant thereof. Alternate in vitro assays quantitate the ability of the inhibitor to bind to SHMT1 and/or SHMT2. Detailed conditions for assaying a compound utilized in this invention as an inhibitor of SHMT1 and/or SHMT2, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of SHMT1 and/or SHMT2 and are therefore useful for treating one or more disorders associated with activity of SHMT1 and/or SHMT2. Thus, in certain embodiments, the present invention provides a method for treating a SHMT1 and/or SHMT2-mediated disorder comprising the step of administering to a patient in need thereof a compound of the present invention, or pharmaceutically acceptable composition thereof.

As used herein, the terms "SHMT1 and/or SHMT2-mediated" disorders, diseases, and/or conditions as used herein means any disease or other deleterious condition in which SHMT1 and/or SHMT2, or a mutant thereof, is known to play a role. Accordingly, another embodiment of the present invention relates to treating or lessening the severity of one or more diseases in which SHMT1 and/or SHMT2, or a mutant thereof, are known to play a role.

In some embodiments, the present invention provides a method for treating one or more disorders, diseases, and/or conditions wherein the disorder, disease, or condition includes, but is not limited to, a cellular proliferative disorder.

Cellular Proliferative Disorders

The present invention features methods and compositions for the diagnosis and prognosis of cellular proliferative disorders (e.g., cancer) and the treatment of these disorders by targeting SHMT1 and/or SHMT2 of the serine biosynthetic pathway. Cellular proliferative disorders described herein include, e.g., cancer, obesity, and proliferation-dependent diseases. Such disorders may be diagnosed using methods known in the art.

Cancer

Cancer includes, in one embodiment, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). In some embodiments, the cancer is melanoma or breast cancer.

Cancers includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the present invention provides a method for treating a tumor in a patient in need thereof, comprising administering to the patient any of the compounds, salts or pharmaceutical compositions described herein. In some embodiments, the tumor comprises any of the cancers described herein. In some embodiments, the tumor comprises melanoma cancer. In some embodiments, the tumor comprises breast cancer. In some embodiments, the tumor comprises lung cancer. In some embodiments the the tumor comprises small cell lung cancer (SCLC). In some embodiments the the tumor comprises non-small cell lung cancer (NSCLC).

In some embodiments, the tumor is treated by arresting further growth of the tumor. In some embodiments, the tumor is treated by reducing the size (e.g., volume or mass) of the tumor by at least 5%, 10%, 25%, 50%, 75%, 90% or 99% relative to the size of the tumor prior to treatment. In some embodiments, tumors are treated by reducing the quantity of the tumors in the patient by at least 5%, 10%, 25%, 50%, 75%, 90% or 99% relative to the quantity of tumors prior to treatment.

Other Proliferative Diseases

Other proliferative diseases include, e.g., obesity, benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, and diabetic retinopathy. Proliferative diseases that are hereby incorporated by reference include those described in U.S. Pat. Nos. 5,639,600 and 7,087,648.

Inflammatory Disorders and Diseases

Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Compounds according to the invention are useful in the treatment of heteroimmune diseases. Examples of such heteroimmune diseases include, but are not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to "morning dipping". "Morning dipping" is a recognized asthmatic syndrome, common to a substantial percentage of asthmatics and characterised by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is an disease of the skin. In some embodiments, the inflammatory disease of the skin is selected from contact dermatitits, atompic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, and other inflammatory or allergic conditions of the skin.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic jubenile idiopathic arthritis (SJIA), Cryopyrin Associated Periodic Syndrome (CAPS), and osteoarthritis.

In some embodiments the inflammatory disease which can be treated according to the methods of this invention is a TH17 mediated disease. In some embodiments the TH17 mediated disease is selected from Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Metabolic Disease

In some embodiments the invention provides a method of treating a metabolic disease. In some embodiments the metabolic disease is selected from Type 1 diabetes, Type 2 diabetes, metabolic syndrome or obesity.

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting SHMT1 and/or SHMT2 activity in a biological sample comprising the step of contacting said biological sample with a compound of this invention, or a composition comprising said compound.

According to another embodiment, the invention relates to a method of inhibiting SHMT1 and/or SHMT2, or a mutant thereof, activity in a biological sample comprising the step of contacting said biological sample with a compound of this invention, or a composition comprising said compound. In certain embodiments, the invention relates to a method of irreversibly inhibiting SHMT1 and/or SHMT2, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Another embodiment of the present invention relates to a method of inhibiting SHMT1 and/or SHMT2 in a patient comprising the step of administering to said patient a compound of the present invention, or a composition comprising said compound.

According to another embodiment, the invention relates to a method of inhibiting SHMT1 and/or SHMT2, or a mutant thereof, activity in a patient comprising the step of administering to said patient a compound of the present invention, or a composition comprising said compound. According to certain embodiments, the invention relates to a method of irreversibly inhibiting SHMT1 and/or SHMT2, or a mutant thereof, activity in a patient comprising the step of administering to said patient a compound of the present invention, or a composition comprising said compound. In other embodiments, the present invention provides a method for treating a disorder mediated by SHMT1 and/or SHMT2, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; Ilmofosine; RO 318220 and RO 320432; GO 6976; Isis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213;

Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™ Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zamestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., $4^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Abbreviations

Ac: acetyl
AcOH: acetic acid
ACN: acetonitrile
Ad: adamantane
AIBN: 2,2'-azo bisisobutyronitrile
Anhyd: anhydrous
Aq: aqueous
$B_2Pin_2$: bis (pinacolato)diboron-4,4,4',4',5,5,5',5'-octamethyl-2,2'-bi(1,3,2-dioxaborolane)
BINAP: 2,2'-bis(diphenylphosphino)-1,1'-binaphthyl BH₃: borane
Bn: benzyl
Boc: tert-butoxycarbonyl
Boc₂O: di-tert-butyl dicarbonate
BPO: benzoyl peroxide
ⁿBuOH: n-butanol
COD: cyclooctadiene
d: days
DAST: diethylaminosulfur trifluoride
dba: dibenzylideneacetone
DBU: 1,8-diazobicyclo[5.4.0]undec-7-ene
DCE: 1,2-dichloroethane
DCM: dichloromethane
DEA: diethylamine
DIBAL-H: diisobutylaluminum hydride
DIPEA or DIEA: N,N-diisopropylethylamine
DMA: N,N-dimethylacetamide
DME: 1,2-dimethoxyethane
DMAP: 4-dimethylaminopyridine
DMF: N,N-dimethylformamide
DMSO: dimethyl sulfoxide
DPPA: diphenylphosphoryl azide
dppf: 1,1'-bis(diphenylphosphino)ferrocene
EDC or EDCI: 1-(3-dimethylaminopropyl)-3-ethylcarbodiimide hydrochloride
ee: enantiomeric excess
ESI: electrospray ionization
EA: ethyl acetate
EtOAc: ethyl acetate
EtOH: ethanol
h or hrs: hours
HATU: N,N,N',N'-tetramethyl-O-(7-azabenzotriazol-1-yl)uronium hexafluorophosphate
HCl: hydrochloric acid
HPLC: high performance liquid chromatography
HOAc: acetic acid
IPA: isopropyl alcohol
KHMDS: potassium hexamethyldisilazide
K₂CO₃: potassium carbonate
LAH: lithium aluminum hydride
LDA: lithium diisopropylamide
m-CPBA: meta-chloroperbenzoic acid
M: molar
MeCN: acetonitrile
MeOH: methanol
Me₂S: dimethyl sulfide
MeONa: sodium methylate
MeI: iodomethane
min: minutes
mL: milliliters
mM: millimolar
mmol: millimoles
MPa: mega pascal
MOMCl: methyl chloromethyl ether
MsCl: methanesulfonyl chloride
MTBE: methyl tert-butyl ether
NaNO₂: sodium nitrite
Na₂SO₄: sodium sulfate
NBS: N-bromosuccinimide
NCS: N-chlorosuccinimide
NaOH: sodium hydroxide
NMO: N-methylmorpholine N-oxide
NMP: N-methylpyrrolidine
NMR: Nuclear Magnetic Resonance
OC: degrees Celsius
Pd/C: palladium on carbon
Pd(OAc)₂: palladium acetate
PBS: phosphate buffered saline
PE: petroleum ether
POCl₃: phosphorus oxychloride
PPh₃: triphenylphosphine
Rel: relative
R.T. or rt: room temperature
sat: saturated
SEMCl: chloromethyl-2-trimethylsilylethyl ether
SFC: supercritical fluid chromatography
SOCl₂: sulfur dichloride
tBuOK: potassium tert-butoxide
TBAB: tetrabutylammonium bromide
TEA: triethylamine
Tf: trifluoromethanesulfonate
TfAA, TFMSA or Tf₂O: trifluoromethanesulfonic anhydride
TFA: trifluoracetic acid
TIPS: triisopropylsilyl
THF: tetrahydrofuran
THP: tetrahydropyran
TLC: thin layer chromatography
TMEDA: tetramethylethylenediamine
pTSA: para-toluenesulfonic acid
Xantphos: 4,5-bis(diphenylphosphino)-9,9-dimethylxanthene
Xphos: 2-dicyclohexylphosphino-2',4',6'-triisopropylbiphenyl General Synthetic Methods The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated. Optical rotations were measured in MeOH.

Proton NMR ($^1$H NMR) is conducted in deuterated solvent. In certain compounds disclosed herein, one or more $^1$H shifts overlap with residual proteo solvent signals; these signals have not been reported in the experimental provided hereinafter.

Analytical instruments used to purify and characterize the compounds of the present invention are summarized in Table 3.

TABLE 3

| Analytical Instruments | |
|---|---|
| LCMS | Shimadzu UFLC MS: LCMS-2020 |
| | Agilent Technologies 1200 series MS: Agilent Technologies 6110 |
| | Agilent Technologies 1200 series MS: LC/MSD VL |
| NMR | BRUKER AVANCE III/400; Frequency (MHz) 400.13; Nucleus: 1H; Number of Transients: 8 |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

For Acidic LCMS Data:

LCMS was recorded on an Agilent 1200 Series LC/MSD or Shimadzu LCMS2020 equipped with electro-spray ionization and quadruple MS detector [ES+ve to give MH$^+$] and equipped with Chromolith Flash RP-18e 25*2.0 mm, eluting with 0.0375 vol % TFA in water (solvent A) and 0.01875 vol % TFA in acetonitrile (solvent B).

For Basic LCMS Data:

LCMS was recorded on an Agilent 1200 Series LC/MSD or Shimadzu LCMS 2020 equipped with electro-spray ionization and quadruple MS detector [ES+ve to give MH$^+$] and equipped with Xbridge C18, 2.1×50 mm columns packed with 5 mm C18-coated silica or Kinetex EVO C18 2.1×30 mm columns packed with 5 mm C18-coated silica, eluting with 0.05 vol % NH$_3$ in water (solvent A) and acetonitrile (solvent B).

INTERMEDIATES (Intermediate A) Ethyl 2-[[2-[2-(2-bromo-4-chloro-phenyl)thiazol-4-yl]acetyl]amino]-2-methyl-propanoate

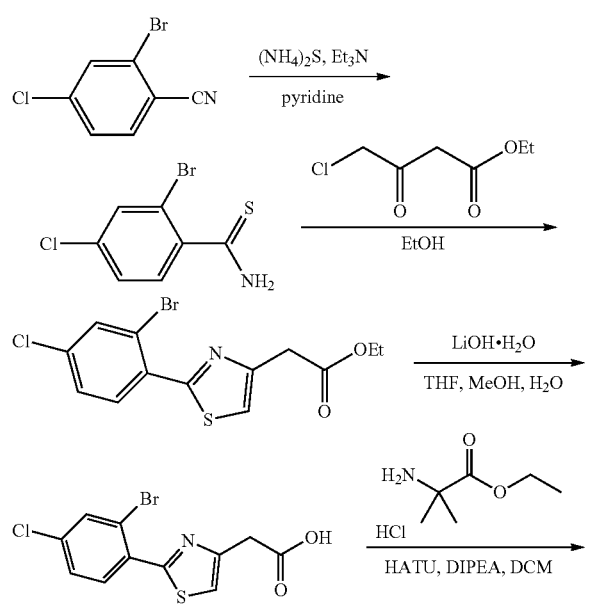

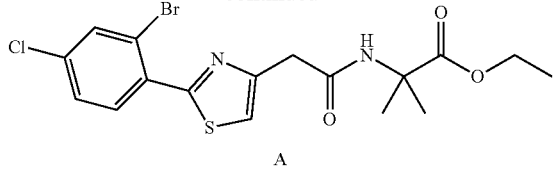

A

Step 1—2-Bromo-4-chloro-benzenecarbothioamide 2-bromo-4-chloro-benzonitrile (11.5 g, 53.1 mmol, CAS #57381-49-4) was dissolved in pyridine (15 mL). Then triethylamine (14.7 mL, 106 mmol) and (NH$_4$)$_2$S (36.2 g, 531 mmol) were added into the mixture. The reaction mixture was stirred at 70° C. for 10 hours in an autoclave. On completion, after being cooled to room temperature, the mixture was diluted with cold water (200 mL). The product was extracted with ethyl acetate (3×200 mL). The organic layer was washed with brine, dried over Na$_2$SO$_4$, and concentrated in vacuo to give the title compound (10.0 g, 75% yield) as a yellowish solid. $^1$H NMR (400 MHz, CDCl$_3$) δ=7.88 (br. s., 1H), 7.58-7.45 (m, 2H), 7.31-7.23 (m, 1H), 7.04 (br. s., 1H).

Step 2—Ethyl 2-[2-(2-bromo-4-chloro-phenyl)thiazol-4-yl]acetate

To a mixture of 2-bromo-4-chloro-benzenecarbothioamide (9.00 g, 35.9 mmol) in EtOH (20 mL) was added ethyl 4-chloro-3-oxo-butanoate (11.8 g, 71.8 mmol, CAS #638-07-3). Then the reaction mixture was stirred at 80° C. for 12 hours. On completion, the reaction mixture was concentrated in vacuo. The reaction mixture was purified by prep-column chromatography (petroleum ether: ethyl acetate=40:1 to 20:1) to give the title compound (11.0 g, 85% yield) as a yellowish solid. $^1$H NMR (400 MHz, CDCl$_3$) δ=8.05 (d, J=8.4 Hz, 1H), 7.73 (d, J=2.0 Hz, 1H), 7.44-7.37 (m, 2H), 4.23 (q, J=7.2 Hz, 2H), 3.93 (s, 2H), 1.32 (t, J=7.2 Hz, 3H).

Step 3—2-[2-(2-Bromo-4-chloro-phenyl)thiazol-4-yl]acetic acid

To a solution of ethyl 2-[2-(2-bromo-4-chloro-phenyl)thiazol-4-yl]acetate (6.00 g, 16.6 mmol) in a mixture of MeOH (30 mL), THF (30 mL) and water (30 mL) was added LiOH·H$_2$O (1.20 g, 49.9 mmol) and the reaction mixture was stirred at 20° C. for 0.5 hour. On completion, the reaction mixture was concentrated in vacuo to remove the THF and MeOH. The mixture was then acidified with 3N HCl solution (4 mL) until pH=3.0. The mixture was then filtered and the filter cake was dried in vacuo to give the title compound (4.70 g, 85% yield) as a yellow solid. LCMS: (ES+) m/z (M+H)$^+$=331.8, tR=0.813. $^1$H NMR (400 MHz, CDCl$_3$) δ=7.97 (d, J=8.4 Hz, 1H), 7.74 (d, J=2.0 Hz, 1H), 7.41 (dd, J=2.0, 8.4 Hz, 1H), 7.36 (s, 1H), 3.97 (s, 2H).

Step 4—Ethyl 2-[[2-[2-(2-bromo-4-chloro-phenyl)thiazol-4-yl]acetyl]amino]-2-methyl-propanoate To a mixture of 2-[2-(2-bromo-4-chloro-phenyl)thiazol-4-yl]acetic acid (4.70 g, 14.1 mmol), diisopropylethylamine (5.48 g, 42.3 mmol) and HATU (6.98 g, 18.3 mmol) in DCM (150 mL) was added ethyl 2-amino-2-methyl-propanoate hydrochloride (2.61 g, 15.5 mmol, CAS #17288-15-2) in one portion and the reaction mixture was stirred at 20° C. for 3 hours. On completion, the reaction mixture was washed with 1N HCl solution (50 mL) and extracted with ethyl acetate (3×100 mL). The organic layer was dried over Na$_2$SO$_4$, filtrated and concentrated in vacuo. The residue was purified by silica gel chromatography (petroleum ether: ethyl acetate=3:1) to give the title compound (5.40 g, 85% yield) as a light yellow solid. $^1$H NMR (400 MHz, CDCl$_3$) δ=8.10 (d, J=8.4 Hz, 1H), 7.74 (d, J=2.4 Hz, 1H), 7.42 (dd, J=2.4, 8.4 Hz, 1H), 7.39 (br. s., 1H), 7.30 (s, 1H), 4.18 (q, J=7.2 Hz, 2H), 3.77 (s, 2H), 1.56 (s, 6H), 1.23 (t, J=7.2 Hz, 3H).

(Intermediate B) 2-Indan-4-yl-4,4,5,5-tetramethyl-1,3,2-dioxaborolane

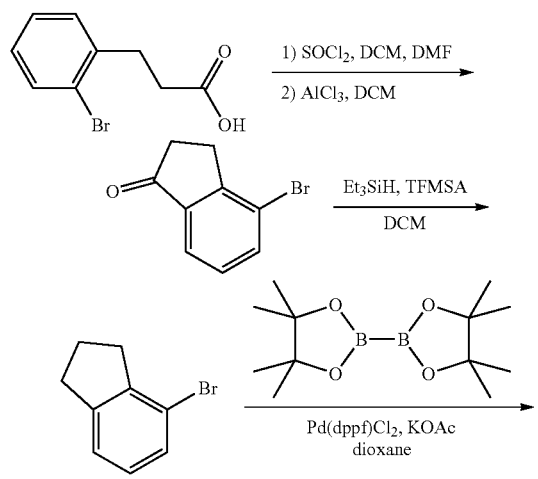

B

Step 1—4-Bromoindan-1-one

To a solution of 3-(2-bromophenyl)propanoic acid (1.20 g, 5.24 mmol, CAS #15115-58-9) in a mixture of solvent dichloromethane (20 mL) and dimethylformamide (3.83 mg, 52.4 umol) was added oxalyl chloride (1.33 g, 10.4 mmol) and the reaction mixture was stirred at 20° C. for 1 hr. On completion, the mixture was concentrated in vacuo and the residue was dissolved in dichloromethane (20 mL) and cooled to 0° C. Then aluminum trichloride (838 mg, 6.29 mmol) was added at 0° C. and the reaction mixture was stirred at 0° C. for 1 hr. On completion, the reaction mixture was poured into 100 mL cool water and extracted with DCM (3×50 mL). The organic layer was dried over Na$_2$SO$_4$, filtered and concentrated in vacuo to give the title compound (1.10 g, 95% yield) as a light yellow solid. $^1$H NMR (400 MHz, CDCl$_3$) δ=7.77 (d, J=7.2 Hz, 1H), 7.73 (d, J=7.2 Hz, 1H), 7.30 (dd, J=7.2, 7.2 Hz, 1H), 3.12 (t, J=7.2 Hz, 2H), 2.75 (t, J=7.2 Hz, 2H).

Step 2—4-Bromoindane

To a solution of 4-bromoindan-1-one (200 mg, 947 umol) in dichloromethane (10 mL) was added a solution of trifluoromethanesulfonic acid (426 mg, 2.84 mmol) in dichloromethane (500 uL) and the reaction mixture was cooled to 0° C. Then triethylsilane (220 mg, 1.90 mmol) in dichloromethane (500 uL) was added dropwise to the reaction mixture and the mixture was stirred at 0° C. for 0.5 hr. TLC detected most starting material remained. Then another batch of trifluoromethanesulfonic acid (426 mg, 2.84 mmol) and triethylsilane (220 mg, 1.90 mmol) was added in turn and the reaction mixture was stirred at 20° C. for 15.5 hrs. On completion, the reaction mixture was diluted with 15 mL DCM and washed with saturated sodium bicarbonate until pH=7. The organic layer was dried over Na$_2$SO$_4$, filtered and concentrated in vacuo. The residue was purified by silica gel chromatography (petroleum ether) to give the title compound (1.00 g, 80% yield) as colorless oil. $^1$H NMR (400 MHz, CDCl$_3$) δ=7.31 (d, J=7.6 Hz, 1H), 7.16 (d, J=7.6 Hz, 1H), 7.02 (dd, J=7.6, 7.6 Hz, 1H), 3.04 (t, J=7.2 Hz, 2H), 2.98 (t, J=7.2 Hz, 2H), 2.11 (m, 2H).

Step 3—2-Indan-4-yl-4,4,5,5-tetramethyl-1,3,2-dioxaborolane

A mixture of 4-bromoindane (60.0 mg, 304 umol), bis(pinacolato)diboron (92.7 mg, 365 umol), potassium acetate (59.7 mg, 608 umol) and Pd(dppf)Cl$_2$ (11.1 mg, 15.2 umol) in dioxane (10 mL) was stirred at 90° C. for 4 hrs under nitrogen. On completion, the reaction mixture was concentrated in vacuo. The residue was purified by silica gel chromatography (petroleum ether:ethyl acetate=50:1) to give the title compound (50.0 mg, 57% yield) as a colorless oil. $^1$H NMR (400 MHz, CDCl$_3$) δ=7.60 (d, J=7.2 Hz, 1H), 7.32 (d, J=7.2 Hz, 1H), 7.14 (dd, J=7.2, 7.2 Hz, 1H), 3.14 (t, J=7.6 Hz, 2H), 2.90 (t, J=7.6 Hz, 2H), 2.05 (m, 2H), 1.34 (s, 12H).

(Intermediate C) 2-(1,3-Dihydroisobenzofuran-4-yl)-4,4,5,5-tetramethyl-1,3,2-dioxaborolane

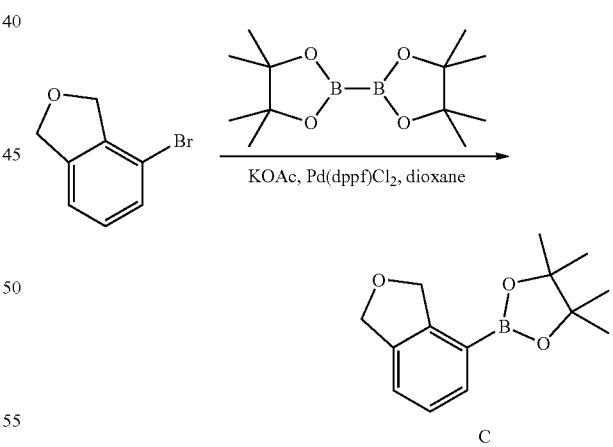

C

Step 1—2-(1,3-Dihydroisobenzofuran-4-yl)-4,4,5,5-tetramethyl-1,3,2-dioxaborolane A mixture of 4-bromo-1,3-dihydroisobenzofuran (250 mg, 1.26 mmol, CAS #1402667-16-6), bis(pinacolato)diboron (637 mg, 2.51 mmol), potassium acetate (246 mg, 2.51 mmol) and Pd(dppf)Cl$_2$ (9.19 mg, 12.5 umol) in dioxane (10 mL) was stirred at 90° C. for 16 hrs under nitrogen. On completion, the reaction mixture was concentrated in vacuo and diluted with 15 mL dichloromethane. The organic layer was washed with water (3×15 mL), dried over anhydrous sodium sulfate, filtered and concentrated in vacuo. The residue was purified by silica gel chromatography (petroleum ether:ethyl acetate=4:1) to give the title compound (300 mg, 90% yield) as a white solid. $^1$H NMR (400 MHz, CDCl$_3$) δ=7.72 (d, J=7.2 Hz, 1H), 7.35 (d, J=7.2 Hz, 1H), 7.31 (t, J=7.2 Hz, 1H), 5.27 (s, 2H), 5.13 (s, 2H), 1.35 (s, 12H).

(Intermediate D) 2-(4-Chloro-2-phenyl-phenyl)-4,4,5,5-tetramethyl-1,3,2-dioxaborolane

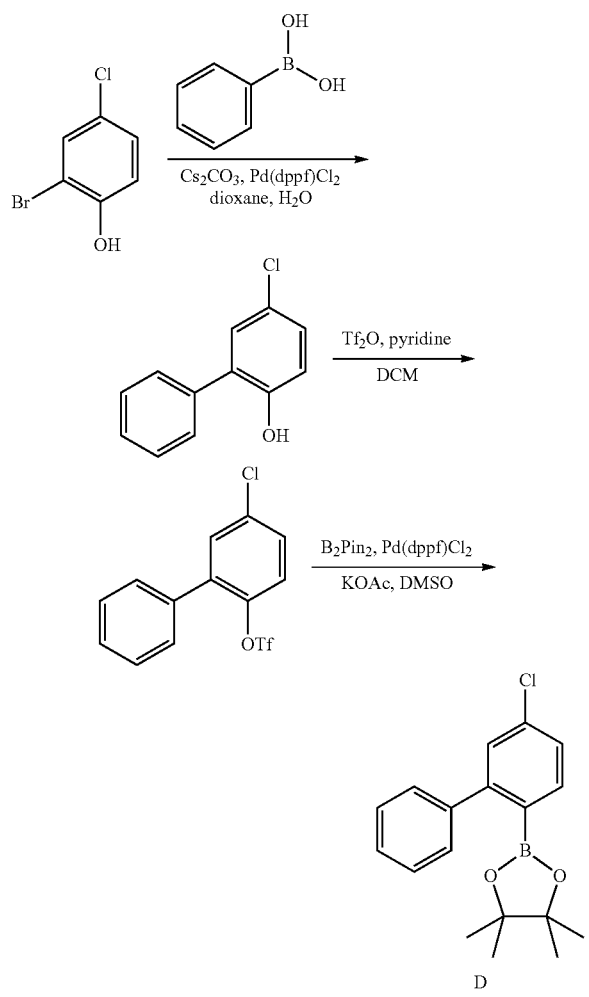

Step 1—4-Chloro-2-phenyl-phenol

A mixture of 2-bromo-4-chloro-phenol (3.00 g, 14.5 mmol), phenylboronic acid (2.12 g, 17.4 mmol), cesium carbonate (9.42 g, 28.9 mmol) and Pd(dppf)Cl$_2$ (529 mg, 723 umol) in dioxane (30 mL) and water (3 mL) was stirred at 90-100° C. for 12 hrs under nitrogen atmosphere. On completion, the reaction mixture was concentrated in vacuo. The residue was diluted with DCM (100 mL) and water (100 mL), then acidified with 1N HCl solution until the pH=4-5. The organic phase was dried over anhydrous sodium sulfate, filtered and concentrated in vacuo. The residue was purified by column chromatography (petroleum ether:ethyl acetate=3:1) to give the title compound (2.60 g, 58% yield) as yellow oil. LCMS: (ES+) m/z (M–H)$^-$=203.0, tR=1.451. $^1$H NMR (400 MHz, CDCl$_3$) δ=7.54-7.49 (m, 2H), 7.47-7.41 (m, 3H), 7.25-7.19 (m, 2H), 6.93 (d, J=8.8 Hz, 1H), 5.18 (s, 1H).

Step 2—(4-Chloro-2-phenyl-phenyl) trifluoromethanesulfonate

To a solution of 4-chloro-2-phenyl-phenol (1.50 g, 7.33 mmol) in DCM (15 mL) was added pyridine (1.16 g, 14.7 mmol) and trifluoromethanesulfonic anhydride (2.48 g, 8.80 mmol) dropwise at 0° C. Then the reaction mixture was warmed to 15° C. and stirred for 1 hour. On completion, the reaction mixture was diluted with DCM (30 mL) and water (30 mL). The organic layer was washed with 1N HCl solution until pH<7, dried over anhydrous sodium sulfate, filtrated and concentrated in vacuo. The residue was purified by column chromatography (petroleum ether: ethyl acetate=10:1) to give the title compound (2.20 g, 89% yield). $^1$H NMR (400 MHz, CDCl$_3$) δ=7.49-7.47 (m, 2H), 7.47-7.44 (m, 4H), 7.41 (dd, J=2.4, 8.8 Hz, 1H), 7.35 (d, J=8.8 Hz, 1H).

Step 3—2-(4-Chloro-2-phenyl-phenyl)-4,4,5,5-tetramethyl-1,3,2-dioxaborolane

A mixture of (4-chloro-2-phenyl-phenyl) trifluoromethanesulfonate (1.23 g, 3.65 mmol), 4,4,5,5-tetramethyl-2-(4,4,5,5-tetramethyl-1,3,2-dioxaborolan-2-yl)-1,3,2-dioxaborolane (1.86 g, 7.31 mmol), Pd(dppf)Cl$_2$ (134 mg, 183 umol) and potassium acetate (717 mg, 7.31 mmol) in DMSO (5 mL) was stirred at 90-100° C. for 16 hours under nitrogen atmosphere. On completion, the reaction mixture was diluted with DCM (100 mL) and water (100 mL). The organic phase was dried over anhydrous sodium sulfate, filtered and concentrated in vacuo. The residue was purified by column chromatography (petroleum ether:ethyl acetate=10:1) to give the title compound (750 mg, 55% yield) as a yellow oil. LCMS: (ES+) m/z (M+1)+=315.0, tR=1.304.

(Intermediate E) Ethyl 2-[[2-(6-bromo-2-pyridyl)acetyl]amino]-2-methyl-propanoate

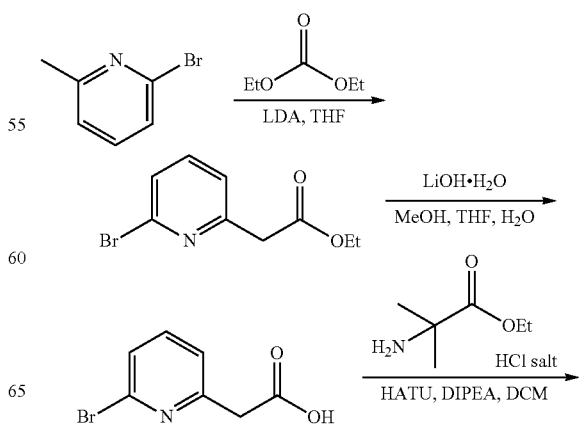

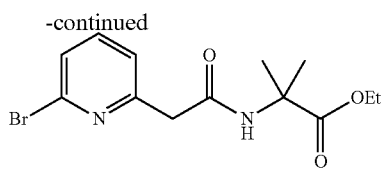

E

Step 1—Ethyl 2-(6-bromo-2-pyridyl)acetate

To a solution of 2-bromo-6-methyl-pyridine (5.00 g, 29.0 mmol, CAS #5315-25-3) in THF (100 mL) was added LDA (2.0 M, 30.5 mL) at −70 OC. After 0.5 hour of stirring at −70° C., diethyl carbonate (5.26 mL, 43.6 mmol) was added. The reaction mixture was slowly warmed to 20° C. and stirred at 20° C. for 4 hours. On completion, the reaction mixture was washed with water (120 mL) and extracted with ethyl acetate (3×150 mL). The organic layer was dried over $Na_2SO_4$, filtered and concentrated in vacuo. The residue was purified by prep-column chromatography (petroleum ether: ethyl acetate=10:1) to give the title compound (5.50 g, 77% yield) as a yellowish oil. $^1H$ NMR (400 MHz, $CDCl_3$) δ=7.50-7.41 (m, 1H), 7.33 (d, J=7.6 Hz, 1H), 7.21 (d, J=7.6 Hz, 1H), 4.11 (q, J=7.2 Hz, 2H), 3.75 (s, 2H), 1.20 (t, J=7.2 Hz, 3H).

Step 2—2-(6-Bromo-2-pyridyl)acetic acid

To a mixture of ethyl 2-(6-bromo-2-pyridyl)acetate (2.00 g, 8.19 mmol) in THF (10 mL), water (10 mL) and MeOH (20 mL) was added LiOH—$H_2O$ (1.03 g, 24.5 mmol). Then the reaction mixture was stirred at 20° C. for 2 hours. On completion, the reaction mixture was concentrated in vacuo. The residue was acidified by 1.0 N HCl to pH=3.0, washed with water (150 mL) and extracted with ethyl acetate (3×150 mL). The organic layer was dried with $Na_2SO_4$, filtered and concentrated in vacuo to give the title compound (1.70 g, 96% yield) as a yellowish solid. $^1H$ NMR (400 MHz, DMSO-$d_6$) δ=12.63 (br. s., 1H), 7.86-7.71 (m, 1H), 7.59 (d, J=8.0 Hz, 1H), 7.46 (d, J=7.6 Hz, 1H), 3.81 (s, 2H).

Step 3—Ethyl 2-[[2-(6-bromo-2-pyridyl)acetyl]amino]-2-methyl-propanoate

To a mixture of 2-(6-bromo-2-pyridyl)acetic acid (500 mg, 2.31 mmol) and ethyl 2-amino-2-methyl-propanoate (426 mg, 2.55 mmol, CAS #17288-15-2) in DMF (10 mL) was added HATU (1.14 g, 3.01 mmol) and DIPEA (897 mg, 6.94 mmol). Then the mixture was stirred at 20° C. for 12 hours. On completion, the reaction mixture was concentrated in vacuo. The residue was washed with water (50 mL) and extracted with ethyl acetate (3×50 mL). The organic layer was dried with $Na_2SO_4$, filtered and concentrated in vacuo. The residue was purified by prep-column chromatography (petroleum ether:ethyl acetate=1:1) to give the title compound (580 mg, 76% yield) as a yellowish oil. LCMS: (ES+) m/z $(M+H)^+$=328.9, tR=0.742.

(Intermediate F) Ethyl 2-[[2-(2-bromo-4-pyridyl)acetyl]amino]-2-methyl-propanoate

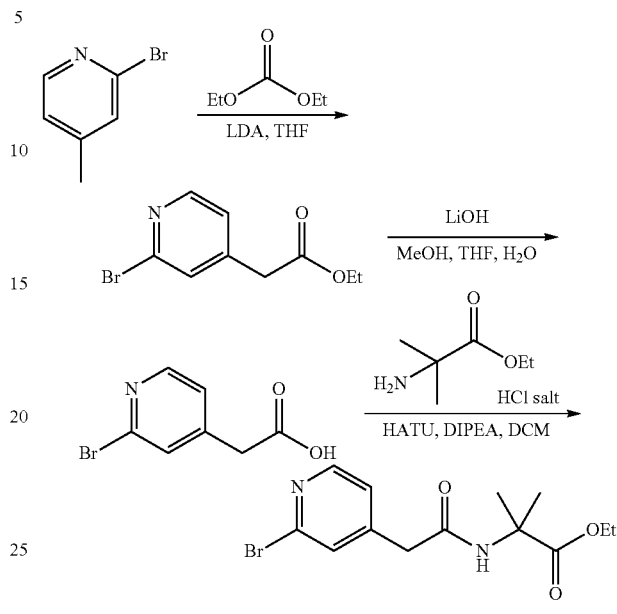

F

Step 1—Ethyl 2-(2-bromo-4-pyridyl)acetate

To a solution of 2-bromo-4-methyl-pyridine (1.00 g, 5.81 mmol CAS #4926-28-7) in THF (15 mL) was added LDA (2 M, 5.81 mL) dropwise at −15° C. under nitrogen and the reaction mixture was stirred at −15° C. for 0.5 hr. Then diethyl carbonate (840 uL, 6.97 mmol) was added dropwise and the reaction mixture was stirred at 20° C. for 0.5 hr. On completion, the reaction mixture was poured into 100 mL cool water and extracted with DCM (3×50 mL). The combined organic layer was dried over $Na_2SO_4$, filtered and concentrated in vacuo. The residue was purified by silica gel chromatography (petroleum ether:ethyl acetate=5:1) to give the title compound (1.00 g, 69% yield) as a light yellow oil. LCMS: (ES+) m/z $(M+H)^+$=245.9, tR=0.749. $^1H$ NMR (400 MHz, $CDCl_3$) δ=8.33 (d, J=5.2 Hz, 1H), 7.45 (d, J=0.8 Hz, 1H), 7.21 (dd, J=0.8, 5.2 Hz, 1H), 4.19 (q, J=7.2 Hz, 2H), 3.60 (s, 2H), 1.28 (t, J=7.2 Hz, 3H).

Step 2—2-(2-Bromo-4-pyridyl)acetic Acid

To a solution of ethyl 2-(2-bromo-4-pyridyl)acetate (1.00 g, 4.10 mmol) in a mixture of THF (5 mL), MeOH (10 mL) and water (5 mL) was added lithium hydroxide (294 mg, 12.3 mmol) and the reaction mixture was stirred at 20° C. for 10 mins. On completion, the reaction mixture was concentrated in vacuo to remove THF and MeOH and diluted with 10 mL water. The aqueous phase was acidified with 2N HCl solution until pH=2. The mixture was filtered and the filter cake was dried in vacuo to give the title compound (850 mg, 90% yield) as a white solid. LCMS: (ES+) m/z $(M+H)^+$=217.9, tR=0.539.

Step 3—Ethyl 2-[[2-(2-bromo-4-pyridyl)acetyl]amino]-2-methyl-propanoate

To a solution of 2-(2-bromo-4-pyridyl)acetic acid (300 mg, 1.39 mmol), diisopropylethylamine (538 mg, 4.17 mmol) and HATU (634 mg, 1.67 mmol) in DCM (15 mL) was added ethyl 2-amino-2-methyl-propanoate (256 mg, 1.53 mmol, HCl salt) and the reaction mixture was stirred at 20° C. for 16 hours. On completion, the reaction mixture was concentrated in vacuo. The residue was purified by silica gel chromatography (petroleum ether:ethyl acetate=1:1) to give the title compound (430 mg, 94% yield) as a light yellow solid. LCMS: (ES$^+$) m/z (M+H)$^+$=329.0, tR=0.679. $^1$H NMR (400 MHz, CDCl$_3$) δ=8.33 (d, J=5.2 Hz, 1H), 7.45 (d, J=1.2 Hz, 1H), 7.22 (dd, J=1.2, 5.2 Hz, 1H), 6.27 (br. s., 1H), 4.20 (q, J=7.2 Hz, 2H), 3.49 (s, 2H), 1.57 (s, 6H), 1.26 (t, J=7.2 Hz, 3H).

(Intermediate G) Ethyl 2-[[2-(4-bromo-2-pyridyl)acetyl]amino]-2-methyl-propanoate

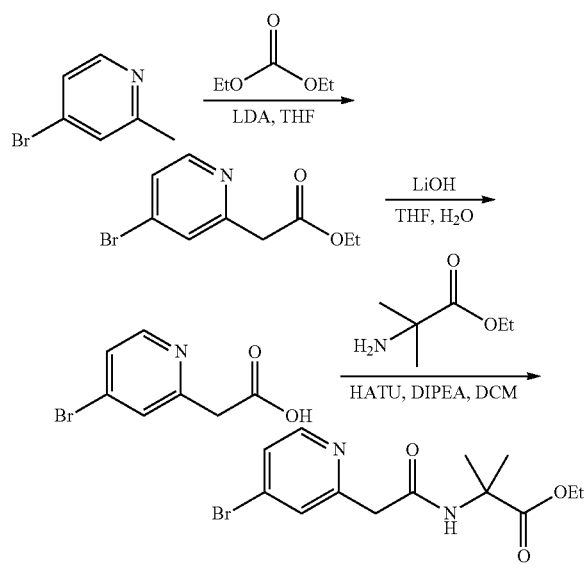

G

Step 1—Ethyl 2-(4-bromo-2-pyridyl)acetate

To a solution of 4-bromo-2-methyl-pyridine (2.00 g, 11.6 mmol, CAS #22282-99-1) and diethyl carbonate (1.65 g, 13.9 mmol, 1.68 mL) in THF (15.0 mL) was added LDA (2 M, 11.63 mL) at −60° C. dropwise. Then the mixture was stirred at −60 OC for 2 hours. On completion, the reaction mixture was quenched by addition of saturated ammonium chloride solution 30 mL at 0° C., and extracted with ethyl acetate 60 mL (3×20 mL). The combined organic layer was dried over anhydrous sodium sulfate, filtered and concentrated under in vacuo to give a residue. The residue was purified by column chromatography (petroleum ether:ethyl acetate=20:1 to 8:1) to give the title compound (1.30 g, 46% yield) as a yellow oil. $^1$H NMR (400 MHz, CDCl$_3$) δ=8.40 (d, J=5.2 Hz, 1H), 7.52 (d, J=1.6 Hz, 1H), 7.40 (dd, J=1.6, 5.2 Hz, 1H), 4.21 (q, J=7.2 Hz, 2H), 3.83 (s, 2H), 1.29 (t, J=7.2 Hz, 3H).

Step 2—2-(4-Bromo-2-pyridyl)acetic Acid

To a solution of ethyl 2-(4-bromo-2-pyridyl)acetate (1.20 g, 4.92 mmol) in THF (15 mL) and water (10 mL) was added LiOH (471 mg, 19.6 mmol). The mixture was stirred at 15° C. for 16 hours. On completion, the reaction mixture was concentrated in vacuo to remove the THF. The residue was acidified with 1 M hydrochloric acid to adjust the pH<5. A fine precipitate was formed which was filtered and dried in vacuo to give the title compound (800 mg, 75% yield) as a yellow solid. $^1$H NMR (400 MHz, DMSO-d$_6$) δ=12.56 (br. s., 1H), 8.39 (d, J=5.2 Hz, 1H), 7.67 (d, J=1.6 Hz, 1H), 7.57 (dd, J=1.6, 5.2 Hz, 1H), 3.77 (s, 2H).

Step 3—Ethyl 2-[[2-(4-bromo-2-pyridyl)acetyl]amino]-2-methyl-propanoate

To a solution of 2-(4-bromo-2-pyridyl)acetic acid (400 mg, 1.85 mmol) in DMF (6.00 mL) was added HATU (844 mg, 2.22 mmol), DIPEA (717 mg, 5.55 mmol, 970 uL) and ethyl 2-amino-2-methyl-propanoate (325 mg, 1.94 mmol, hydrochloride salt) and the mixture was stirred at 15° C. for 16 hours. On completion, the reaction mixture was poured into water 40 mL and extracted with dichloromethane 60 mL (3×20 mL). The combined organic phase was dried over anhydrous Na$_2$SO$_4$, filtered and concentrated in vacuo to get a residue. The residue was purified by column chromatography (dichloromethane:ethyl acetate=9:1 to 9:4) to give the title compound (460 mg, 75% yield) as a yellow oil. $^1$H NMR (400 MHz, CDCl$_3$) δ=8.32 (d, J=5.2 Hz, 1H), 7.46 (br. s., 1H), 7.42 (d, J=1.6 Hz, 1H), 7.32 (dd, J=1.6, 5.2 Hz, 1H), 4.09 (q, J=7.2 Hz, 2H), 3.60 (s, 2H), 1.46 (s, 6H), 1.14 (t, J=7.2 Hz, 3H).

(Intermediate H) Ethyl 2-[[2-(2-bromopyrimidin-4-yl)acetyl]amino]-2-methyl-propanoate

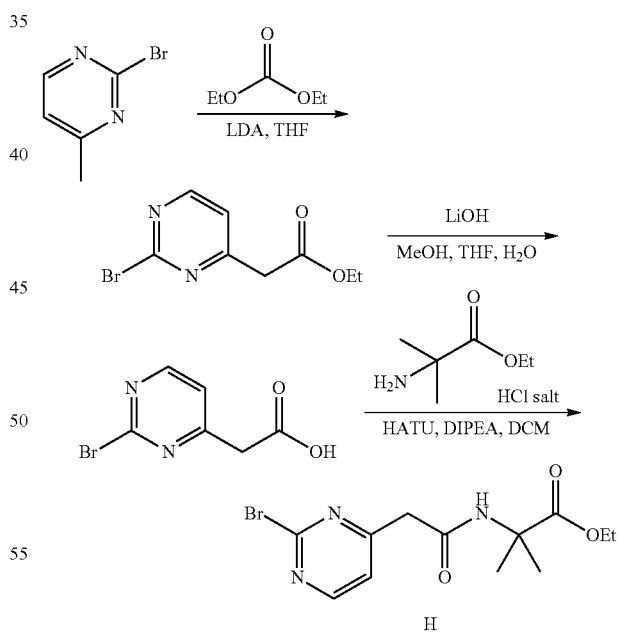

H

Step 1—Ethyl 2-(2-bromopyrimidin-4-yl)acetate

To a LiHMDS solution (52.0 mL, 1 M in THF) was added a solution of 2-bromo-4-methyl-pyrimidine (3.00 g, 17.3 mmol) in tetrahydrofuran (50 mL) slowly at −70° C. under nitrogen gas. The reaction mixture was stirred at −70 OC for 5 mins. Then diethyl carbonate (3.07 g, 26.0 mmol) was added. The resulting reaction mixture was stirred at 20° C. for 12 hrs. On completion, the reaction mixture was quenched with saturated ammonium chloride (50 mL) and extracted with ethyl acetate (3×200 mL). The combined organic layers were washed with brine (100 mL), dried over anhydrous sodium sulfate, filtered and concentrated in vacuo to give black oil. The black oil was purified by silica gel chromatography (petroleum ether:ethyl acetate=10:1) to give the title compound (3.48 g, 82% yield) as a colorless solid. $^1$H NMR (400 MHz, CDCl$_3$) δ=8.54-8.53 (d, J=5.2 Hz, 1H), 7.39 (d, J=5.2 Hz, 1H), 4.20 (q, J=7.2 Hz, 2H), 3.82 (s, 2H), 1.30 (t, J=7.2 Hz, 3H).

Step 2—2-(2-Bromopyrimidin-4-yl)acetic Acid

To a solution of ethyl 2-(2-bromopyrimidin-4-yl)acetate (3.00 g, 12.2 mmol) in MeOH (30 mL), THF (30 mL) and water (20 mL) was added lithium hydroxide (879 mg, 36.7 mmol) and the reaction mixture was stirred at 15° C. for 16 hrs. On completion, the reaction mixture was concentrated in vacuo to remove the THF and MeOH. The aqueous phase was acidified with 1 N HCl solution until pH=4-5. The residue was concentrated in vacuo and triturated with acetone (30 mL), filtered and concentrated in vacuo to give the title compound (1.5 g, 56% yield) as a yellow oil. LCMS: (ES$^+$) m/z (M+1)+=218.9, tR=0.158.

Step 3—Ethyl 2-[[2-(2-bromopyrimidin-4-yl)acetyl]amino]-2-methyl-propanoate

To a solution of 2-(2-bromopyrimidin-4-yl)acetic acid (600 mg, 2.76 mmol), HATU (1.37 g, 3.59 mmol) and N,N-diisopropylethylamine (1.07 g, 8.29 mmol) in DCM (40 mL) was added ethyl 2-amino-2-methyl-propanoate (399 mg, 2.38 mmol, HCl salt). The reaction mixture was stirred at 15° C. for 16 hrs. On completion, the reaction mixture was quenched with water (50 mL) and acidified with 1 N HCl solution until pH=5-6. The organic phase was dried over anhydrous sodium sulfate, filtered and concentrated in vacuo. The residue was purified by column chromatography (petroleum ether:ethyl acetate=1:1) to give the title compound (100 mg, 11% yield) as a yellow oil. $^1$H NMR (400 MHz, CDCl$_3$) δ=8.51 (d, J=5.2 Hz, 1H), 7.39 (d, J=5.2 Hz, 1H), 7.03 (br. s., 1H), 4.18 (q, J=7.2 Hz, 2H), 3.67 (s, 2H), 1.56 (s, 6H), 1.23 (t, J=7.2 Hz, 3H).

(Intermediate I) Ethyl 2-methyl-2-[[2-[3-(4,4,5,5-tetramethyl-1,3,2-dioxaborolan-2-yl)phenyl]acetyl]amino] propanoate

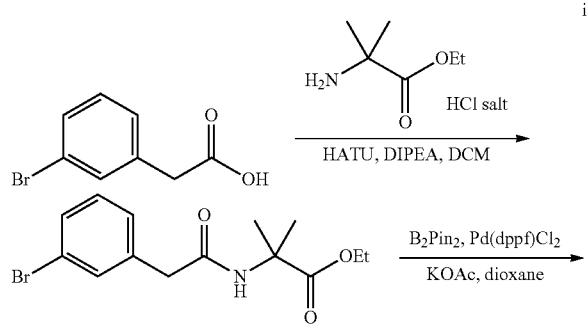

Step 1—Ethyl 2-[[2-(3-bromophenyl)acetyl]amino]-2-methyl-propanoate

To a solution of 2-(3-bromophenyl)acetic acid (5.00 g, 23.3 mmol, CAS #1878-67-7), HATU (11.5 g, 30.2 mmol) and diisopropylethylamine (9.01 g, 69.8 mmol) in DCM (100 mL) was added ethyl 2-amino-2-methyl-propanoate (4.29 g, 25.6 mmol, HCl salt). The reaction mixture was stirred at 15° C. for 16 hrs. On completion, the reaction mixture was washed with 1N HCl solution until pH=6. The organic layer was dried over sodium sulfate, filtered and concentrated in vacuo. The residue was purified by silica gel chromatography (petroleum ether: ethyl acetate=5:1) to give the title compound (3.00 g, 39% yield) as a white solid. LCMS: (ES$^+$) m/z (M)$^+$=328.0, tR=0.746.

Step 2—Ethyl 2-methyl-2-[[2-[3-(4,4,5,5-tetramethyl-1,3,2-dioxaborolan-2-yl)phenyl]acetyl]amino] propanoate To a mixture of ethyl 2-[[2-(3-bromophenyl)acetyl]amino]-2-methyl-propanoate (3.00 g, 9.14 mmol), 4,4,5,5-tetramethyl-2-(4,4,5,5-tetramethyl-1,3,2-dioxaborolan-2-yl)-1,3,2-dioxaborolane (2.79 g, 10.9 mmol) and potassium acetate (1.79 g, 18.2 mmol) in dioxane (50 mL) was added Pd(dppf)Cl$_2$ (334 mg, 457 umol) and the reaction mixture was stirred at 90° C. for 16 hrs. On completion, the reaction mixture was concentrated in vacuo. The residue was purified by flash (petroleum ether:ethyl acetate=3:1) to give the title compound (3.00 g, 87% yield) as a light yellow solid. LCMS: (ES$^+$) m/z (M+1)$^+$=376.2, tR=0.854. $^1$H NMR (400 MHz, CDCl$_3$) δ=7.74 (d, J=6.8 Hz, 1H), 7.70 (s, 1H), 7.44-7.41 (m, 1H), 7.41-7.37 (m, 1H), 4.17 (q, J=7.2 Hz, 2H), 3.57 (s, 2H), 1.51 (s, 6H), 1.37 (s, 12H), 1.24 (t, J=7.2 Hz, 3H).

(Intermediate J) [4-Chloro-2-(p-tolyl)phenyl] trifluoromethanesulfonate

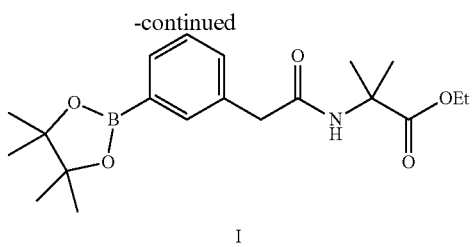

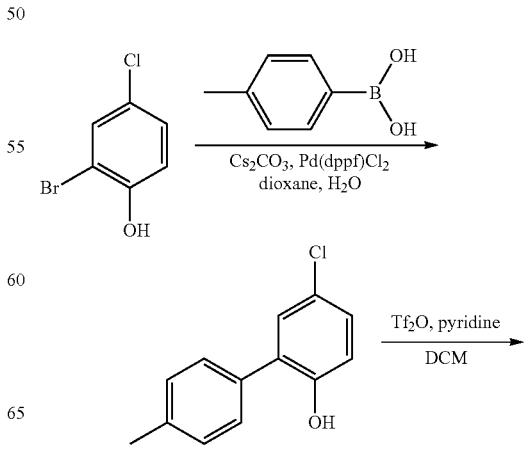

-continued

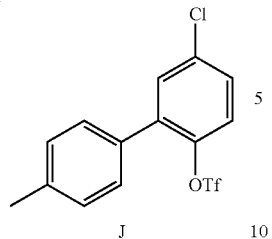

J

Step 1—4-Chloro-2-(p-tolyl)phenol

To a mixture of p-tolylboronic acid (1.44 g, 10.6 mmol), 2-bromo-4-chloro-phenol (2.00 g, 9.64 mmol, CAS #695-96-5) and cesium carbonate (6.28 g, 19.3 mmol) in a mixture of dioxane (30 mL) and water (3 mL) was added Pd(dppf)Cl$_2$ (352 mg, 482 umol) and the reaction mixture was stirred at 90° C. for 16 hrs under nitrogen. On completion, the reaction mixture was concentrated in vacuo and diluted with 100 mL DCM and 100 mL water. The mixture was acidified with 1N HCl solution until pH=3. The organic layer was washed with brine (3×50 mL), dried over sodium sulfate, filtered and concentrated in vacuo. The residue was purified by silica gel chromatography (petroleum ether: ethyl acetate=5:1) to give the title compound (1.90 g, 81% yield) as a light yellow oil. LCMS: (ES+) m/z (M−H)$^-$=217.0, tR=1.516. $^1$H NMR (400 MHz, CDCl$_3$) δ=7.36-7.30 (m, 4H), 7.23-7.17 (m, 2H), 6.94-6.89 (d, J=7.2 Hz, 1H), 5.19 (s, 1H), 2.43 (s, 3H).

Step 2—[4-Chloro-2-(p-tolyl)phenyl] trifluoromethanesulfonate

To a solution of 4-chloro-2-(p-tolyl)phenol (1.00 g, 4.57 mmol) in DCM (15 mL) was added pyridine (723 mg, 9.15 mmol) and the solution was cooled to 0° C. Trifluoromethanesulfonic anhydride (0.9 mL, 5.49 mmol) was added dropwise and then the reaction mixture was warmed to 15° C. and stirred for 1 hr. On completion, the reaction mixture was diluted with DCM (20 mL) and water (20 mL), then acidified with 1 N HCl solution until pH=6. The layers were separated and the organic phase was washed with saturated brine, dried over anhydrous sodium sulfate, filtered and concentrated in vacuo. The residue was purified by column chromatography (petroleum ether:ethyl acetate=10:1) to give the title compound (1.4 g, 87% yield) as a yellow oil. $^1$H NMR (400 MHz, CD$_3$Cl) δ=7.46 (d, J=2.4 Hz, 1H), 7.36 (d, J=2.4 Hz, 1H), 7.33 (d, J=3.6 Hz, 2H), 7.31-7.26 (m, 3H), 2.42 (s, 3H).

(Intermediate K)
[4-Chloro-2-(3-cyanophenyl)phenyl] trifluoromethanesulfonate

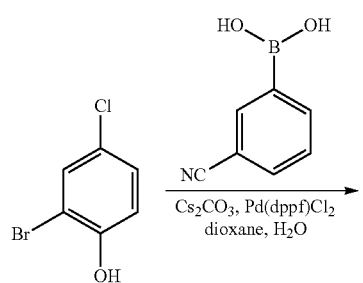

-continued

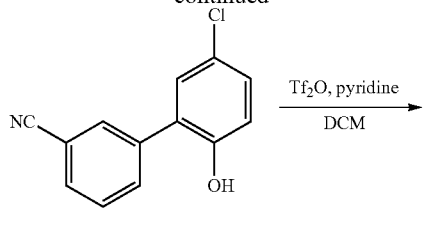

K

Step 1—3-(5-Chloro-2-hydroxy-phenyl)benzonitrile

To a mixture of 2-bromo-4-chloro-phenol (1.00 g, 4.82 mmol), (3-cyanophenyl)boronic acid (708 mg, 4.82 mmol) in dioxane (30 mL) and water (3 mL) was added cesium carbonate (3.14 g, 9.64 mmol) and Pd(dppf)Cl$_2$(176 mg, 241 umol). Then the mixture was stirred at 70° C. for 12 hrs under nitrogen atmosphere. On completion, the reaction mixture was concentrated in vacuo. The residue was diluted with water (100 mL) and EtOAc (100 mL). The organic layer separated and was dried over sodium sulfate, filtered and concentrated in vacuo. The residue was purified by column chromatography (petroleum ether:ethyl acetate=10:1) to give the title compound (500 mg, 45% yield) as a yellow solid. LCMS: (ES+) m/z (M−H)$^-$=228.0, tR=1.36.

Step 2—[4-Chloro-2-(3-cyanophenyl)phenyl] trifluoromethanesulfonate

To a solution of 3-(5-chloro-2-hydroxy-phenyl)benzonitrile (600 mg, 2.61 mmol) in DCM (15 mL) was added pyridine (413 mg, 5.23 mmol), and the solution was cooled to 0° C. Trifluoromethanesulfonic anhydride (885 mg, 3.14 mmol) was added dropwise and then the reaction mixture was warmed to 15° C. and stirred for 1 hour. On completion, the reaction mixture was diluted with DCM (20 mL) and water (20 mL). The organic phase was separated and washed with saturated brine, dried over anhydrous sodium sulfate, filtered and concentrated in vacuo. The residue was purified by column chromatography (petroleum ether:ethyl acetate=10:1) to give the title compound (600 mg, 64% yield) as a yellow oil. $^1$H NMR (400 MHz, CDCl$_3$) δ=7.78-7.75 (m, 1H), 7.75 (d, J=1.6 Hz, 1H), 7.72-7.68 (m, 1H), 7.63 (d, J=8.0 Hz, 1H), 7.51-7.45 (m, 2H), 7.38 (d, J=8.8 Hz, 1H).

(Intermediate L) [4-Chloro-2-(4-fluorophenyl)phenyl] trifluoromethanesulfonate

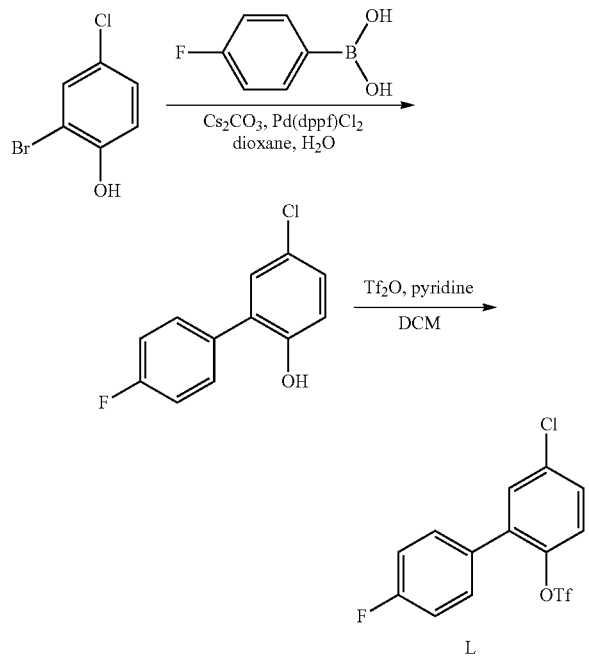

Step 1—4-Chloro-2-(4-fluorophenyl)phenol

To a mixture of 2-bromo-4-chloro-phenol (2.00 g, 9.64 mmol), (4-fluorophenyl)boronic acid (1.62 g, 11.6 mmol) and cesium carbonate (6.28 g, 19.3 mmol) in dioxane (20 mL) and water (2 mL) was added Pd(dppf)Cl$_2$ (353 mg, 482 umol) and the reaction mixture was stirred at 90-100° C. for 16 hrs under nitrogen. On completion, the reaction mixture was concentrated in vacuo. The residue was diluted with DCM (50 mL) and water (50 mL), and acidified with 1 N HCl solution until pH=4-5. The organic phase separated and was dried over anhydrous sodium sulfate, filtered and concentrated in vacuo. The residue was purified by silica gel chromatography (petroleum ether:ethyl acetate=5:1) to give the title compound (1.70 g, 79% yield) a as yellow oil. $^1$H NMR (400 MHz, CDCl$_3$) δ=7.48-7.40 (m, 2H), 7.24-7.16 (m, 4H), 6.94-6.89 (m, 1H), 5.04 (s, 1H)

Step 2—[4-Chloro-2-(4-fluorophenyl)phenyl] trifluoromethanesulfonate

To a solution of 4-chloro-2-(4-fluorophenyl)phenol (1.10 g, 4.94 mmol) in DCM (15 mL) was added pyridine (782 mg, 9.88 mmol) and the solution was cooled to 0° C. Trifluoromethanesulfonic anhydride (1.67 g, 5.93 mmol) was added dropwise and then the reaction mixture was warmed to 15° C. and stirred for 1 hr. On completion, the reaction mixture was diluted with DCM (20 mL) and water (20 mL), and acidified with 1 N HCl solution until pH=6. The organic phase was separated and washed with brine, dried over anhydrous sodium sulfate, filtered and concentrated in vacuo. The residue was purified by column chromatography (petroleum ether:ethyl acetate=10:1) to give the title compound (1.60 g, 91% yield) as a colorless oil. 1H NMR (400 MHz, CDCl$_3$) δ=7.47-7.39 (m, 4H), 7.33 (d, J=2.0, 1H), 7.21-7.14 (m, 2H).

(Intermediate M) 4-Chloro-3-phenyl-pyridine

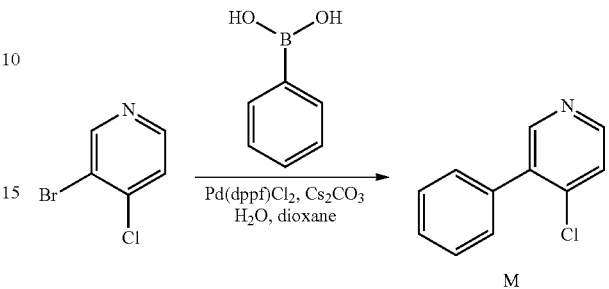

A mixture of 3-bromo-4-chloro-pyridine (4.00 g, 20.8 mmol, CAS #36593-42-1), phenylboronic acid (3.04 g, 24.9 mmol), cesium carbonate (13.5 g, 41.6 mmol) and Pd(dppf)Cl$_2$ (760 mg, 1.04 mmol) in dioxane (40 mL) and water (4 mL) was stirred at 60-70° C. for 5 hrs under nitrogen atmosphere. On completion, the reaction mixture was concentrated in vacuo, then diluted with DCM (30 mL) and water (30 mL). The organic phase separated and was dried over anhydrous sodium sulfate, filtered and concentrated in vacuo. The residue was purified by column chromatography (petroleum ether: ethyl acetate=5:1) to give the title compound (2.6 g, 63% yield) as a yellow oil. LCMS: (ES$^+$) m/z (M+1)$^+$=190.0, tR=0.656. $^1$H NMR (400 MHz, CDCl$_3$) δ=8.57 (s, 1H), 8.49 (d, J=5.2 Hz, 1H), 7.52-7.49 (m, 1H), 7.48-7.46 (m, 4H), 7.44 (d, J=5.2 Hz, 1H).

(Intermediate N) Ethyl 2-[2-(2-bromo-4-methoxy-phenyl)thiazol-4-yl]acetate

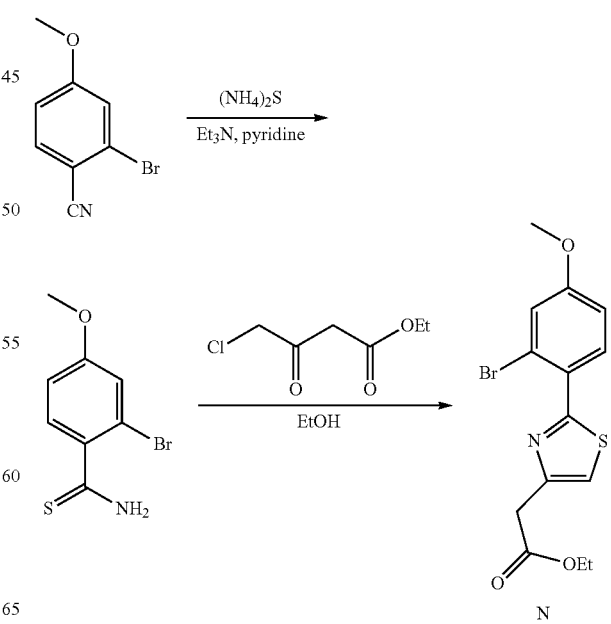

Step 1—2-Bromo-4-methoxy-benzenecarbothioamide

A mixture of 2-bromo-4-methoxy-benzonitrile (1.00 g, 4.72 mmol, CAS #42872-73-1), triethylamine (954 mg, 9.44 mmol) and ammonia hydrogen sulfide (3.22 g, 47.2 mmol) in pyridine (15 mL) was stirred at 70° C. for 16 hours in a 100 mL autoclave. On completion, the reaction mixture was concentrated in vacuo. The residue was purified by silica gel chromatography (petroleum ether:ethyl acetate=10:1) to give the title compound (850 mg, 64% yield) as a yellow solid. $^1$H NMR (400 MHz, CDCl$_3$) δ=7.92 (br. s., 1H), 7.71 (d, J=8.8 Hz, 1H), 7.20 (br. s., 1H), 7.08 (d, J=2.4 Hz, 1H), 6.87 (dd, J=2.4, 8.8 Hz, 1H), 3.83 (s, 3H).

Step 2—Ethyl 2-[2-(2-bromo-4-methoxy-phenyl)thiazol-4-yl]acetate

To a solution of 2-bromo-4-methoxy-benzenecarbothioamide (750 mg, 3.05 mmol) in EtOH (5 mL) was added ethyl 4-chloro-3-oxo-butanoate (899 mg, 5.46 mmol), and the reaction mixture was stirred at 80° C. for 16 hours. On completion, the reaction mixture was concentrated in vacuo to remove EtOH. The residue was purified by silica gel chromatography (petroleum ether:ethyl acetate=50:1 to 3:1) to give the title compound (760 mg, 70% yield) as a yellow solid. $^1$H NMR (400 MHz, CDCl$_3$) δ=7.99 (d, J=8.8 Hz, 1H), 7.31 (s, 1H), 7.23 (d, J=2.4 Hz, 1H), 6.95 (dd, J=2.4, 8.8 Hz, 1H), 4.25 (q, J=7.2 Hz, 2H), 3.92 (s, 2H), 3.87 (s, 3H), 1.32 (t, J=7.2 Hz, 3H).

(Intermediate O) Ethyl 2-(2-(2-bromo-4,5-dichlorophenyl)thiazol-4-yl)acetate

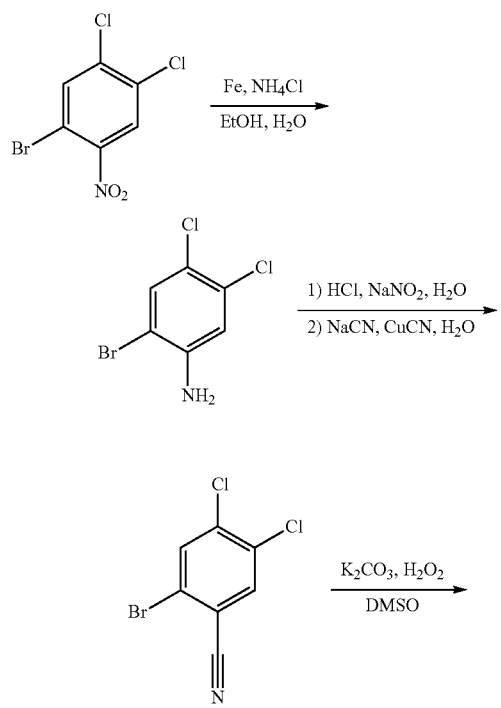

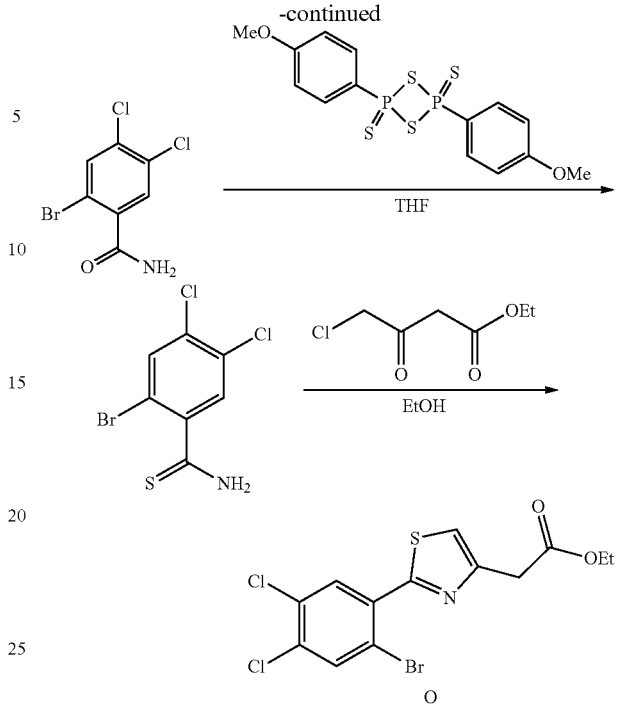

Step 1—2-Bromo-4,5-dichloroaniline

To a solution of 1-bromo-4,5-dichloro-2-nitro-benzene (5.00 g, 18.5 mmol, CAS #93361-94-5) in ethanol (30 mL) and water (10 mL) was added ammonium chloride (523 mg, 9.78 mmol) and iron powder (4.90 g, 87.7 mmol) at 60° C. The reaction mixture was stirred at 78° C. for 12 hrs. On completion, the reaction mixture was diluted with ethanol (50 mL), filtered and concentrated in vacuo to remove the ethanol. Water (20 mL) was added to the residue and was extracted with ethyl acetate (3×50 mL). The combined organic layer was washed with brine (30 mL), dried over anhydrous sodium sulfate, filtered and concentrated in vacuo to give a white solid. The white solid was purified by silica gel chromatography (petroleum ether: ethyl acetate=10:1) to give the title compound (3.80 g, 85% yield) as a white solid. $^1$H NMR (400 MHz, CDCl$_3$) δ=7.48 (s, 1H), 6.85 (s, 1H), 4.26-4.08 (br. s, 2H).

Step 2—2-Bromo-4,5-dichlorobenzonitrile

To a suspension of 2-bromo-4,5-dichloro-aniline (6.50 g, 27.0 mmol) in water (14 mL) was added concentrated HCl (12 M, 8.99 mL) and the resulting mixture was cooled to 0° C. with vigorous stirring. Then, a solution of NaNO$_2$ (2.79 g, 40.5 mmol) in water (2 mL) was added dropwise while maintaining the internal temperature below 4° C. After 30 min, the mixture containing the diazonium salt was slowly added, through an addition funnel and maintaining the temperature below 5° C., over a stirred solution of CuCN (3.38 g, 37.8 mmol) and NaCN (3.97 g, 80.9 mmol) in water (14 mL). Once the addition was finished, the reaction mixture was allowed to warm to 20° C. and vigorous stirring was maintained for 4 hours. On completion, saturated sodium bicarbonate solution was added to the mixture to adjust the pH>8, and the aqueous phase was extracted with dichloromethane (3×50 mL). The combined organic layers were washed with brine (2×50 mL), dried over anhydrous sulfate sodium and concentrated in vacuo to give a brown solid. The brown solid was purified by silica gel chromatography (petroleum ether:dichloromethane=100:1) to give the title compound (4.00 g, 59% yield) as a yellow solid. $^1$H NMR (400 MHz, CDCl$_3$) δ=7.82 (s, 1H), 7.75 (s, 1H).

Step 3—2-Bromo-4,5-dichlorobenzamide

To a mixture of 2-bromo-4,5-dichloro-benzonitrile (1.00 g, 3.99 mmol) and hydrogen peroxide (1.36 g, 39.9 mmol, 1.15 mL) in dimethylsulfoxide (5 mL) was added potassium carbonate (220 mg, 1.59 mol) in one portion at 15° C. Then the mixture was heated to 60° C. (oil-bath temperature) and stirred for 3 hours. On completion, the reaction mixture was diluted with water (10 mL), filtered and the filter cake was dried in vacuo to give the title compound (1.06 g, 99% yield) as a yellow solid. LCMS: (ES+) m/z (M+1)+=269.9.

Step 4—2-Bromo-4,5-dichlorobenzothioamide

To a solution of 2-bromo-4,5-dichloro-benzamide (1.06 g, 3.94 mmol) in tetrahydrofuran (10 mL) was added 2,4-bis(4-methoxyphenyl)-2,4-dithioxo-1,3,2,4dithiadiphosphetane (Lawesson's reagent, 1.59 g, 3.94 mmol) under a nitrogen. The reaction mixture was stirred at 70° C. for 5 hrs. On completion, the reaction mixture was diluted with water (20 mL) and extracted with ethyl acetate (3×100 mL). The combined organic layer was washed with brine (100 mL), dried over with anhydrous sodium sulfate, filtered and concentrated in vacuo to give the residue. The residue was purified by silica gel chromatography (petroleum ether:ethyl acetate=10:1) to give the title compound (765 mg, 68% yield) as a yellow solid. $^1$H NMR (400 MHz, CDCl$_3$) δ=7.80 (br. s., 1H), 7.71 (s, 1H), 7.69 (s, 1H), 7.05 (br. s., 1H).

Step 5—Ethyl 2-(2-(2-bromo-4,5-dichlorophenyl)thiazol-4-yl)acetate

To a solution of 2-bromo-4,5-dichloro-benzenecarbothioamide (765 mg, 2.68 mmol) in ethanol (10 mL) was added ethyl 4-chloro-3-oxo-butanoate (882 mg, 5.36 mmol). The reaction mixture was stirred at 80° C. for 12 hrs. On completion, the reaction mixture was concentrated in vacuo to give a residue. The residue was triturated with tert-butyl methyl ether (5 mL) to give the title compound (815 mg, 77% yield) as a white solid. $^1$H NMR (400 MHz, CDCl$_3$) δ=8.27 (s, 1H), 7.80 (s, 1H), 7.41 (s, 1H), 4.24 (q, J=7.2 Hz, 2H), 3.92 (s, 2H), 1.31 (t, J=7.2 Hz, 3H).

(Intermediate P) Ethyl 2-[2-(2-bromo-4-chloro-5-methoxy-phenyl)thiazol-4-yl]acetate

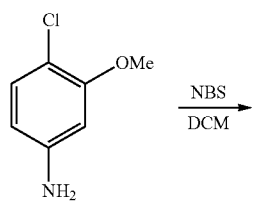

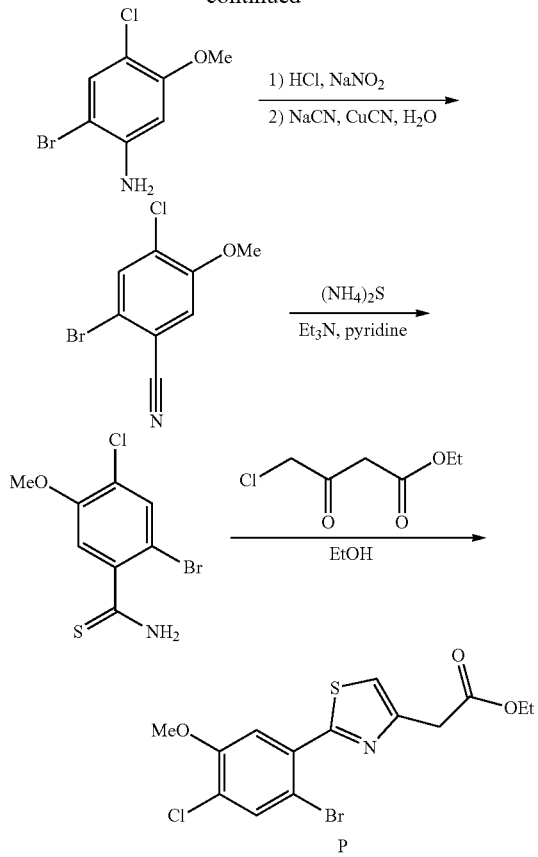

Step 1—2-Bromo-4-chloro-5-methoxy-aniline

A solution of 4-chloro-3-methoxy-aniline (7.00 g, 44.4 mmol) dissolved in dichloromethane (100 mL) at 5° C. was treated portions with NBS (8.14 g, 45.7 mmol) over 1 hour, then warmed to 20° C. and stirred at 20° C. for 2 hours. On completion, a 5% aqueous Na$_2$SO$_3$ solution (100 mL) was added and the mixture was stirred for 10 minutes. The layers were separated and the organic layer was washed with water and saturated brine, dried over anhydrous Na$_2$SO$_4$, filtered and concentrated in vacuo. The getting residue was purified by column chromatography (petroleum ether: ethyl acetate=3:1) to give the title compound (9.00 g, 85% yield) as a dark brown solid. $^1$H NMR (400 MHz, CD$_3$Cl) δ=7.37 (s, 1H), 6.35 (s, 1H), 4.13 (br. s., 2H), 3.83 (s, 3H).

Step 2—2-Bromo-4-chloro-5-methoxy-benzonitrile

To a suspension of 2-bromo-4-chloro-5-methoxy-aniline (9.00 g, 38.1 mmol) in water (140 mL) was added concentrated HCl (12.7 mL) and the resulting mixture was cooled to 0° C. with vigorous stirring. Then, a solution of sodium nitrite (3.94 g, 57.0 mmol) dissolved in water (20 mL) was added dropwise while maintaining the internal temperature below 4° C. After 30 minutes, the mixture containing the diazonium salt was slowly added, through an addition funnel and maintaining the temperature below 5° C., over a stirred solution of CuCN (4.77 g, 53.3 mmol) and NaCN (5.60 g, 114 mmol) dissolved in water (140 mL). Once the addition was finished, the reaction mixture was allowed to warm to 20° C. and a vigorous stirring was maintained for 4 hours.

On completion, saturated sodium bicarbonate solution was added to the mixture to adjust the pH>8, and the aqueous phase was extracted with dichloromethane 900 mL (3×300 mL). The combined organic extracts were washed with brine and concentrated in vacuo. The residue was triturated with petroleum ether and ethyl acetate (10:1) to give the title compound (3.80 g, 40% yield) as a yellow solid. ¹H NMR (400 MHz, CD₃Cl) δ=7.69 (s, 1H), 7.16 (s, 1H), 3.95 (s, 3H).

Step 3—2-Bromo-4-chloro-5-methoxy-benzenecarbothioamide

A mixture of 2-bromo-4-chloro-5-methoxy-benzonitrile (3.00 g, 12.8 mmol), triethylamine (2.46 g, 24.3 mmol, 3.37 mL) and ammonia sulfide (8.29 g, 121 mmol, 8.29 mL) in pyridine (45.0 mL) was stirred at 70° C. for 16 hours in a 100 mL autoclave. On completion, the reaction mixture was concentrated in vacuo. The residue was diluted with water (90 mL) and extracted with dichloromethane (3×60 mL). The combined organic phase was dried over anhydrous sodium sulfate, filtered and concentrated in vacuo to give a residue. The residue was purified by column chromatography (petroleum ether: ethyl acetate=5:1 to 3:1) to give the title compound (1.70 g, 49% yield) as a yellow solid. ¹H NMR (400 MHz, CD₃Cl) δ=7.90 (br. s., 1H), 7.57 (s, 1H), 7.26 (s, 1H), 7.16 (br. s., 1H), 3.94 (s, 3H).

Step 4—Ethyl 2-[2-(2-bromo-4-chloro-5-methoxyphenyl)thiazol-4-yl]acetate

To a solution of 2-bromo-4-chloro-5-methoxy-benzenecarbothioamide (600 mg, 2.14 mmol) in ethanol (15.0 mL) was added ethyl 4-chloro-3-oxo-butanoate (528 mg, 3.21 mmol). The mixture was stirred at 70° C. for 16 hours. On completion, the reaction mixture was concentrated in vacuo to remove the solvent. The residue was triturated with petroleum ether:dichloromethane (50:1) to give the title compound (540 mg, 64% yield) as a yellow solid. ¹H NMR (400 MHz, CD₃Cl) δ=7.74 (s, 1H), 7.70 (s, 1H), 7.40 (s, 1H), 4.25 (q, J=7.2 Hz, 2H), 4.00 (s, 3H), 3.95 (s, 2H), 1.32 (t, J=7.2 Hz, 3H).

(Intermediate Q) Ethyl 2-[2-(5-phenyl-2,3-dihydro-1,4-benzodioxin-6-yl)thiazol-4-yl]acetate

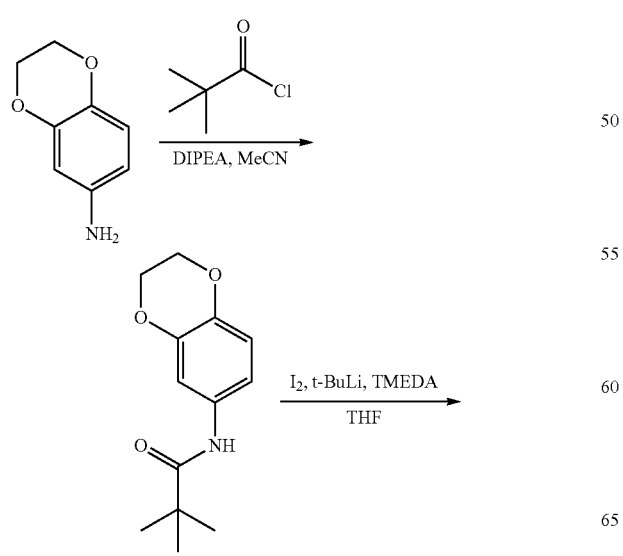

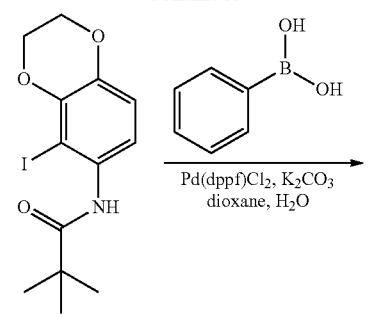

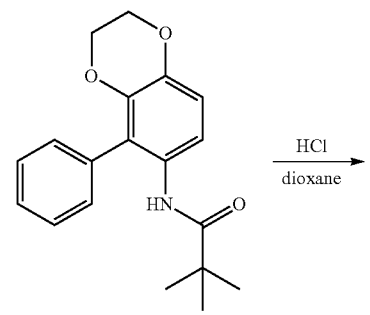

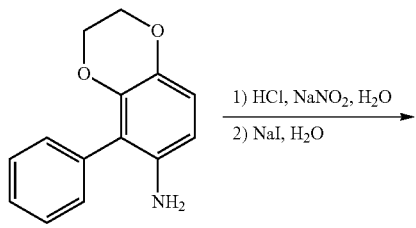

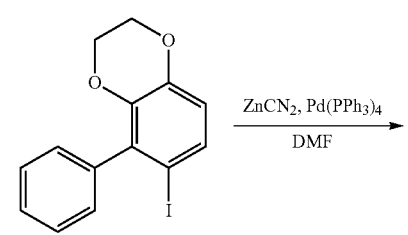

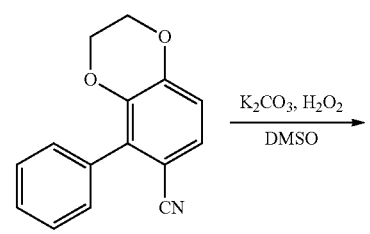

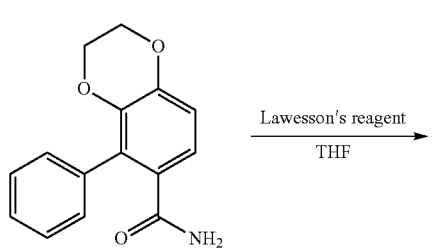

-continued

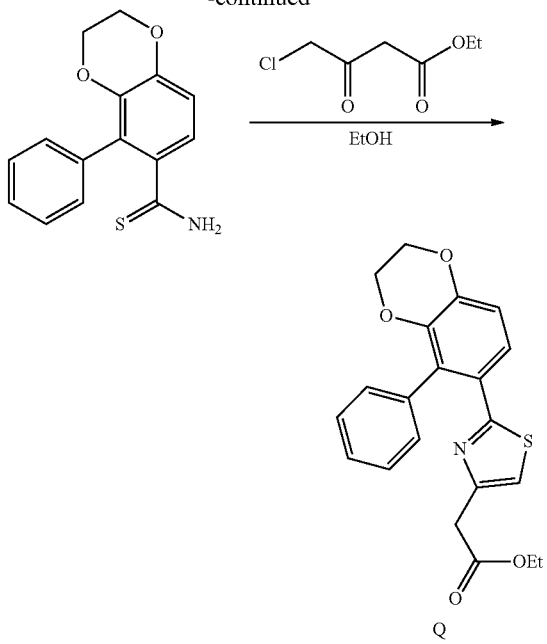

Step 1—N-(2,3-dihydro-1,4-benzodioxin-6-yl)-2,2-dimethyl-propanamide

To a solution of 2,3-dihydro-1,4-benzodioxan-6-amine (20.0 g, 132 mmol, CAS #22013-33-8) and diisopropylethylamine (20.5 g, 158 mmol) in acetonitrile (100 mL) was added 2,2-dimethylpropanoyl chloride (17.5 g, 145 mmol) and the reaction mixture was stirred at 15° C. for 0.5 hrs. Then the reaction mixture was stirred at 45° C. for 2.5 hrs. On completion, the reaction mixture was concentrated in vacuo and the residue was diluted with 500 mL of DCM. The organic layer was separated and washed with 1N HCl solution until the pH=6. The organic layer was dried over $Na_2SO_4$, filtered and concentrated in vacuo. The residue was triturated with MTBE (500 mL) to give the title compound (30.0 g, 96% yield) as a white solid. $^1$H NMR (400 MHz, CDCl$_3$) δ=7.20 (br. s., 1H), 7.18 (d, J=2.4 Hz, 1H), 6.91 (dd, J=2.4, 8.8 Hz, 1H), 6.82 (d, J=8.8 Hz, 1H), 4.29-4.21 (m, 4H), 1.31 (s, 9H).

Step 2—N-(5-iodo-2,3-dihydro-1,4-benzodioxin-6-yl)-2,2-dimethyl-propanamide

To a solution of N-(2,3-dihydro-1,4-benzodioxin-6-yl)-2,2-dimethyl-propanamide (7.00 g, 29.7 mmol) and tetramethylethylenediamine (10.3 g, 89.2 mmol) in THF (400 mL) was added t-BuLi (1.3 M, 68.6 mL) dropwise at −78° C., then reaction mixture was stirred at −30° C. for 2 hrs under nitrogen. Next, the reaction mixture was cool to −70° C. and iodine (22.6 g, 89.2 mmol) in THF (200 mL) was added dropwise. Finally, the reaction mixture was warmed to 0° C. over 2 hrs, then stirred at 20° C. for 12 hrs. On completion, the reaction mixture was quenched by saturated sodium thiosulfate solution (300 mL) and concentrated in vacuo to remove the THF. The aqueous phase was extracted with DCM (3×500 mL), dried over $Na_2SO_4$, filtered and concentrated in vacuo. The residue was purified by silica gel chromatography (petroleum ether: ethyl acetate=5:1) to give the title compound (4.00 g, 37% yield) as an off-white solid. $^1$H NMR (400 MHz, CDCl$_3$) δ=7.76 (d, J=8.8 Hz, 1H), 7.71 (br. s., 1H), 6.89 (d, J=8.8 Hz, 1H), 4.40-4.32 (m, 2H), 4.27-4.21 (m, 2H), 1.37 (s, 9H).

Step 3—2,2-Dimethyl-N-(5-phenyl-2,3-dihydro-1,4-benzodioxin-6-yl)propanamide A mixture of N-(5-iodo-2,3-dihydro-1,4-benzodioxin-6-yl)-2,2-dimethyl-propanamide (3.30 g, 9.14 mmol), potassium carbonate (2.53 g, 18.2 mmol), Pd(dppf)Cl$_2$ (334 mg, 457 umol) and phenylboronic acid (1.23 g, 10.0 mmol) in dioxane (100 mL) and water (10 mL) was stirred at 90° C. for 4 hrs under nitrogen. On completion, the reaction mixture was concentrated in vacuo. The residue was purified by flash (petroleum ether: ethyl acetate=10:1) to give the title compound (2.80 g, 98% yield) as a white solid $^1$H NMR (400 MHz, CDCl$_3$) δ=7.79 (d, J=8.8 Hz, 1H), 7.55-7.48 (m, 2H), 7.46-7.41 (m, 1H), 7.33-7.29 (m, 2H), 7.02 (br. s., 1H), 6.90 (d, J=8.8 Hz, 1H), 4.27-4.23 (m, 2H), 4.22-4.19 (m, 2H), 1.01 (s, 9H).

Step 4—5-Phenyl-2,3-dihydro-1,4-benzodioxin-6-amine

To a solution of 2,2-dimethyl-N-(5-phenyl-2,3-dihydro-1,4-benzodioxin-6-yl)propanamide (2.80 g, 8.99 mmol) in dioxane (50 mL) was added concentrated hydrochloric acid (12 M, 77 mL) and the reaction mixture was stirred at 110° C. for 16 hrs. On completion, the reaction mixture was concentrated in vacuo. The residue was triturated with 50 mL of MTBE to give the title compound (2.20 g, 92% yield, HCl salt) as an off-white solid. $^1$H NMR (400 MHz, DMSO-d$_6$) δ=9.65 (br. s., 3H), 7.52-7.42 (m, 3H), 7.42-7.37 (m, 2H), 7.05 (d, J=8.0 Hz, 1H), 7.00 (d, J=8.0 Hz, 1H), 4.27-4.23 (m, 2H), 4.21-4.16 (m, 2H).

Step 5—6-Iodo-5-phenyl-2,3-dihydro-1,4-benzodioxine

To a solution of 5-phenyl-2,3-dihydro-1,4-benzodioxin-6-amine (2.20 g, 8.34 mmol, HCl salt) in water (150 mL) was added concentrated hydrochloric acid (12 M, 1.39 mL) and the reaction mixture was stirred at 0° C. for 10 min. Then a solution of sodium nitrite (748 mg, 10.8 mmol) in water (30 mL) was added dropwise and the reaction mixture was stirred at 0° C. for 0.5 hr. Finally, a solution of sodium iodide (2.76 g, 18.4 mmol) in water (0.5 mL) was added and the reaction mixture was stirred at 20° C. for 0.5 hr. On completion, the reaction mixture was extracted with ethyl acetate (3×100 mL). The combined organic layer was dried over $Na_2SO_4$, filtered and concentrated in vacuo. The residue was purified by silica gel chromatography (petroleum ether:ethyl acetate=20:1) to give the title compound (2.20 g, 78% yield) as a yellow solid. $^1$H NMR (400 MHz, CDCl$_3$) δ=7.52-7.39 (m, 4H), 7.27-7.22 (m, 2H), 6.69 (d, J=8.4 Hz, 1H), 4.29-4.23 (m, 2H), 4.23-4.16 (m, 2H).

Step 6—5-Phenyl-2,3-dihydro-1,4-benzodioxine-6-carbonitrile

To a mixture of 6-iodo-5-phenyl-2,3-dihydro-1,4-benzodioxine (1.00 g, 2.96 mmol) and zinc cyanide (1.04 g, 8.88 mmol) in DMF (15.00 mL) was added Pd(PPh$_3$)$_4$ (341 mg, 296 umol) and the reaction mixture was stirred at 130° C. for 16 hrs. On completion, the reaction mixture was diluted with 300 mL water and extracted with ethyl acetate (3×100 mL). The combined organic layer was dried over $Na_2SO_4$, filtered and concentrated in vacuo. The residue was purified by flash (petroleum ether: ethyl acetate=5:1) to give the title compound (650 mg, 92% yield) as a white solid. $^1$H NMR (400 MHz, CDCl$_3$) δ=7.45-7.32 (m, 5H), 7.20 (d, J=8.4 Hz, 1H), 6.86 (d, J=8.4 Hz, 1H), 4.29-4.21 (m, 2H), 4.20-4.13 (m, 2H).

Step 7—5-Phenyl-2,3-dihydro-1,4-benzodioxine-6-carboxamide

To a solution of 5-phenyl-2,3-dihydro-1,4-benzodioxine-6-carbonitrile (650 mg, 2.74 mmol) and potassium carbonate (151 mg, 1.10 mmol) in DMSO (10 mL) was added hydrogen peroxide (2.82 mL, 28%) dropwise and the reaction mixture was stirred at 50° C. for 16 hrs. On completion, the reaction mixture was diluted with 40 mL water and extracted with ethyl acetate (3×20 mL). The combined organic layer was dried over Na$_2$SO$_4$, filtered and concentrated in vacuo to give the title compound (650 mg, 93% yield) as a light yellow solid. LCMS: (ES+) m/z (M+H)$^+$=256.0, tR=0.600.

Step 8—5-Phenyl-2,3-dihydro-1,4-benzodioxine-6-carbothioamide

To a solution of 5-phenyl-2,3-dihydro-1,4-benzodioxine-6-carboxamide (550 mg, 2.15 mmol) in THF (15 mL) was added 2,4-bis(4-methoxyphenyl)-2,4-dithioxo-1,3,2,4dithiadiphosphetane (1.04 g, 2.58 mmol) and the reaction mixture was stirred at 66° C. for 16 hrs under nitrogen. On completion, the reaction mixture was concentrated in vacuo. The residue was purified by silica gel chromatography (petroleum ether:ethyl acetate=5:1) to give the title compound (330 mg, 41% yield) as a light yellow solid. LCMS: (ES+) m/z (M+H)$^+$=272.1, tR=1.167.

Step 9—Ethyl 2-[2-(5-phenyl-2,3-dihydro-1,4-benzodioxin-6-yl)thiazol-4-yl]acetate To a solution of 5-phenyl-2,3-dihydro-1,4-benzodioxine-6-carbothioamide (330 mg, 1.22 mmol) in EtOH (20 mL) was added ethyl 4-chloro-3-oxo-butanoate (359 mg, 2.18 mmol) and the reaction mixture was stirred at 80° C. for 6 hours. On completion, the reaction mixture was concentrated in vacuo to remove the EtOH. The residue was purified by column chromatography (petroleum ether:ethyl acetate=3:1) to give the title compound (250 mg, 97% yield). LCMS: (ES$^+$) m/z (M+1)$^+$=382.1, tR=0.802. $^1$H NMR (400 MHz, CDCl$_3$) δ=7.65 (d, J=8.8 Hz, 1H), 7.46-7.37 (m, 3H), 7.30-7.26 (m, 2H), 6.98 (d, J=8.8 Hz, 1H), 6.96 (s, 1H), 4.32-4.27 (m, 2H), 4.24-4.21 (m, 2H), 4.15 (q, J=7.2 Hz, 2H), 3.79 (s, 2H), 1.28 (t, J=7.2 Hz, 3H).

(Intermediate R) Cyclobutylmethyl(trifluoro)boranuide potassium Salt

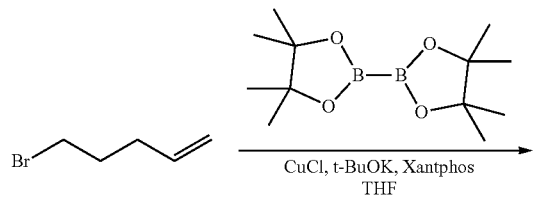

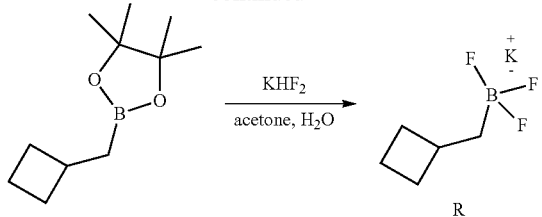

Step 1—2-(Cyclobutylmethyl)-4,4,5,5-tetramethyl-1,3,2-dioxaborolane

Copper chloride (220 mg, 2.23 mmol), 4,4,5,5-tetramethyl-2-(4,4,5,5-tetramethyl-1,3,2-dioxaborolan-2-yl)-1,3,2-dioxaborolane (16.9 g, 66.8 mmol), and Xantphos (1.29 g, 2.23 mmol) were placed in an oven-dried reaction flask. THF (50.0 mL) and a solution of t-BuOK (7.50 g, 66.8 mmol) in THF (5.00 mL) were then added in the flask under nitrogen. Then 5-bromopent-1-ene (8.30 g, 55.7 mmol) was added dropwise while the solution was heated to 30° C. and the mixture was stirred at 30° C. for 18 hrs. On completion, the reaction mixture was passed through a short silica gel column eluting with hexane (200 mL). The crude mixture was further purified by flash column chromatography (SiO$_2$, PE/EA, 100:0-96:4) to give the title compound (9.20 g, 71% yield, 85% purity) as a colorless oil. $^1$H NMR (400 MHz, CDCl$_3$, δ=2.47 (m, 1H), 2.04-2.11 (m, 2H), 1.72-1.85 (m, 2H), 1.54-1.64 (m, 2H), 1.23 (s, 12H), 0.94 (d, J=7.8 Hz, 2H).

Step 2—Cyclobutylmethyl(trifluoro)boranuide potassium Salt

To a mixture of 2-(cyclobutylmethyl)-4,4,5,5-tetramethyl-1,3,2-dioxaborolane (6.00 g, 30.6 mmol) and KHF$_2$ (7.17 g, 91.8 mmol) in acetone (30.0 mL) was added water (30.0 mL) dropwise at 0° C. Then the reaction mixture was warmed to 15° C., and stirred at 15° C. for 2.5 hrs. On completion, the solvent was removed under reduced pressure. The residue was dissolved in acetone, and diethyl ether was added. The precipitate was filtered to give the title product (5.00 g, 74.26% yield) as a white solid $^1$H NMR (400 MHz, D2O) δ=2.04 (m, 1H), 1.77 (m, 2H), 1.59-1.42 (m, 2H), 1.37-1.24 (m, 2H), 0.17 (m, 2H)

(Intermediate S) Iodo(tetrahydropyran-4-yl)zinc

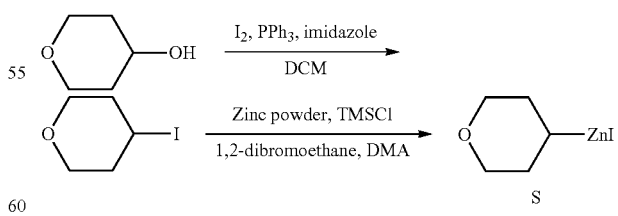

Step 1—4-Iodotetrahydropyran

To a solution of tetrahydropyran-4-ol (15.0 g, 146 mmol, 14.71 mL) in dichloromethane (600 mL) was added PPh$_3$ (50.0 g, 191 mmol) and imidazole (15.0 g, 220 mmol). The mixture was stirred at 0° C. and iodine (44.7 g, 176 mmol) was added in portions under a nitrogen atmosphere. Finally, the mixture was stirred at 15° C. for 16 hours. On completion, the reaction mixture was filtered and the filtrate was concentrated in vacuo to get a residue. The residue was diluted with water (150 mL) and extracted with ethyl acetate (3×150 mL). The combined organic layers were dried over anhydrous Na₂SO₄, filtered and concentrated in vacuo to give a residue. The residue was purified by column chromatography (petroleum ether:dichloromethane=1:0 to 2:1) to give the title compound (16.0 g, 51% yield) as a colorless oil. ¹H NMR (400 MHz, CDCl₃) δ=4.48-4.41 (m, 1H), 3.80 (td, J=4.4, 11.6 Hz, 2H), 3.56-3.46 (m, 2H), 2.20-2.09 (m, 4H).

Step 2—Iodo(tetrahydropyran-4-yl)zinc

To a suspension of zinc powder (1.85 g, 28.3 mmol) in redistilled DMA (3.00 mL) under a nitrogen atmosphere was cautiously added a mixture of 1,2-dibromoethane (442 mg, 2.36 mmol, 178 uL) and TMSCl (256 mg, 2.36 mmol, 298 uL) over 10 min at 20° C. The temperature of the reaction mixture rose to about 60° C. during this period. After stirring for 15 min, a solution of 4-iodotetrahydropyran (5.00 g, 23.5 mmol) in redistilled DMA (8.00 mL) was added over 30 min and stirring was continued for an additional 30 min. The temperature of reaction mixture rose to 70° C. during this period. On completion, the reaction mixture was filtered and the filtrate was used into the next step directly.

(Intermediate T) (1-(Tert-butoxycarbonyl)piperidin-4-yl)zinc(II) iodide

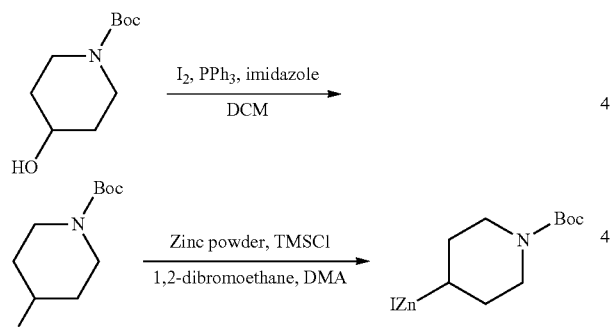

Step 1—Tert-butyl 4-iodopiperidine-1-carboxylate

To a mixture of tert-butyl 4-hydroxypiperidine-1-carboxylate (30.0 g, 149 mmol, CAS #109384-19-2), imidazole (13.1 g, 193 mmol) and PPh₃ (46.9 g, 178 mmol) in DCM (500 mL) was added iodine (45.4 g, 178 mmol) in portions at 0° C. and the reaction mixture was stirred at 25° C. for 16 hrs under nitrogen. On completion, the reaction mixture was filtered and the filtrate was washed with Na₂SO₃ solution until the organic layer was colorless. The organic layer was dried over Na₂SO₄, filtered and concentrated in vacuo. The residue was purified by flash column chromatography (petroleum ether:ethyl acetate=20:1) to give the title compound (42.0 g, 90% yield) as a white solid. ¹H NMR (400 MHz, CDCl₃) δ=4.48-4.42 (m, 1H), 3.64-3.56 (m, 2H), 3.32-3.58 (m, 2H), 2.08-1.97 (m, 4H), 1.46 (s, 9H).

Step 2—(1-(Tert-butoxycarbonyl)piperidin-4-yl)zinc (II) iodide

To a mixture of zinc powder (1.26 g, 19.2 mmol) in dimethylacetamide (10 mL) was added TMSCl (174 mg, 1.61 mmol) and 1,2-dibromoethane (301 mg, 1.61 mmol) at 60° C. under nitrogen. Then tert-butyl 4-iodopiperidine-1-carboxylate (5.00 g, 16.0 mmol) in dimethylacetamide (5 mL) was added at 70° C. and the reaction mixture was stirred at 70° C. for 0.5 hr. The green liquid (1 M) was for the next step directly.

(Intermediate U) Ethyl 2-[2-(4-chloro-2-phenylphenyl)-1,3-thiazol-4-yl]acetate

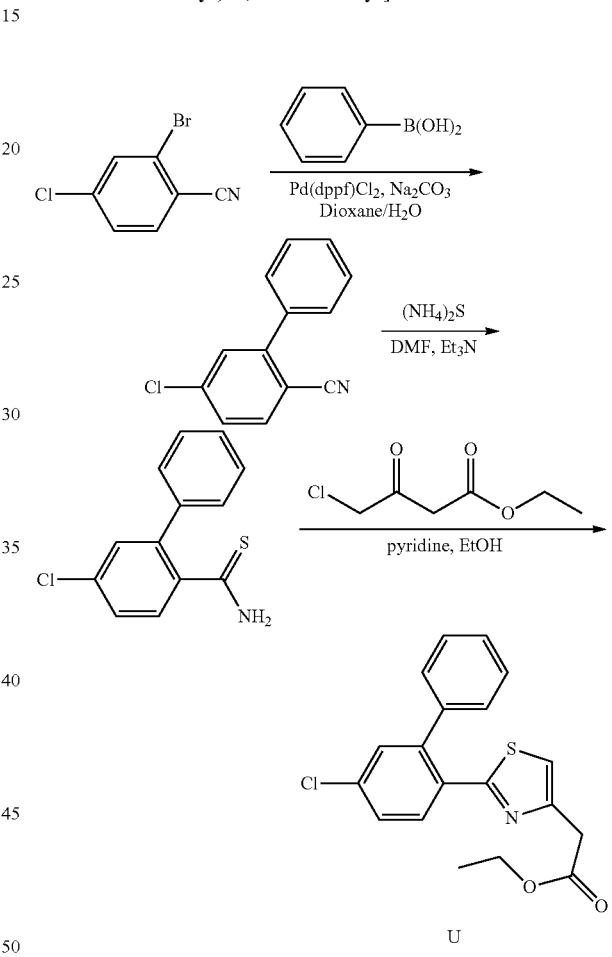

Step 1: 4-Chloro-2-phenylbenzonitrile

Into a 19-mL sealed tube was placed 2-bromo-4-chlorobenzonitrile (216 mg, 1.00 mmol), dioxane (1.5 mL), water (0.3 mL), Pd(dppf)Cl₂ (36 mg, 0.05 mmol), Na₂CO₃ (318 mg, 2.97 mmol), and phenylboronic acid (148 mg, 1.21 mmol). The resulting solution was stirred for 16 h at 95° C. The reaction was then quenched by the addition of 25 mL of water. The resulting solution was extracted with ethyl acetate (3×15 mL) and the organic layers were combined. The organic layer was washed with brine (25 mL), dried over anhydrous sodium sulfate and filtered. The filtrate was concentrated under vacuum. The residue purified via a silica gel chromatography with ethyl acetate/petroleum ether (1:20). This resulted in 50 mg (23% yield) of 4-chloro-2- phenylbenzonitrile as a white solid. ¹H NMR (400 MHz, DMSO-d6, ppm): δ 8.00 (d, J=8.4 Hz, 1H), 7.74 (d, J=2.1 Hz, 1H), 7.68 (dd, J=8.3, 2.2 Hz, 1H), 7.65-7.59 (m, 2H), 7.58-7.48 (m, 3H), 4.04 (dd, J=1.9, 1.0 Hz, 1H).

Step 2:
4-Chloro-2-phenylbenzene-1-carbothioamide

Into a 250-mL 3-necked round-bottom flask was placed 4-chloro-2-phenylbenzonitrile (5.1 g, 23.87 mmol), triethylamine (7.25 g, 71.7 mmol), a solution of (NH₄)₂S (60.0 g, 71.0 mmol, 8% wt in water) and N,N-dimethylformamide (150 mL). The resulting solution was stirred for 120 min at 50° C. The reaction was then quenched by the addition of 600 mL of water. The resulting solution was extracted with ethyl acetate (3×250 mL) and the organic layers were combined. The resulting mixture was washed with water (3×250 mL) and brine (250 mL). The organic layer was dried over anhydrous sodium sulfate, filtered and the filtrate was concentrated under vacuum. The residue was purified by silica gel chromatography with (ethyl acetate/hexane=1:5). This resulted in 6 g (73% purity, 74% yield) of 4-chloro-2-phenylbenzene-1-carbothioamide as yellow oil. LCMS: (ES+) m/z (M+H)⁺=248.1, tR=1.504.

Step 3: Ethyl 2-[2-(4-chloro-2-phenylphenyl)-1,3-thiazol-4-yl]acetate

Into a 250-mL 3-necked round-bottom flask was placed 4-chloro-2-phenylbenzene-1-carbothioamide (3.00 g, 8.80 mmol, 73% purity), pyridine (2.08 g, 26.3 mmol), ethanol (60 mL), and ethyl 4-chloro-3-oxobutanoate (3.98 g, 24.2 mmol). The resulting solution was stirred for 48 h at 80° C. in an oil bath. On completion, the mixture was concentrated under vacuum. The residue was purified by silica gel chromatography with ethyl acetate/petroleum ether (1:10). This resulted in 2.5 g (71% yield) of ethyl 2-[2-(4-chloro-2-phenylphenyl)-1,3-thiazol-4-yl]acetate as a light yellow solid. LCMS: (ES+) m/z (M+H)⁺=358.1, tR=1.778.

(Intermediate V) Ethyl 2-(2,4-dichlorophenyl)-1,3-thiazole-4-carboxylate

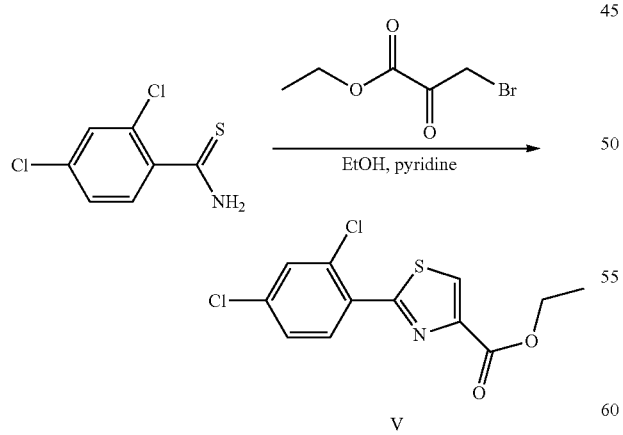

Into a 250-mL round-bottom flask was placed 2,4-dichlorobenzene-1-carbothioamide (4.0 g, 19 mmol, CAS #2775-38-4), ethyl 3-bromo-2-oxopropanoate (10.0 g, 51 mmol), ethanol (20 mL) and pyridine (4.8 g, 61 mmol). The resulting solution was stirred overnight at 80° C. On completion, the reaction mixture was cooled to rt and concentrated under vacuum. The residue was purified by silica gel chromatography with ethyl acetate/petroleum ether (1:5). This resulted in 2.0 g (31% yield) of ethyl 2-(2,4-dichlorophenyl)-1,3-thiazole-4-carboxylate as a yellow solid. LCMS: m/z=302.0 [M+1]⁺, tR=1.3 min. ¹H-NMR: (300 MHz, Chloroform-d) δ 8.32 (s, 1H), 7.54 (d, J=2.1 Hz, 1H), 7.39 (dd, J=8.6, 2.1 Hz, 1H), 4.48 (q, J=7.1 Hz, 2H), 1.45 (t, J=7.1 Hz, 3H).

(Intermediate W) Ethyl 2-(4-chloro-2-phenylphenyl)-1,3-thiazole-4-carboxylate

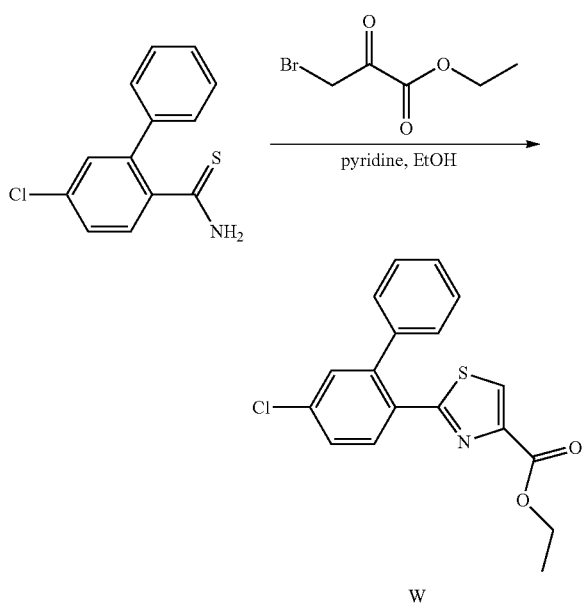

Into a 250-mL 3-necked round-bottom flask was placed 4-chloro-2-phenylbenzene-1-carbothioamide (3.00 g, 8.84 mmol, 73% purity, synthesized from Steps 1-2 of Intermediate U), pyridine (2.08 g, 26.3 mmol), ethanol (60 mL), and ethyl 3-bromo-2-oxopropanoate (5.28 g, 27.1 mmol). The resulting solution was stirred for 48 h at 80° C. On completion, the mixture was concentrated under vacuum. The residue purified by silica gel chromatography with ethyl acetate/petroleum ether (1:10). This resulted in 1.5 g (49% yield) of ethyl 2-(4-chloro-2-phenylphenyl)-1,3-thiazole-4-carboxylate as a white solid. LCMS: (ES+) m/z (M+H)⁺=344.0, tR=1.771.

(Intermediate X) Ethyl 2-(2-(2,4-dichlorophenyl)thiazol-4-yl)acetate

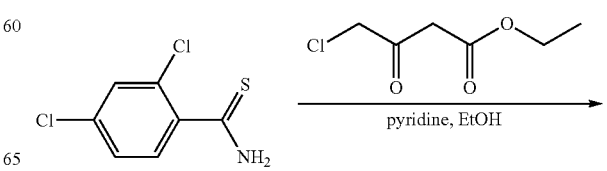

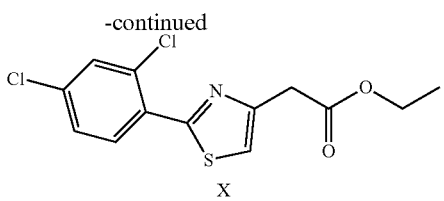

X

Into a 250-mL round-bottom flask was placed 2,4-dichlorobenzene-1-carbothioamide (2.0 g, 9.7 mmol), pyridine (3 mL), ethanol (100 mL) and ethyl 4-chloro-3-oxobutanoate (4.8 g, 29 mmol). The resulting solution was stirred for 12 h at 80° C. in an oil bath. On completion, the reaction mixture was cooled to rt then concentrated under vacuum. The resulting solution was extracted with ethyl acetate (3×200 mL) and the organic layers combined. The organic layer was washed with brine (3×100 mL), dried over anhydrous sodium sulfate, filtered and concentrated in vacuo. The residue was purified by silica gel chromatography with ethyl acetate/petroleum ether (1/10). This resulted in 1.0 g (33% yield) of ethyl 2-[2-(2,4-dichlorophenyl)-1,3-thiazol-4-yl]acetate as a yellow solid. LCMS: m/z=316.0 [M+1]⁺.

(Intermediate Y) Ethyl 2-[2-(4-chloro-3-phenylphenyl)-1,3-thiazol-4-yl]acetate

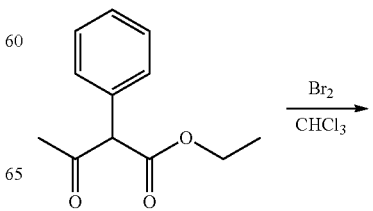

Y

Step 1: 3-bromo-4-chlorobenzene-1-carbothioamide

Into a 250-mL round-bottom flask was placed 3-bromo-4-chlorobenzonitrile (2.1 g, 9.7 mmol), (NH₄)₂S (8% wt in water, 36.7 mmol, 25 mL), N,N-dimethylformamide (40 mL) and triethylamine (4 mL). The resulting solution was stirred for 1 h at 50° C. in an oil bath. On completion, the reaction was cooled to rt and was diluted 100 mL of with water. The solid precipitate was collected by filtration. This resulted in 2.2 g (91% yield) of 3-bromo-4-chlorobenzene-1-carbothioamide as a yellow solid. LCMS: (ES+) m/z (M+H)+=249.9, tR=0.967.

Step 2: Ethyl 2-[2-(3-bromo-4-chlorophenyl)-1,3-thiazol-4-yl]acetate

Into a 250-mL round-bottom flask was placed ethyl 4-chloro-3-oxobutanoate (2.9 g, 17.6 mmol), 3-bromo-4-chlorobenzene-1-carbothioamide (2.2 g, 8.8 mmol), pyridine (2 mL) and ethanol (50 mL). The resulting solution was stirred for 12 h at 90° C. in an oil bath. On completion, the mixture was concentrated under vacuum. The resulting solution was diluted with DCM (50 mL). The resulting mixture was washed with hydrogen chloride (4N, 3×100 mL) then brine (500 mL). The mixture was dried over anhydrous sodium sulfate, filtered and concentrated in vacuo. The residue purified by silica gel chromatography with ethyl acetate/petroleum ether (1:45). This resulted in 1.4 g (44% yield) of ethyl 2-[2-(3-bromo-4-chlorophenyl)-1,3-thiazol-4-yl]acetate as a white solid. LCMS: (ES+) m/z (M+H)+=362.0, tR=1.653.

Step 3: Ethyl 2-[2-(4-chloro-3-phenylphenyl)-1,3-thiazol-4-yl]acetate

Into a 30-mL vial purged and maintained with an inert atmosphere of nitrogen, was placed a solution of ethyl 2-[2-(3-bromo-4-chlorophenyl)-1,3-thiazol-4-yl]acetate (1.0 g, 2.8 mmol) in dioxane (10 mL). A solution of sodium carbonate (886 mg, 8.36 mmol) in water (1 mL), Pd(dppf)Cl₂ dichloromethane (228 mg, 0.279 mmol) and phenylboronic acid (408 mg, 3.35 mmol) were added. The resulting solution was stirred for 2 h at 95° C. On completion, the reaction mixture was cooled to rt and diluted with water (50 mL). The resulting solution was extracted with ethyl acetate (3×30 mL) and the organic layers combined. The organics were washed with sodium chloride (100 mL), dried over anhydrous sodium sulfate, filtered and concentrated under vacuum. The crude product was purified by Flash-Prep-HPLC with the following conditions (IntelFlash-1): Column, silica gel; mobile phase, water/ACN=100/0 increasing to water/ACN=40/60 within 25 min; Detector, UV 254 nm). This resulted in 757 mg (76% yield) of ethyl 2-[2-(4-chloro-3-phenylphenyl)-1,3-thiazol-4-yl]acetate as a light yellow solid. LCMS: (ES+) m/z (M+H)⁺=358.1, tR=1.788.

(Intermediate Z) Ethyl 2-[2-(2,4-dichlorophenyl)-1,3-thiazol-4-yl]-2-phenylacetate -continued

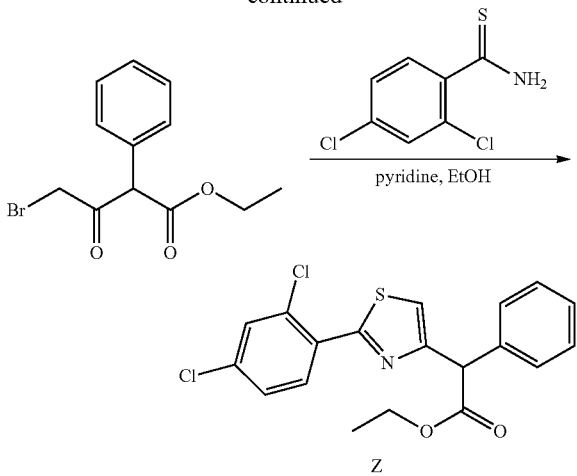

Step 1: Ethyl 4-bromo-3-oxo-2-phenylbutanoate

Into a 100-mL round-bottom flask was placed ethyl 3-oxo-2-phenylbutanoate (925 mg, 4.49 mmol, CAS #5413-05-8), bromine (718 mg, 4.49 mmol) and chloroform (25 mL). The resulting solution was stirred for 1 h at 25° C. The reaction was then quenched by the addition of NaHSO₃ solution (50 mL). The resulting solution was extracted with ethyl acetate (3×100 mL) and the organic layers combined. The organic layer was washed with brine (3×50 mL, dried over anhydrous sodium sulfate, filtered and concentrated under vacuum. This resulted in 1 g (78% yield) of ethyl 4-bromo-3-oxo-2-phenylbutanoate as yellow oil. (ES+) m/z (M+H)+=285.0, tR=1.093

Step 2: Ethyl 2-[2-(2,4-dichlorophenyl)-1,3-thiazol-4-yl]-2-phenylacetate

Into a 100-mL round-bottom flask was placed ethyl 4-bromo-3-oxo-2-phenylbutanoate (1.39 g, 4.87 mmol), pyridine (1.16 g, 14.66 mmol), ethanol (50 mL), and 2,4-dichlorobenzene-1-carbothioamide (2.00 g, 9.70 mmol, CAS #2775-38-4). The resulting solution was stirred for 12 h at 80° C. in an oil bath. On completion, the reaction mixture was cooled to rt and concentrated under vacuum. The resulting solution was extracted with ethyl acetate (3×50 mL) and the organic layers combined. The organic layer was washed with brine (3×50 mL), dried over anhydrous sodium sulfate, filtered and concentrated in vacuo. This resulted in 3 g (crude) of ethyl 2-[2-(2,4-dichlorophenyl)-1,3-thiazol-4-yl]-2-phenylacetate as brown oil. LCMS: (ES+) m/z (M+H)+=360.1, tR=0.819.

(Intermediate AA) Ethyl 2-[2-(3-bromophenyl)acetamido]acetate as a white solid

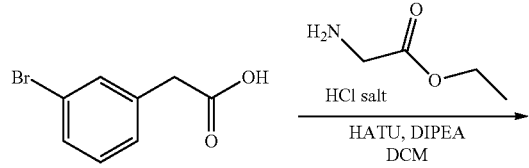

-continued

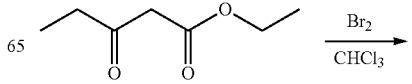

AA

Into a 100-mL round-bottom flask was placed 2-(3-bromophenyl)acetic acid (1.0 g, 4.7 mmol, CAS #1876-67-7), ethyl 2-aminoacetate (776 mg, 7.53 mmol, HCl salt), HATU (3.53 g, 9.30 mmol), DIPEA (1.80 g, 13.95 mmol) and dichloromethane (60 mL). The resulting solution was stirred for 1 h at 25° C. On completion, the reaction mixture was washed with water (3×50 mL) and brine (50 mL). The mixture was dried over anhydrous sodium sulfate and concentrated under vacuum. The residue was purified by C-18 reversed-phase column chromatography with H₂O:ACN (1/1). This resulted in 1.12 g (80% yield) of ethyl 2-[2-(3-bromophenyl)acetamido]acetate as a white solid. LCMS: (ES+) m/z (M+H)+=300.0, tR=0.825.

Ethyl 2-[2-(2,4-dichlorophenyl)-1,3-thiazol-4-yl]propanoate (Intermediate AB)

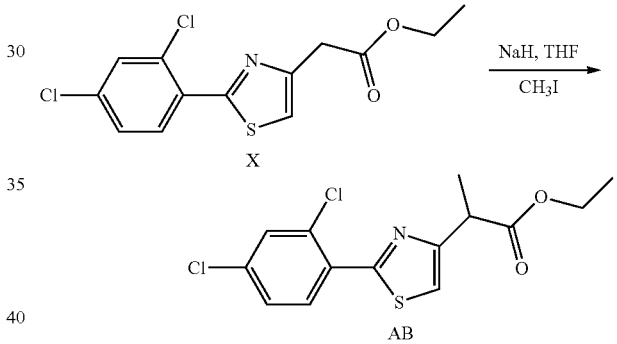

Into a 50-mL round-bottom flask was placed ethyl 2-[2-(2,4-dichlorophenyl)-1,3-thiazol-4-yl]acetate (500 mg, 1.58 mmol, Intermediate X), sodium hydride (190 mg, 7.92 mmol), and tetrahydrofuran (20 mL). The resulting solution was stirred for 1 h at 0° C. in a water/ice bath. Then iodomethane (270 mg, 1.90 mmol) was added with stirring, and the reaction was stirred for an additional 3 hrs at 25° C. The reaction was then quenched by the addition of 50 mL of NH₄Cl. The solution was then extracted with ethyl acetate (3×100 mL) and the organic layers combined. The organic layer was washed with 100 mL of brine, dried over anhydrous sodium sulfate, filtered and concentrated under vacuum. This resulted in 500 mg (96% yield) of ethyl 2-[2-(2,4-dichlorophenyl)-1,3-thiazol-4-yl]propanoate as yellow oil. LCMS: (ES+) m/z (M+H)+=330.1, tR=1.528.

(Intermediate AC) Ethyl 2-[2-(2,4-dichlorophenyl)-5-methyl-1,3-thiazol-4-yl]acetate

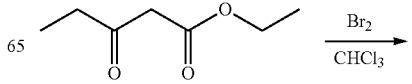

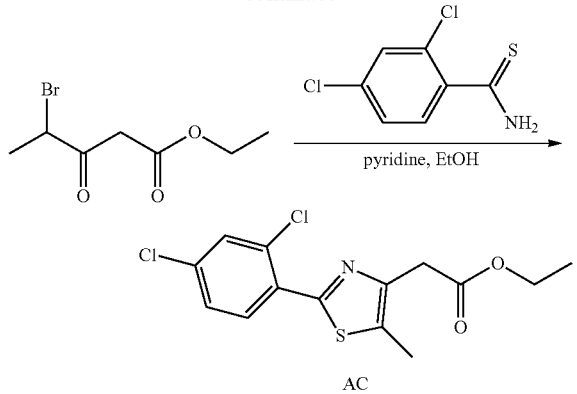

AC

Step 1: Ethyl 4-bromo-3-oxopentanoate

Into a 250-mL round-bottom flask, was placed ethyl 3-oxopentanoate (5.0 g, 35 mmol, CAS #4949-44-4), bromine (5.6 g, 35 mmol) and chloroform (100 mL). The resulting solution was stirred for 12 h at 25° C. The reaction was then quenched by the addition of NaHSO$_3$. The resulting solution was extracted with dichloromethane (3×200 mL) and the organic layers combined. The organic layer was washed with brine (3×100 mL), dried over anhydrous sodium sulfate, filtered and concentrated under vacuum. This resulted in 6.5 g (84% yield) of ethyl 4-bromo-3-oxopentanoate as yellow oil. LCMS: (ES+) m/z (M+H)$^+$=223.0, tR=0.875.

Step 2: Ethyl 2-[2-(2,4-dichlorophenyl)-5-methyl-1,3-thiazol-4-yl]acetate

Into a 250-mL round-bottom flask, was placed ethyl 4-bromo-3-oxopentanoate (1.09 g, 4.89 mmol), pyridine (1 mL), ethanol (20 mL) and 2,4-dichlorobenzene-1-carbothioamide (1.00 g, 4.85 mmol, CAS #2775-38-4). The resulting solution was stirred for 12 h at 80° C. in an oil bath. On completion, the reaction mixture was cooled to rt and concentrated under vacuum. The resulting solution was extracted with ethyl acetate (3×100 mL) and the organic layers combined. The organic layer was washed with brine (3×50 mL), dried over anhydrous sodium sulfate, filtered and concentrated in vacuo. The residue was purified by silica gel chromatography with ethyl acetate/petroleum ether (1/10). This resulted in 600 mg (37%) of ethyl 2-[2-(2,4-dichlorophenyl)-5-methyl-1,3-thiazol-4-yl]acetate as a yellow solid. $^1$H NMR (300 MHz, Chloroform-d) δ 8.21 (d, J=8.6 Hz, 1H), 7.50 (d, J=2.1 Hz, 1H), 7.34 (dd, J=8.6, 2.1 Hz, 1H), 4.22 (q, J=7.1 Hz, 2H), 3.84 (s, 2H), 2.49 (s, 3H), 1.30 (t, J=7.1 Hz, 3H).

(Intermediate AD) Ethyl 2-[2-(4-chloro-2-ethenylphenyl)-1,3-thiazol-4-yl]acetate

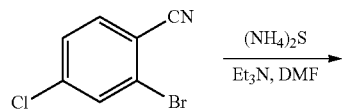

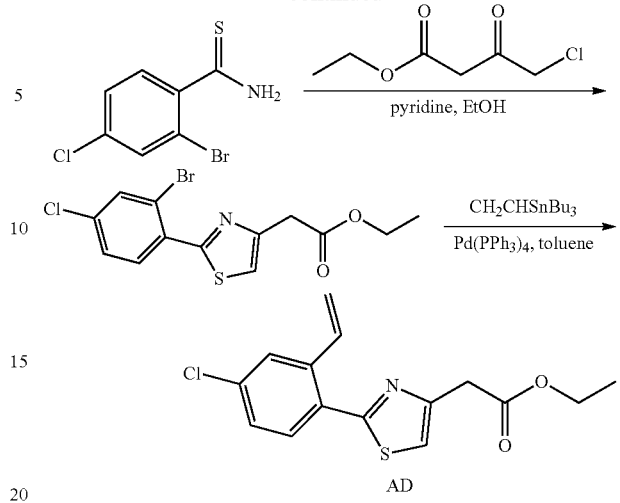

AD

Step 1: 2-bromo-4-chlorobenzene-1-carbothioamide

Into a 250-mL round-bottom flask was placed 2-bromo-4-chlorobenzonitrile (10.0 g, 46 mmol), (NH$_4$)$_2$S (21.6 g, 71.0 mmol, 8% wt in water), triethylamine (14.1 g, 140 mmol) and N,N-dimethylformamide (20 mL). The resulting solution was stirred for 2 h at 50° C. On completion, the reaction was cooled to rt and quenched by the addition of 20 mL of water. The resulting solution was extracted with 60 mL of ethyl acetate. The organic layer was washed with 40 mL of water, 60 mL of brine, dried over anhydrous sodium sulfate, filtered and concentrated in vacuo. This resulted in 11 g (95% yield) of 2-bromo-4-chlorobenzene-1-carbothioamide as a yellow solid. LCMS (ESI): m/z=251.8 [M+1]$^+$, tR=0.84 min.

Step 2: Ethyl 2-[2-(2-bromo-4-chlorophenyl)-1,3-thiazol-4-yl]acetate

Into a 25-mL round-bottom flask was placed 2-bromo-4-chlorobenzene-1-carbothioamide (11.0 g, 44 mmol), ethyl 4-chloro-3-oxobutanoate (14.5 g, 88 mmol), pyridine (10.4 g, 132 mmol), and ethanol (30 mL). The resulting solution was stirred for 5 h at 80° C. On completion, the reaction was cooled to rt then quenched by the addition of 10 mL of water. The resulting solution was extracted with 60 mL of ethyl acetate. The organic layer was washed with 30 mL of hydrogen chloride solution (5N), 60 mL of brine, dried over anhydrous sodium sulfate, filtered and concentrated in vacuo. The residue was purified by silica gel chromatography with ethyl acetate/petroleum ether (1:1). This resulted in 12 g (76% yield) of ethyl 2-[2-(2-bromo-4-chlorophenyl)-1,3-thiazol-4-yl]acetate as a yellow solid. LCMS (ESI): m/z=362.05 [M+1]$^+$, tR=1.2 min.

Step 3: Ethyl 2-[2-(4-chloro-2-ethenylphenyl)-1,3-thiazol-4-yl]acetate

Into a 250-mL round-bottom flask was placed ethyl 2-[2-(2-bromo-4-chlorophenyl)-1,3-thiazol-4-yl]acetate (4.5 g, 12 mmol), toluene (50 mL), Pd(PPh$_3$)$_4$(3.59 g, 3.1 mmol), and tributyl(ethenyl)stannane (5.16 g, 16.3 mmol). The resulting solution was stirred for 3 h at 110° C. On completion, the reaction was cooled to rt then quenched by the addition of 20 mL of water. The resulting solution was extracted with 450 mL of ethyl acetate. The organic layer was washed with 50 mL of brine, dried over sodium sulfate, filtered and concentrated in vacuo. The residue was then purified by silica gel chromatography with ethyl acetate/petroleum ether (10:1). This resulted in 3.1 g (81% yield) of ethyl 2-[2-(4-chloro-2-ethenylphenyl)-1,3-thiazol-4-yl]acetate as a yellow solid. LCMS (ES): m/z=308.15 [M+1]+, tR=1.2 min.

(Intermediate AE) Ethyl 2-[2-[4-chloro-2-(propan-2-yl)phenyl]-1,3-thiazol-4-yl]acetate

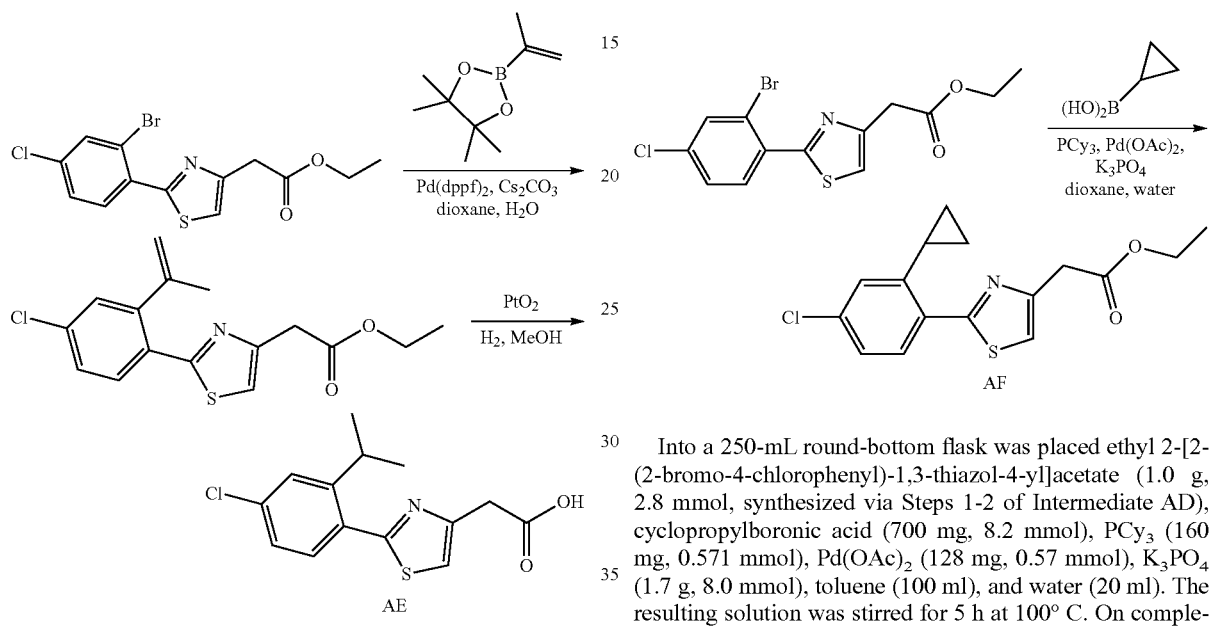

Step 1: Ethyl 2-[2-[4-chloro-2-(prop-1-en-2-yl)phenyl]-1,3-thiazol-4-yl]acetate

Into a 25-mL round-bottom flask purged and maintained with an inert atmosphere of nitrogen, was placed ethyl 2-[2-(2-bromo-4-chlorophenyl)-1,3-thiazol-4-yl]acetate (500 mg, 1.39 mmol, synthesized via Steps 1-2 of Intermediate AD), 4,4,5,5-tetramethyl-2-(prop-1-en-2-yl)-1,3,2-dioxaborolane (463.7 mg, 2.76 mmol), Pd(dppf)₂ (101 mg, 0.123 mmol), cesium carbonate (1.4 g, 4.3 mmol), dioxane (8 mL), and water (2 mL). The resulting solution was stirred for 2 h at 80° C. On completion, the reaction mixture was cooled to rt then quenched by the addition of 10 mL of water. The resulting solution was extracted with 50 mL of ethyl acetate. The organic layer was washed with 20 mL of brine, dried over anhydrous sodium sulfate, filtered and concentrated in vacuo. The residue was purified by silica gel chromatography with ethyl acetate/petroleum ether (1:1). This resulted in 350 mg (78% yield) of ethyl 2-[2-[4-chloro-2-(prop-1-en-2-yl)phenyl]-1,3-thiazol-4-yl]acetate as a yellow liquid. LCMS: m/z=322.0 [M+1]+, tR=1.8 min. ¹H NMR (400 MHz, Chloroform-d) δ 7.83 (d, J=8.4 Hz, 1H), 7.38-7.24 (m, 4H), 5.28 (s, 1H), 5.13 (s, 1H), 4.24 (q, J=7.1 Hz, 2H), 3.92 (s, 2H), 1.93 (s, 3H), 1.31 (t, J=7.1 Hz, 3H).

Step 2: Ethyl 2-[2-[4-chloro-2-(propan-2-yl)phenyl]-1,3-thiazol-4-yl]acetate

Into a 25-mL round-bottom flask, was placed ethyl 2-[2-[4-chloro-2-(prop-1-en-2-yl)phenyl]-1,3-thiazol-4-yl]acetate (100 mg, 0.31 mmol), PtO₂ (200 mg), and methanol (10 mL) and the reaction vessel was purged with hydrogen. The resulting solution was stirred under hydrogen for 13 h at room temperature. On completion, the solids were filtered and the resulting mixture was concentrated under vacuum. This resulted in 80 mg (80% yield) of ethyl 2-[2-[4-chloro-2-(propan-2-yl)phenyl]-1,3-thiazol-4-yl]acetate as a yellow liquid. LCMS: m/z=324.0 [M+1]+, tR=1.8 min (Intermediate AF) Ethyl 2-[2-(4-chloro-2-cyclopropylphenyl)-1,3-thiazol-4-yl]acetate

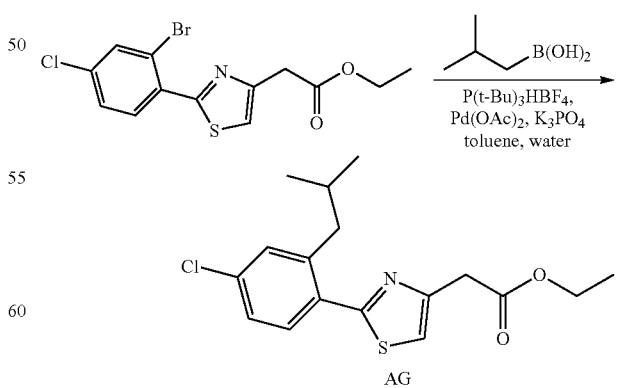

Into a 250-mL round-bottom flask was placed ethyl 2-[2-(2-bromo-4-chlorophenyl)-1,3-thiazol-4-yl]acetate (1.0 g, 2.8 mmol, synthesized via Steps 1-2 of Intermediate AD), cyclopropylboronic acid (700 mg, 8.2 mmol), PCy₃ (160 mg, 0.571 mmol), Pd(OAc)₂ (128 mg, 0.57 mmol), K₃PO₄ (1.7 g, 8.0 mmol), toluene (100 ml), and water (20 ml). The resulting solution was stirred for 5 h at 100° C. On completion, the reaction mixture was concentrated under vacuum. The residue was purified by silica gel chromatography with ethyl acetate/petroleum ether (1:3). This resulted in 700 mg (71% yield) of ethyl 2-[2-(4-chloro-2-cyclopropylphenyl)-1,3-thiazol-4-yl]acetate as a yellow solid. LCMS: m/z=322.1 [M+1]+, tR=1.2 min.

(Intermediate AG) Ethyl 2-[2-[4-chloro-2-(2-methylpropyl)phenyl]-1,3-thiazol-4-yl]acetate Into a 20-mL pressure tank reactor was placed ethyl 2-[2-(2-bromo-4-chlorophenyl)-1,3-thiazol-4-yl]acetate (100 mg, 0.28 mmol, synthesized via Steps 1-2 of Intermediate AD), toluene (10 mL), water (1 mL), K$_3$PO$_4$ (200 mg, 0.94 mmol), Pd(OAC)$_2$ (30 mg, 0.133 mmol), P(t-Bu)$_3$HBF$_4$ (45 mg, 0.156 mmol), and (2-methylpropyl)boronic acid (85 mg, 0.83 mmol). The resulting solution was stirred for 2 h at 100° C. in an oil bath. On completion, the reaction mixture was filtered and concentrated under vacuum. The residue was purified by silica gel chromatography with ethyl acetate/petroleum ether (3:7). This resulted in 70 mg (75% yield) of ethyl 2-[2-[4-chloro-2-(2-methylpropyl)phenyl]-1,3-thiazol-4-yl]acetate as yellow oil. LCMS: (ES+) m/z (M+H)$^+$=338.0, tR=1.472.

(Intermediate AH) Ethyl 2-(2-bromo-1,3-thiazol-4-yl)acetate

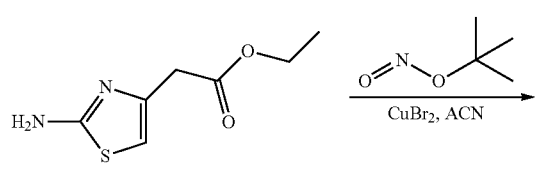

Into a 100-mL round-bottom flask purged and maintained with an inert atmosphere of nitrogen, was placed a solution of CuBr$_2$ (6.5 g, 29.4 mmol) in ACN (20 mL) and tert-butyl nitrite (4.8 mL, 40 mmol). This was followed by the addition of ethyl 2-(2-amino-1,3-thiazol-4-yl)acetate (5.0 g, 27 mmol, CAS #53266-94-7) at −20 OC. The resulting solution was stirred for 1.5 h at room temperature. On completion, the reaction mixture was diluted with 100 mL of water. The resulting solution was extracted with ethyl acetate (3×30 mL) and the organic layers combined. The organic layer was washed with 100 mL of brine, dried over anhydrous sodium sulfate, filtered and concentrated under vacuum. The crude product was purified by flash-prep-HPLC with the following conditions (IntelFlash-1): Column, silica gel; mobile phase, water/ACN=100/0 increasing to water/ACN=60/40 within 20 min. This resulted in 1.8 g (27% yield) of ethyl 2-(2-bromo-1,3-thiazol-4-yl)acetate as a brown liquid. LCMS (ESI): m/z=249.9 [M+1]$^+$, tR=0.84 min. Ethyl 2-[2-(2,4-dichlorophenyl)-1,3-thiazol-4-yl]-2-methylpropanoate (Intermediate AI)

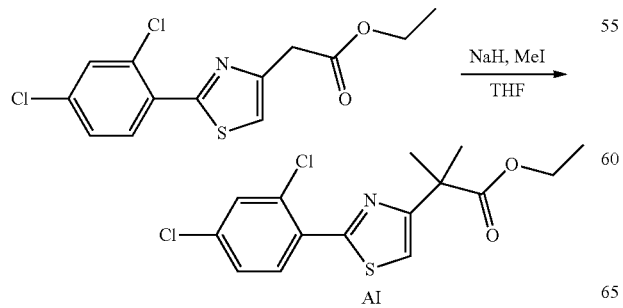

Into a 25-mL round-bottom flask was placed a solution of ethyl 2-[2-(2,4-dichlorophenyl)-1,3-thiazol-4-yl]acetate (100 mg, 0.32 mmol, Intermediate X) in tetrahydrofuran (20 mL) and the mixture was cooled to 0° C. Then sodium hydride (63 mg, 2.6 mmol, 60%) was added followed by iodomethane (225 mg, 1.6 mmol). The resulting solution was stirred for 3 h at 0° C. in a water/ice bath. The reaction was then stirred an additional 16 hrs at rt. On completion, the reaction mixture was quenched with 20 mL of water and was concentrated under vacuum. The residue was extracted with ethyl acetate (3×20 mL) and the organic layers combined. The organic layer was washed with of brine (3×40 mL), dried over anhydrous sodium sulfate, filtered and concentrated in vacuo. This resulted in 70 mg of ethyl 2-[2-(2,4-dichlorophenyl)-1,3-thiazol-4-yl]-2-methylpropanoate which was used directly without further purification. LCMS: m/z=344.0 [M+1]$^+$, tR=1.4 min.

(Intermediate AJ) 2-(4-Chloronaphthalen-1-yl)-4,4,5,5-tetramethyl-1,3,2-dioxaborolane

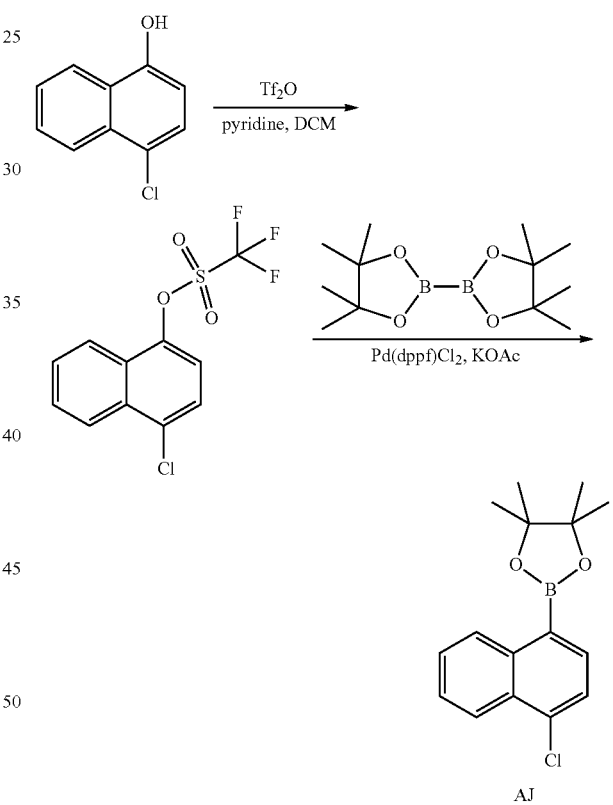

Step 1: 4-Chloronaphthalen-1-yl trifluoromethanesulfonate

Into a 100-mL round-bottom flask was placed 4-chloronaphthalen-1-ol (2 g, 11.20 mmol), (trifluoromethane)sulfonyl trifluoromethanesulfonate (6.6 g, 23 mmol), dichloromethane (50 mL), and pyridine (2.2 g, 28 mmol). The resulting solution was stirred for 30 min at 0° C. On completion, the reaction was quenched by the addition of 100 mL of water. The resulting solution was extracted with dichloromethane (3×50 mL) and the organic layers combined. The organic layer was washed with 100 mL of brine, dried over anhydrous sodium sulfate, filtered and concentrated under vacuum. The residue was purified by silica gel chromatography with ethyl acetate/petroleum ether (1:20). This resulted in 2.2 g (63% yield) of 4-chloronaphthalen-1-yl trifluoromethanesulfonate as yellow oil. $^1$H NMR (300 MHz, DMSO-d6, ppm): δ 8.35-8.27 (m, 1H), 8.09-8.01 (m, 1H), 7.95-7.83 (m, 3H), 7.72 (d, J=8.4 Hz, 1H).

Step 2: 2-(4-chloronaphthalen-1-yl)-4,4,5,5-tetramethyl-1,3,2-dioxaborolane

Into a 100-mL round-bottom flask was placed 4-chloronaphthalen-1-yl trifluoromethanesulfonate (310 mg, 1.00 mmol), 4,4,5,5-tetramethyl-2-(tetramethyl-1,3,2-dioxaborolan-2-yl)-1,3,2-dioxaborolane (510 mg, 2.01 mmol), dichloropalladium; bis(triphenylphosphane) (70 mg, 0.10 mmol), potassium acetate (294 mg, 3.00 mmol), and dioxane (50 mL). The resulting solution was stirred for 8 h at 80° C. On completion, the reaction was cooled to rt then quenched by the addition of 250 mL of water. The resulting solution was extracted with ethyl acetate (3×100 mL) and the organic layers combined. The organic layer was washed with 200 mL of brine, dried over anhydrous sodium sulfate, filtered and concentrated under vacuum. The crude product was purified by flash-prep-HPLC with the following conditions (IntelFlash-1): Column, silica gel; mobile phase, MeCN: Water=1:5 increasing to MeCN:Water=10:1 within 120 min. This resulted in 0.15 g (52% yield) of 2-(4-chloronaphthalen-1-yl)-4,4,5,5-tetramethyl-1,3,2-dioxaborolane as a white solid. $^1$H NMR (300 MHz, DMSO-d6, ppm): δ 8.79-8.68 (m, 1H), 8.31-8.20 (m, 1H), 7.94 (d, J=7.5 Hz, 1H), 7.77-7.65 (m, 3H), 1.38 (s, 12H).

(Intermediate AK) Ethyl 2-[2-(2-bromo-1,3-thiazol-4-yl)acetamido]acetate

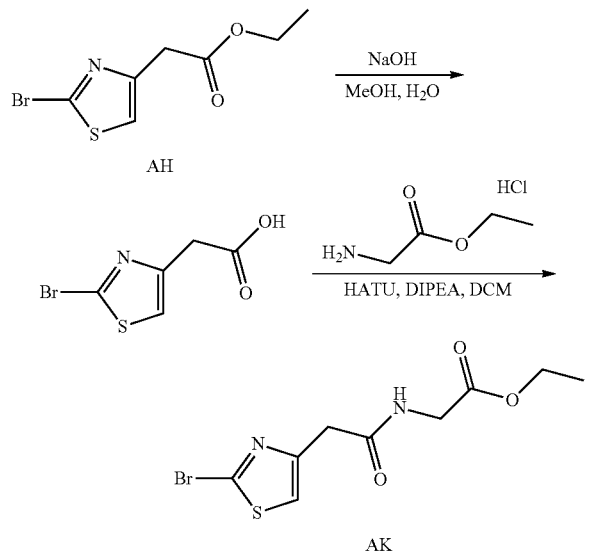

Step 1: 2-(2-Bromo-1,3-thiazol-4-yl)acetic Acid

Into a 100-mL round-bottom flask was placed ethyl 2-(2-bromo-1,3-thiazol-4-yl)acetate (500 mg, 2.00 mmol, Intermediate AH), sodium hydroxide (100 mg, 2.50 mmol), methanol (5 mL) and water (5 mL). The resulting solution was stirred for 2 h at room temperature. On completion, the resulting mixture was concentrated under vacuum. The reaction was then quenched by the addition of 20 mL of water. The resulting solution was washed with dichloromethane (3×20 mL). The pH of the aqueous layer was adjusted to 3 with hydrogen chloride (3 mol/L). The resulting solution was extracted with ethyl acetate (3×20 mL) and the organic layers combined and concentrated in vacuo. This resulted in 430 mg (87% yield) of 2-(2-bromo-1,3-thiazol-4-yl)acetic acid as a yellow solid. $^1$H NMR (300 MHz, Methanol-d$_4$) δ 7.42 (t, J=0.8 Hz, 1H), 3.80 (d, J=0.8 Hz, 2H).

Step 2: Ethyl 2-[2-(2-bromo-1,3-thiazol-4-yl)acetamido]acetate

Into a 100-mL round-bottom flask was placed 2-(2-bromo-1,3-thiazol-4-yl)acetic acid (430 mg, 1.94 mmol), ethyl 2-aminoacetate (HCl salt, 153 mg, 1.48 mmol), HATU (1.14 g, 3.00 mmol), DIPEA (780 mg, 6.04 mmol) and dichloromethane (5 mL). The resulting solution was stirred overnight at room temperature. On completion, the reaction mixture was extracted with dichloromethane (3×20 mL) and the organic layers combined. The organic layer was washed with water (3×20 mL), dried over anhydrous sodium sulfate, filtered and concentrated under vacuum. The residue was purified by silica gel chromatography with ethyl acetate/ petroleum ether (2:1). This resulted in 380 mg (57% yield) of ethyl 2-[2-(2-bromo-1,3-thiazol-4-yl)acetamido]acetate as a light yellow solid. $^1$H NMR (300 MHz, Chloroform-d) δ 7.17 (s, 1H), 6.91 (s, 1H), 4.22 (q, J=7.1 Hz, 2H), 4.05 (d, J=5.2 Hz, 2H), 3.76 (s, 2H), 1.29 (t, J=7.1 Hz, 3H).

(Intermediate AL) Ethyl 2-[2-(4-chloro-2-ethylphenyl)-1,3-thiazol-4-yl]acetate

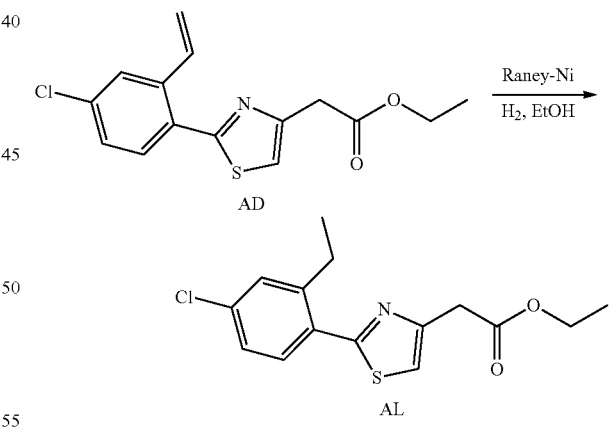

Into a 25-mL round-bottom flask was placed ethyl 2-[2-(4-chloro-2-ethenylphenyl)-1,3-thiazol-4-yl]acetate (100 mg, 0.32 mmol, Intermediate AD), Raney nickel (20 mg) and ethanol (10 mL). The flask was purged with hydrogen gas and resulting solution was stirred for 30 min at room temperature. On completion, the solids were filtered and the filtrate concentrated under reduced pressure. The residue was purified by silica gel chromatography with ACN/Water (50/100). This resulted in 50 mg (50% yield) of ethyl 2-[2-(4-chloro-2-ethylphenyl)-1,3-thiazol-4-yl]acetate as a yellow solid. LCMS: (ES+) m/z (M+H)$^+$=310.0, tR=1.218.

GENERAL METHODS

Example 1. Synthesis of 2-[[2-[2-[4-Chloro-2-(3-cyanophenyl)phenyl]thiazol-4-yl]acetyl]amino]-2-methyl-propanoic Acid, I-1, (Method 1)

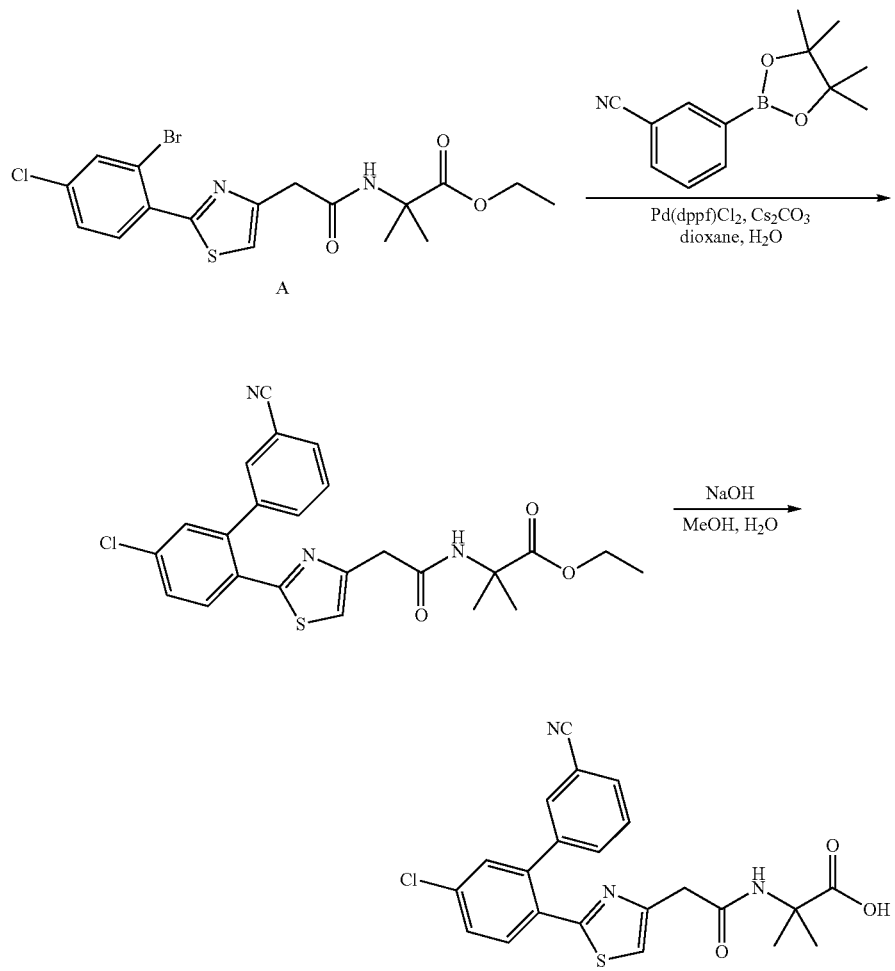

Step 1—Ethyl 2-[[2-[2-[4-chloro-2-(3-cyanophenyl)phenyl]thiazol-4-yl]acetyl]amino]-2-methyl-propanoate To a mixture of ethyl 2-[[2-[2-(2-bromo-4-chloro-phenyl)thiazol-4-yl]acetyl]amino]-2-methyl-propanoate (100 mg, 224 umol) in dioxane (6 mL) and water (700 uL) was added 3-(4,4,5,5-tetramethyl-1,3,2-dioxaborolane-2-yl)benzonitrile (66.8 mg, 291 umol, CAS #214360-48-2), Pd(dppf)Cl$_2$ (1.64 mg, 2.24 umol) and Cs$_2$CO$_3$ (146 mg, 448 umol). Then the mixture was stirred at 90-110° C. for 16 hours under nitrogen. On completion, the reaction mixture was concentrated in vacuo. The residue was washed with water (30 mL) and extracted with ethyl acetate (3×30 mL). The organic layer was dried with Na$_2$SO$_4$, filtered and concentrated in vacuo to give the title compound (110 mg, 90% purity, 94% yield) as yellowish oil. The product was used to the next step directly without further purification. LCMS: (ES+) m/z (M+H)$^+$=468.0, tR=0.939.

Step 2—2-[[2-[2-[4-Chloro-2-(3-cyanophenyl)phenyl]thiazol-4-yl]acetyl]amino]-2-methyl-propanoic Acid To a mixture of ethyl 2-[[2-[2-[4-chloro-2-(3-cyanophenyl)phenyl]thiazol-4-yl]acetyl]amino]-2-methyl-propanoate (110 mg, 235 umol) in a mixture solvent of MeOH (2 mL) and water (2 mL) was added NaOH (28.2 mg, 705 umol) and the reaction mixture was stirred at 20° C. for 16 hours. On completion, the reaction mixture was concentrated in vacuo. The residue was adjusted to pH~4-7 by 1.0 N HCl. The residue was purified by prep-HPLC (column: Boston Green ODS 150*30 5 u; mobile phase: [water (0.225% FA)-ACN]; B % (ACN): 41%-71%, 10 min) to give the title compound I-1 (45.3 mg, 43% yield) as white solid. LCMS: (ES+) m/z (M+H)$^+$=440.0, tR=0.844. $^1$H NMR (400 MHz, DMSO-d$_6$) δ=8.29 (s, 1H), 8.03 (d, J=8.4 Hz, 1H), 7.95-7.86 (m, 2H), 7.65 (d, J=8.4 Hz, 1H), 7.63-7.57 (m, 2H), 7.54 (s, 1H), 7.37 (s, 1H), 3.56 (s, 2H), 1.35 (s, 6H).

Compounds synthesized via Method 1 using the appropriate ester and boronic acid/ester intermediates are shown below in Table 4.

TABLE 4

Compounds Synthesized via Method 1 using the appropriate ester and boronic acid/ester intermediates

| Example # | Compound Number | Intermediate Ester | Intermediate Boronic Acid/Ester | LCMS (ES+) m/z (M + H)+ | HNMR (400 MHz, DMSO-d6) δ |
|---|---|---|---|---|---|
| 2[a] | I-41 | AA | (2,4-dichlorophenyl) boronic acid | 338.1 | (MeOD) 7.56 (t, J = 1.2 Hz, 1H), 7.48-7.27 (m, 6H), 3.77 (s, 2H), 3.66 (s, 2H) |
| 3[b] | I-6 | A | (3-chlorophenyl) boronic acid | 449.0 | 12.27 (br. s., 1H), 8.31 (s, 1H), 8.02 (d, J = 8.4 Hz, 1H), 7.62 (dd, J = 2.0, 8.4 Hz, 1H), 7.56-7.48 (m, 2H), 7.47-7.41 (m, 2H), 7.35 (s, 1H), 7.24 (d, J = 7.2 Hz, 1H), 3.58 (s, 2H), 1.36 (s, 6H) |
| 4[c] | I-4 | A | 4,4,5,5-tetramethyl-2-(m-tolyl)-1,3,2-dioxaborolane | 429.0 | 12.23 (br. s., 1H), 8.32 (s, 1H), 8.02 (d, J = 8.4 Hz, 1H), 7.57 (dd, J = 2.4, 8.4 Hz, 1H), 7.40 (d, J = 2.4 Hz, 1H), 7.33-7.23 (m, 3H), 7.14 (s, 1H), 7.05 (d, J = 7.2 Hz, 1H), 3.58 (s, 2H), 2.32 (s, 3H), 1.35 (s, 6H) |
| 5 | I-14 | A | B | 455.0 | 12.26 (br. s., 1H), 8.30 (s, 1H), 8.19 (d, J = 8.4 Hz, 1H), 7.59 (dd, J = 2.4, 8.4 Hz, 1H), 7.37-7.32 (m, 2H), 7.30-7.24 (m, 2H), 7.04 (d, J = 7.2 Hz, 1H), 3.58 (s, 2H), 2.90 (t, J = 7.2 Hz, 2H), 2.53 (t, J = 7.2 Hz, 2H), 1.88 (m, 2H), 1.36 (s, 6H) |
| 6[d] | I-7 | A | C | 457.0 | 8.32 (s, 1H), 8.12 (d, J = 8.4 Hz, 1H), 7.61 (dd, J = 2.4, 8.4 Hz, 1H), 7.47-7.39 (m, 3H), 7.30 (s, 1H), 7.20 (dd, J = 2.4, 6.0 Hz, 1H), 5.05 (s, 2H), 4.59 (s., 2H), 3.59 (s, 2H), 1.36 (s, 6H) |
| 7[b] | I-9 | A | (2,3-dimethylphenyl) boronic acid | 443.0 | 8.32 (s, 1H), 8.25 (d, J = 8.8 Hz, 1H), 7.59 (dd, J = 2.4, 8.8 Hz, 1H), 7.33-7.27 (m, 2H), 7.25 (s, 1H), 7.24-7.18 (m, 1H), 7.02 (d, J = 7.6 Hz, 1H), 3.57 (s, 2H), 2.27 (s, 3H), 1.83 (s, 3H), 1.35 (s, 6H) |
| 8[e] | I-12 | A | (3-ethylphenyl) boronic acid | 443.0 | 12.23 (br. s., 1H), 8.31 (s, 1H), 8.02 (d, J = 8.4 Hz, 1H), 7.58 (dd, J = 2.4, 8.4 Hz, 1H), 7.42 (d, J = 2.4 Hz, 1H), 7.38-7.31 (m, 1H), 7.31-7.25 (m, 2H), 7.13 (s, 1H), 7.09 (d, J = 7.6 Hz, 1H), 3.57 (s, 2H), 2.60 (q, J = 7.6 Hz, 2H), 1.35 (s, 6H), 1.14 (t, J = 7.6 Hz, 3H) |
| 9[f] | I-18 | E | D | 409.0 | 8.34 (br. s., 1H), 7.69 (d, J = 8.4 Hz, 1H), 7.57 (dd, J = 2.4, 8.4 Hz, 1H), 7.51-7.42 (m, 2H), 7.35-7.25 (m, 3H), 7.19 (d, J = 7.6 Hz, 1H), 7.14-7.10 (m, 2H), 6.68 (s, 1H), 3.61 (s, 2H), 1.37 (s, 6H) |
| 10[g] | I-20 | F | D | 409.1 | 8.40 (d, J = 4.8 Hz, 1H), 8.07 (br. s., 1H), 7.60 (d, J = 8.4 Hz, 1H), 7.56 (dd, J = 2.0, 8.4 Hz, 1H), 7.48 (d, J = 2.0 Hz, 1H), 7.29-7.23 (m, 3H), 7.14 (dd, J = 1.2, 4.8 Hz, 1H), 7.10 (m, 2H), 6.96 (s, 1H), 3.28 (s, 2H), 1.31 (s, 6H) |
| 11[h] | I-23 | G | D | 409.0 | 8.27-8.20 (m, 2H), 7.59 (dd, J = 2.0, 8.4 Hz, 1H), 7.51 (d, J = 2.0 Hz, 1H), 7.46 (d, J = 8.4 Hz, 1H), 7.33-7.26 (m, 3H), 7.24 (s, 1H), 7.18-7.11 (m, 2H), 6.82-6.76 (m, 1H), 3.54 (s, 2H), 1.34 (s, 6H) |

TABLE 4-continued

Compounds Synthesized via Method 1 using the appropriate ester and boronic acid/ester intermediates

| Example # | Compound Number | Intermediate Ester | Intermediate Boronic Acid/Ester | LCMS (ES+) m/z (M + H)+ | HNMR (400 MHz, DMSO-d6) δ |
|---|---|---|---|---|---|
| 12[i] | I-29 | H | D | 410.0 | 8.52 (d, J = 5.2 Hz, 1H), 8.04 (s, 1H), 7.86 (d, J = 8.4 Hz, 1H), 7.58 (dd, J = 1.6, 8.4 Hz, 1H), 7.50 (d, J = 1.6 Hz, 1H), 7.30 (d, J = 5.2 Hz, 1H), 7.27-7.20 (m, 3H), 7.08-7.06 (m, 2H), 3.53 (s, 2H), 1.35 (s, 6H) |

[a]Step 2 was run at rt for 2 hrs then the pH was adjusted to 4 with AcOH instead of HCl. The final product was purified by Prep-HPLC with the following conditions: Column, X Select C18, 19 * 150 mm, 5 um; mobile phase, A:Water/0.05% NH$_4$HCO$_3$, mobile phase B: ACN.
[b]The final product purified by prep-HPLC: column: Phenomenex Synergi C18 150 * 25 * 10 um; mobile phase: [water (0.1% TFA)-ACN].
[c]Step 1 was run at 90-100° C. for 64 hours. In the final step after the mixture was acidified, thiourea (resin) (100 mg) was added and the mixture was stirred at 20° C. for 3 hours. After filtering and concentrating, the final product was purified via prep-HPLC: column: Phenomenex Synergi C18 150 * 25 * 10 um; mobile phase: [water (0.1% TFA)-ACN].
[d]After Step 1was complete, the reaction mixture was concentrated in vacuo and the intermediate was purified by prep-TLC (petroleum ether:ethyl acetate = 1:1). The final product was purified by prep-HPLC: column: Phenomenex Synergi C18 150 * 25 * 10 um; mobile phase: [water (0.05% HCl)-ACN].
[e]The intermediate after Step 1 was purified by prep-TLC (petroleum ether:ethyl acetate = 1:1). The final product was purified by prep-HPLC: column: Phenomenex Synergi C18 150 * 25 * 10 um; mobile phase: [water (0.1% TFA)-ACN].
[f]The intermediate from Step 1 was purified by prep-TLC (petroleum ether:ethyl acetate = 2:1).
[g]The intermediate of Step 1 was purified by prep-TLC (petroleum ether:ethyl acetate = 1:2). The final product was purified by prep-HPLC: column: Phenomenex Synergi C18 150 * 25 * 10 um; mobile phase: [water (0.225% FA)-ACN].
[h]The intermediate from Step 1 was purified by column chromatography (petroleum ether:ethyl acetate = 5:1 to 1:1). The final product was purified by prep-HPLC (column: Phenomenex Synergi C18 150 * 25 * 10 um; mobile phase: [water (0.225% FA)-ACN]; B %: 25%-55%, 10 min).
[i]The intermediate from Step 1 was purified by column chromatography (petroleum ether:ethyl acetate = 5:1). The final product was purified by prep-HPLC (column: Boston Green ODS 150 * 30 5 u; mobile phase: [water(0.225% FA)-ACN])(HPLC ran twice for purification).

Example 13. Synthesis of 2-[[2-[5-(4-Chloro-2-phenyl-phenyl)-3-pyridyl]acetyl]amino]-2-methyl-propanoic Acid, I-17

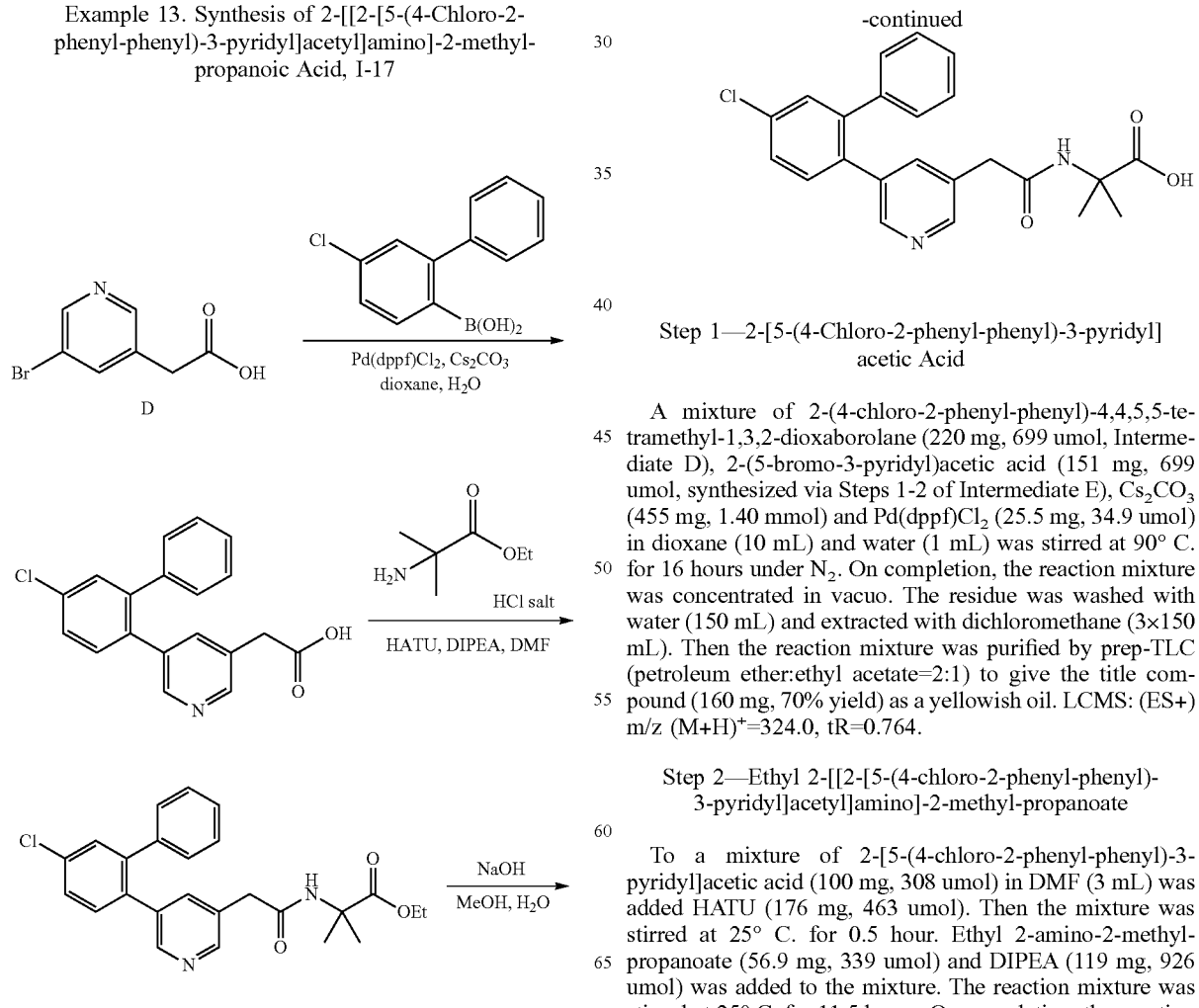

Step 1—2-[5-(4-Chloro-2-phenyl-phenyl)-3-pyridyl]acetic Acid

A mixture of 2-(4-chloro-2-phenyl-phenyl)-4,4,5,5-tetramethyl-1,3,2-dioxaborolane (220 mg, 699 umol, Intermediate D), 2-(5-bromo-3-pyridyl)acetic acid (151 mg, 699 umol, synthesized via Steps 1-2 of Intermediate E), Cs$_2$CO$_3$ (455 mg, 1.40 mmol) and Pd(dppf)Cl$_2$ (25.5 mg, 34.9 umol) in dioxane (10 mL) and water (1 mL) was stirred at 90° C. for 16 hours under N$_2$. On completion, the reaction mixture was concentrated in vacuo. The residue was washed with water (150 mL) and extracted with dichloromethane (3×150 mL). Then the reaction mixture was purified by prep-TLC (petroleum ether:ethyl acetate=2:1) to give the title compound (160 mg, 70% yield) as a yellowish oil. LCMS: (ES+) m/z (M+H)$^+$=324.0, tR=0.764.

Step 2—Ethyl 2-[[2-[5-(4-chloro-2-phenyl-phenyl)-3-pyridyl]acetyl]amino]-2-methyl-propanoate To a mixture of 2-[5-(4-chloro-2-phenyl-phenyl)-3-pyridyl]acetic acid (100 mg, 308 umol) in DMF (3 mL) was added HATU (176 mg, 463 umol). Then the mixture was stirred at 25° C. for 0.5 hour. Ethyl 2-amino-2-methyl-propanoate (56.9 mg, 339 umol) and DIPEA (119 mg, 926 umol) was added to the mixture. The reaction mixture was stirred at 25° C. for 11.5 hours. On completion, the reaction mixture was concentrated in vacuo. The residue was washed with water (30 mL), extracted with dichloromethane (3×50 mL). The organic layer was separated and dried with Na$_2$SO$_4$, filtered and concentrated in vacuo. The residue was purified by prep-TLC (ethyl acetate) to give the title compound (110 mg, 59% yield) as a yellowish oil. LCMS: (ES+) m/z (M+H)$^+$=437.1, tR=0.823.

Step 3—2-[[2-[5-(4-Chloro-2-phenyl-phenyl)-3-pyridyl]acetyl]amino]-2-methyl-propanoic Acid To a mixture of ethyl 2-[[2-[5-(4-chloro-2-phenyl-phenyl)-3-pyridyl]acetyl]amino]-2-methyl-propanoate (100 mg, 228.87 umol) in MeOH (3 mL) and water (1.2 mL) was added NaOH (27.4 mg, 686 umol). Then the mixture was stirred at 25° C. for 12 hours. On completion, the reaction mixture was concentrated in vacuo. The residue was adjusted to pH=6.0 with 2.0 N hydrochloric acid. Then the mixture was purified by prep-HPLC (column: Boston Green ODS 150*30 5 u; mobile phase: [water (0.225% FA)-ACN]; B %: 26%-56%, 10 min) to give the title compound 1-17 (25.0 mg, 26% yield) as a white solid. LCMS: (ES+) m/z (M+H)$^+$=409.0, tR=0.755. $^1$H NMR (400 MHz, DMSO-d$_6$) δ=8.29-8.26 (m, 2H), 8.00 (d, J=2.4 Hz, 1H), 7.59 (dd, J=2.4, 8.4 Hz, 1H), 7.53 (t, J=2.4 Hz, 1H), 7.51 (d, J=2.4 Hz, 1H), 7.47 (d, J=8.4 Hz, 1H), 7.33-7.25 (m, 3H), 7.18-7.09 (m, 2H), 3.40 (s, 2H), 1.33 (s, 6H).

Example 14. Synthesis of 2-[2-[3-(4-chlorophenyl)phenyl]acetamido]-2-methylpropanoic Acid, I-30

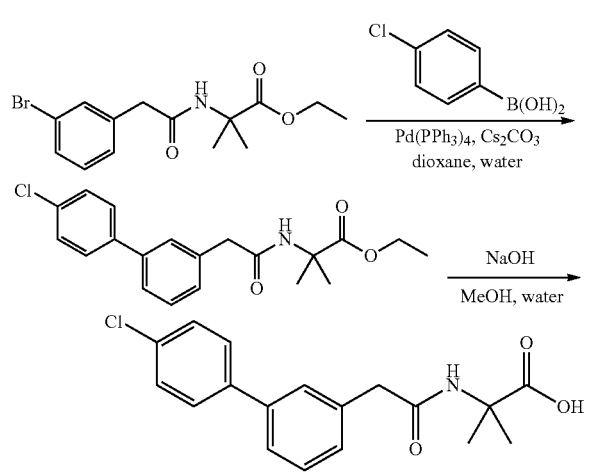

Step 1: Ethyl 2-[2-[3-(4-chlorophenyl)phenyl]acetamido]-2-methylpropanoate

Into a 50-mL round-bottom flask purged and maintained with an inert atmosphere of nitrogen, was placed ethyl 2-[2-(3-bromophenyl)acetamido]-2-methylpropanoate (70 mg, 0.21 mmol, synthesized via Step 1 of Intermediate I), dioxane (10 mL), water (2 mL), (4-chlorophenyl)boronic acid (40 mg, 0.26 mmol), cesium carbonate (139 mg, 0.43 mmol), and Pd(PPh$_3$)$_4$(24.6 mg, 0.02 mmol). The resulting solution was stirred for 12 h at 80° C. in an oil bath. On completion, the reaction mixture was cooled to rt and concentrated under vacuum. The resulting solution was then extracted with ethyl acetate (3×50 mL) and the organic layers combined. The organic layer was washed with water 3×50 mL, brine (2×50 mL), dried over anhydrous sodium sulfate, filtered and concentrated under vacuum. This resulted in 70 mg (91% yield) of ethyl 2-[2-[3-(4-chlorophenyl)phenyl]acetamido]-2-methylpropanoate as yellow oil. LCMS: (ES+) m/z (M+H)$^+$=360.0, tR=1.038.

Step 2: 2-[2-[3-(4-chlorophenyl)phenyl]acetamido]-2-methylpropanoic Acid

Into a 50-mL round-bottom flask was placed ethyl 2-[2-[3-(4-chlorophenyl)phenyl]acetamido]-2-methylpropanoate (80 mg, 0.22 mmol), methanol (20 mL), water (10 mL) and sodium hydroxide (48 mg, 1.20 mmol). The resulting solution was stirred for 2 h at 25° C. On completion, the mixture was concentrated under vacuum. The resulting solution was washed with dichloromethane (3×50 mL). The aqueous layer was then adjusted to pH=4 with AcOH. The resulting solution was extracted with ethyl acetate (3×50 mL) and the organic layers combined. The organic layer was washed with brine (3×50 mL), dried over anhydrous sodium sulfate, filtered and concentrated in vacuo. The crude product was purified by prep-HPLC with the following conditions: Column, X Select C18, 19*150 mm, 5 um; mobile phase, mobile phase A: Water/0.05% NH4HCO3, Mobile Phase B: ACN. This resulted in 17.5 mg (24% yield) of 2-[2-[3-(4-chlorophenyl)phenyl]acetamido]-2-methylpropanoic acid 1-30 as an off-white solid. LCMS: m/z=332.10 [M+1]$^+$. tR: 1.14 min. HNMR: (300 MHz, Methanol-d4) δ 7.69-7.26 (m, 8H), 3.60 (s, 2H), 1.51 (s, 6H).

Example 15. Synthesis of 2-[[2-[3-[4-Chloro-2-(p-tolyl)phenyl]phenyl]acetyl]amino]-2-methyl-propanoic Acid, I-3, (Method 2)

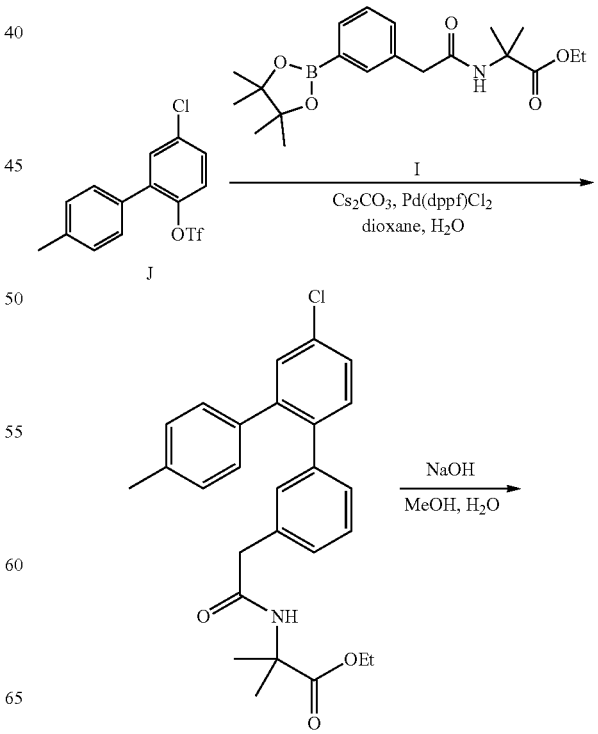

-continued

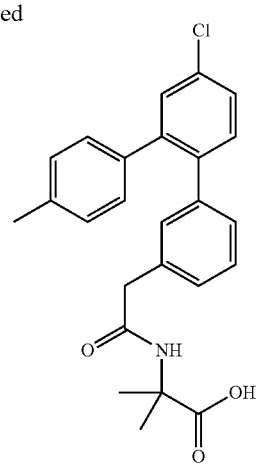

Step 1—Ethyl 2-[[2-[3-[4-chloro-2-(p-tolyl)phenyl]phenyl]acetyl]amino]-2-methyl-propanoate A mixture of [4-chloro-2-(p-tolyl)phenyl] trifluoromethanesulfonate (300 mg, 855 umol, Intermediate J), ethyl 2-methyl-2-[[2-[3-(4,4,5,5-tetramethyl-1,3,2-dioxaborolan-2-yl)phenyl]acetyl]amino]propanoate (353 mg, 941 umol, Intermediate I), cesium carbonate (558 mg, 1.71 mmol) and Pd(dppf)Cl$_2$ (31.3 mg, 42.8 umol) in dioxane (5 mL) and water (500 uL) was stirred at 100-110° C. for 16 hrs under nitrogen atmosphere. On completion, the reaction mixture was concentrated in vacuo, then DCM (20 mL) and water (20 mL) were added. The phases were separated and the organic phase was dried over anhydrous sodium sulfate, filtered and concentrated in vacuo. The residue was purified by column chromatography (petroleum ether:ethyl acetate=1:1) to give the title compound (50.0 mg, 13% yield) as a yellow oil. LCMS: (ES$^+$) m/z (M+1)$^+$=450.1, tR=1.056.

Step 2—2-[[2-[3-[4-Chloro-2-(p-tolyl)phenyl]phenyl]acetyl]amino]-2-methyl-propanoic Acid To a solution of ethyl 2-[[2-[3-[4-chloro-2-(p-tolyl)phenyl]phenyl]acetyl]amino]-2-methyl-propanoate (50.0 mg, 111 umol) in MeOH (5 mL) and water (2 mL) was added sodium hydroxide (13.3 mg, 333 umol). The reaction mixture was stirred at 15° C. for 16 hrs. On completion the reaction mixture was concentrated in vacuo. The residue was adjusted to pH~4-7 by 1.0 N HCl and the residue was purified by prep-HPLC (column: Boston Green ODS 150*30 5 u; mobile phase: [water (0.225% FA)-ACN]) to give the title compound I-3 (3.87 mg, 8% yield) as white solid. LCMS: (ES$^+$) m/z (M+23)$^+$=444.1, tR=1.245. $^1$H NMR (400 MHz, DMSO-d$_6$) δ=8.04 (br s, 1H), 7.50 (dd, J=2.4, J=8.0, 1H), 7.40 (d, J=2.0 Hz, 1H), 7.38 (d, J=8.4 Hz, 1H), 7.15 (s, 1H), 7.13-7.07 (m, 2H), 7.07-7.03 (m, 2H), 7.03-6.97 (m, 2H), 6.78 (td, J=2.0, 6.0 Hz, 1H), 3.35 (s, 2H), 2.25 (s, 3H), 1.32 (s, 6H).

Example 16. Synthesis of 2-[[2-[3-[2-(3-Carbamoylphenyl)-4-chloro-phenyl]phenyl]acetyl]amino]-2-methyl-propanoic Acid, I-19

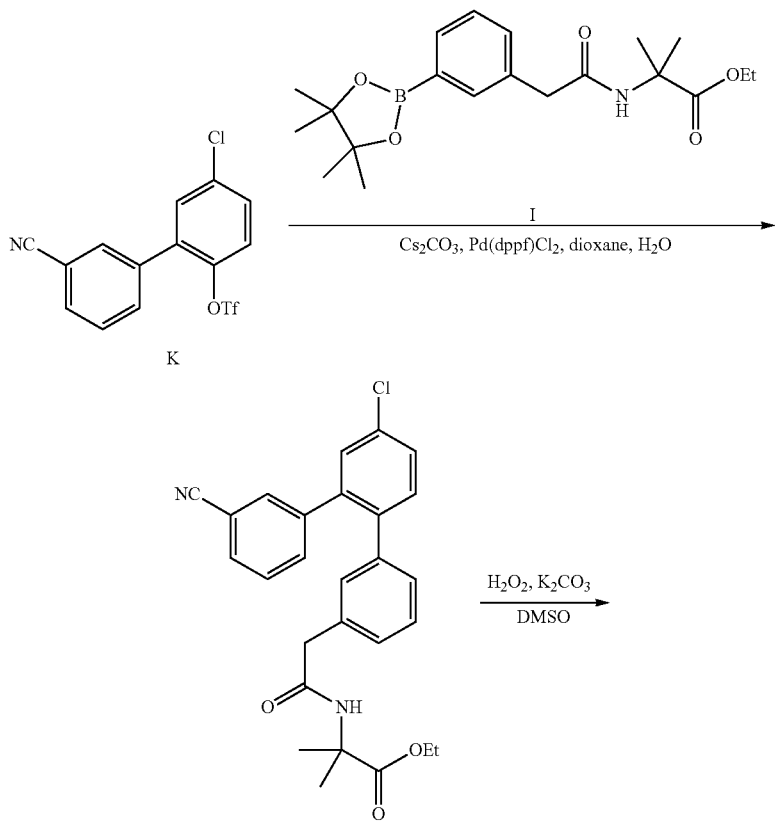

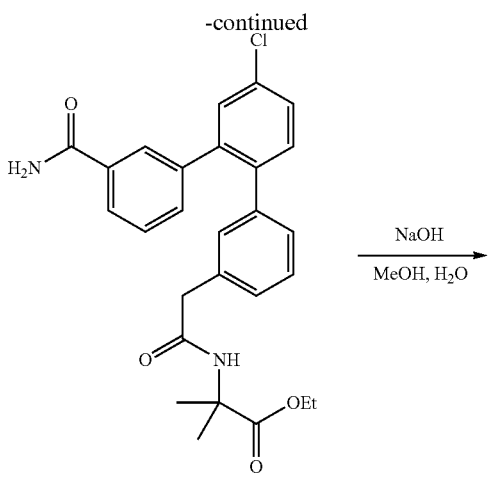

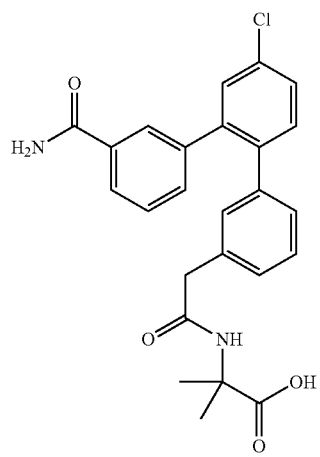

Step 1—Ethyl 2-[[2-[3-[4-chloro-2-(3-cyanophenyl)phenyl]phenyl]acetyl]amino]-2-methyl-propanoate Following the conditions of Step 1 of Method 2, [4-chloro-2-(3-cyanophenyl)phenyl] trifluoromethanesulfonate (250 mg, 691 umol, Intermediate K) was coupled with ethyl 2-methyl-2-[[2-[3-(4,4,5,5-tetramethyl-1,3,2-dioxaborolan-2-yl) phenyl]acetyl]amino]propanoate (285 mg, 760 umol, Intermediate I) and the reaction mixture was stirred at 90-100° C. for 5 hours. The title compound was purified by column chromatography (petroleum ether: ethyl acetate=1:1) to give a yellow oil (100 mg, 31% yield). LCMS: (ES+) m/z (M+1)+=461.0, tR=0.998.

Step 2—Ethyl 2-[[2-[3-[2-(3-carbamoylphenyl)-4-chloro-phenyl]phenyl]acetyl]amino]-2-methyl-propanoate To a solution of ethyl 2-[[2-[3-[4-chloro-2-(3-cyanophenyl)phenyl]phenyl]acetyl]amino]-2-methyl-propanoate (100 mg, 217 umol) and potassium carbonate (60.0 mg, 434 umol) in dimethyl sulfoxide (10 mL) was added hydrogen peroxide (246 mg, 2.17 mmol, 30% solution). The reaction mixture was stirred at 60° C. for 16 hours. On completion, the reaction mixture was diluted with water (30 mL), and extracted with DCM (3×30 mL). The organic phase was dried over anhydrous sodium sulfate, filtered and concentrated in vacuo to give the title compound (100 mg 76% yield) as a white solid. LCMS: (ES+) m/z (M+1)+=479.1, (M+23)+=501.0. tR=0.856.

Step 3—2-[[2-[3-[2-(3-Carbamoylphenyl)-4-chlorophenyl]phenyl]acetyl]amino]-2-methyl-propanoic Acid Ethyl 2-[[2-[3-[2-(3-carbamoylphenyl)-4-chloro-phenyl]phenyl]acetyl]amino]-2-methyl-propanoate (100 mg, 209 umol) was hydrolized as described in Step 2 of Method 2. The title compound 1-19 was purified by prep-HPLC (column: Boston Green ODS 150*30 5 u; mobile phase: [water (0.225% FA)-ACN]) to give a white solid (12.2 mg, 13% yield). LCMS: (ES+) m/z (M+1)+=451.0, tR=0.802. $^1$H NMR (400 MHz, DMSO-$d_6$) δ=8.09-7.89 (m, 2H), 7.82 (s, 1H), 7.73 (d, J=8.0 Hz, 1H), 7.57-7.50 (m, 2H), 7.44 (d, J=8.0 Hz, 1H), 7.32 (s, 1H), 7.24 (t, J=7.6 Hz, 1H), 7.17-7.04 (m, 3H), 6.79 (d, J=6.4 Hz, 1H), 3.36 (s, 2H), 1.32 (s, 6H).

Example 17. Synthesis of 2-[[2-[3-[4-Chloro-2-(4-fluorophenyl)phenyl]phenyl]acetyl]amino]-2-methyl-propanoic Acid, I-15

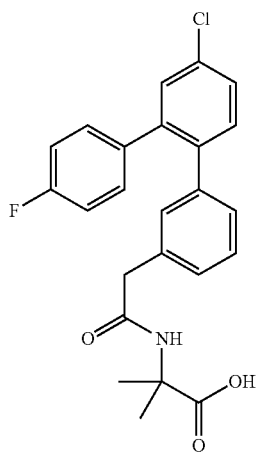 [SMILES: CC(C)(NC(=O)Cc1cccc(-c2ccc(Cl)cc2-c2ccc(F)cc2)c1)C(=O)O]

[4-chloro-2-(4-fluorophenyl)phenyl] trifluoromethanesulfonate (300 mg, 846 umol, Intermediate L) and ethyl 2-methyl-2-[[2-[3-(4,4,5,5-tetramethyl-1,3,2-dioxaborolan-2-yl)phenyl]acetyl]amino] propanoate (349 mg, 930 umol, Intermediate I) were coupled under the conditions described in Method 2. The final product was purified by prep-HPLC (column: Boston Green ODS 150*30 5 u; mobile phase: [water (0.225% FA)-ACN]) to give the title compound I-15 (4.23 mg, 9% yield) as white solid. LCMS: (ES+) m/z (M+23)+=448.1, tR=1.207. $^1$H NMR (400 MHz, DMSO-$d_6$) δ=8.03 (s, 1H), 7.52 (dd, J=2.0, 8.0 Hz, 1H), 7.45 (d, J=2.4 Hz, 1H), 7.40 (d, J=8.4 Hz, 1H), 7.17-7.04 (m, 7H), 6.85-6.77 (m, 1H), 3.34 (s, 2H), 1.32 (s, 6H).

Example 18. Synthesis of 2-[[2-[2-(4-Methoxy-2-phenyl-phenyl)thiazol-4-yl]acetyl]amino]-2-methyl-propanoic Acid, I-13, (Method 3)

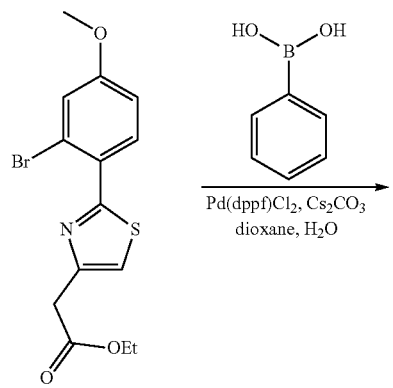

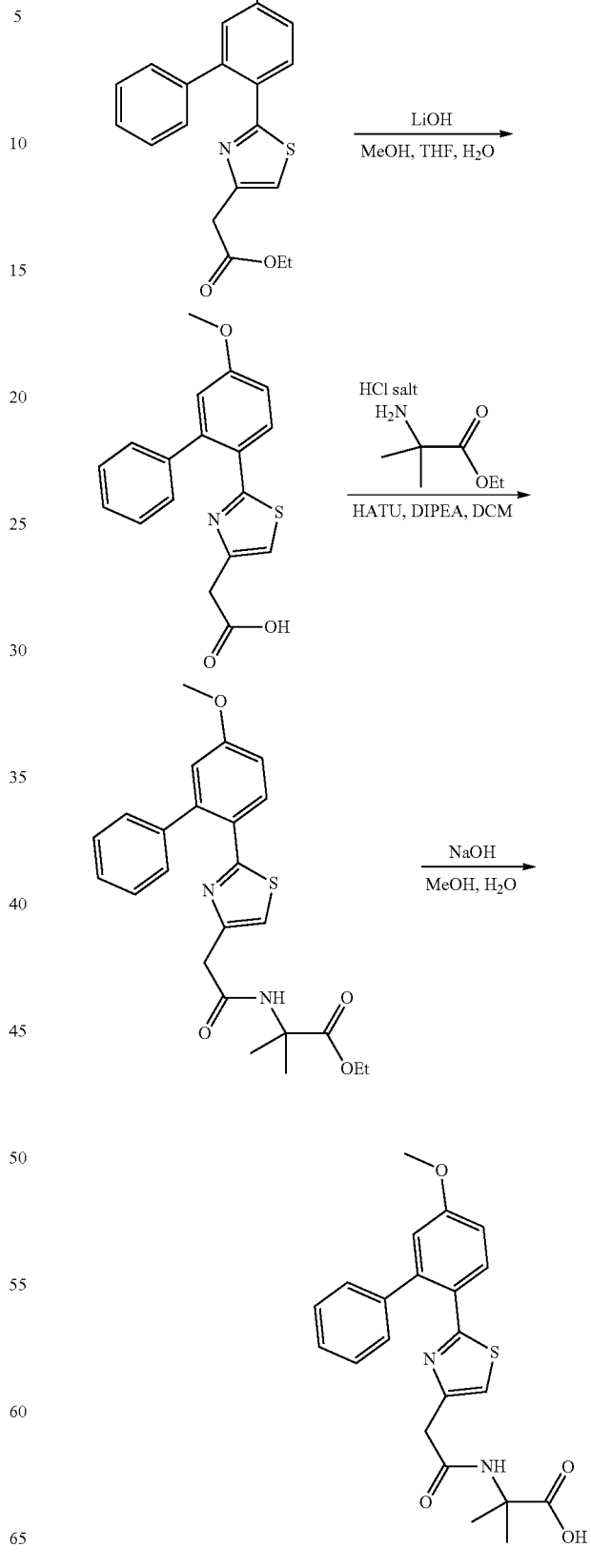

Step 1—Ethyl 2-[2-(4-methoxy-2-phenyl-phenyl)thiazol-4-yl]acetate

A mixture of ethyl 2-[2-(2-bromo-4-methoxy-phenyl)thiazol-4-yl]acetate (150 mg, 421 umol, Intermediate N), phenylboronic acid (56.5 mg, 463 umol), Pd(dppf)Cl$_2$ (3.08 mg, 4.21 umol) and cesium carbonate (274 mg, 842 umol) in a mixture solvent of dioxane (5 mL) and water (500 uL) was stirred at 90-100° C. for 64 hours under nitrogen atmosphere. On completion, the reaction mixture was concentrated in vacuo to give the title compound (150 mg, 80% yield) as a yellow oil. LCMS: (ES+) m/z (M+1)+=354.2, tR=0.857.

Step 2—2-[2-(4-Methoxy-2-phenyl-phenyl)thiazol-4-yl]acetic Acid

To a mixture of ethyl 2-[2-(4-methoxy-2-phenyl-phenyl)thiazol-4-yl]acetate (149 mg, 421 umol) in a solvent mixture of THF (4 mL), MeOH (4 mL) and water (4 mL) was added lithium hydroxide (50.4 mg, 2.11 mmol) and the reaction mixture was stirred at 15° C. for 16 hours. On completion, the reaction mixture was acidified with 1N HCl solution until pH=4 and concentrated in vacuo to remove the MeOH and THF. The aqueous phase was extracted with DCM (3×10 mL), dried over anhydrous sodium sulfate, filtered and concentrated in vacuo to give the title compound (150 mg, 83% yield) as a black brown oil. LCMS: (ES+) m/z (M+1)+=326.0, tR=0.806.

Step 3—Ethyl 2-[[2-[2-(4-methoxy-2-phenyl-phenyl)thiazol-4-yl]acetyl]amino]-2-methyl-propanoate To a mixture of 2-[2-(4-methoxy-2-phenyl-phenyl)thiazol-4-yl]acetic acid (200 mg, 615 umol) and HATU (304 mg, 799 umol) in DCM (20 mL) was added ethyl 2-amino-2-methyl-propanoate (88.7 mg, 529 umol, HCl salt) and diisopropylethylamine (322 uL, 1.84 mmol) in one portion and the reaction mixture was stirred at 20° C. for 16 hours. On completion, the reaction mixture was diluted with DCM (10 mL) and washed with 1N HCl solution. The organic layer was separated and dried over anhydrous sodium sulfate, filtered and concentrated in vacuo. The residue was purified by silica gel chromatography (petroleum ether:ethyl acetate=20:1 to 1:2) to give the title compound (180 mg, 38% yield). LCMS: (ES+) m/z (M+1)+=439.2, tR=0.917.

Step 4—2-[[2-[2-(4-Methoxy-2-phenyl-phenyl)thiazol-4-yl]acetyl]amino]-2-methyl-propanoic Acid To a solution of ethyl 2-[[2-[2-(4-methoxy-2-phenyl-phenyl) thiazol-4-yl]acetyl]amino]-2-methyl-propanoate (180 mg, 410 umol) in a mixture solvent of MeOH (10 mL) and water (10 mL) was added sodium hydroxide (49.3 mg, 1.23 mmol). The reaction mixture was stirred at 15° C. for 16 hours. On completion, the reaction mixture was acidified with 1N HCl until pH=5-6 and concentrated in vacuo to give a residue. The residue was purified by prep-HPLC (column: Welch Ultimate AQ-C18 150*30 mm*5 um; mobile phase: [water (0.1% TFA)-ACN]) to give the title compound 1-13 (56.6 mg, 34% yield). LCMS: (ES+) m/z (M+1)+=411.0, tR=0.816. $^1$H NMR (400 MHz, DMSO-d$_6$) δ=8.30 (s, 1H), 7.92 (d, J=8.8 Hz, 1H), 7.43-7.38 (m, 3H), 7.29-7.25 (m, 2H), 7.18 (s, 1H), 7.08 (dd, J=2.8, 8.8 Hz, 1H), 6.86 (d, J=2.8 Hz, 1H), 3.84 (s, 3H), 3.54 (s, 2H), 1.35 (s, 6H).

Example 19. Synthesis of Ethyl 2-(2-(2-(4,5-dichloro-[1,1'-biphenyl]-2-yl)thiazol-4-yl)acetamido)-2-methylpropanoate, 1-22

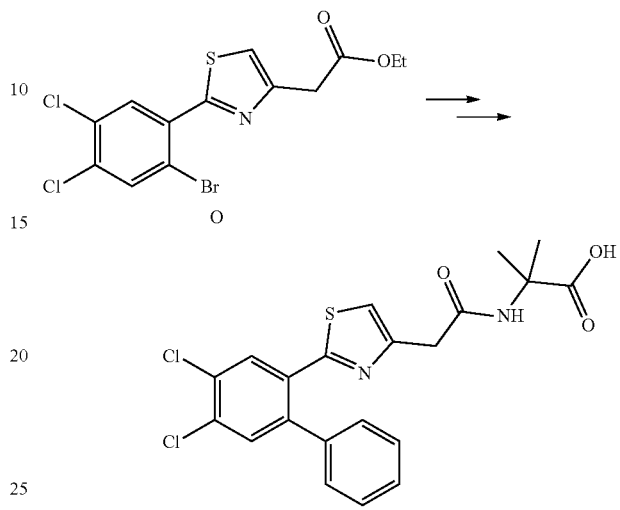

Ethyl 2-(2-(2-(4,5-dichloro-[1,1'-biphenyl]-2-yl)thiazol-4-yl)acetamido)-2-methylpropanoate was synthesized according to Method 3. Ethyl 2-[2-(2-bromo-4,5-dichloro-phenyl)thiazol-4-yl]acetate (400 mg, 1.01 mmol, Intermediate O) and phenylboronic acid (123 mg, 1.01 mmol) were coupled according to Method 3 Step 1 where the reaction mixture was stirred at 80° C. for 12 hours. In the third step, 2-[2-(4,5-dichloro-2-phenyl-phenyl)thiazol-4-yl]acetic acid (220 mg, 604 umol) dissolved in N,N-dimethylformamide (5 mL), was added N-di(isopropyl)ethylamine (234 mg, 1.81 mmol) and HATU and stirred for 0.5 hr. Then the ethyl 2-amino-2-methyl-was added and the reaction was complete after 0.5 hr where the work-up procedure follows Method 3, Step 3. The final compound was purified by prep-HPLC (column: Boston Green ODS 150*30 5 u; mobile phase: [water (0.225% FA)-ACN]; B %: 55%-85%, 10 min) to give the title compound 1-22 (88.0 mg, 36% yield) as a white solid. LCMS: (ES+) m/z (M+1)+=448.9. $^1$H NMR (400 MHz, DMSO-d$_6$) D=12.26 (br. s, 1H), 8.32 (s, 1H), 8.22 (s, 1H), 7.64 (s, 1H), 7.52-7.40 (m, 3H), 7.35 (s, 1H), 7.33-7.28 (m, 2H), 3.61-3.56 (m, 2H), 1.36 (s, 6H).

Example 20. Synthesis of 2-[[2-[2-(4-chloro-5-methoxy-2-phenyl-phenyl)thiazol-4-yl]acetyl]amino]-2-methyl-propanoic Acid, I-8

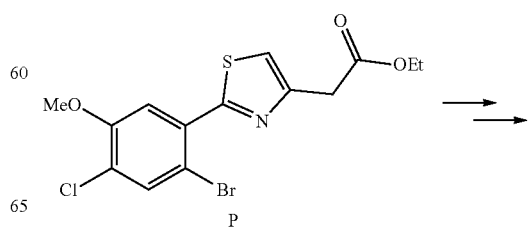

287

-continued

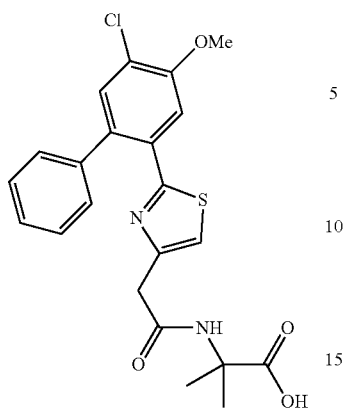

2-[[2-[2-(4-chloro-5-methoxy-2-phenyl-phenyl)thiazol-4-yl]acetyl]amino]-2-methyl-propanoic acid was synthesized according to Method 3. Ethyl 2-[2-(2-bromo-4-chloro-5-methoxy-phenyl)thiazol-4-yl]acetate (250 mg, 640 umol, Intermediate P) and phenylboronic acid (117 mg, 960 umol) were coupled according to Method 3 Step 1 where the reaction mixture was stirred at 90° C. for 16 hours. The final 2-[[2-[2-(4-chloro-5-methoxy-2-phenyl-phenyl)thiazol-4-yl]acetyl]amino]-2-methyl-propanoic acid was purified by prep-HPLC (column: Phenomenex Synergi C18 150*25*10 um; mobile phase: [water (0.05% HCl)-ACN]; B %: 48%-72%, 8 min) to afford I-8 as a white solid (164 mg, 64% yield). LCMS: (ES+) m/z (M+1)+=445.0, tR=0.856. $^1$H NMR (400 MHz, DMSO-$d_6$) δ=12.2 (br. s., 1H), 8.35 (s, 1H), 7.68 (s, 1H), 7.45-7.39 (m, 4H), 7.32 (s, 1H), 7.27 (dd, J=3.2, 6.4 Hz, 2H), 3.97 (s, 3H), 3.60 (s, 2H), 1.37 (s, 6H).

Example 21. Synthesis of 2-Methyl-2-[[2-[2-(5-phenyl-2,3-dihydro-1,4-benzodioxin-6-yl)thiazol-4-yl]acetyl]amino] propanoic Acid, I-2

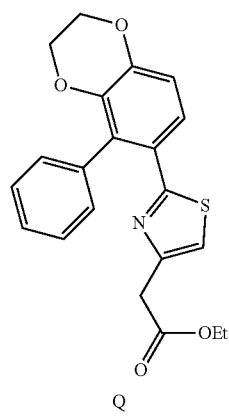

288

-continued

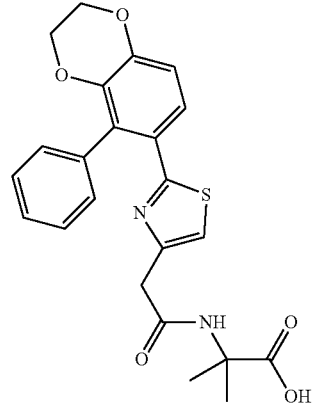

2-Methyl-2-[[2-[2-(5-phenyl-2,3-dihydro-1,4-benzodioxin-6-yl)thiazol-4-yl]acetyl]amino] propanoic acid was synthesized via Steps 2-4 of Method 3 starting from ethyl 2-[2-(5-phenyl-2,3-dihydro-1,4-benzodioxin-6-yl)thiazol-4-yl]acetate (Intermediate Q). The final product was purified by prep-HPLC (column: Boston Green ODS 150*30 5 u; mobile phase: [water 0.225% FA)-ACN]) to give the title compound I-2 (38 mg, 81% yield) as white solid. LCMS: (ES+) m/z (M+1)+=439.1, tR=0.742.1H NMR (400 MHz, DMSO-$d_6$) δ=8.23 (s, 1H), 7.61 (d, J=8.8 Hz, 1H), 7.45-7.37 (m, 3H), 7.25-7.17 (m, 2H), 7.13 (s, 1H), 6.99 (d, J=8.8 Hz, 1H), 4.31-4.24 (m, 2H), 4.21-4.14 (m, 2H), 3.51 (s, 2H), 1.34 (s, 6H).

Example 22. Synthesis of (Method 4)—(2-[2-[2-(4-chloro-2-phenylphenyl)-1,3-thiazol-4-yl]acetamido] acetic Acid, I-34

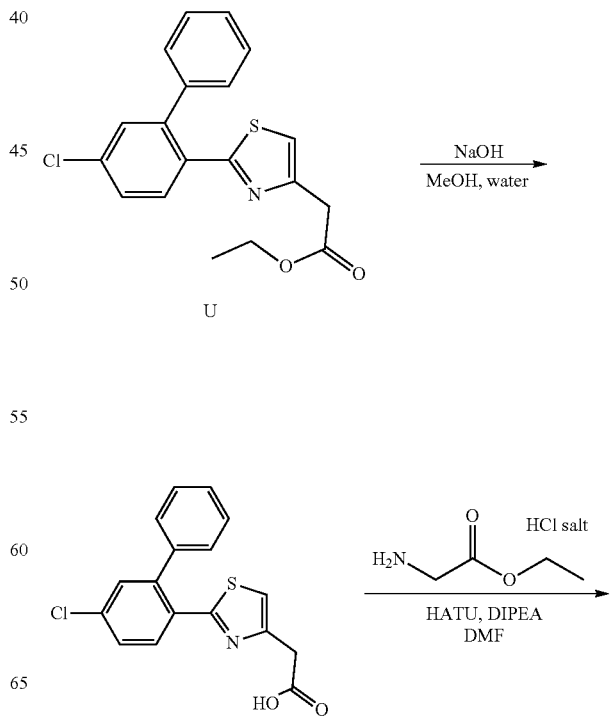

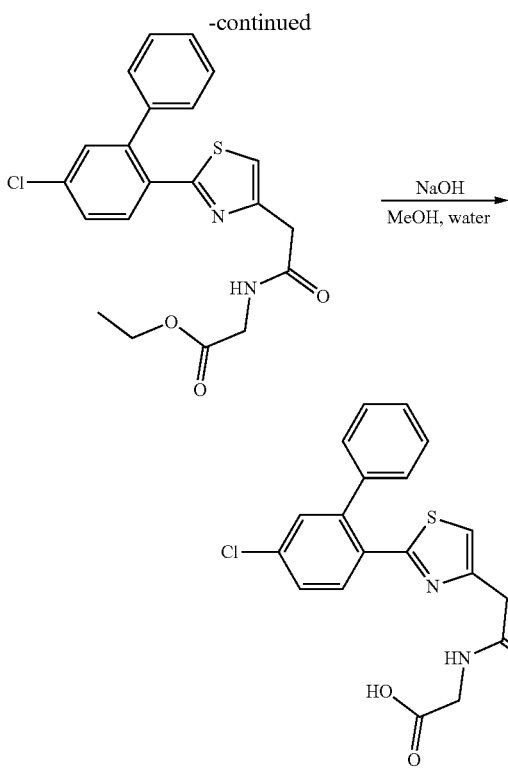

Step 1: 2-[2-(4-Chloro-2-phenylphenyl)-1,3-thiazol-4-yl]acetic Acid

Into a 100-mL round-bottom flask was placed ethyl 2-[2-(4-chloro-2-phenylphenyl)-1,3-thiazol-4-yl]acetate (1.5 g, 4.2 mmol, Intermediate U), sodium hydroxide (840 mg, 21.0 mmol), methanol (15 mL), and water (15 mL). The resulting solution was stirred for 30 min at 50° C. On completion, the reaction mixture was cooled to rt and HCl (12M aq.) was added to adjust the pH=3. The solid was filtered out and dried under vacuum. This resulted in 1.2 g (87% yield) of 2-[2-(4-chloro-2-phenylphenyl)-1,3-thiazol-4-yl]acetic acid as a white solid. LCMS: (ES+) m/z (M+H)$^+$=330.1, tR=0.884.

Step 2: Ethyl 2-[2-[2-(4-chloro-2-phenylphenyl)-1,3-thiazol-4-yl]acetamido]acetate Into a 100-mL round-bottom flask was placed 2-[2-(4-chloro-2-phenylphenyl)-1,3-thiazol-4-yl]acetic acid (800 mg, 2.43 mmol), ethyl 2-aminoacetate hydrochloride (676 mg, 4.84 mmol) diisopropylethylamine (1.25 g, 9.67 mmol), dichloromethane (50 mL), and HATU (1.85 g, 4.86 mmol). The resulting solution was stirred for 16 h at rt. The reaction was then quenched with 100 mL of water. The resulting solution was extracted with dichloromethane (3×50 mL) and the organic layers combined. The organic layer was washed with brine (100 mL), dried over anhydrous sodium sulfate, filtered, and the filtrate was concentrated under vacuum. The residue was purified by silica gel chromatography with ethyl acetate/petroleum ether (1:10). This resulted in 0.84 g (83% yield) of ethyl 2-[2-[2-(4-chloro-2-phenylphenyl)-1,3-thiazol-4-yl]acetamido]acetate as an off-white solid. LCMS: (ES+) m/z tR=1.052.

Step 3: 2-[2-[2-(4-Chloro-2-phenylphenyl)-1,3-thiazol-4-yl]acetamido]acetic Acid Into a 25-mL round-bottom flask was placed ethyl 2-[2-[2-(4-chloro-2-phenylphenyl)-1,3-thiazol-4-yl]acetamido] acetate (200 mg, 0.48 mmol), sodium hydroxide (100 mg, 2.50 mmol), methanol (2.5 mL) and water (2.5 mL). The resulting solution was stirred for 30 min at room temperature. On completion, the solution was adjusted to pH=3 with hydrogen chloride (6M in water). The solid precipitate was collected by filtration. The crude product was stirred in MeOH (1.5 mL) for 1 hr. The solution was then filtered again and the filter cake was washed with MeOH (1 mL×2). This resulted in 42.5 mg (23% yield) of 2-[2-[2-(4-chloro-2-phenylphenyl)-1,3-thiazol-4-yl]acetamido]acetic acid 1-34 as a white solid. LCMS (ES+) m/z (M+H)$^+$387.05, tR=2.008. $^1$H NMR (300 MHz, DMSO-d$_6$, ppm) δ: 12.76 (s, 1H), 8.31 (t, J=5.9 Hz, 1H), 8.02 (d, J=8.5 Hz, 1H), 7.58 (dd, J=8.6, 2.3 Hz, 1H), 7.42 (dd, J=5.7, 2.3 Hz, 4H), 7.36 (s, 1H), 7.29 (dd, J=6.6, 2.9 Hz, 2H), 3.77 (d, J=5.7 Hz, 2H), 3.63 (s, 2H).

Table 5 below shows compounds synthesized via Method 4 using the appropriate ester and amine intermediates.

TABLE 5

Compounds Synthesized via Method 4 using the appropriate ester and amine intermediates

| Example # | Compound Number | Intermediate Ester | Intermediate Amine | LCMS (ES+) m/z (M + H)+ | HNMR (400 MHz, MeOD-d$_4$) δ |
|---|---|---|---|---|---|
| 23$^a$ | I-66 | Z | ethyl 2-aminoacetate (HCl salt) | 421.0 | 8.34 (dt, J = 8.6, 3.2 Hz, 1H), 7.67-7.42 (m, 5H), 7.40-7.20 (m, 3H), 5.25 (s, 1H), 3.93-3.73 (m, 2H) |
| 24$^b$ | I-28 | X | methyl 1-aminocyclo-butane-1-carboxylate (HCl salt) | 385.1 | 8.25 (d, J = 8.5 Hz, 1H), 7.66 (d, J = 2.2 Hz, 1H), 7.60 (s, 1H), 7.50 (dd, J = 8.6, 2.2 Hz, 1H), 3.82 (s, 2H), 2.61 (dtd, J = 14.4, 5.7, 2.3 Hz, 2H), 2.43 (tdd, J = 9.8, 7.3, 2.3 Hz, 2H), 2.16-1.96 (m, 2H) |

TABLE 5-continued

Compounds Synthesized via Method 4 using the appropriate ester and amine intermediates

| Example # | Compound Number | Intermediate Ester | Intermediate Amine | LCMS (ES+) m/z (M + H)+ | HNMR (400 MHz, MeOD-$d_4$) δ |
|---|---|---|---|---|---|
| 25[c] | I-67 | X | (2S,3R)-methyl 2-amino-3-methyl-pentanoate (HCl salt) (CAS: 18598-74-8) | 401.0 | 8.29 (d, J = 8.6 Hz, 1H), 7.67 (d, J = 2.1 Hz, 1H), 7.59 (s, 1H), 7.50 (dd, J = 8.6, 2.2 Hz, 1H), 4.42 (d, J = 5.3 Hz, 1H), 3.92-3.83 (m, 2H), 1.93 (ddd, J = 10.1, 7.0, 4.6 Hz, 1H), 1.61-1.49 (m, 1H), 1.23 (dd, J = 11.1, 4.7 Hz, 1H), 1.00-0.86 (m, 6H). |
| 26[d] | I-36 | Y | ethyl 2-aminoacetate (HCl salt) | 387.1 | (DMSO-$d_6$) 8.13 (t, J = 5.3 Hz, 3H), 8.00-7.85 (m, 2H), 7.69 (d, J = 8.3 Hz, 1H), 7.64-7.39 (m, 6H), 3.65 (d, J = 5.3 Hz, 2H) |
| 27[e] | I-45 | X | methyl 1-aminocyclo-propane-1-carboxylate | 371.0 | 8.18 (d, J = 8.6 Hz, 1H), 7.70-7.61 (m, 2H), 7.49 (dd, J = 8.6, 2.2 Hz, 1H), 4.80 (s, 1H), 3.81 (s, 2H), 3.16 (s, 1H), 1.48 (q, J = 4.4 Hz, 2H), 1.07 (q, J = 4.4 Hz, 2H), 0.93 (s, 1H) |
| 28[e] | I-24 | X | ethyl 2-amino-2-methyl-propanoate (HCl salt) | 373.0 | 8.32 (d, J = 8.6 Hz, 1H), 7.67-7.44 (m, 3H), 3.77 (d, J = 0.8 Hz, 2H), 1.53 (s, 6H) |
| 29[f] | I-38 | AB | ethyl 2-aminoacetate (HCl salt) | 359.0 | 8.27 (d, J = 8.6 Hz, 1H), 7.70-7.57 (m, 2H), 7.48 (dd, J = 8.6, 2.1 Hz, 1H), 4.11-3.87 (m, 3H), 1.62 (d, J = 7.2 Hz, 3H) |
| 30[g] | I-33 | AC | ethyl 2-amino-2-methyl-propanoate (HCl salt) | 387.0 | (DMSO-$d_6$) 12.19 (s, 1H), 8.31 (s, 1H), 8.17 (d, J = 8.6 Hz, 1H), 7.81 (d, J = 2.1 Hz, 1H), 7.57 (dd, J = 8.6, 2.2 Hz, 1H), 3.64 (s, 2H), 2.44 (s, 3H), 1.37 (s, 6H) |
| 31[h] | I-5 | U | ethyl 2-amino-2-methyl-propanoate (HCl salt) | 415.0 | 8.01 (d, J = 8.4 Hz, 1H), 7.54 (dd, J = 8.4, 2.2 Hz, 1H), 7.46-7.35 (m, 4H), 7.34-7.23 (m, 3H), 3.69 (s, 2H), 1.54 (s, 6H) |
| 32[f] | I-27 | AL | ethyl 2-amino-2-methyl-propanoate (HCl salt) | 367.1 | 7.57 (d, J = 8.3 Hz, 1H), 7.53-7.37 (m, 2H), 7.32 (dd, J = 8.3, 2.2 Hz, 1H), 3.77 (d, J = 0.9 Hz, 2H), 2.93 (q, J = 7.5 Hz, 2H), 1.52 (s, 6H), 1.17 (t, J = 7.5 Hz, 3H) |
| 33[i] | I-25 | AE | ethyl 2-amino-2-methyl-propanoate (HCl salt) | 381.2 | 7.56-7.45 (m, 3H), 7.31 (dd, J = 8.3, 2.2 Hz, 1H), 3.77 (d, J = 0.9 Hz, 2H), 3.55 (p, J = 6.8 Hz, 1H), 1.54 (s, 6H), 1.23 (d, J = 6.8 Hz, 6H |
| 34[j] | I-26 | AF | ethyl 2-amino-2-methyl-propanoate (HCl salt) | 379.2 | 7.71 (dd, J = 8.7, 2.6 Hz, 1H), 7.52 (s, 1H), 7.31 (d, J = 8.4 Hz, 1H), 7.16 (s, 1H), 3.79 (d, J = 2.6 Hz, 2H), 2.35 (s, 1H), 1.53 (d, J = 2.6 Hz, 6H), 1.04 (d, J = 8.1 Hz, 2H), 0.77 (d, J = 5.2 Hz, 2H) |

TABLE 5-continued

Compounds Synthesized via Method 4 using the appropriate ester and amine intermediates

| Example # | Compound Number | Intermediate Ester | Intermediate Amine | LCMS (ES+) m/z (M + H)+ | HNMR (400 MHz, MeOD-d₄) δ |
|---|---|---|---|---|---|
| 35[k] | I-21 | AG | ethyl 2-amino-2-methyl-propanoate (HCl salt) | 395.0 | 7.67-7.57 (m, 1H), 7.49 (d, J = 0.8 Hz, 1H), 7.39-7.28 (m, 2H), 3.76 (d, J = 0.8 Hz, 2H), 2.84 (d, J = 7.2 Hz, 2H), 1.74 (m, 1H), 1.54 (s, 6H), 0.84 (d, J = 6.6 Hz, 6H) |

[a]Step 1 was run at rt for 1 hr, then during the work up AcOH was used instead of HCl to adjust the pH to 5. This solution was extracted with ethyl acetate and concentrated to give the intermediate as a yellow oil. The third step also used AcOH to adjust the pH to 4 and after an aqeuous work up the residue was purified by prep-HPLC with the following conditions: Column: X Select C18, 19 * 150 mm, 5 um; mobile phase, Mobile Phase A: water/0.05% NH₄HCO₃, Mobile Phase B: ACN.
[b]Step 2 was run at 60° C. for 1 hr. Step 3 was run at rt for 7 hrs. The final product was purified by prep-HPLC: Column, XBridge Shield RP18 OBD, 5 um, 19 * 150 mm; mobile phase, water/0.05% NH₃ and ACN (7.0% ACN up to 25.0% in 7 min).
[c]Step 2 was run at rt for 1 hr. In Step 3, lithium hydroxide was used instead of sodium hydroxide and the reaction was run at rt for 2 days.
[d]Step 1 was run at 60° C. for 1 hr. Step 2 was run for 5 hr at rt. The final product was purified by prep-HPLC with the following conditions: Column: XBridge Prep C18 OBD, 19 * 150 mm, 5 um, C-0013; mobile phase A: water (10 mmol/NH₄HCO₃) Phase B: ACN.
[e]Step 3 was run at rt for 8 hrs. The final product was purified by prep-HPLC with the following conditions: Column, XBridge Prep C18 OBD, 19 * 150 mm, 5 um, C-0013; mobile phase, Phase A: water (0.05% NH₃) Phase B: ACN.
[f]Step 1 was run at rt for 2 hrs. Step 3 was run at rt for 2 hrs and the final product was purified by Prep-HPLC with the following conditions: Column: X Select C18, 19 * 150 mm, 5 um; mobile phase, Phase A: water/0.05% NH₄HCO₃, Phase B: ACN.
[g]Step 1-3 were run at rt, for 1-2 hrs.
[h]Step 2 was run at rt for 2 hrs. Step 3 was run at rt for 5 hrs.
[i]Only Steps 2-3 were performed as the ester was reduced as part of the synthesis to acid Intermediate AE. Step 3 was run at rt for 5 hrs.
[j]Step 1-3 were run at rt for 3 hrs. The final product was purified by Prep-HPLC with the following conditions (Column, XBridge Prep C18 OBD, 19 x 150 mm 5 um; mobile phase, water (0.05% NH₃) and ACN (15.0% ACN up to 34.0% in 7 min).
[k]Step 1 was run at rt for 1 hr, Step 2 at rt for 2 hrs, and Step 3 at rt for 1 hr. The final product was purified by Prep-HPLC with the following conditions: Column, XBridge Shield RP18 OBD, 5 um, 19 * 150 mm; mobile phase, water (0.05% NH₃) and ACN (10.0% ACN up to 30.0% in 8 min).

Example 36. Synthesis of 2-[2-[2-(2,4-dichlorophenyl)-1,3-thiazol-4-yl]-2-methylpropanamido]acetic Acid, I-64

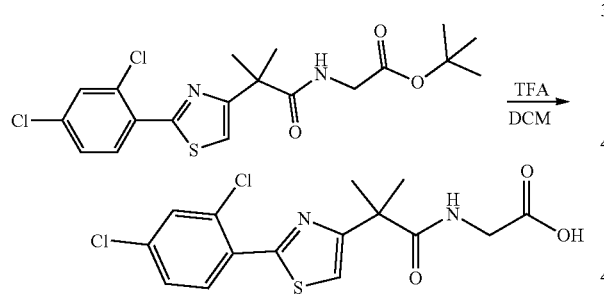

Into a 25-mL round-bottom flask, was placed tert-butyl 2-[2-[2-(2,4-dichlorophenyl)-1,3-thiazol-4-yl]-2-methylpropanamido]acetate (10 mg, 0.02 mmol, synthesized via Method 4, Steps 1-2, starting with ethyl 2-[2-(2,4-dichlorophenyl)-1,3-thiazol-4-yl]-2-methylpropanoate, Intermediate AI in Step 1 which was run at rt for 2 days, and using tert-butyl 2-aminoacetate in Step 2 which was run at rt for 3 hrs), dichloromethane (1.5 mL) and trifluoroacetic acid (0.5 mL). The resulting solution was stirred for 2 hrs at room temperature. On completion, the reaction mixture was concentrated under vacuum. The crude product was purified by prep-HPLC under the following conditions: Column, XBridge Prep OBD C18 Column, 19*150 mm 5 um; mobile phase, water (0.05% NH₃) and ACN (3.0% ACN up to 8.0% in 10 min). This resulted in 4.8 mg (55% yield) of 2-[2-[2-(2,4-dichlorophenyl)-1,3-thiazol-4-yl]-2-methylpropanamido]acetic acid I-64 as a white solid. LCMS: m/z=373 [M+1]⁺, rT=1.52 min. ¹H NMR (300 MHz, Methanol-d4) δ 8.39 (tt, J=5.4, 2.5 Hz, 1H), 7.64 (p, J=2.4 Hz, 2H), 7.51 (dq, J=8.4, 2.6 Hz, 1H), 3.80 (q, J=2.5 Hz, 2H), 1.69 (q, J=2.5 Hz, 6H).

OTHER METHODS

Example 37. Synthesis of 2-[[2-[2-[4-Chloro-2-(cyclobutylmethyl)phenyl]thiazol-4-yl]acetyl]amino]-2-methyl-propanoic Acid, I-10

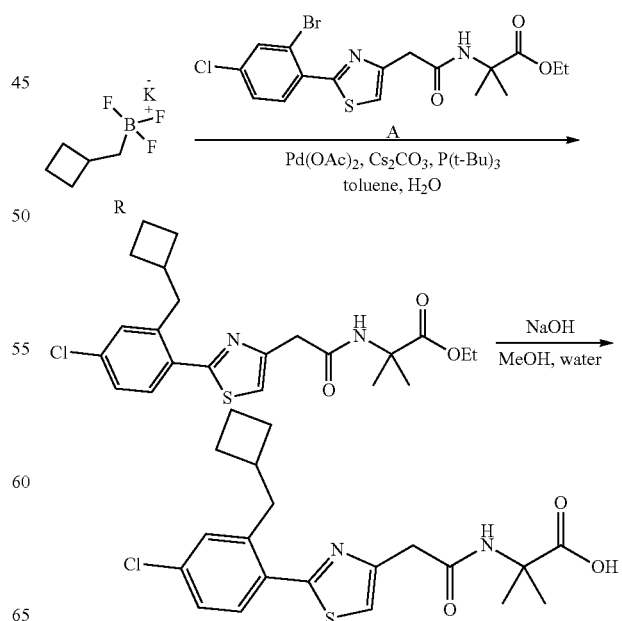

Step 1—Ethyl 2-[[2-[2-[4-chloro-2-(cyclobutylmethyl)phenyl]thiazol-4-yl]acetyl]amino]-2-methyl-propanoate To a mixture of ethyl 2-[[2-[2-(2-bromo-4-chloro-phenyl)thiazol-4-yl]acetyl]amino]-2-methyl-propanoate (500 mg, 1.12 mmol), cyclobutylmethyl(trifluoro)boranuide potassium salt (1.18 g, 6.72 mmol), Pd(OAc)$_2$ (50.3 mg, 224 umol), and P(t-Bu)$_3$ (250 mg, 1.24 mmol) in toluene (20.0 mL) was added Cs$_2$CO$_3$ aq (1.5 M/L, 2.24 mL). The resulting mixture was stirred at 100° C. under nitrogen for 6 hrs. On completion, the reaction mixture was diluted with water and extracted with ethyl acetate. The organic layer was dried over sodium sulfate and concentrated in vacuo. The residue was purified by silica gel chromatography (PE:EA=10/1 to 5/1) to give the title compound (380 mg, 58% yield) as a yellow solid. LCMS: (ES+) m/z (M+H)$^+$=435.2, tR=1.025.

Step 2—2-[[2-[2-[4-Chloro-2-(cyclobutylmethyl)phenyl]thiazol-4-yl]acetyl]amino]-2-methyl-propanoic Acid To a solution of ethyl 2-[[2-[2-[4-chloro-2-(cyclobutylmethyl)phenyl]thiazol-4-yl]acetyl]amino]-2-methyl-propanoate (300 mg, 689.69 umol) in a mixture solvent of MeOH (5.00 mL) and water (5.00 mL) was added NaOH (82.8 mg, 2.07 mmol) at 20° C. The reaction mixture was stirred at 20° C. for 18 hrs. On completion, the reaction mixture was acidified with 1N HCl solution until pH=5. The mixture was extracted with DCM (50 mL) and the organic layer was dried over sodium sulfate and concentrated in vacuo. The residue was purified by prep-HPLC (column: Phenomenex Synergi C18 150*25*10 um; mobile phase: [water (0.225% FA)-ACN]; B %: 48%-78%, 10 min) to give 180 mg impure product. The impure product was purified by SFC (column: OD (250 mm*30 mm, 10 um); mobile phase: [NH$_3$-MeOH]) to give the title compound I-10 (119 mg, 42% yield) as a white solid. LCMS: (ES+) m/z (M+H)$^+$=407.1, tR=0.922.$^1$H NMR (400 MHz, CD$_3$OD) δ=7.59 (d, J=8.4 Hz, 1H), 7.49 (s, 1H), 7.36-7.28 (m, 2H), 3.77 (s, 2H), 3.03 (d, J=7.6 Hz, 2H), 2.52 (td, J=7.6, 15.6 Hz, 1H), 2.01-1.91 (m, 2H), 1.87-1.75 (m, 2H), 1.73-1.62 (m, 2H), 1.54 (s, 6H).

Example 38. Synthesis of 2-[[2-[2-(4-Chloro-2-tetrahydropyran-4-yl-phenyl)thiazol-4-yl]acetyl]amino]-2-methyl-propanoic Acid, I-16

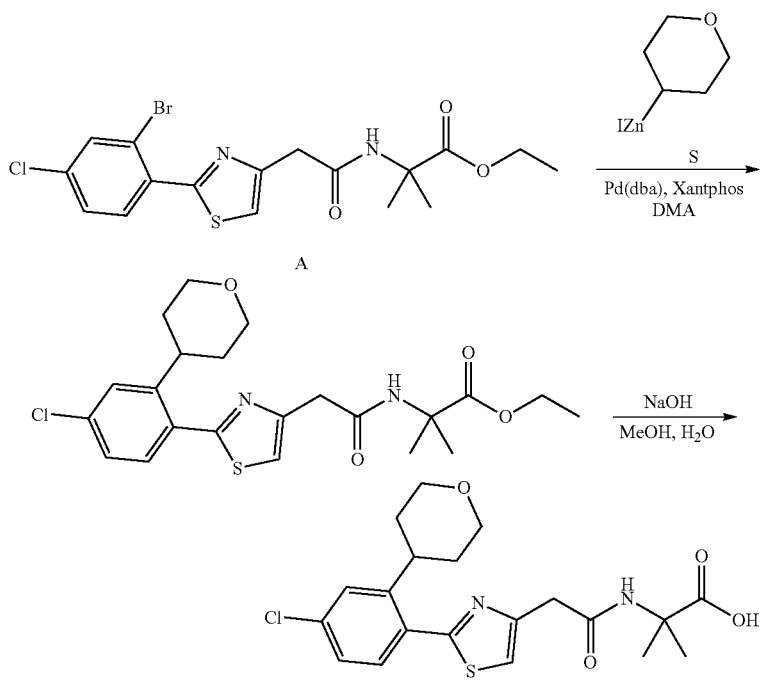

Step 1—Ethyl 2-[[2-[2-(4-chloro-2-tetrahydropyran-4-yl-phenyl)thiazol-4-yl]acetyl]amino]-2-methyl-propanoate To a solution of ethyl 2-[[2-[2-(2-bromo-4-chloro-phenyl)thiazol-4-yl]acetyl]amino]-2-methyl-propanoate (600 mg, 1.35 mmol) in DMA (10.0 mL) was added Pd(dba)$_2$ (38.8 mg, 67.5 umol), Xantphos (39.0 mg, 67.5 umol) and iodo(tetrahydropyran-4-yl)zinc (4.05 mL, 1M). The mixture was degassed and purged with nitrogen gas 3 times, and stirred at 80° C. for 1 hour under nitrogen gas atmosphere. On completion, the reaction mixture was poured into a saturated NH$_4$Cl solution (30 mL), then filtered through a pad of Celite. The filtrate was extracted with ethyl acetate (3×10 mL), and the combined organic phase was collected, dried over anhydrous Na$_2$SO$_4$, filtered and concentrated in vacuo to get a residue. The residue was purified by prep-HPLC (column: Welch Ultimate AQ-C18 150*30 mm*5 um; mobile phase: [water (0.1% TFA)-ACN]; B %: 46%-76%, 13 min) to give the title compound (310 mg, 50% yield) as a colorless gum. $^1$H NMR (400 MHz, CD$_3$Cl) δ=7.51 (d, J=8.4 Hz, 1H), 7.41 (d, J=2.0 Hz, 1H), 7.31 (s, 1H), 7.30-7.27 (m, 1H), 7.22 (s, 1H), 4.17 (q, J=7.2 Hz, 2H), 4.05 (dd, J=3.6, 11.4 Hz, 2H), 3.81 (s, 2H), 3.48-3.41 (m, 3H), 1.89-1.68 (m, 4H), 1.56 (s, 6H), 1.25 (t, J=7.2 Hz, 3H).

297

Step 2—2-[[2-[2-(4-Chloro-2-tetrahydropyran-4-yl-phenyl)thiazol-4-yl]acetyl]amino]-2-methyl-propanoic Acid To a solution of ethyl 2-[[2-[2-(4-chloro-2-tetrahydropyran-4-yl-phenyl)thiazol-4-yl]acetyl]amino]-2-methyl-propanoate (310 mg, 687 umol) in methanol (15.0 mL) and water (6.00 mL) was added sodium hydroxide (110 mg, 2.75 mmol). The mixture was stirred at 15° C. for 16 hours. On completion, the reaction mixture was acidified with 1 M hydrochloride acid to adjust the pH to below 7, and then concentrated in vacuo to give a residue. The residue was purified by prep-HPLC (column: Welch Ultimate AQ-C18 150*30 mm*5 um; mobile phase: [water (0.1% TFA)-ACN]; B %: 32%-62%, 13 min) to give the title compound 1-16 (128 mg, 43% yield) as a white solid. LCMS: (ES+) m/z (M+H)+=423.2, tR=0.742. 1H NMR (400 MHz, DMSO-$d_6$) δ=8.32 (s, 1H), 7.60 (d, J=8.4 Hz, 1H), 7.54 (s, 1H), 7.53 (d, J=2.0 Hz, 1H), 7.41 (dd, J=2.0, 8.4 Hz, 1H), 3.90 (dd, J=2.8, 11.6 Hz, 2H), 3.67 (s, 2H), 3.55 (tt, J=3.6, 11.6 Hz, 1H), 3.36 (dt, J=2.0, 11.6 Hz, 2H), 1.79-1.61 (m, 4H), 1.38 (s, 6H).

Example 39. Synthesis of 2-[[2-[2-[4-Chloro-2-(4-piperidyl)phenyl]thiazol-4-yl]acetyl]amino]-2-methyl-propanoic Acid, I-31

298

Step 1—Tert-butyl 4-[5-chloro-2-[4-[2-[(2-ethoxy-1,1-dimethyl-2-oxo-ethyl)amino]-2-oxo-ethyl]thiazol-2-yl]phenyl]piperidine-1-carboxylate To a solution of ethyl 2-[[2-[2-(2-bromo-4-chloro-phenyl)thiazol-4-yl]acetyl]amino]-2-methyl-propanoate (1.30 g, 2.92 mmol), XantPhos (67.5 mg, 116 umol) and Pd(dba)$_2$ (67.1 mg, 116 umol) in dimethylacetamide (15 mL) was added (1-tert-butoxycarbonyl-4-piperidyl)-iodo-zinc (8.76 mL, 1 M) and the reaction mixture was stirred at 80° C. for 1 hr under nitrogen. On completion, the reaction mixture was poured into 100 mL cool water and extracted with DCM (3×50 mL). The combined organic layer was dried over Na$_2$SO$_4$, filtered and concentrated in vacuo. The residue was purified by silica gel chromatography (petroleum ether:ethyl acetate=3:1) to give the title compound (600 mg, 27% yield) as a yellow solid. LCMS: (ES+) m/z (M+H)+=550.3, tR=1.116.

Step 2—Ethyl 2-[[2-[2-[4-chloro-2-(4-piperidyl)phenyl]thiazol-4-yl]acetyl]amino]-2-methyl-propanoate To a solution of tert-butyl 4-[5-chloro-2-[4-[2-[(2-ethoxy-1,1-dimethyl-2-oxo-ethyl)amino]-2-oxo-ethyl]thiazol-2-yl]phenyl]piperidine-1-carboxylate (400 mg, 727 umol) in

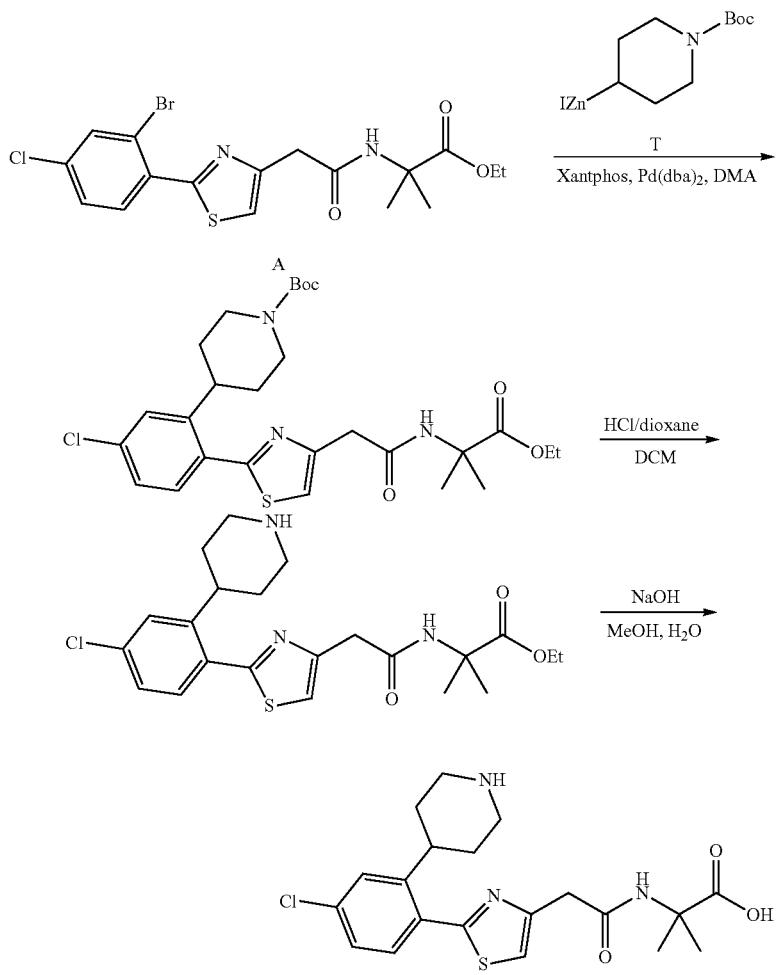

DCM (6 mL) was added HCl/dioxane (4 M, 908 uL) and the reaction mixture was stirred at 20° C. for 10 min. On completion, the reaction mixture was concentrated in vacuo. The residue was triturated with 10 mL MTBE, filtered and the filter cake was dried in vacuo to give the title compound (350 mg, 90% yield, HCl salt) as a yellow solid. LCMS: (ES+) m/z (M+H)$^+$=450.1, tR=0.700.

Step 3—2-[[2-[2-[4-Chloro-2-(4-piperidyl)phenyl]thiazol-4-yl]acetyl]amino]-2-methyl-propanoic Acid To a solution of ethyl 2-[[2-[2-[4-chloro-2-(4-piperidyl)phenyl]thiazol-4-yl]acetyl]amino]-2-methyl-propanoate (150 mg, 308 umol) in a mixture of MeOH (6 mL) and water (2 mL) was added sodium hydroxide (74.0 mg, 1.9 mmol) and the reaction mixture was stirred at 25° C. for 16 hrs. On completion, the reaction mixture was acidified by 1N HCl solution until the pH=4 and concentrated in vacuo. The residue was purified by prep-HPLC (column: Phenomenex Synergi C18 150*25*10 um; mobile phase: [water (0.05% HCl)-ACN]) to give the title compound 1-31 (32.0 mg, 22% yield, HCl salt) as a white solid. LCMS: (ES+) m/z (M+H)$^+$=422.1, tR=0.661. $^1$H NMR (400 MHz, DMSO-d6) δ=9.05 (br s, 2H), 8.41 (s, 1H), 7.64 (d, J=8.4 Hz, 1H), 7.55 (s, 1H), 7.46 (dd, J=2.0, 8.4 Hz, 1H), 7.41 (d, J=2.0 Hz, 1H), 3.70 (s, 2H), 3.66-3.59 (m, 1H), 3.33-3.28 (m, 2H), 2.94-2.90 (m, 2H), 1.99-1.88 (m, 4H), 1.38 (s, 6H).

Example 40. Synthesis of 2-[[2-[2-[2-(1-Acetyl-4-piperidyl)-4-chloro-phenyl]thiazol-4-yl]acetyl]amino]-2-methyl-propanoic Acid, I-11

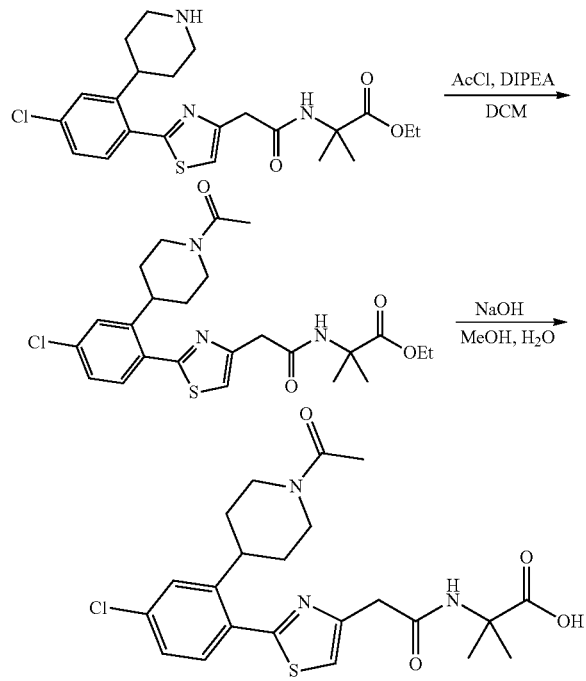

Step 1—Ethyl 2-[[2-[2-[2-(1-acetyl-4-piperidyl)-4-chloro-phenyl]thiazol-4-yl]acetyl]amino]-2-methyl-propanoate To a solution of ethyl 2-[[2-[2-[4-chloro-2-(4-piperidyl)phenyl]thiazol-4-yl]acetyl]amino]-2-methyl-propanoate (150 mg, 308 umol, HCl salt, synthesized via Steps 1-2 of Example 42) and diisopropylethylamine (119 mg, 925 umol) in DCM (3 mL) was added acetyl chloride (29.0 mg, 370 umol) and the reaction mixture was stirred at 20° C. for 10 min. On completion, the reaction mixture was diluted with 10 mL DCM and acidified with 1N HCl solution until the pH=6. The layers were separated and the organic layer was concentrated in vacuo to give the title compound (150 mg, 95% yield) as a light yellow solid. LCMS: (ES+) m/z (M+H)$^+$=492.1, tR=0.873.

Step 2—2-[[2-[2-[2-(1-Acetyl-4-piperidyl)-4-chloro-phenyl]thiazol-4-yl]acetyl]amino]-2-methyl-propanoic Acid To a solution of ethyl 2-[[2-[2-[2-(1-acetyl-4-piperidyl)-4-chloro-phenyl]thiazol-4-yl]acetyl]amino]-2-methyl-propanoate (150 mg, 304 umol) in a mixture of MeOH (6 mL) and water (3 mL) was added sodium hydroxide (60.9 mg, 1.52 mmol) and the reaction mixture was stirred at 25° C. for 16 hrs. On completion, the reaction mixture was acidified by 1N HCl solution until pH=4 and concentrated in vacuo. The residue was purified by prep-HPLC (column: Phenomenex Synergi C18 150*25*10 um; mobile phase: [water (0.225% FA)-ACN]) to give the title compound I-11 (56.0 mg, 39% yield) as a white solid. LCMS: (ES+) m/z (M+H)$^+$=464.0, tR=0.973. $^1$H NMR (400 MHz, DMSO-d$_6$) δ=8.20 (s, 1H), 7.62 (d, J=8.4 Hz, 1H), 7.57 (s, 1H), 7.53 (d, J=2.0 Hz, 1H), 7.41 (dd, J=2.0, 8.4 Hz, 1H), 4.52-4.50 (m, 1H), 3.90-3.88 (m, 1H), 3.68 (s, 2H), 3.58-3.51 (m, 2H), 3.06-3.00 (m, 1H), 2.02 (s, 3H), 1.81-1.74 (m, 2H), 1.73-1.63 (m, 1H), 1.54-1.48 (m, 1H), 1.38 (s, 6H).

Example 41. Synthesis of 2-(2-[2-[2-(carbamoylmethyl)-4-chlorophenyl]-1,3-thiazol-4-yl]acetamido)acetic Acid, I-65

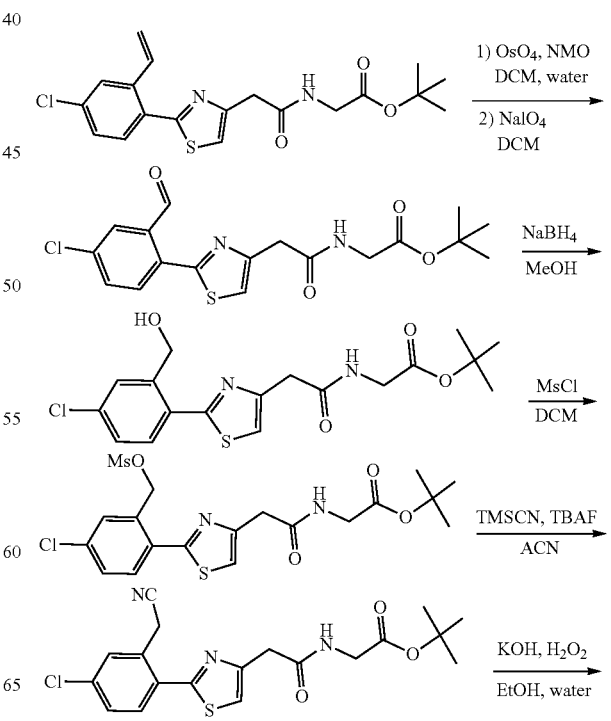

-continued

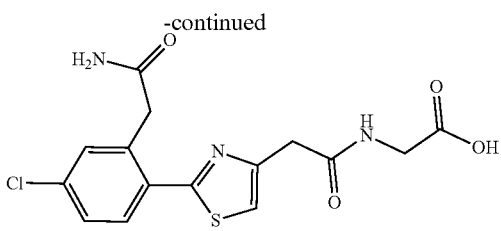

Step 1: Tert-butyl 2-[2-[2-(4-chloro-2-formylphenyl)-1,3-thiazol-4-yl]acetamido]acetate Into a 250-mL round-bottom flask, was placed a solution of tert-butyl 2-[2-[2-(4-chloro-2-ethenylphenyl)-1,3-thiazol-4-yl]acetamido]acetate (3.0 g, 7.6 mmol, synthesized via Method 4, Steps 1-2, starting from Intermediate AD as the ester starting material and coupling amine tert-butyl 2-aminoacetate at rt over 8 hrs in Step 2) in DCM/water=5/1 (60 mL), and NMO (642 mg, 5.49 mmol). This was followed by the addition of tetraoxoosmium (197 mg, 0.77 mmol) and the mixture was stirred at r.t. for 8 h. On completion, the reaction was then quenched by the addition of 50 mL of water. The resulting solution was extracted with dichloromethane (3×50 mL) and the organic layers combined and concentrated under vacuum. To this residue was added a solution of sodium periodate (4.9 g, 22.91 mmol) in dichloromethane (60 mL). The resulting solution was stirred for 2 h at room temperature. On completion, the reaction was quenched by the addition of 50 mL of water. The resulting solution was extracted with dichloromethane (3×50 mL) and the organic layers combined and concentrated under vacuum. This resulted in 3 g (crude) of tert-butyl 2-[2-[2-(4-chloro-2-formylphenyl)-1,3-thiazol-4-yl]acetamido]acetate as a black solid. LCMS: (ES+) m/z (M+H)$^+$=395.1, tR=1.092

Step 2: Tert-butyl 2-(2-[2-[4-chloro-2-(hydroxymethyl)phenyl]-1,3-thiazol-4-yl]acetamido) acetate Into a 250-mL round-bottom flask was placed a solution of tert-butyl 2-[2-[2-(4-chloro-2-formylphenyl)-1,3-thiazol-4-yl]acetamido]acetate (3 g, 7.60 mmol) in methanol (100 mL) and NaBH$_4$ was added (870 mg, 22.9 mmol). The resulting solution was stirred for 1 h at room temperature. On completion, the reaction was then quenched by the addition of 50 mL of water. The resulting mixture was concentrated under vacuum then was extracted with dichloromethane (3×50 mL) and the organic layers combined and concentrated under vacuum. The residue was purified by silica gel chromatography with water/ACN (100/40). This resulted in 1.9 g (63% yield) of tert-butyl 2-(2-[2-[4-chloro-2-(hydroxymethyl)phenyl]-1,3-thiazol-4-yl]acetamido)acetate as a black solid. LCMS: (ES+) m/z (M+H)$^+$=397.0, tR=1.425

Step 3: Tert-butyl 2-[2-(2-[4-chloro-2-[(methanesulfonyloxy)methyl]phenyl]-1,3-thiazol-4-yl)acetamido]acetate Into a 250-mL round-bottom flask was placed a solution of tert-butyl 2-(2-[2-[4-chloro-2-(hydroxymethyl)phenyl]-1,3-thiazol-4-yl]acetamido)acetate (1.9 g, 4.8 mmol) in dichloromethane (50 mL), then methanesulfonyl chloride (1.1 g, 0.74 mL, 9.6 mmol) and triethylamine (970 mg, 1.2 mL, 9.59 mmol) were added. The resulting solution was stirred for 3 hrs at room temperature. On completion, the reaction was quenched by the addition of 50 mL of water. The resulting solution was extracted with dichloromethane (3×100 mL) and the organic layers combined and concentrated under vacuum. This resulted in 800 mg (crude) of tert-butyl 2-[2-(2-[4-chloro-2-[(methanesulfonyloxy)methyl]phenyl]-1,3-thiazol-4-yl)acetamido]acetate as a blue solid. LCMS: (ES+) m/z (M+H)$^+$=475.0, tR=2.074.

Step 4: Tert-butyl 2-(2-[2-[4-chloro-2-(cyanomethyl)phenyl]-1,3-thiazol-4-yl]acetamido) acetate Into a 100-mL round-bottom flask was placed a solution of tert-butyl 2-[2-(2-[4-chloro-2-[(methanesulfonyloxy)methyl]phenyl]-1,3-thiazol-4-yl)acetamido]acetate (300 mg, 0.63 mmol) in ACN (25 mL), and trimethylsilanecarbonitrile (124 mg, 1.25 mmol) and TBAF (595 mg, 1.89 mmol) were added. The resulting solution was stirred for 30 min at room temperature. On completion, the reaction was extracted with dichloromethane (3×10 mL) and the organic layers combined and concentrated in vacuo. The residue was purified by silica gel chromatography with Water/ACN (100/40). This resulted in 30 mg (12% yield) of tert-butyl 2-(2-[2-[4-chloro-2-(cyanomethyl)phenyl]-1,3-thiazol-4-yl]acetamido)acetate as a black solid. LCMS: (ES+) m/z (M+H)$^+$=406.0, tR=1.044.

Step 5: 2-(2-[2-[2-(Carbamoylmethyl)-4-chlorophenyl]-1,3-thiazol-4-yl]acetamido)acetic acid Into a 50-mL round-bottom flask was placed a solution of tert-butyl 2-(2-[2-[4-chloro-2-(cyanomethyl)phenyl]-1,3-thiazol-4-yl]acetamido)acetate (25 mg, 0.06 mmol) in ethanol/water=5/1 (15 mL), potassium hydroxide (13 mg, 0.23 mmol), and hydrogen peroxide (5 mL, 30%). The resulting solution was stirred for 16 h at room temperature. The mixture was washed with sat. NaHSO$_3$ solution, extracted with dichloromethane (3×20 mL) and the organic layers combined and concentrated in vacuo. The crude product was purified by prep-HPLC with the following conditions: Column, XBridge Prep C18 OBD Column 19*150 mm SumC-0013; mobile phase, Phase A:water (0.05% NH$_3$) Phase B:ACN. This resulted in 1.4 mg (6% yield) of 2-(2-[2-[2-(carbamoylmethyl)-4-chlorophenyl]-1,3-thiazol-4-yl]acetamido)acetic acid I-65 as a white solid. LCMS m/z=368.0 [M+1]$^+$, rT=1.504. $^1$H-NMR (300 MHz, Methanol-d4, ppm): δ 7.70 (d, J=8.3 Hz, 1H), 7.55-7.37 (m, 3H), 3.99-3.81 (m, 6H).

Example 42. Synthesis of 2-(2-[2-[4-chloro-2-(2-hydroxyethyl)phenyl]-1,3-thiazol-4-yl]acetamido) acetic Acid, I-70

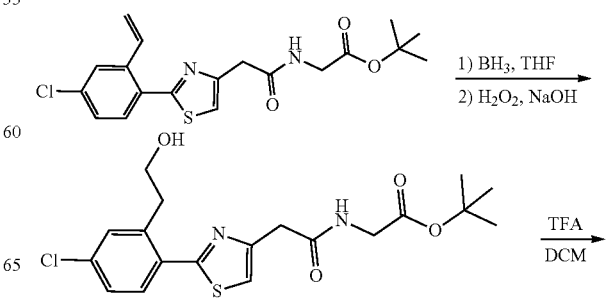

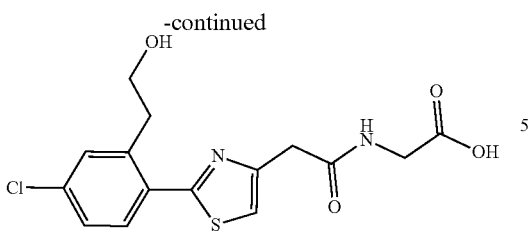

Step 1: tert-butyl 2-(2-[2-[4-chloro-2-(2-hydroxy-ethyl)phenyl]-1,3-thiazol-4-yl]acetamido) acetate Into a 250-mL 3-necked round-bottom flask, was placed tert-butyl 2-[2-[2-(4-chloro-2-ethenylphenyl)-1,3-thiazol-4-yl]acetamido]acetate (2.3 g, 5.9 mmol, synthesized as described above in Example 41), BH$_3$ (20 mL, 20 mmol, BH$_3$-THF solution, 1M) and tetrahydrofuran (60 mL). The resulting solution was stirred for 12 h at 25° C. Then hydrogen peroxide (796 mg, 7 mmol, 30% in water) and sodium hydroxide (936 mg, 23.4 mmol) were added with stirring, and the reaction was stirred for an additional 2 h at 25° C. On completion, the reaction mixture was extracted with ethyl acetate (3×200 mL) and the organic layers combined. The organic layer was washed with brine (3×100 mL), dried over anhydrous sodium sulfate, filtered and concentrated under vacuum. The crude product was purified by flash-prep-HPLC with the following conditions (Intel-Flash-1): Column, silica gel; mobile phase, ACN/H$_2$O=1/1. This resulted in 530 mg (22% yield) of tert-butyl 2-(2-[2-[4-chloro-2-(2-hydroxyethyl)phenyl]-1,3-thiazol-4-yl]acetamido)acetate as yellow oil. LCMS: (ES+) m/z (M+H)$^+$=411.0, tR=1.093.

Step 2: 2-(2-[2-[4-chloro-2-(2-hydroxyethyl)phenyl]-1,3-thiazol-4-yl]acetamido)acetic acid Into a 50-mL round-bottom flask, was placed tert-butyl 2-(2-[2-[4-chloro-2-(2-hydroxyethyl)phenyl]-1,3-thiazol-4-yl]acetamido)acetate (100 mg, 0.24 mmol), trifluoroacetic acid (0.5 mL) and dichloromethane (4 mL). The resulting solution was stirred for 1 h at 25° C. On completion, the resulting mixture was concentrated under vacuum. The crude product was purified by prep-HPLC with the following conditions (Column: X Select C18, 19*150 mm, 5 um); Mobile phase A:water/0.05% NH$_4$HCO$_3$, Mobile Phase B: ACN. This resulted in 14.8 mg (17% yield) of 2-(2-[2-[4-chloro-2-(2-hydroxyethyl)phenyl]-1,3-thiazol-4-yl]acetamido)acetic acid I-70 as a white solid. LCMS: m/z=355.00 [M+1]$^+$, tR 1.64 min. $^1$H-NMR: (300 MHz, Methanol-d4) δ 7.71-7.59 (m, 2H), 7.53 (d, J=2.2 Hz, 1H), 7.40 (dd, J=8.3, 2.2 Hz, 1H), 3.99 (s, 2H), 3.93-3.77 (m, 4H), 3.12 (t, J=6.5 Hz, 2H).

Example 43. Synthesis of 2-[2-[2-(2,3-dihydro-1,4-benzodioxin-6-yl)-1,3-thiazol-4-yl]acetamido]acetic Acid, I-62

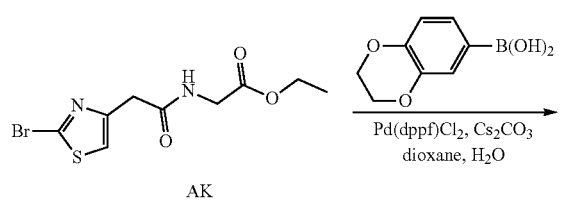

Into a 100-mL round-bottom flask, was placed ethyl 2-[2-(2-bromo-1,3-thiazol-4-yl)acetamido]acetate (310 mg, 1.0 mmol, Intermediate AK), (2,3-dihydro-1,4-benzodioxin-6-yl)boronic acid (225 mg, 1.25 mmol, CAS #: 164014-95-3), Pd(dppf)Cl$_2$ (83.7 mg, 0.11 mmol), cesium carbonate (978 mg, 3 mmol), water (2 mL) and dioxane (5 mL). The resulting solution was stirred for 3 h at 80° C. On completion, the reaction was cooled to rt then quenched by the addition of 20 mL of water. The solids were filtered out and the resulting solution was washed with dichloromethane (3×20 mL) and the aqueous layers combined. The aqueous layer was adjusted to pH=3 with hydrogen chloride (3 mol/L). The solid precipitate was collected by filtration and dried under vacuum. This resulted in 89.5 mg (26% yield) of 2-[2-[2-(2,3-dihydro-1,4-benzodioxin-6-yl)-1,3-thiazol-4-yl]acetamido]acetic acid 1-62 as a white solid. LCM: m/z=335 [M+1]$^+$, rT=1.488. $^1$H NMR (300 MHz, Methanol-d$_4$) δ 7.50-7.37 (m, 2H), 7.33 (d, J=0.9 Hz, 1H), 6.92 (d, J=8.4 Hz, 1H), 4.30 (s, 4H), 3.98 (s, 2H), 3.80 (d, J=0.8 Hz, 2H

Example 44. Synthesis of 2-[2-[2-(4-chloronaphthalen-1-yl)-1,3-thiazol-4-yl]acetamido]acetic Acid, I-40

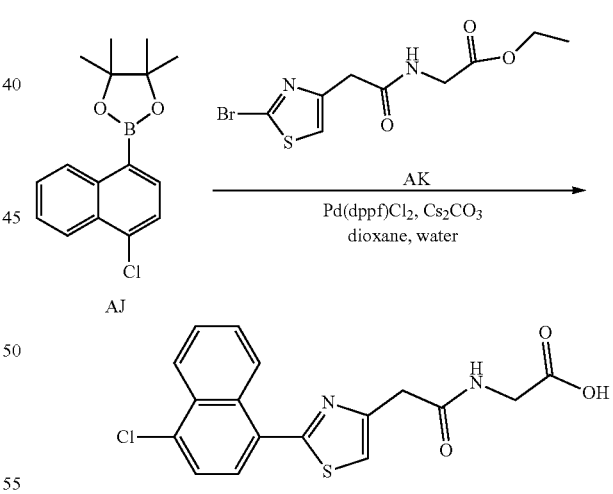

Into a 30-mL sealed tube was placed 2-(4-chloronaphthalen-1-yl)-4,4,5,5-tetramethyl-1,3,2-dioxaborolane (105 mg, 0.36 mmol, Intermediate AJ), ethyl 2-[2-(2-bromo-1,3-thiazol-4-yl)acetamido]acetate (93 mg, 0.30 mmol, Intermediate AK), Pd(dppf)Cl$_2$(11 mg, 0.02 mmol), cesium carbonate (294 mg, 0.90 mmol), dioxane (4.5 mL) and water (1 mL). The resulting solution was stirred for 5.5 h at 90° C. On completion, the reaction was cooled to rt then quenched by the addition of 15 mL of water. The resulting solution was washed with ethyl acetate (2×5 mL). The pH value of the aqueous solution was adjusted to 3 with hydrogen chloride (6M). The solid precipitate was collected by filtration. The crude product was purified by prep-HPLC with the following conditions. Column: Xbridge Prep C18 OBD Column 19×15 mm 5uMC-0013; mobile phase: Phase A: water, Phase B: ACN. This resulted in 0.0194 g (18% yield) of 2-[2-[2-(4-chloronaphthalen-1-yl)-1,3-thiazol-4-yl]acetamido]acetic acid 1-40 as an off-white solid. LCMS: m/z=361.05 [M+1]$^+$, tR=1.121 $^1$H NMR (300 MHz, Methanol-d4): δ 8.72 (dd, J=7.7, 2.1 Hz, 1H), 8.38 (dd, J=7.6, 2.1 Hz, 1H), 7.85-7.57 (m, 5H), 4.01 (s, 2H), 3.93 (s, 2H).

SHMT1 and SHMT2 Activity Assays

Full length human cytosolic Serine Hydroxymethyl transferase 1 (SHMT1, residues 1-483 in Uniport ID P34896) was expressed as an N-terminal His6 tagged protein and purified in *E. coli* using nickel capture followed by size-exclusion chromatography. Human mitochondrial SHMT2 (residues 30-504 in Uniprot ID P34897) with mitochondrial leader sequence deleted was expressed as an N-terminal His$_6$ tagged protein and purified in *E. coli* using nickel capture followed by size-exclusion chromatography.

Serine hydroxymethyltransferases catalyze the reversible hydroxymethylation of glycine to serine, with methylene tetrahydrofolate (CH$_2$-THF) providing the additional carbon. SHMT1 and SHMT2 activity was determined by measuring serine production from glycine and CH$_2$-THF using mass spectroscopy. Briefly, 15 ul of 0.5 mM glycine and 0.2 mM CH$_2$-THF in 20 mM TEA, pH8.0, 0.2 mM NADPH were added to 384 well plate containing 0, 0.05 mM, 0.005 mM or 0.0005 mM of inhibitor. 15 ul of SHMT1 or 2 were added to initiate the reaction. The plate was incubated for 60 minutes at room temperature and the reaction was quenched by the addition of 30 ul of 10% trichloroacetic acid. Serine produced was analyzed using Rapidfire 360 and API4000$^+$ in the positive ion mode.

Purification of *Arabidopsis thaliana* SHMT

The following buffers were used during the purification protocol:

Buffer a (Lysis and Wash Buffer):

| |
|---|
| 20 mM Na-Phosphat (pH 7.4) |
| 500 mM NaCl |
| 40 mM Imidazole |
| 1.0 mM L-Serine |
| 0.5 mM Pyridoxal-5-phosphate |
| 0.5 mM DTT |

Buffer B (Elution Buffer):

| |
|---|
| 20 mM Na-Phosphat (pH 7.4) |
| 500 mM NaCl |
| 250 mM Imidazole |
| 1.0 mM L-Serine |
| 0.5 mM Pyridoxal-5-phosphate |
| 0.5 mM DTT |

Cell Lysis

All procedures were conducted at 4° C. or on ice. Pellets were suspended in Buffer A containing 1 mg/ml DNAse+ Complete EDTA-free protease inhibitor tablet. Cells were lysed using sonication or a French Press device, using standard settings. Lysis was centrifuged at 40000×g for 25 minutes. The supernatant was filtered (0.22 μM) before loading onto a Ni-NTA column.

Purification:

A gravity flow column containing Ni-NTA resin was equilibrated with 10 CV Buffer A and loaded with filtered cell lysate. The column was then washed with 10 CV Buffer A. Elution was afforded using Buffer B and collected manually as mini-factions. EDTA was added after elution to a final concentration of 1 mM. Fractions were pooled on the basis of the correct band for SHMT visualised via SDS-PAGE and staining.

Determination of the ED$_{50}$ SHMT was carried out as described hereinunder.

Activity Assay:

SHMT Assay Buffer:

| |
|---|
| 50 mM KH$_2$PO$_4$ (pH 7.4) |
| 2.0 mM NAD+ |
| 7.5 mM OTT |
| 0.3 mM Tetrahydrofolic acid |
| 4% DMSO |

Reaction Start: 20 mM L-Serine

The rate of N5,N10-CH$_2$-THF formation catalyzed by SHMT was monitored at 340 nm by coupling with excess N5,N10-CH$_2$-THF dehydrogenase, which converts NAD+ to NADH. Reactions were initiated by adding 20 mM L-Serine. Inhibition of initial velocity was determined by adding various inhibitors of the SHMT reaction and monitored as described. Reactions were measured in a Bio Tek micro titer plate reader following the change in absorption with the formation of NADH for 30 minutes.

Table 6 shows the inhibitory activity (IC$_{50}$) of selected compounds of this invention in the SHMT1 and SHMT2 activity inhibition assay. The compound numbers correspond to the compound numbers in Table 1. Compounds having an activity designated as "A" provided inhibitory activity (IC$_{50}$) of <1 μM; compounds designated as "B" provided inhibitory activity (IC$_{50}$) of 1-10 μM; compounds designated as "C" provided inhibitory activity (IC$_{50}$) of 10-100 μM; compounds designated as "D" provided inhibitory activity (IC$_{50}$) of 100-500 PM, and compounds designated as "E" provided inhibitory activity (IC$_{50}$) of >500 μM.

TABLE 6

SHMT1 and SHMT2 inhibitory activity (IC$_{50}$)

| Compound Number | SHMT1 IC50 (uM) | SHMT2 IC50 (uM) |
|---|---|---|
| I-1 | A | A |
| I-2 | A | B |
| I-3 | A | A |
| I-4 | A | A |
| I-5 | A | A |
| I-6 | A | A |
| I-7 | A | A |
| I-8 | A | A |
| I-9 | A | A |
| I-10 | A | A |
| I-11 | B | A |
| I-12 | B | A |
| I-13 | B | A |
| I-14 | B | A |
| I-15 | B | A |
| I-16 | B | A |
| I-17 | B | A |
| I-18 | B | A |
| I-19 | B | A |
| I-20 | B | A |
| I-21 | B | A |
| I-22 | B | A |
| I-23 | B | B |
| I-24 | B | A |
| I-25 | B | A |

TABLE 6-continued

SHMT1 and SHMT2 inhibitory activity (IC$_{50}$)

| Compound Number | SHMT1 IC50 (uM) | SHMT2 IC50 (uM) |
|---|---|---|
| I-26 | C | B |
| I-27 | C | B |
| I-28 | C | B |
| I-29 | C | B |
| I-30 | C | B |
| I-31 | C | B |
| I-32 | C | C |
| I-33 | C | B |
| I-34 | C | C |
| I-35 | C | C |
| I-36 | C | C |
| I-37 | C | B |
| I-38 | C | C |
| I-39 | C | C |
| I-40 | C | C |
| I-41 | C | C |
| I-42 | C | D |
| I-43 | C | C |
| I-44 | C | D |
| I-45 | C | C |
| I-46 | C | C |
| I-47 | D | D |
| I-48 | D | D |
| I-49 | D | D |
| I-50 | D | D |
| I-51 | D | D |
| I-52 | D | D |
| I-53 | D | C |
| I-54 | D | D |
| I-55 | D | D |
| I-56 | D | D |
| I-57 | D | C |
| I-58 | D | D |
| I-59 | D | D |
| I-60 | D | D |
| I-61 | D | C |
| I-62 | D | D |
| I-63 | D | D |
| I-64 | D | D |
| I-65 | D | D |
| I-66 | D | E |
| I-67 | D | D |
| I-68 | D | D |
| I-69 | D | D |
| I-70 | D | D |
| I-71 | D | D |

I claim:
1. A compound of Formula II-a:

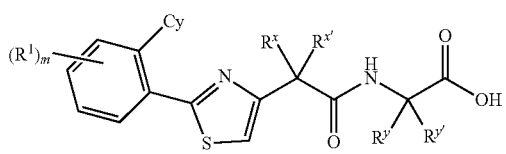

II-a or a pharmaceutically acceptable salt thereof, wherein:
each $R^1$ is independently halogen, —CN, —NO$_2$, —OR, —Cy, or an optionally substituted C$_{1-6}$ aliphatic group; or
two $R^1$ groups can be taken together with their intervening atoms to form a 5-8 membered partially unsaturated or aryl fused ring having 0-3 heteroatoms independently selected from nitrogen, oxygen or sulfur;

each R is independently hydrogen or an optionally substituted group selected from C$_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

each Cy is independently an optionally substituted group selected from a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

$R^x$ and $R^y$ are independently hydrogen or an optionally substituted group selected from C$_{1-6}$ aliphatic or phenyl;

$R^{x'}$ and $R^{y'}$ are independently hydrogen or C$_{1-4}$ alkyl; or

Ry and Ry' can be taken together with their intervening atoms to form a 3-6 membered saturated ring having 0-3 heteroatoms independently selected from nitrogen, oxygen or sulfur; and m is 1, 2, 3, or 4.

2. The compound according to claim 1, wherein each of $R^1$ is independently halogen, —CN, —OR, —Cy, or an optionally substituted C$_{1-6}$ aliphatic group.

3. The compound according to claim 1, wherein two $R^1$ groups are taken together with their intervening atoms to form a 5-8 membered partially unsaturated fused ring having 0-3 heteroatoms independently selected from nitrogen, oxygen or sulfur.

4. The compound according to claim 1, wherein $R^x$ and $R^y$ are independently hydrogen or an optionally substituted group selected from C$_{1-6}$ aliphatic.

5. The compound according to claim 1, wherein $R^{x'}$ and $R^{y'}$ are independently hydrogen or C$_{1-2}$ alkyl.

6. The compound according to claim 1, wherein m is 1, 2, or 3.

7. The compound according to claim 1, wherein $R^y$ and $R^{y'}$ are taken together with their intervening atoms to form a 3-6 membered saturated carbocyclic ring.

8. The compound according to claim 1, wherein each of $R^1$ is independently chloro or —Cy.

9. The compound according to claim 8, wherein m is 1 or 2.

10. The compound according to claim 1, wherein said compound is selected from one of the following compounds:

I-1
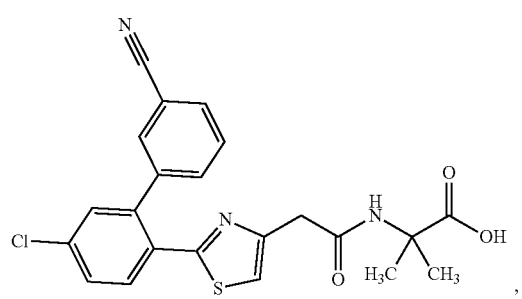
I-2
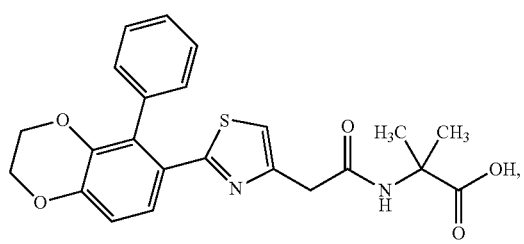
I-4
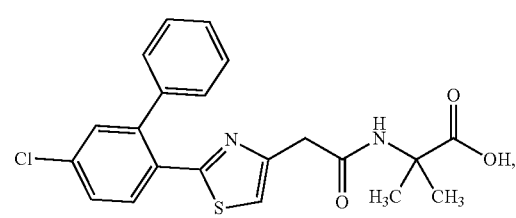
I-5
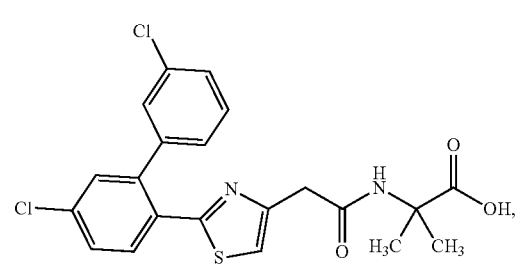
I-6
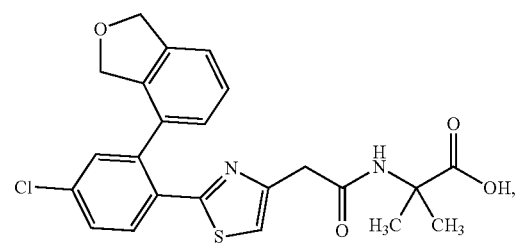
I-7
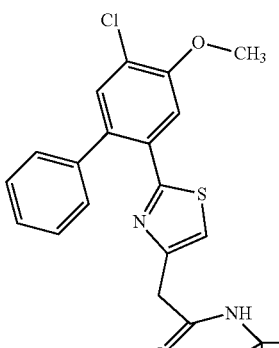
-continued
I-8
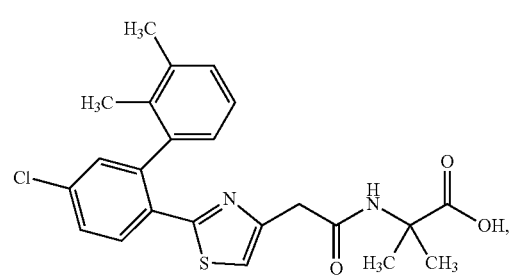
I-9
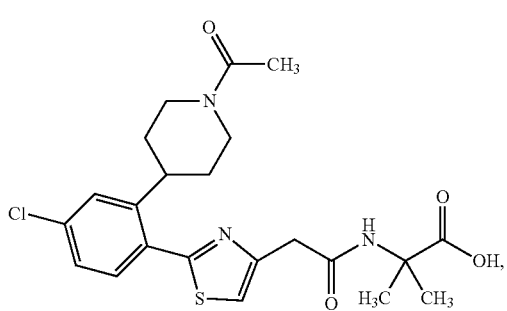
I-11
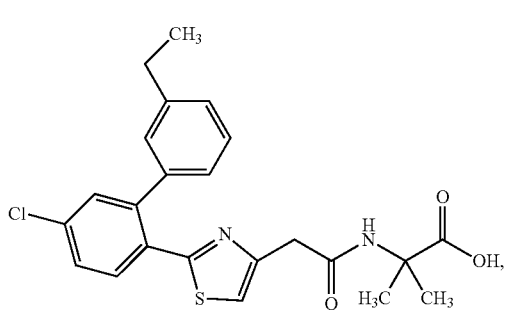
I-12
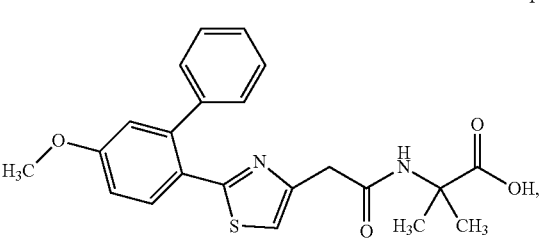
I-13

I-14
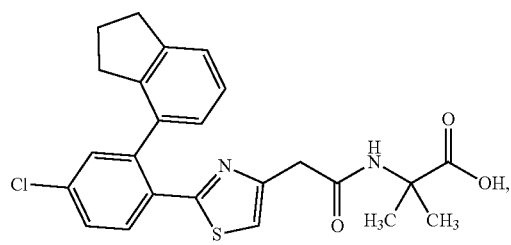
I-16
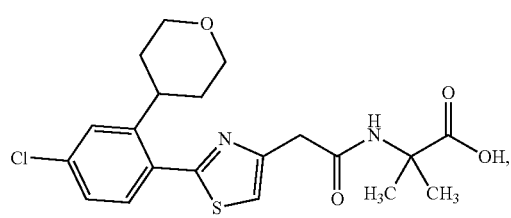
I-22
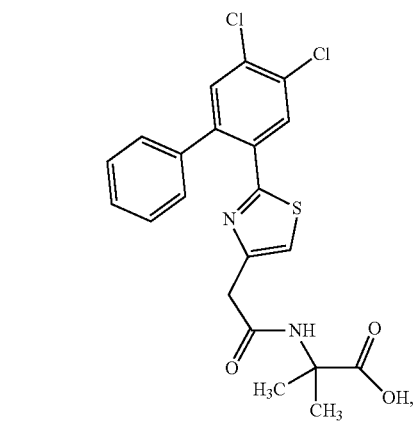
I-26
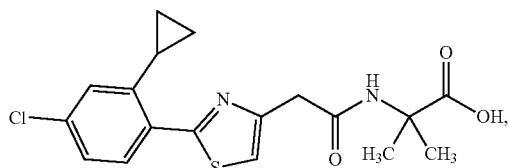
I-31
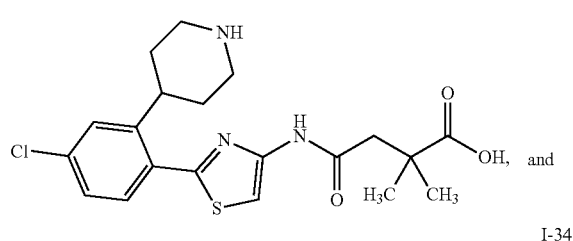 and
I-34
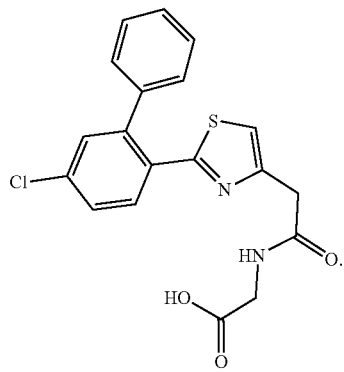
11. A pharmaceutically acceptable composition comprising a compound of claim 1, and a pharmaceutically acceptable carrier, adjuvant, or vehicle.
* * * * *